(12) United States Patent
Peacock et al.

(10) Patent No.: US 10,806,887 B2
(45) Date of Patent: Oct. 20, 2020

(54) PATIENT INTERFACE AND COMPONENT PARTS

(71) Applicant: Fisher & Paykel Healthcare Limited, Auckland (NZ)

(72) Inventors: Mathew Ian Peacock, Auckland (NZ); Laurence Gulliver, Auckland (NZ); Jason Allan Klenner, Auckland (NZ); Brent Ian Laing, Auckland (NZ); Sooji Hope Clarkson, Auckland (NZ); Mark Thomas O'Connor, Auckland (NZ); Milanjot Singh Assi, Auckland (NZ); Aidan James Moyle, Auckland (NZ); Andrew Rolf Drain, Auckland (NZ); Christi Nicol Enslin, Auckland (NZ); Olivia Grace Curtis, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 839 days.

(21) Appl. No.: 15/319,657

(22) PCT Filed: Jun. 18, 2015

(86) PCT No.: PCT/IB2015/054585
§ 371 (c)(1),
(2) Date: Dec. 16, 2016

(87) PCT Pub. No.: WO2015/193833
PCT Pub. Date: Dec. 23, 2015

(65) Prior Publication Data
US 2017/0151409 A1 Jun. 1, 2017

Related U.S. Application Data

(60) Provisional application No. 62/110,146, filed on Jan. 30, 2015, provisional application No. 62/096,028, (Continued)

(51) Int. Cl.
*A61M 16/08* (2006.01)
*A61M 16/06* (2006.01)
(Continued)

(52) U.S. Cl.
CPC .... *A61M 16/0816* (2013.01); *A61M 16/0066* (2013.01); *A61M 16/021* (2017.08);
(Continued)

(58) Field of Classification Search
CPC .......... A61M 16/0683; A61M 16/0694; A61M 16/0633–0655; A61M 16/0816; A44B 11/2573; A44B 11/2534
See application file for complete search history.

(56) References Cited

U.S. PATENT DOCUMENTS

| | | | |
|---|---|---|---|
| 3,585,692 A * | 6/1971 | Le Mire | A44B 11/2534 24/635 |
| 3,682,171 A | 9/1972 | Dali et al. | |

(Continued)

FOREIGN PATENT DOCUMENTS

| | | |
|---|---|---|
| AU | 2012265597 | 1/2013 |
| CN | 2286558 | 7/1998 |

(Continued)

OTHER PUBLICATIONS

International Search Report; PCT/IB2015/054585; dated Jan. 7, 2016; 7 pages.
(Continued)

*Primary Examiner* — Valerie L Woodward
(74) *Attorney, Agent, or Firm* — Knobbe Martens Olson and Bear LLP

(57) ABSTRACT

A patient interface and component parts which may include: a component such as a clip for supporting a gas supply tube to the interface; a buckle may be provided at an end of a headgear strap for releasable attachment to the interface; a
(Continued)

manifold part of a patient interface may be attachable to the interface in a manner allowing for adjustment or re-orientation such that an associated gas supply conduit is re-routed to be to a left- or a right-side of the interface (or user); one or a pair of support side arms of the interface may be configured to be twisted or bent so as to more comfortably accommodate the shape of a user's face upon which they are to be located in use; parts of a manifold at the connection of a gas supply tube to the interface may be configured to be of a multi-part manifold assembly.

20 Claims, 115 Drawing Sheets

Related U.S. Application Data filed on Dec. 23, 2014, provisional application No. 62/096,073, filed on Dec. 23, 2014, provisional application No. 62/096,414, filed on Dec. 23, 2014, provisional application No. 62/096,404, filed on Dec. 23, 2014, provisional application No. 62/054,846, filed on Sep. 24, 2014, provisional application No. 62/013,957, filed on Jun. 18, 2014, provisional application No. 62/013,912, filed on Jun. 18, 2014.

(51) Int. Cl.
  *A61M 16/16* (2006.01)
  *A61M 16/00* (2006.01)
  *A61M 16/10* (2006.01)
  *A44B 11/25* (2006.01)

(52) U.S. Cl.
  CPC .... *A61M 16/0666* (2013.01); *A61M 16/0683* (2013.01); *A61M 16/0875* (2013.01); *A61M 16/109* (2014.02); *A61M 16/1095* (2014.02); *A61M 16/16* (2013.01); *A44B 11/2592* (2013.01); *A61M 16/0672* (2014.02); *A61M 2205/3331* (2013.01); *A61M 2205/3368* (2013.01); *A61M 2205/42* (2013.01); *A61M 2205/581* (2013.01); *A61M 2205/582* (2013.01); *A61M 2205/583* (2013.01); *A61M 2205/584* (2013.01); *A61M 2209/082* (2013.01); *A61M 2209/088* (2013.01)

(56) References Cited

U.S. PATENT DOCUMENTS

| | | | |
|---|---|---|---|
| 4,831,694 A * | 5/1989 | Kong | A44B 11/266 24/606 |
| 6,003,213 A * | 12/1999 | Keller | A44B 11/2534 24/615 |
| 6,119,694 A | 9/2000 | Correa et al. | |
| 6,463,637 B1 | 10/2002 | Carnahan | |
| 6,560,830 B1 * | 5/2003 | Chi | A44B 11/266 24/616 |
| 7,942,150 B2 | 5/2011 | Guney | |
| 2005/0028822 A1 | 2/2005 | Sleeper et al. | |
| 2005/0072428 A1 | 4/2005 | Ho et al. | |
| 2005/0199240 A1 * | 9/2005 | Hall | A61M 16/06 128/206.26 |
| 2007/0107169 A1 | 5/2007 | Kung | |
| 2007/0114794 A1 | 5/2007 | Frost et al. | |
| 2007/0163600 A1 | 7/2007 | Hoffman | |
| 2009/0044808 A1 | 2/2009 | Guney et al. | |
| 2009/0078259 A1 | 3/2009 | Kooij et al. | |
| 2009/0100652 A1 | 4/2009 | Mok | |
| 2010/0019107 A1 | 1/2010 | McCloud | |
| 2010/0136501 A1 | 6/2010 | Schuetz | |
| 2011/0067704 A1 | 3/2011 | Kooij et al. | |
| 2012/0090079 A1 | 4/2012 | Lebel et al. | |
| 2012/0090622 A1 | 4/2012 | Chang | |
| 2012/0227220 A1 * | 9/2012 | Fiedler | A01K 27/005 24/459 |
| 2012/0234319 A1 * | 9/2012 | Eifler | A61M 16/0683 128/202.27 |

FOREIGN PATENT DOCUMENTS

| | | |
|---|---|---|
| DE | 20 2013 005712 | 9/2013 |
| EP | 3157603 | 4/2017 |
| GB | 1434431 | 5/1976 |
| JP | 2004-000573 | 1/2000 |
| JP | 2003-93113 | 4/2003 |
| JP | 2010-213936 | 9/2010 |
| WO | WO 1996/013685 | 5/1996 |
| WO | WO 2012/024740 | 3/2012 |
| WO | WO 13/042004 | 3/2013 |
| WO | WO 2014/142681 A1 | 9/2014 |
| WO | WO 15/193833 | 12/2015 |

OTHER PUBLICATIONS

EPO Extended Search Report; dated Jan. 5, 2018; 8 pages.
Australian Examination report in Application No. 2015275717 dated Jun. 19, 2019 in 3 pages.
Chinese office action dated Oct. 12, 2018 in patent application No. 201580032853.6.
Japanese official action dated Jul. 3, 2019 in patent application No. 2016-573771.
Extended European Search Report dated Sep. 19, 2019 in application No. 19177474.4.

\* cited by examiner

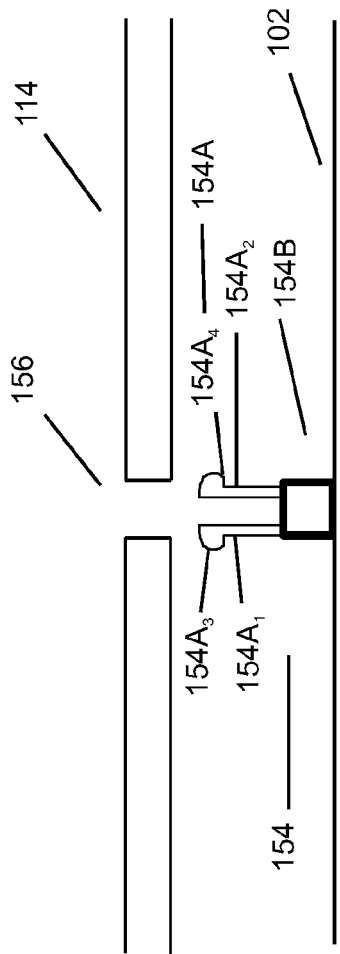
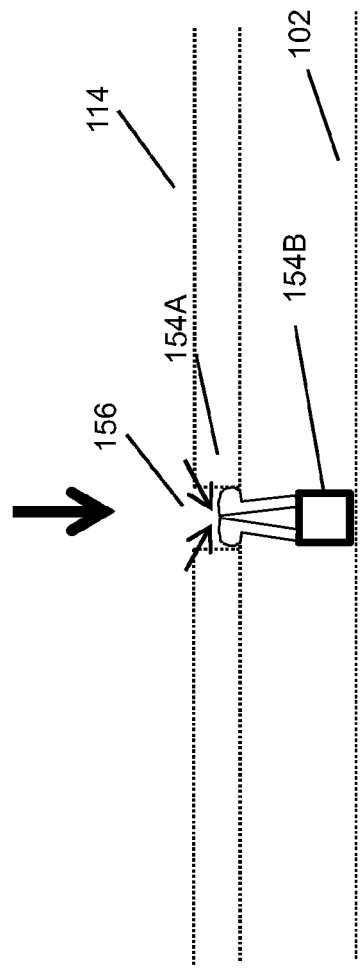
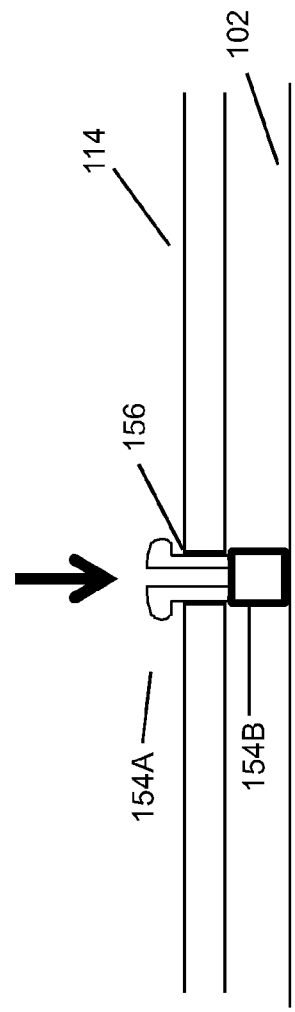
FIGURE 4A
FIGURE 4B
FIGURE 4C

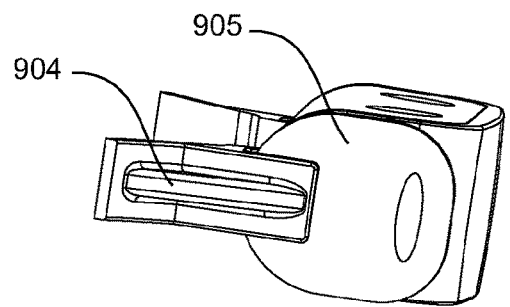
FIGURE 10G
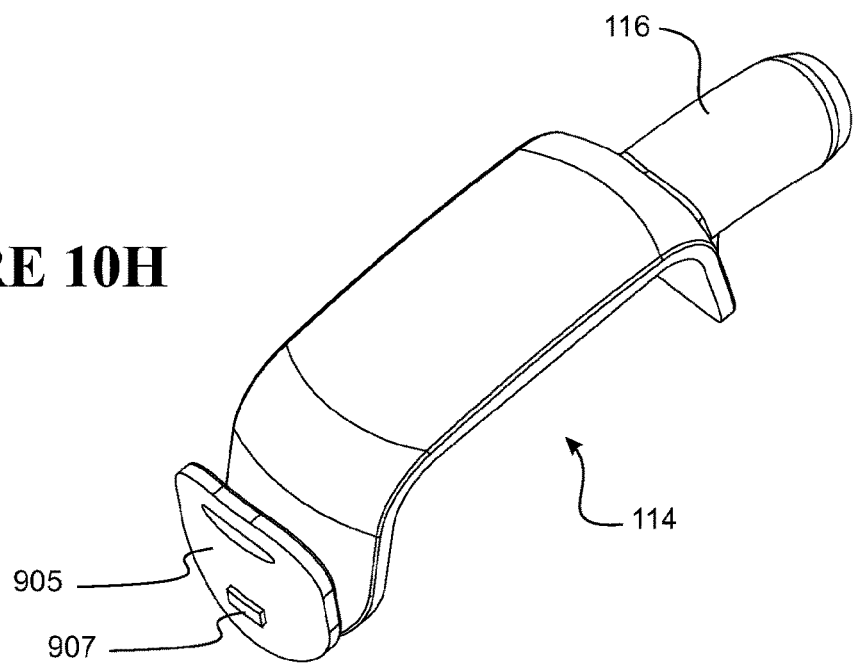
FIGURE 10H
FIGURE 10I
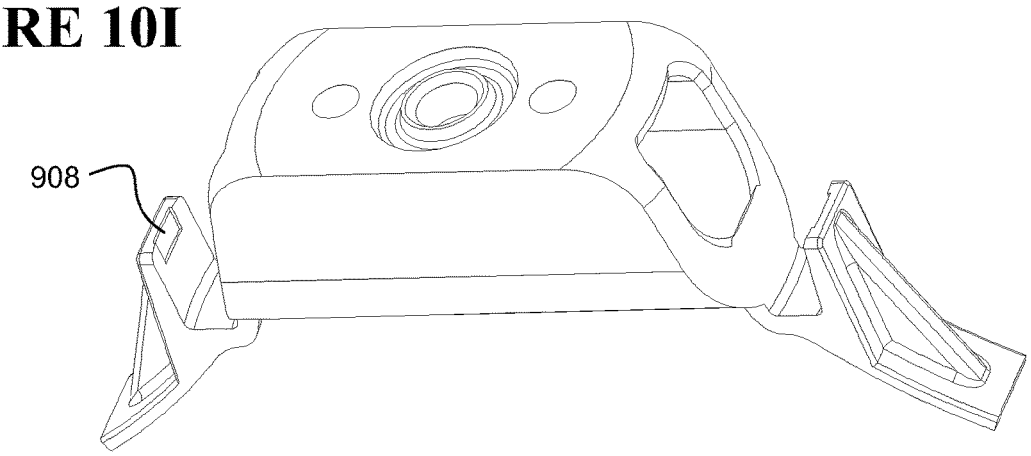

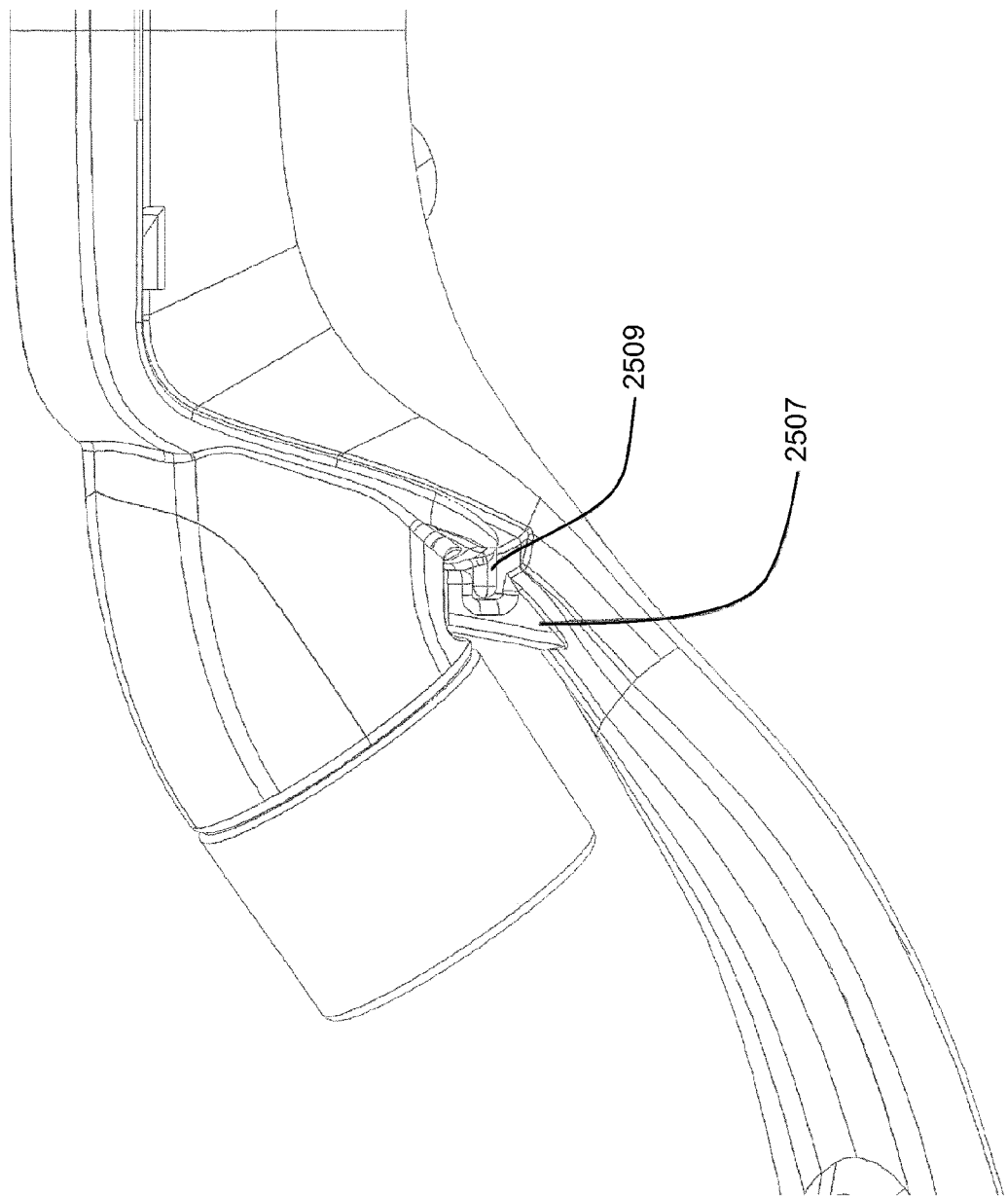

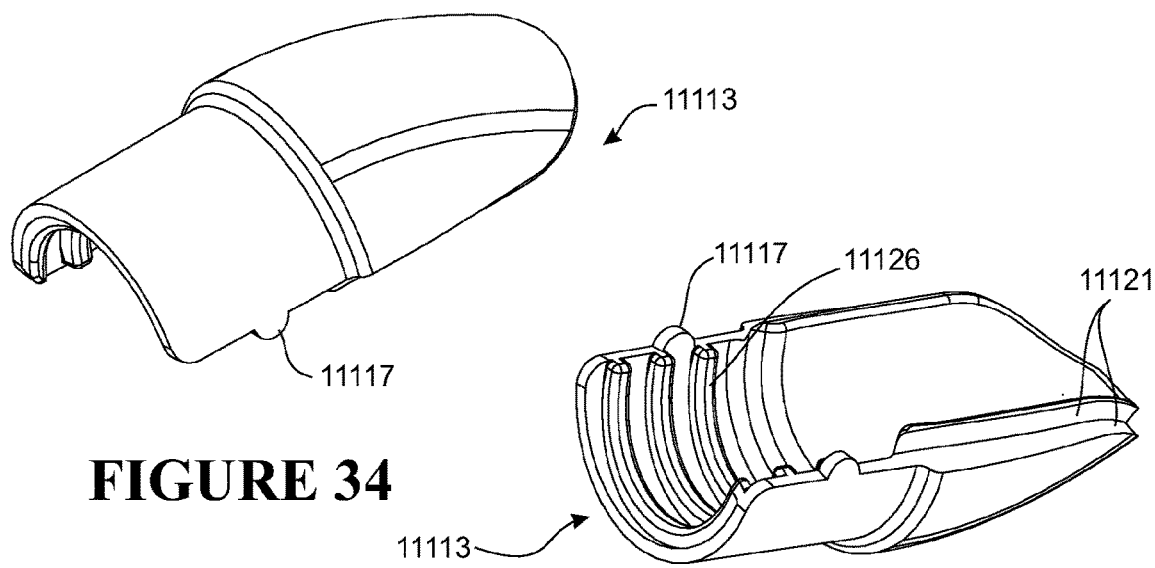
FIGURE 34
FIGURE 35
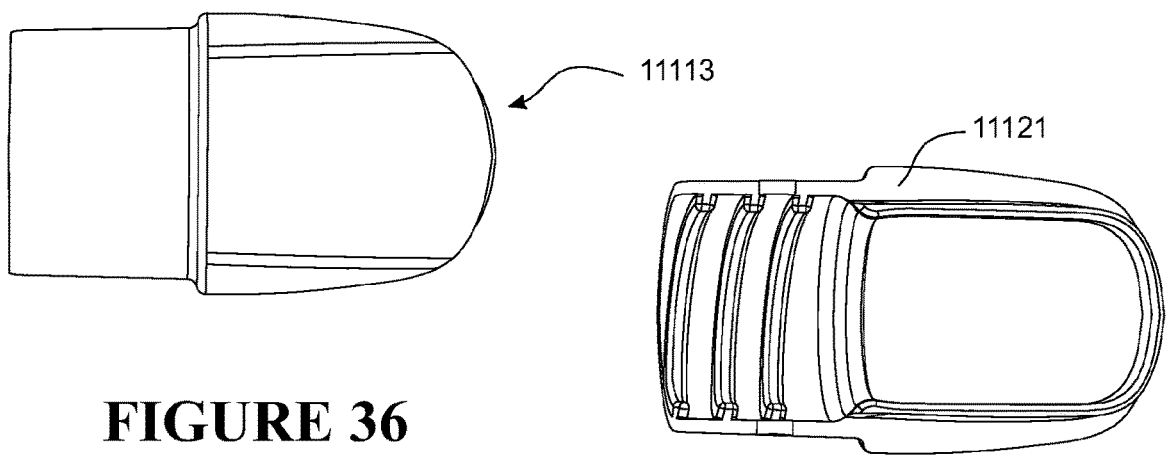
FIGURE 36
FIGURE 37
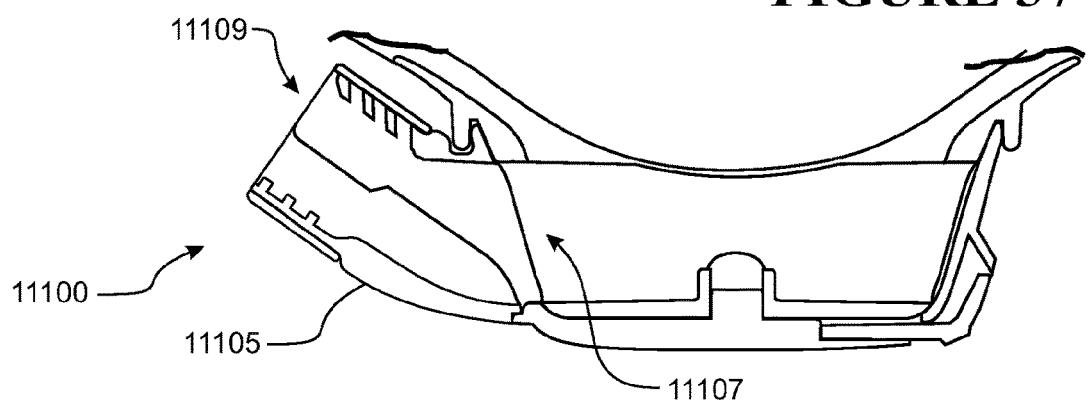
FIGURE 38

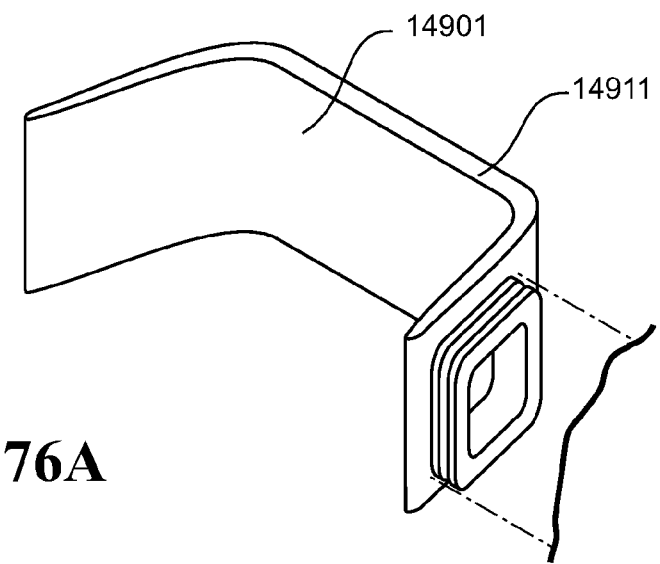
FIGURE 76A
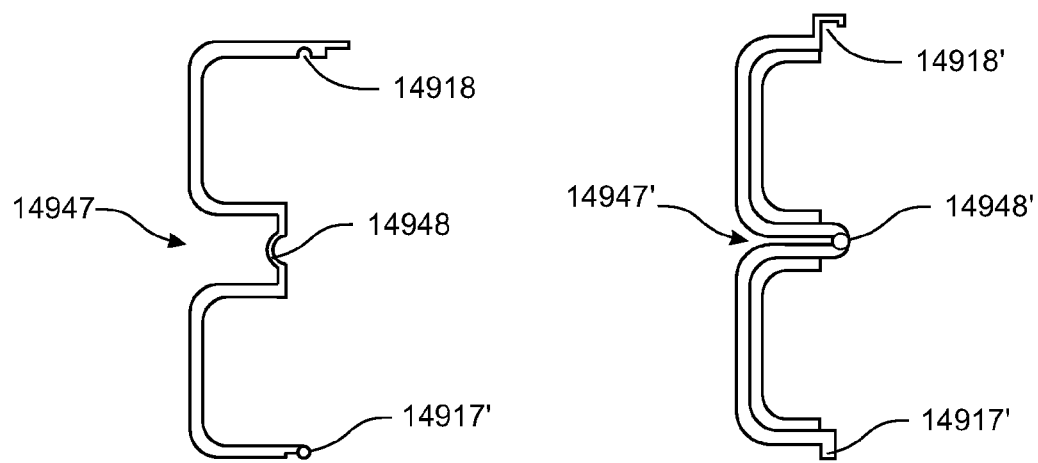
FIGURE 76B FIGURE 76C

(A)

(B)

PATIENT INTERFACE AND COMPONENT PARTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to components for medical applications, particularly medical breathing circuits, surgical insufflation systems, medical feeding apparatus, and/or medical monitoring apparatus, including but not limited to components associated with or forming parts of a patient interface for delivery of gases to a user's airway.

In one particular aspect, the disclosure relates to a component for receiving a tube or cable, such as a breathing tube for use in the inspiratory and/or expiratory limb of a breathing circuit, a tube associated with a surgical insufflation system, or a tube associated with a medical feeding apparatus, a cable associated with such apparatus, or a cable associated with medical monitoring apparatus, or any combination of any two or more thereof.

In another aspect, the disclosure relates to a connector, such as a releasable connector for releasably connecting two components together, including but not limited to a connector for releasably connecting headgear of a patient interface to a patient interface itself.

In another aspect, the disclosure generally relates to gas therapy, in particular to patient interfaces for providing gas therapy.

BACKGROUND

In certain medical applications, such as with assisted breathing or provision of breathable gases to a person (or animal), the gases to be provided and inhaled are preferably delivered in a condition having humidity near saturation level and at close to body temperature (usually at a temperature between 33° C. and 37° C.). Alternatively, the delivery of gases may be for CPAP or BIPAP purposes, where the gases may or may not be humidified in advance of delivery to the person (or animal).

In facilitating delivery of gases to a patient in such preferred conditions, breathing tubes (or medical tubes) may be used, including patient interfaces and components associated with such tubes or interfaces. Such tubes, interfaces or other such components may take various shapes and configurations.

In terms of tubes, one generally used configuration is an externally corrugated tube.

In various instances, such tubing is advantageously placed or positioned in certain locations relative to the patient or user. For example, the tubing may need to be held in a position or supported such that the weight of the tubing does not exert undesirable forces on the patient or user or other associated medical devices they may be using, such as masks or other interfaces. Enabling the positioning, support and adjustment of tubing between various further positions or supported positions for patients or users would be beneficial.

Other medical applications, such as surgical insufflation systems, medical feeding apparatus, and medical monitoring apparatus, similarly involve the positioning of tubes conveying nutrition, hydration and/or gases, and/or cables conveying patient information. Enabling the positioning, support and adjustment of tubing and cables in such applications would also be beneficial.

In terms of other components, releasable connectors, such as two part connectors of the type having male and female parts, may provide useful solutions for connecting two components together (e.g. one component is attached or attachable in some way to the male part and another component is attached or attachable in some way to the female part). The disclosure herein provides a further alternative for such a releasable connector.

Medical breathing circuits with a patient interface at the patient or user end often require multiple components to be connected together or attached to each other in a way which allow for a configurable adaptation for the patient or user. For example, patient interfaces such as full face masks, nasal masks, oro-nasal masks or nasal cannula configurations typically utilise associated headgear or straps for retaining the patient interface in position, or at least for holding certain components together for an assembled state of the medical breathing circuit or the patient interface itself.

In various instances, a person may wish to adjust, remove or attach a patient interface from the in-use position or the associated headgear. A releasable connector may be useful to enabling such adjustment or connection or disconnection of headgear from a patient interface. The ease of use and security of the connection are important factors when considering connectors of this type.

In terms of yet other components which may be associated with a patient interface for example, a patient dealing with respiratory illness, for example chronic obstructive pulmonary disease (COPD), can have difficulty engaging in effective respiration. This difficulty may be the result of a variety of causes, including a breakdown of lung tissue, dysfunctions of the small airways, excessive accumulation of sputum, infection, genetic disorders, or cardiac insufficiency. With some respiratory illnesses, it is useful to provide the patient with a therapy that can improve the ventilation of the patient. The patient can be provided with high flow therapy using a respiratory therapy system that includes a gases source, a patient interface that may be used to transmit gas to an airway of a patient, and a conduit extending between the gas source and the patient interface. The gases may be heated and humidified before being delivered to the patient.

In terms of yet other components which may be associated with a patient interface, for example, in many environments, the gas source can be positioned in a limited number of locations relative to the patient. As such, conduits that extend from the gas source to the patient interface can lie in inconvenient or uncomfortable positions, such as on the patient's chest or neck. Additionally, in some cases, if the conduit is not optimally oriented with respect to at least the patient interface, the convenience or efficacy of the therapy delivered could be compromised. For example, excessive pulling or torque forces upon the conduit could force the patient interface away from the patient, could cause the conduit to be dislodged from the patient interface or the gas source, or could cause the gas source to fall off a table or other support. In addition, flow of gases through the patient interface can be noisy, which can irritate or cause discomfort to the patient.

It is therefore an object of the present disclosures to provide further options or alternatives and/or which will go at least some way towards addressing the foregoing problems or which will at least provide the industry and/or public with a useful choice.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

Further aspects and advantages of the present disclosure will become apparent from the ensuing description which is given by way of example only.

SUMMARY

It is an object of the present disclosure to provide a component for use in a medical application that will at least go some way towards improving on the above or which will at least provide the public or the medical profession with a useful choice.

In a first aspect, the present disclosure relates broadly to a component (herein a "clip") comprising
   a body for receiving at least one tube and/or at least one cable, and
   an attachment for removeably engaging a mounting portion of a patient interface.

It should be understood that any of the following embodiments may relate to any one of the first to fourth aspects of the disclosure described above and below, alone or in any combination of any two or more.

In at least some embodiments the component is for use in a medical application, including but not limited to a medical breathing circuit, a surgical insufflation system, a feeding apparatus, and/or a monitoring apparatus.

In at least some embodiments the component is for use with a tube in a medical breathing circuit.

In at least some embodiments the component is for retaining or positioning a tube in a medical breathing circuit relative to a patient, for the purpose of improving the patient's breathing, or comfort, or for other related purposes including, for example, improving the stability of the patient interface on the patient when forces are applied to the patient interface and/or the tube. In relation to a patient's comfort, alternative positioning allows for a reduction in pressure or a relocation of pressure exerted by the tube, associated patient interface, and/or other components of the medical breathing circuit, for example.

In at least some embodiments the component is for use with a tube in a medical breathing circuit and comprises
   a body for receiving a tube in a medical breathing circuit, and
   an attachment for removeably engaging a mounting portion of a patient interface associated with the tube.

In at least some embodiments the component is for use with a tube in a surgical insufflation system or a feeding apparatus, and/or a cable in a monitoring apparatus.

In at least some embodiments the component is for retaining or positioning a tube in a surgical insufflation system or a feeding apparatus, and/or a cable in a monitoring apparatus relative to a patient, for the purpose of improving the patient's comfort, or for other related purposes including, for example, improving the stability of the patient interface on the patient when forces are applied to the patient interface and/or the tube and/or the cable.

It should be understood that any reference to a tube below may alternatively be read as a reference to a cable, such as a cable in a medical monitoring apparatus, as described herein.

In at least some embodiments the body is movable along a length of the at least one tube and/or the at least one cable or is fixed relative to the at least one tube and/or the at least one cable. In at least some embodiments the body is slidable along the length of the at least one tube and/or the at least one cable, and/or rotatable about the periphery of the at least one tube and/or the at least one cable, and/or rotatable along the length of the at least one tube and/or the at least one cable. In at least some embodiments the body is rotatable about the periphery of the at least one tube and/or the at least one cable while remaining fixed relative to the ends of the at least one tube and/or the at least one cable.

In at least some embodiments the body is arranged to at least partially surround or to surround a perimeter of the at least one tube and/or the at least one cable.

In at least some embodiments the body comprises at least one arm that is arranged to at least partially surround or to surround a perimeter of the at least one tube and/or the at least one cable. In at least some embodiments the at least one arm is shaped or curved to at least partially surround or to surround a perimeter of the at least one tube and/or the at least one cable. In at least some embodiments the at least one arm is substantially resistant to deformation or is resiliently flexible.

In at least some embodiments the body comprises two arms that are arranged to at least partially surround or, separately or together, surround a perimeter of the at least one tube and/or the at least one cable. In at least some embodiments the arms are shaped or curved to at least partially surround or to surround a perimeter of the at least one tube and/or the at least one cable. In at least some embodiments the arms are substantially resistant to deformation or are resiliently flexible.

In at least some embodiments the body comprises an annular, substantially annular, square, substantially square, or rectilinear portion that is arranged to at least partially surround or to surround a perimeter of the at least one tube and/or the at least one cable.

In at least some embodiments an internal surface of the body is engageable with the one or more external surface recesses of the at least one tube, such as those recesses of a corrugated tube or a tube with a helically recessed surface region.

In at least some embodiments the internal surface of the body comprises one or more projections engageable with one or more corresponding recesses of the at least one tube. In at least some embodiments the internal surface of the body comprises a first projection engageable with a first recess and a second projection engageable with the same or another recess.

In at least some embodiments the body is pivotably, rotatably, or removably connected to the attachment, or any combination of any two or more thereof.

In at least some embodiments the attachment comprises at least one arm or at least one lug that are arranged to engage a mounting portion on a patient interface. In at least some embodiments the mounting portion is shaped to receive the at least one arm or the at least one lug. In at least some embodiments the arm engages a corresponding projection on the mounting portion, optionally with a snap engagement. In at least some embodiments the lug engages a corresponding recess on the mounting portion, optionally with a snap engagement.

In at least some embodiments the at least one arm and/or the at least one lug are substantially resistant to deformation or are resiliently flexible.

In at least some embodiments the attachment is oriented in the same plane as the body.

In at least some embodiments the attachment is rotated or skewed with respect to the body.

In at least some embodiments the at least one arm comprises a projection or lug. In at least some embodiments the projection or lug engages a corresponding projection or recess on the mounting portion, in at least some embodiments with a snap engagement.

In at least some embodiments the attachment comprises two arms that are arranged to engage a mounting portion. In at least some embodiments the mounting portion is shaped to receive them. In at least some embodiments the mounting portion is similarly or identically shaped to receive them.

In at least some embodiments the two arms extend from the body to define a space therebetween.

In at least some embodiments the two arms extend from the same point or substantially adjacent points on the body. In at least some embodiments each arm initially extends from the body in a direction away from the other arm. Alternatively, each arm extends from the body in a direction substantially toward the other arm, or each arm extends from the body in a direction substantially parallel with each other or each respective arm.

In at least some embodiments the arms are substantially the same length or are different lengths.

In at least some embodiments the attachment comprises two arms and one arm is shaped, or both arms are shaped to engage a corresponding projection on the mounting portion, optionally with a snap engagement.

In at least some embodiments the arm or arms comprise an angled portion shaped to engage a corresponding projection on the mounting portion, optionally with a snap engagement.

In at least some embodiments the attachment comprises two arms, each arm comprises an angled portion, and each angled portion extends towards the other arm, or into or towards the space between the arms.

In at least some embodiments the attachment comprises two arms, each arm extending from the same point or substantially adjacent points on the body, each arm initially extending from the body in a direction away from the other arm, and each arm comprising an angled portion that extends substantially towards the other arm, or into or towards the space between the arms.

In at least some embodiments the attachment comprises two arms and one arm comprises a projection or lug, or both arms comprise a projection or lug.

In at least some embodiments the projection or lug engages a corresponding recess on the mounting portion, in at least some embodiments with a snap engagement.

In at least some embodiments the attachment comprises two arms and a projection or lug on one arm, or on each arm, extends substantially towards the other arm, or into or towards the space between the arms.

In at least some embodiments the attachment comprises two arms, each arm extending from the same point or substantially adjacent points on the body, each arm initially extending from the body in a direction away from the other arm, and each arm comprising a projection or lug that extends substantially towards the other arm, or into or towards the space between the arms. Alternatively, the attachment comprises two arms, each arm extending from the same point or substantially adjacent points on the body, each arm extending from the body in a direction toward the other arm, and each arm comprising a projection or lug that extends substantially outwardly or away from the other arm.

In at least some embodiments the mounting portion comprises one or more shaped projections, and/or one or more slots or recesses arranged to engage the attachment. Alternatively the mounting portion comprises one or more slots or recesses or apertures as a female part of the mounting portion for receiving of an engagement by the attachment. Further, one or more mounting portions may comprise one or more bevels or chamfers or tapered lead-in shaped portions or sections, or angled bosses on the female and male portions. Any one or more of these, or other geometries, may be utilised for the mounting portion to assist with insertion of an arm or arms or orientation of the arm or arms for insertion within the mounting portion and/or may assist in providing for a more securely or more positively retained arm or arms within a mounting portion. For example, the mounting portion may be of a shape which is to be provided in contact with an arm or arms, as well as other parts of the attachment.

In at least some embodiments the mounting portion is integral with a patient interface, in at least some embodiments with an auxiliary part of a patient interface.

In at least some embodiments the mounting portion is removably attachable to a patient interface, in at least some embodiments to an auxiliary part of a patient interface.

In at least some embodiments the mounting portion is, is integral with, or is removably attachable to a strap attached or attachable to a patient interface.

In at least some embodiments the mounting portion comprises a projection shaped to engage the space defined between the arms of the attachment. Alternatively, the mounting portion comprises a female mounting portion or aperture shaped to engage outer surfaces or lugs of the arms of the attachment.

In at least some embodiments the female mounting portion or aperture is oriented or shaped in an off-set manner or is angled relative to the patient interface, such that when the attachment of the body is engaged to or with the female mounting portion or aperture, a tube connected to the body is substantially aligned with an arm or frame of the patient interface. In at least some embodiments in this manner the tube follows the shape of a cannula frame arm and provides the visual appearance of the tube entering or being connected with a manifold or fluid connection port of a patient interface in a "straight" manner.

In at least some embodiments the mounting portion comprises a projection shaped to engage and substantially fill the space between the arms of the attachment.

In at least some embodiments the mounting portion comprises at least one projection arranged to engage at least one arm of the attachment. In at least some embodiments the mounting portion comprises a projection arranged to engage each arm. In at least some embodiments the projection or projections are arranged to engage the arms with a snap engagement.

In at least some embodiments the mounting portion comprises at least one recess or slot or aperture arranged to engage a lug. In at least some embodiments the mounting portion comprises a recess or slot or aperture arranged to engage each lug, either individually or communally. In at least some embodiments the recess or recesses or slot or slots or aperture is/are arranged to engage the lugs with a snap engagement.

In at least some embodiments the attachment provides sensory feedback to an operator when the attachment engages the mounting portion, in at least some embodiments with a snap engagement.

In at least some embodiments the attachment provides sensory feedback to an operator when a lug on the attachment engages a recess on the mounting portion, in at least some embodiments with a snap engagement.

In at least some embodiments the sensory feedback is audible feedback, tactile feedback, or both.

In at least some embodiments the attachment is arranged to emit a readily audible sound when the attachment engages the mounting portion, in at least some embodiments with a snap engagement.

In at least some embodiments the attachment is arranged to undergo a readily tactile movement or emit a readily tactile vibration when the attachment engages the mounting portion, in at least some embodiments with a snap engagement.

In at least some embodiments the component further comprises at least one retainer portion for retaining of at least one accessory.

In at least some embodiments the at least one accessory is at least one tube and/or at least one cable and/or at least one lanyard. For example, the at least one accessory may comprise a gas line, a gas monitoring line including but not limited to a gas sampling line or a line for measuring end tidal volume, a hydration tube, a feeding tube, a nasogastric tube, a cable including but not limited to an electrical cable or a sensor cable (such as a temperature probe cable), or a lanyard, or any combination of any two or more thereof.

In at least some embodiments the at least one accessory is a temperature probe cable.

In at least some embodiments the at least one retainer portion is an annular, substantially annular, square, substantially square, or rectilinear portion that receives the at least one accessory.

In at least some embodiments the at least one retainer portion is a C-shaped portion that receives the at least one accessory.

In at least some embodiments the at least one retainer portion is an annular portion that receives the at least one accessory.

In at least some embodiments the at least one retainer portion is a recessed region of the component.

In at least some embodiments the at least one retainer portion extends from the body.

In at least some embodiments the patient interface is a nasal mask, oral mask, oronasal mask, nasal cannula, or full-face mask.

In at least some embodiments the patient interface is a nasal cannula.

In at least some embodiments the patient interface comprises one or more head straps or two or more head straps. In at least some embodiments, where two or more head straps are present, the two or more head straps independently comprise a single strap or two or more straps, any of which may be bifurcated.

In at least some embodiments the tube is a medical breathing tube, including a corrugated tube or a tube with a helically recessed surface region. For example, a medical breathing tube as defined by International standard ISO 5367:2000(E) (Fourth edition, Jun. 6, 2000).

In at least some embodiments the tube is an insufflation tube.

In at least some embodiments the tube is a nasogastric tube.

In at least some embodiments the cable is a sensor cable.

In at least some embodiments the component comprises
a body for receiving at least one tube and/or at least one cable, in at least some embodiments a tube in a medical breathing circuit, the body comprising an annular, substantially annular, square, substantially square, or rectilinear portion that is arranged to at least partially surround or to surround a perimeter of the at least one tube and/or the at least one cable, and an attachment for removeably engaging a mounting portion on a patient interface associated with the at least one tube and/or the at least one cable, the attachment comprising one or two arms that extend from the body to define a space therebetween, each arm comprising an angled portion extending into or towards the space defined by the arms, such that the arms are arranged to engage a mounting portion on a patient interface, and each angled portion engages a corresponding projection on the mounting portion with a snap engagement.

Alternatively, the component comprises
a body for receiving at least one tube and/or at least one cable, such as a tube in a medical breathing circuit, the body comprising an annular, substantially annular, square, substantially square, or rectilinear portion that is arranged to at least partially surround or to surround a perimeter of the at least one tube and/or the at least one cable, and an attachment for removeably engaging a mounting portion on a patient interface associated with the at least one tube and/or the at least one cable, the attachment comprising at least one arm or alternatively multiple arms that extend from the body to define a space therebetween, each arm comprising an angled portion or lug portion extending outwardly or away from the arms, such that the arms are arranged to engage a mounting portion on a patient interface, and each angled portion or lug portion engages a corresponding projection on the mounting portion with a snap engagement. In an embodiment the attachment comprises two arms.

In at least some embodiments the component comprises
a body for receiving at least one tube and/or at least one cable, in at least some embodiments a tube in a medical breathing circuit, the body comprising an annular, substantially annular, square, substantially square, or rectilinear portion that is arranged to at least partially surround or to surround a perimeter of the at least one tube and/or the at least one cable, and
an attachment for removeably engaging a mounting portion on a patient interface associated with the at least one tube and/or the at least one cable, the attachment comprising one or two arms that extend from the body to define a space therebetween, each arm comprising a projection or lug extending into or towards the space defined by the arms, such that the arms are arranged to engage a mounting portion on a patient interface, and each projection or lug engages a corresponding recess on the mounting portion with a snap engagement.

Alternatively, the component comprises
a body for receiving at least one tube and/or at least one cable, such as a tube in a medical breathing circuit, the body comprising an annular, substantially annular, square, substantially square, or rectilinear portion that is arranged to at least partially surround or to surround a perimeter of the at least one tube and/or the at least one cable, and
an attachment for removeably engaging a mounting portion on a patient interface associated with the at least one tube and/or the at least one cable, the attachment comprising at least one arm alternatively multiple arms that extend from the body to define a space therebetween, each arm comprising a projection or lug extending away from or outwardly from the arms, such that the arms are arranged to engage a mounting portion on a patient interface, and each projection or lug engages a corresponding recess on the mounting portion with a snap engagement. In an embodiment the attachment comprises two arms.

In a second aspect, the present disclosure relates broadly to a tube, such as a tube for use in a medical breathing circuit, the tube (as herein described) is coupled to a component as herein described, the component being optionally removeably engaged to a mounting portion as herein described, the mounting portion being removably attachable to a patient interface in a medical breathing circuit.

In a third aspect, the present disclosure relates broadly to a patient interface (as herein described), such as for use in a medical breathing circuit, the patient interface comprising a mounting portion, such as those herein described, integral with or removably attached to the patient interface, and a component as herein described removeably engaged to the mounting portion.

In a fourth aspect, the present disclosure relates broadly to a kit comprising a component as herein described and any two or more of:
- a patient interface as herein described, optionally comprising an integral mounting portion as herein described,
- a mounting portion as herein described, and
- instructions for assembly and/or use.

The various aspects and embodiments of a component referred to above as a "clip" may be provided for use in relation to securement or retention or support of an item (e.g. a breathing tube) to a mounting portion, for example a patient interface (optionally in the form of a nasal cannula) can comprise of such a "clip" for receiving of such a component as described above. It will also be appreciated that such a "clip" and a respectively described mounting portion, can be provided in combination with a side arm of a nasal cannula patient interface.

In addition, the "clip" described above in relation to each of the first to fourth aspects may be provided in for integration or combination with one or more of the other aspects described below in relation to patient interface or component parts for assembling of a patient interface.

It is an object of the present disclosure to provide a connector, such as for use with a patient interface as part of a medical breathing circuit, that will at least go some way towards improving on the above or which will at least provide the public or the medical profession with a useful choice.

In a fifth aspect, the present disclosure relates broadly to a connector (herein a "buckle") comprising:
- a first connector part;
- a second connector part;
- a detent for securing the first connector part and the second connector part together;
- a slide moveable relative to the first connector part and/or the second connector part between:
  - a secured position in which the detent is substantially inhibited from moving and releasing the first connector part from the second connector part; and
  - a free position in which the detent is able to move to release the first connector part from the second connector part.

It should be understood that any of the following embodiments may relate to any one of the aspects of the disclosure described above and below, alone or in any combination of any two or more.

In some embodiments the connector further comprises a biasing means for urging the slide towards the secured position.

In some embodiments the biasing means comprises a resilient leg.

In some embodiments the biasing means comprises a pair of resilient legs. Alternatively the legs move away from each other as the slide moves towards the free position. Alternatively the legs may move towards each other as the slide moves towards the free position.

In some embodiments the biasing means and detent are integrally formed together.

In some embodiments the detent comprises a resilient arm. Optionally the resilient arm is biased towards engagement with the first connector part.

In some embodiments the detent comprises a pair of resilient arms. Optionally the pair of resilient arms are biased towards engagement with the first connector part.

In some embodiments the resilient arms are spaced apart and are biased towards each other.

In some embodiments the or each resilient arm comprises a protrusion for engagement with a complementary notch of the first connector part.

In some embodiments the slide comprises a lug for engagement with the biasing means. Optionally the lug comprises outwardly tapered surfaces.

In some embodiments the slide comprises a protrusion for engagement with the detent for substantially inhibiting movement and release of the first connector part from the second connector part.

In some embodiments the slide comprises two protrusions for engagement with the detent for substantially inhibiting movement and release of the first connector part from the second connector part.

In some embodiments the slide comprises a stop for locating the slide and second connector part in the secured configuration.

In some embodiments the slide comprises a sleeve.

In some embodiments the slide enables a single-handed operation to move from the secured position to the free position.

In some embodiments the first connector part comprises a notch.

In some embodiments the first connector part comprises a pair of notches.

In some embodiments the first connector part is a substantially planar component.

In some embodiments the first connector part is a substantially rigid component.

In some embodiments the first connector part comprises a clip.

In some embodiments the first connector part is located on a patient interface.

In some embodiments the first connector part is attached to, or integrally formed with or as, a patient interface or a part of a patient interface.

In some embodiments the first connector part is attached to, or integrally formed with or as, a part of an arm of a patient interface. For example, an arm may be a side arm extending outwardly from a central manifold region or a nasal prong or pair of nasal prongs of a nasal cannula.

In some embodiments the second connector part comprises a location feature for locating the biasing means.

In some embodiments the second connector part comprises a guide feature for guiding the first connector part.

In some embodiments the second connector part has a guide feature for guiding the slide.

In some embodiments the second connector part comprises a carrier for carrying the detent and/or biasing means.

In some embodiments the carrier is formed with a slot and a headstrap of the headgear has an opening, the slot and opening being arranged for receiving the first connector part.

In a sixth aspect, the present disclosure relates broadly to a connector comprising:
- a first connector part;
- a detent for securing the first connector part and a second connector part together;
- a slide moveable relative to the first connector part between:
- a secured position in which the detent is substantially inhibited from moving and releasing the first connector part from the second connector part; and
- a free position in which the detent is able to move to release the first connector part from the second connector part.

In a seventh aspect, the present disclosure relates broadly to a patient interface for use in a medical breathing circuit, the patient interface comprising a connector of the second aspect.

The sixth and/or seventh aspects may comprise one or more of the features described above in relation to the fifth aspect.

The various aspects and embodiments of a component referred to above as a "buckle" may be provided for use in relation to securement or retention or support of an item (e.g. a headgear or strap end to an end of a side arm of a patient interface, such as a nasal cannula). However, it will also be appreciate the "buckle" described above may be utilised to provide for a releasable connection point between other facilities of a patient interface. It will also be appreciated that such a "buckle" can be provided in combination with a side arm of a nasal cannula patient interface or the end of a headgear portion of a strap for a headgear to connect with a patient interface.

In a further embodiment, the "clip" as described above may find particular application when used on a nasal cannula or frame of a nasal cannula, allowing for relative ease of connection or attachment and disconnection or removal of headgear as a conduit or tube retained or supported by the "clip" can be retained or supported in a position, location or orientation so as to be avoid entanglement with the headgear. Further, the "buckle" as described herein can also be connected or disconnected from the end of an arm of a patient interface such as a nasal cannula as any tube or conduit is effectively neatly stowed and supported in a position or location avoiding entanglement with the headgear and without getting in the way of a user trying to locate and operate the releasable buckle.

In addition, the "buckle" described above in relation to each of the fifth to seventh aspects may be provided in for integration or combination with one or more of the other aspects described below in relation to patient interface or component parts for assembling of a patient interface.

In many environments, the gases source can be positioned in a limited number of locations relative to the patient. As such conduits that extend from the gas source to the patient interface can lie in inconvenient or uncomfortable positions, such as on the patient's chest or neck. Additionally, in some cases if the conduit is not optimally oriented with respect to at least the patient interface, the convenience or efficacy of the therapy delivered could be compromised. For example, excessive pulling or torque forces upon the conduit could force the patient interface away from the patient, cause the conduit to be dislodged from the patient interface or the gas source, or cause the gas source to fall off a table or other support.

Certain features, aspects and advantages of at least one of the embodiments disclosed herein apply to an eighth aspect and include the realization that a patient interface can comprise a rotatable assembly adapted to receive gases from a gas source (herein a "swivel manifold").

In some embodiments, the patient interface can comprise a manifold adapted to receive gases that is rotatably secured to a frame adapted to channel gases to a user.

In some embodiments, the manifold may communicate gases to the frame only in certain rotational orientations, and/or may be rotationally locked in place in certain rotational orientations relative to the frame.

In some embodiments, if the manifold is rotationally locked in place relative to the frame, a release mechanism may be used to 'unlock' the patient interface and allow for further rotational movement of the manifold relative to the frame. The rotatable assembly may then allow for a conduit linked to the interface to be positioned in a plurality of orientations relative to the interface and/or gas source, which can improve the convenience and/or efficacy of the respiratory therapy delivered.

Thus, in accordance with certain features, aspects and advantages of at least one of the embodiments disclosed herein, a patient interface is disclosed. For example, in a ninth aspect, the present disclosure relates to a patient interface that may comprise a nasal cannula. The patient interface may comprise a frame adapted to be positioned on the face of a user. The frame may comprise a gas chamber adapted to channel a gas to the user. The patient interface may also comprise a manifold rotatably secured to the frame and adapted to receive a gas from a gas source. The manifold may be rotatably secured to the frame in such a way that the range of rotary or rotational motion between the manifold and the frame is limited, e.g. limited to less than 360 degrees of rotation.

In some embodiments, the range of rotational motion between the manifold and the frame may be limited to about 180 degrees.

In some embodiments, the frame may comprise a stop that limits the range of rotary motion (e.g. the rotary motion of the manifold relative to the frame).

In some embodiments, the manifold may comprise an axle structure about which the manifold may pivot relative to the frame. In some such embodiments, the axle structure may protrude through an aperture in the frame. In alternative embodiments, the frame may comprise an axle structure that protrudes through an aperture in the manifold.

Additionally, in accordance with certain features, aspects and advantages of at least one of the embodiments disclosed herein, a patient interface is disclosed. In a tenth aspect, the patient interface may comprise a nasal cannula. The patient interface may comprise a frame adapted to be positioned on the face of a user. The frame may comprise a gas chamber adapted to channel a gas to the user. The patient interface may also comprise a manifold rotatably secured to the frame and adapted to receive a gas from a gas source. The patient interface may be configured such that non-rotary motion of the manifold relative to the frame is limited.

In some embodiments, the frame further comprises a post adapted to limit non-rotary motion of the manifold relative to the frame.

In some embodiments, the range of non-rotary motion of the manifold relative to the frame is limited only in some rotational orientations.

Additionally, in accordance with certain features, aspects and advantages of at least one of the embodiments disclosed herein, a patient interface is disclosed. The patient interface may comprise a nasal cannula. In an eleventh aspect, the patient interface may comprise a frame adapted to be positioned on the face of a user. The frame may comprise a gas chamber adapted to channel a gas to the user. The patient interface may also comprise a manifold rotatably secured to the frame and adapted to receive a gas from a gas source. The patient interface may be configured such that the manifold is not permitted to further rotate relative to the frame in at least one rotational orientation. The patient interface may be configured to lock the rotational orientation of the manifold relative to the frame after a certain rotational orientation has been achieved. The patient interface may comprise a release mechanism adapted to permit rotary motion of the manifold relative to the frame when the manifold is not normally permitted to rotate relative to the frame. The release mechanism may unlock the fixed rotational orientation of the manifold relative to the frame. After unlocking, the patient interface may again permit rotation of the manifold relative to the frame.

In some embodiments, the release mechanism may comprise a manually depressible button. The button can be depressed to unlock a fixed rotational orientation. The button may be positioned on the frame. In some alternative embodiments, the button may be positioned within the frame.

In some embodiments, the manifold may comprise a boss adapted to rotatably move in a complementary track of the frame, and the track may comprise detention regions that can restrain the motion of the boss.

Additionally, in accordance with certain features, aspects and advantages of at least one of the embodiments disclosed herein, a patient interface is disclosed. The patient interface may comprise a combination of the features disclosed above or elsewhere in this disclosure.

In some embodiments, the patient interfaces disclosed above or elsewhere in this disclosure may comprise a manifold comprising a boss adapted to rotatably move in a complementary track of the frame.

In some embodiments, the patient interfaces disclosed above or elsewhere in this disclosure may comprise a manifold that is permanently rotatably secured to the frame.

In some embodiments, the patient interfaces disclosed above or elsewhere in this disclosure may comprise a manifold configured to cooperate with the frame to channel gas to the gas chamber only in some or certain orientations (e.g. rotary or rotational orientations, of for example the manifold relative to the frame).

In some embodiments, the patient interfaces disclosed above or elsewhere in this disclosure may comprise a frame comprising a relatively rigid section and a relatively flexible section. In some such embodiments, the relatively flexible section of the frame may be overmoulded onto a face contacting portion of the relatively rigid section of the frame. In some such embodiments, the patient interface may comprise a nasal delivery element adapted to be inserted into a nare or the nares of the user. The nasal delivery element may extend from the relatively flexible section of the frame.

In some embodiments, the patient interfaces disclosed above or elsewhere in this disclosure may comprise a nasal delivery element adapted to be inserted into a nare of the user. The nasal delivery element may extend from the frame.

In a twelfth aspect, the present disclosure relates broadly to a patient interface comprising:

a frame section adapted to be positioned on the face of a user, the frame section comprising a gases chamber adapted to channel gases to the user and a nasal delivery element extending from the gases chamber adapted to be located in a nare of the user; and a manifold rotatably secured to the frame section, the manifold being configured to rotate relative to the frame section, the manifold comprising an axle structure about which rotational motion between the manifold and frame section can occur.

In some embodiments, the axle structure protrudes through an aperture in the frame section.

In some embodiments, the manifold is rotatably secured to the frame section in such a way that the range of rotary motion between the manifold and the frame section is limited.

In some embodiments, the frame section comprises a stop that limits the range of rotary motion.

In some embodiments, the patient interface further comprises a nasal delivery element extending from the gases chamber adapted to be located in a nare of the user.

In some embodiments, the frame section further comprising a track, the track configured to guide rotation of the manifold relative to the frame section.

In some embodiments, the interface further comprises a retention mechanism, the retention mechanism being disposed on the frame section, the retention mechanism configured to retain the manifold in an operational position such that a pneumatic seal is created between the manifold and the gases chamber.

In some embodiments, the retention mechanism is a post extending outwardly from the frame section, the post being configured to retain the manifold between the frame section and the post when the manifold is in the operational position.

In some embodiments, the patient interface comprises a release mechanism, the release mechanism configured to release the manifold from an operational position such that the manifold can rotate relative to the frame section.

In some embodiments, the release mechanism comprises a button, the button disposed on the manifold, the button comprising a boss portion that is configured to engage with and move within a substantial portion of the track as the manifold rotates.

In some embodiments, the track comprises one or more detention regions positioned at the end of the track, the boss configured engage the detention regions to lock the manifold in the operational position.

In some embodiments, the release mechanism comprises a release body, the release body moveable within a recess within the manifold, the release body being moveable from an unbiased position to a biased position, the release body being in the unbiased position when the manifold is in the operational position.

In some embodiments, the release body comprises one or side arms, the recess comprising one or more end regions shaped to correspond to the one or more side arms, the side arms being configured to move into the end regions to release the boss portion from the detention regions and allow the manifold to rotate.

In some embodiments, the side arms are configured to splay outwardly to release the boss portion from the detention regions.

In some embodiments, the side arms are configured to splay inwardly to release the boss portion from the detention regions.

In some embodiments, the patient interface further comprises at least one nasal delivery element extending from the gases chamber, each nasal delivery adapted to be located in a nare of the user.

In some embodiments, the at least one nasal delivery element comprises two nasal delivery elements.

In a thirteenth aspect, the present disclosure relates broadly to a patient interface comprising:
- a frame section adapted to be positioned on the face of a user, the frame section comprising a gases chamber adapted to channel gases to the user;
- a manifold rotatably relative to the frame section and adapted to receive gases from a gases source; and
- a retention mechanism, the retention mechanism being disposed on the frame section and the retention mechanism configured to limit the non-rotational motion of the manifold relative to the frame section.

In some embodiments, the retention mechanism comprises a post adapted to retain the manifold.

In some embodiments, the retention mechanism limits non-rotational motion of the manifold relative to the frame section only in some rotational orientations.

In some embodiments, the retention mechanism seals a gases passageway extending between the manifold and the gases chamber only in some rotational orientations.

In some embodiments, the patient interface further comprises a nasal delivery element extending from the gases chamber, the nasal delivery element being adapted to be located in a nare of the user.

In some embodiments, the manifold is rotatably secured to the frame section.

In some embodiments, the retention mechanism is disposed on the frame section.

In some embodiments, the retention mechanism is integrally formed with the frame section.

In some embodiments, the retention mechanism is disposed on the manifold.

In some embodiments, the retention mechanism is integrally formed with the manifold.

In some embodiments, the retention mechanism comprises a first retention feature disposed on the manifold and a second retention feature disposed on the frame section.

In some embodiments, the first retention feature comprises a first hook having a generally vertically extending portion and a generally horizontally extending portion extending from the generally vertically extending portion in a direction towards the manifold and the second retention features comprises a second hook having a generally vertically extending portion and a generally horizontally extending portion extending from the generally vertically extending portion in a direction away from the manifold.

In some embodiments, the first retention feature comprises a first hook having a generally vertically extending portion and a generally horizontally extending portion extending from the generally vertically extending portion in a direction away from the manifold and the second retention features comprises a second hook having a generally vertically extending portion and a generally horizontally extending portion extending from the generally vertically extending portion in a direction towards from the manifold.

In some embodiments, the first retention feature is integrally formed with the manifold.

In some embodiments, the second retention feature is integrally formed with the frame section.

In some embodiments, the first retention feature is integrally formed with the frame section.

In some embodiments, the second retention feature is integrally formed with the manifold.

In a fourteenth aspect, the present disclosure relates broadly to a patient interface comprising:
- a frame section adapted to be positioned on the face of a user, the frame section comprising a gases chamber adapted to channel gases to the user; and
- a manifold rotatably rotatable relative to the frame section and adapted to receive gases from a gases source; and
- a release mechanism;
- wherein the patient interface is configured such that the manifold is rotationally locked in at least one rotational orientation of the manifold relative to the frame section, and
- wherein the release mechanism is adapted to unlock motion of the manifold relative to the frame section when the manifold is rotationally locked.

In some embodiments, the release mechanism comprises a button.

In some embodiments, the button is positioned on the manifold.

In some embodiments, the button is linked to a release body comprising a boss configured to rotatably move in a track located on the frame.

In some embodiments, the track comprises a detention region that locks the rotational movement of the boss, and wherein actuating the button causes the boss to leave the detention region.

In some embodiments, the release body comprises an biased state and an unbiased state, and wherein actuating the button causes the release body to transition from the biased state to the unbiased state.

In some embodiments, releasing the button causes the release body to transition from the unbiased state to the biased state.

In some embodiments, the release body comprises at least one side arm that is forced around a lug bump section in the frame in the biased state.

In some embodiments, the release mechanism comprises a lever or arm.

In some embodiments, the lever or arm is positioned on the frame.

In some embodiments, the lever or arm comprises a protuberance and the manifold has a complementary recess, slot, or aperture for receiving the protuberance.

In some embodiments, the lever or arm is positioned on the manifold.

In some embodiments, the manifold comprises a flexible section or hinge.

In some embodiments, the lever or arm comprises a protuberance and the frame has a complementary recess, slot, or aperture for receiving the protuberance.

In some embodiments, the lever or arm comprises a biased state and an unbiased state, and wherein actuating the lever or arm causes the lever or arm to transition from the biased state to the unbiased state.

In some embodiments, releasing the lever or arm causes the lever or arm to transition from the unbiased state to the biased state.

In some embodiments, the lever or arm has a flexible section.

In some embodiments, the entire lever or arm is flexible.

In some embodiments, the manifold is rotatably secured to the frame section.

In a fifteenth aspect, the present disclosure relates broadly to a patient interface comprising:

a frame section adapted to be positioned on the face of a user, the frame section comprising a gases chamber adapted to channel a gas to the user;

a manifold rotatable relative to the frame section and adapted to receive gases from a gases source; and a retention mechanism, the retention mechanism being disposed on the frame section and the retention mechanism configured to limit the non-rotational motion of the manifold relative to the frame section; and a release mechanism;

wherein the patient interface is configured such that the manifold is rotationally locked in at least one rotational orientation of the manifold relative to the frame section, and wherein the release mechanism is adapted to unlock motion of the manifold relative to the frame section when the manifold is rotationally locked.

In some embodiments, the retention mechanism and release mechanism are a combined mechanism that limits the non-rotational motion of the manifold relative to the frame section and is adapted to unlock motion of the manifold relative to the frame section when the manifold is rotationally locked.

In a sixteenth aspect, the present disclosure relates broadly to a patient interface comprising:

a frame section adapted to be positioned on the face of a user, the frame section comprising a gases chamber adapted to channel gases to the user;

a manifold secured to the frame section and adapted to receive gases from a gases source; and headgear adapted to secure the frame section to the head of the user, wherein the headgear comprises a bifurcatable section.

In some embodiments, the bifurcatable section rests on the back of the head of the user.

In some embodiments, the bifurcatable strap comprises a pair of straps linked by bridging regions.

In some embodiments, the bridging regions are thinner or integrally weaker than the straps.

In a seventeenth aspect, the present disclosure relates broadly to a patient interface comprising:

a frame section adapted to be positioned on the face of a user, the frame section comprising a gases chamber adapted to channel gases to the user;

a manifold secured to the frame section and adapted to receive gases from a gases source; and headgear adapted to secure the frame section to the head of the user, wherein the headgear comprises a user-contacting section with frictional elements.

In some embodiments, the user-contacting section rests on the back and/or sides of the head of the user.

In some embodiments, the frictional elements comprise markings. The markings may be printed.

In an eighteenth aspect, the present disclosure relates broadly to a patient interface comprising:

a frame section adapted to be positioned on the face of a user, the frame comprising a gas chamber adapted to channel a gas to the user;

a manifold secured to the frame and adapted to receive a gas from a gas source;

headgear adapted to secure the frame to the head of the user; and a headgear retaining mechanism actuatable to tighten or loosen the headgear, wherein the headgear comprises markings adapted to inform the user as to the tightness or fit of the headgear when used in cooperation with the headgear retaining mechanism.

In some embodiments, it may be particularly contemplated that headgear comprising of said markings, when used in combination with the "buckle" as herein described, provides for an advantageous co-operation. An indication of the fitment or tightness of headgear when retained or secured upon a user additionally provides a reference point or points for subsequent adjustment of headgear for fitment to a user, including an applied tightness or tension.

In some embodiments, the frame comprises a relatively rigid section and a relatively flexible section.

In some embodiments, the relatively flexible section of the frame is overmoulded onto a face contacting portion of the relatively rigid section of the frame.

In some embodiments, the patient interface further comprises a nasal delivery element adapted to be inserted into a nare or the nares of a patient, the nasal delivery element extending from the relatively flexible section of the frame.

In some embodiments, the patient interface further comprises a nasal delivery element adapted to be inserted into a nare or the nares of a patient, the nasal delivery element extending from the gases chamber.

The various aspects and embodiments of a component referred to above as a "swivel manifold" may be provided for use in relation to a component forming a part of a patient interface, for example such as a nasal cannula. However, it will also be appreciate the "swivel manifold" described above may be utilised to provide for an adjustable and side swappable manifold or gases delivery element to be integrated with a patient interface, for example as a part of a nasal cannula.

In addition, the "swivel manifold" described above in relation to each of the eighth to eighteenth aspects may be provided in for integration or combination with one or more of the other aspects described below in relation to patient interface or component parts for assembling of a patient interface.

In a nineteenth aspect, there is a patient interface, such as a nasal cannula, comprising a headgear in the form of at least one strap, said strap in-use, being splittable or bifurcatable to provide an upper strap part and a lower strap part of said headgear, in combination with any one or more of the aspects or embodiment as described herein.

In a twentieth aspect, there is a patient interface, such as a nasal cannula, wherein a manifold or manifold assembly is rotatably coupled or configured as a rotatable connection to the patient interface or a frame portion of said patient interface, such that in-use a gas supply conduit in fluid connection with said manifold is orientable to a left-side or a right-side of a user of said patient interface.

In a twenty-first aspect, there is a patient interface, such as a nasal cannula, wherein a manifold or manifold assembly is of a push-fit type configuration receivable by a gases chamber of said patient interface for receiving of a said gas supply and directing to an outlet or outlets, to be inserted into or removed from said gases chamber, said push-fit type configuration manifold in-use being in fluid connection with a gas supply conduit supplying of said gas supply, the push-fit type configuration manifold being receivable by said gases chamber from either, or both, of a left-side or a right-side of said patient interface or connected so as to orient said gas supply conduit to a left-side or a right-side of a user of said patient interface.

In combination with the aspects described herein, the "clip" as described herein allows for particular co-operation with either a "swivel manifold" or "swivel" manifold assembly or a push-fit type configuration of a manifold or manifold assembly, in that such adjustable orientation of the manifold and associated gas supply conduit allows for an effective "side swapping" of the gas supply conduit relative to the interface and user. As such, user comfort may be improved as well as the potential for less interrupted therapy delivery to the user or a user is less likely to interfere with the patient interface and associated parts, which may interfere with therapy delivery (i.e. a user may take the interface off or tubes may become wrapped or entangled with a user or objects in their vicinity). For example, the ability to swap sides from which gas delivery or supply conduit are provided with respect to the interface and user can help with improved operational or more optimal positioning by clipping the tube into the "clip" into the mounting portion or a receiving portion of said "clip" onto an arm or part of the interface. In some configurations, side arms of a nasal cannula interface can include such mounting portions or receiving portions on each arm at approximately the same location on each arm to allow the "clip" to be connectable to a side arm and retain the tube in the same location on each such arm.

The clip of the first to fourth aspects, or the buckle of the fifth to the seventh aspects, or the swivel manifold of the eighth to eighteenth aspects, of the headgear of the nineteenth aspect, or the patient interface of the twentieth or twenty-first aspects may be combined with the any one or more of the other aspects disclosed herein.

It is an object of the present disclosure to provide a patient interface for use in a medical application that will at least go some way towards improving on the above or which will at least provide the public or the medical profession with a useful choice.

In a twenty-second aspect, the present disclosure relates broadly to a patient interface (the patient interface comprising herein of a "tapered manifold portion") comprising:
- a frame section adapted to be positioned on the face of a user, the frame section comprising a gases chamber adapted to channel gases to the user and a nasal delivery element extending from the gases chamber adapted to be located in a nare of the user;
- a manifold assembly operatively securable to the frame section, the manifold assembly having a manifold and a manifold inlet, the manifold inlet having a tapered lumen in which an end proximal to the manifold has an area greater than an area of an end of the lumen distal the manifold.

In some embodiments the manifold assembly comprises a first component and a second component engageable with the first component such that:
the first component forms at least part of the manifold, at least part of the manifold inlet, or at least part of the manifold and at least part of the manifold inlet,
and the second component forms at least part of the manifold, at least part of the manifold inlet, or at least part of the manifold and at least part of the manifold inlet.

In some embodiments the first component has a manifold inlet portion, and the second component is a or has a manifold inlet portion, the manifold inlet portion of the first component and the manifold inlet portion of the second component being engageable to form the manifold inlet.

In some embodiments the manifold portion is formed by the first component having a manifold portion.

In some embodiments the first component comprises at least one location feature and the second component comprises at least one complementary location feature.

In some embodiments the at least one location feature of the first component comprises a protrusion and the at least one location feature of the second component comprises a complementary recess or aperture.

In some embodiments the first component has an internally threaded portion corresponding to an externally threaded portion of a conduit or tube.

In some embodiments the first component has a smooth, non-threaded portion.

In some embodiments the second component has an internally threaded portion corresponding to an externally threaded portion of a conduit or tube.

In some embodiments the second component has a smooth, non-threaded portion.

In some embodiments there may further comprise a fastening component.

In some embodiments the fastening component comprises a collar.

In some embodiments the collar is a substantially annular component.

In some embodiments the collar has a tapered internal surface for engaging with an exterior surface of the manifold inlet portion of the first component and an exterior surface of the manifold inlet portion of the second component.

In some embodiments the first component has a manifold portion, and the second component has a manifold portion, the manifold portion of the first component and the manifold portion of the second component being engageable to form at least part of the manifold.

In some embodiments the manifold portion of the first component and the manifold portion of the second component are engageable to form the entire manifold.

In some embodiments there may further comprise a third component engageable with the first component and/or second component to form at least part of the manifold.

In some embodiments there may further comprise a third component engageable with the first component and/or second component to form the entire manifold.

In some embodiments the first component has a manifold inlet portion forming at least part of the manifold inlet.

In some embodiments the first component has a manifold inlet portion forming the entire manifold inlet.

In some embodiments the first component forms at least a major portion of the manifold and the second component forms at least a major portion of the manifold inlet.

In some embodiments the first component forms the entire manifold and the second component forms the entire manifold inlet.

In some embodiments the first component has a manifold portion and a manifold inlet portion, and the second component has a manifold portion and a manifold inlet portion, the manifold portion of the first component and the manifold portion of the second component being engageable to form at least part of the manifold, and the manifold inlet portion of the first component and the manifold inlet portion of the second component being engageable to form at least part of the manifold inlet.

In some embodiments the first component forms at least a major part of the manifold, the second component forms at least part of the manifold inlet.

In some embodiments there may further comprise a third component, the third component engageable with the second component to form at least part of the manifold inlet.

In some embodiments the first component forms the entire manifold.

In some embodiments the first component forms at least part of the manifold, the second component forms at least a major part of the manifold inlet.

In some embodiments there may further comprise a third component, the third component engageable with the first component to form at least part of the manifold.

In some embodiments the second component forms the entire manifold inlet.

In some embodiments part of the first component comprises a relatively rigid material and another part of the first component comprises a relatively soft and/or flexible material.

In some embodiments the first component comprises a relatively rigid component.

In some embodiments the first component comprises a relatively soft and/or flexible component.

In some embodiments part of the second component comprises a relatively rigid material and another part of the second component comprises a relatively soft and/or flexible material.

In some embodiments the second component is a relatively rigid component.

In some embodiments the second component is a relatively soft and/or flexible component.

In some embodiments part of the second component comprises a relatively rigid material and another part of the second component comprises a relatively soft and/or flexible material.

In some embodiments there may further comprise one or more seals and/or gaskets.

In some embodiments the one or more seals and/or gaskets is/are integrally formed with the first and/or second component.

In some embodiments the one or more seals and/or gaskets is/are a separate component from the first and second components.

In some embodiments the first component and second component are integrally formed together with a live hinge.

In some embodiments the first component and second component are separate components.

In some embodiments the first component is engaged with the second component.

In some embodiments the first component is engaged with the second component by one or more of: ultrasonic welding, RF welding, heat staking, stitching, an adhesive substance, hook and loop fasteners, zip fasteners, clips, snap fits, and press fits.

In some embodiments the manifold assembly is formed from a series of modular components.

In another embodiment, said manifold or manifold assembly provides for a relatively smooth gases flow path into the manifold or manifold assembly, optionally such a path having a relatively reduced flow restriction. For example, reduction in flow restriction helps to minimise or reduce one or more of: noise (e.g. noise from flow of gases through the manifold or manifold assembly and/or into a gases chamber and delivery outlets of the patient interface), turbulent flows, separation of flows in the lead in to the manifold or gases chamber from a connector at a downstream end of a gases supply tube or conduit in connection with the patient interface, and/or makes manufacturing such component parts easier.

In another embodiment, the manifold or manifold assembly as described above allows for a side swapping manifold to be provided in combination with a patient interface, such as a nasal cannula. For example, such a combination with a side swapping manifold, because they are formed together, may allow the lead in to be swapped from side to side too.

The various aspects and embodiments of a component referred to above as a "tapered manifold portion" may be provided for use in relation to a component forming a part of a patient interface, for example such as a nasal cannula. However, it will also be appreciate the "tapered manifold portion" described above may be utilised to provide for an alternative lead-in or lumen portion for delivery of gases to a manifold portion of a patient interface and may be integrated with a patient interface or a manifold portion, including but not limited to a "swivel manifold", for example as a part of a nasal cannula.

In addition, the "tapered manifold portion" described above in relation to the twenty-second aspect may be provided in for integration or combination with one or more of the other aspects described below in relation to patient interface or component parts for assembling of a patient interface.

In a twenty-third aspect the disclosure relates to a patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms comprising a curve or bend upwardly along their length (herein "twisted side arms").

More specifically each side arm may have an inner first portion and an outer second portion which extends at an angle upwardly relative to the inner first portion.

In at least some embodiments at least a part of the outer second portion extends at an angle of about 20 and about 70 degrees to relative to the angle of the inner first portion, or may be between about 5 and about 85 degrees, or may be about 10 to about 80, about 15 to 75, about 25 to about 65, about 30 to about 60, about 35 to about 55, about 40 to about 50 degrees.

In at least some embodiments the side arms are shaped to engage the wearer's face below the cheek bones.

In a twenty-fourth aspect the disclosure relates to a patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms having an inner first portion extending laterally or laterally and rearwardly from the manifold at a first angle to the manifold and an outer second portion extending from the first portion and rearwardly at a relatively shallower or a relatively deeper angle relative to the manifold, for example the angle being made with reference to a line of reference drawn through the manifold body extending from a left-side to a right-side of the manifold body (or vice versa) when considered from a top (or bottom) view of the interface.

Typically the side arms are resiliently flexible or semi-rigid side arms.

In at least some embodiments the inner first portion of each of said side arm extends at an angle to the manifold body of between about 30 or about 50 or about 70 degrees and the outer second portion extends from the first portion at an angle of between about 150 and about 170 or about 180 degrees relative to the angle of the inner first portion, or the outer second portion extends from the first portion at an angle of between about 30 and 10 or about 0 degrees relative to the manifold body.

In at least some embodiments the side arms also comprise a bend upwardly along their length. In at least some embodiments the outer second portion of each of said side arm upwardly extends at an angle to the inner first portion.

In at least some embodiments the first portion and second portion of the elongate wing portions are joined by an intermediate curved portion.

In at least some embodiments a side arm comprises a part twisted portion, such that a cross-section shape orthogonally through the wing portion is part twisted anti-clockwise or clockwise at a part of the wing portion closer to an outer end thereof than a part closer to the manifold body.

In at least some embodiments the cross-section shape orthogonally through the side arms is part twisted anti-clockwise or clockwise up to about 60 degrees or up to about 45 degrees, or between about 2 and about 20 degrees or between about 2 and 50 degrees, the twist and orientation being when considered from a top or a bottom view of the interface, and depending on which side arm is being considered.

In at least some embodiments a major part or all of the part twisted shape is in said second outer portion of each side arm.

In at least some embodiments a cross-section area of each side arm reduces along the length of the side arm.

In a twenty-fifth aspect the disclosure relates to a patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms comprising a part twisted portion, such that a cross-section shape orthogonally through the wing portion is part twisted anti-clockwise or clockwise at a part of the wing portion closer to an outer end thereof than a part closer to the manifold body.

In at least some embodiments the cross-section shape orthogonally through the side arms is part twisted anti-clockwise or clockwise up to about 60 degrees or up to about 45 degrees, or between about 2 and about 20 degrees or between about 2 and 50 degrees, when considered from a top or a bottom view of the interface, and depending on which side arm is being considered.

In at least some embodiments a major part or all of the part twisted shape is in said second outer portion of each side arm.

In at least some embodiments a cross-section area of each side arm reduces along the length of the side arm.

Typically the patient interface also comprises headgear. Headgear may be formed of an elastic material such as an elastic textile material for example.

Typically a distal end of each side arm comprises a formation configured to releasably couple a complementary connector of a headgear.

The term "cheek" as used in this specification and claims means any region on the user's face at or adjacent the cheekbone, and may include any region to the side of and/or below the cheekbone and/or may include any other region between by the periphery of the corresponding eye, ear and nose of the user.

The terms "upward", "across", and "rearward" as used in this specification in relation to an interface mean (unless the context indicates otherwise) approximately vertical, transversely horizontal, and front to back horizontal through or in relation to the interface when worn by a user standing upright.

The various aspects and embodiments of a component referred to above as "twisted side arms" may be provided for use in relation to a component forming a part of a patient interface, for example such as a nasal cannula. However, it will also be appreciate the "twisted side arms" described above may be utilised to provide for an alternative system or configuration of a patient interface.

In addition, the "twisted side arms" described above in relation to each of the twenty-third to twenty-fifth aspects may be provided in for integration or combination with one or more of the other aspects described below in relation to patient interface or component parts for assembling of a patient interface.

In addition, in a further embodiment, the disclosure herein in relation to a "clip" is provided in combination with a patient interface, such as a nasal cannula, that comprises of the "twisted frame arms" as described herein.

In a further embodiment, the twisted or bent or curved nature of the frame or a side arm of a patient interface may facilitate the relative positioning of a mounting portion or receiving portion for the "clip" in a manner such that, in use, the "clip" when engaged with a side arm, allows for a tube or conduit supported or retained by said "clip" to provide the appearance or visual appearance of being aligned with the side arm of interface or such that the tube or conduit is positions and supported to extend away from the interface in a manner that is substantially parallel to a user's face, and optionally does not cause additional loading on a manifold or manifold assembly or any section thereof. Preferably, the frame or side arms of the interface may be twisted to allow or facilitate transmission of load or applied forces therein away from such a manifold section.

In a twenty-sixth aspect, the present disclosure relates broadly to a patient interface comprising:
 a frame adapted to be positioned on the face of a user, the frame comprising a gas chamber to channel gases to the user, and
 a manifold assembly adapted to receive gases from a gas source, the manifold assembly and frame adapted so that the manifold assembly can engage the frame from both the left hand side and the right hand side of the frame to deliver the gases to the gas chamber.

In some embodiments the manifold assembly comprises an inlet for interfacing with or attaching to a conduit and an outlet or opening to communicate with the gas chamber.

In some embodiments the frame comprises a first gas inlet at a left hand side of the gas chamber and a second gas inlet at a right hand side of the gas chamber, the manifold assembly adapted to be inserted into the gas chamber via both of the first and second gas inlets.

In some embodiments the manifold assembly comprises a sealing surface at or towards each end of the manifold assembly to seal with the first and second gas inlets.

In some embodiments the frame or the manifold assembly comprises resilient material to form a seal between the manifold assembly and the frame to substantially prevent gas flow through the first and second gas inlets between the frame and the manifold assembly.

In some embodiments the frame comprises a resilient material within the gases chamber to contact sealing surfaces of the manifold assembly.

In some embodiments the resilient material is integrally formed with a face contacting part of the frame.

In some embodiments the manifold assembly outlet faces rearwardly when the manifold assembly is fitted to the frame.

In some embodiments the resilient face contacting part of the frame is unsupported by the manifold assembly in an upper lip area so that the face contacting part in the region of the manifold outlet provides a cushion to sit against the user's upper lip.

In some embodiments the patient interface comprises a clip for securing a tube and/or a cable to the patient interface according to or as described in one or more of the other aspects of the present invention described herein.

In some embodiments the patient interface comprises one or two buckles or connectors for attaching headgear to the frame according to or as described in one or more of the other aspects of the present invention described herein.

In some embodiments the patient interface comprises headgear for securing the frame to the head of a user according to or as described in one or more of the other aspects of the present invention described herein.

In some embodiments the manifold assembly comprises a manifold inlet as described in one or more of the other aspects of the present invention described herein.

In some embodiments, a headgear may be provided having a slit extending along or through a section of said headgear, such that said slit may be opened or split-apart in use.

In some embodiments, a headgear may be provided comprising of two side straps extending toward rear of a user's head, two rear strap portions, an upper rear strap portion and a lower rear strap portion, the upper and lower rear strap portion allowing for retention of a patient interface onto a user's the face in use, yet while maintaining one or a pair of nasal prongs for delivery of a supplied gas(es) into the nostrils and/or for reducing any pressure applied on the underside of the user's nose, septum or philtrum.

In some embodiments, the upper and lower rear strap portion of a headgear are moveable relative to each other and may be configured to allow for auto or a self-adjustment of fitting to the head, headgear fitting in a position to minimize forces on the septum of the nose while maintaining prongs in nose.

In still further embodiments, in combination with any one or more of the above aspects or other embodiments, a conduit or tube may be provided in combination. Such a conduit or tube providing gases to the patient interface, or that which is provided in fluid communication or in connection with a manifold or manifold assembly. Such a conduit may be formed of a breathable and flexible type. Such a gases conduit may be additionally crush-resistant and/or may be made of a material that reduces or may minimise noise generation when the conduit is moved or bent, such noises are sometimes referred to as a "crinkling" sound. In this embodiment, the conduit may comprise of an elongate film spirally wrapped with an elongate reinforcing member to form the conduit's lumen. The conduit may also be of the type which is extruded to form the conduit. In various embodiments, breathable material(s) can be used in the construction of the conduit to assist with expelling of any accumulated condensate (e.g. from "rain-out") in the conduit. In various embodiments, the reinforcing member may help to prevent or reduce crushing and/or kinking of the tube, or at least the potential for crushing and/or kinking during use. The lumen of the conduit may comprise of an inner bore that is substantially smooth so as to reduce resistance to flow and/or minimise surface features upon which condensation may accumulate or pool.

It should be understood that any of the following embodiments may relate to the any one or more of the aspects of the disclosure described above, alone or in any combination of any two or more, or combinations of the various embodiments described herein in providing for assemblies and combinations.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This disclosure may also be said broadly to consist in the parts, elements and features referred to or indicated in the specification of the application, individually or collectively, and any or all combinations of any two or more said parts, elements or features, and where specific integers are mentioned herein which have known equivalents in the art to which this disclosure relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both.

The disclosure consists in the foregoing and also envisages constructions of which the following gives examples only.

BRIEF DESCRIPTION OF THE DRAWINGS

Various embodiments of the disclosure will be described by way of example only and with reference to the following drawings.

FIGS. 4A-4C show a way in which a frame of a patient interface may be rotatably secured to a manifold.

FIGS. 10A-10I show an alternative embodiment of components for the patient interface;

FIGS. 26A-26D show an alternative embodiment of the components for the patient interface.

FIG. 34 is a top perspective view of the second component of the manifold assembly of FIG. 29;

FIG. 35 is an underside perspective view of the second component of FIG. 34;

FIG. 36 is a top view of the second component of FIG. 34;

FIG. 37 is an underside view of the second component of FIG. 34;

FIG. 38 is a partial cross sectional view of the manifold assembly of FIG. 29;

FIGS. 76A to 76C show a thirty-third embodiment manifold assembly;

FIG. 121 (B) is a front view of the embodiment of FIGS. 117-120 that is attached to a mounting portion integral with an auxiliary portion of patient interface.

FIG. 122 is a perspective view of a patient interface incorporating the first embodiment of the connector.

FIG. 123 is a perspective view of the embodiment of the connector of FIG. 122.

FIG. 124 is a cross sectional view of the connector of FIG. 123, before the clip is engaged with the detent.

FIG. 125 is a cross sectional view of the connector of FIG. 123, showing the initial stages of the clip being engaged with the detent.

FIG. 126 is a cross sectional view of the connector of FIG. 123 showing the slide in the secured position.

FIG. 127 is a cross sectional view of the connector of FIG. 123 showing the slide in a free position.

FIG. 128 is a cross sectional view of the connector of FIG. 123 showing the clip removed from the carrier.

FIG. 129 is a cross sectional view of one half of the slide of the first embodiment.

FIG. 130 is a cross sectional view of the other half of the slide of the first embodiment.

FIG. 131 is a perspective view of the carrier of the first embodiment.

FIG. 132 is a perspective view of the clip of the first embodiment.

FIG. 133 is a cross sectional view of a second embodiment connector, before the clip is engaged with the detent.

Figure 133:
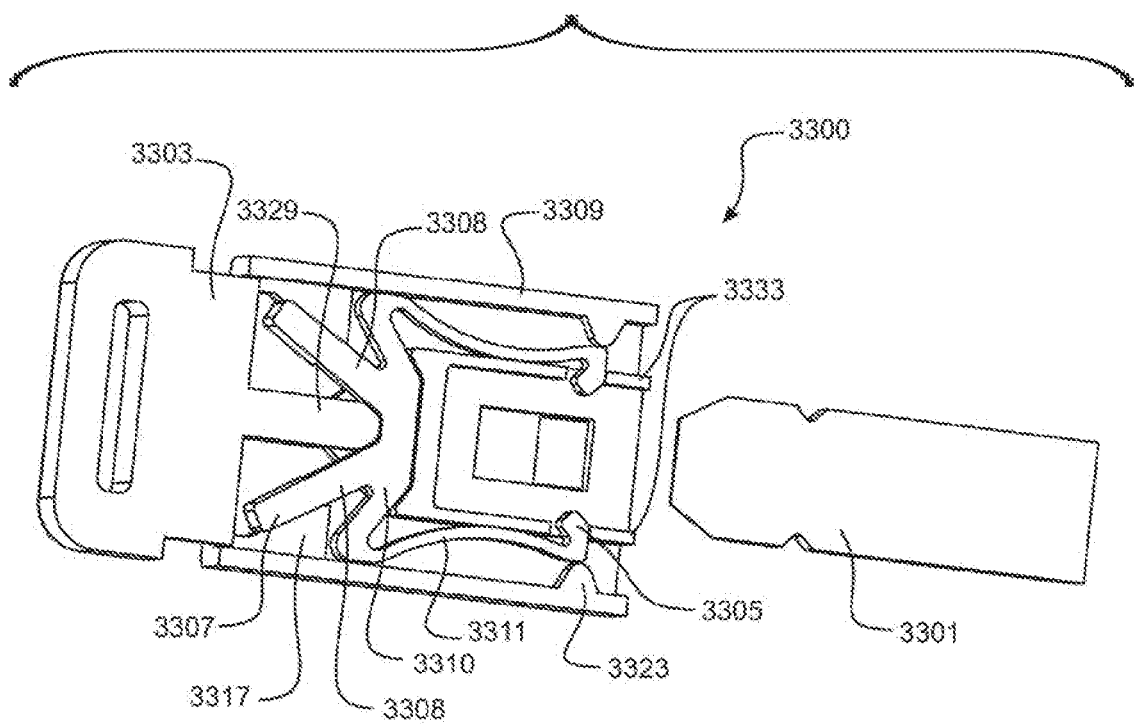
Figure 134:
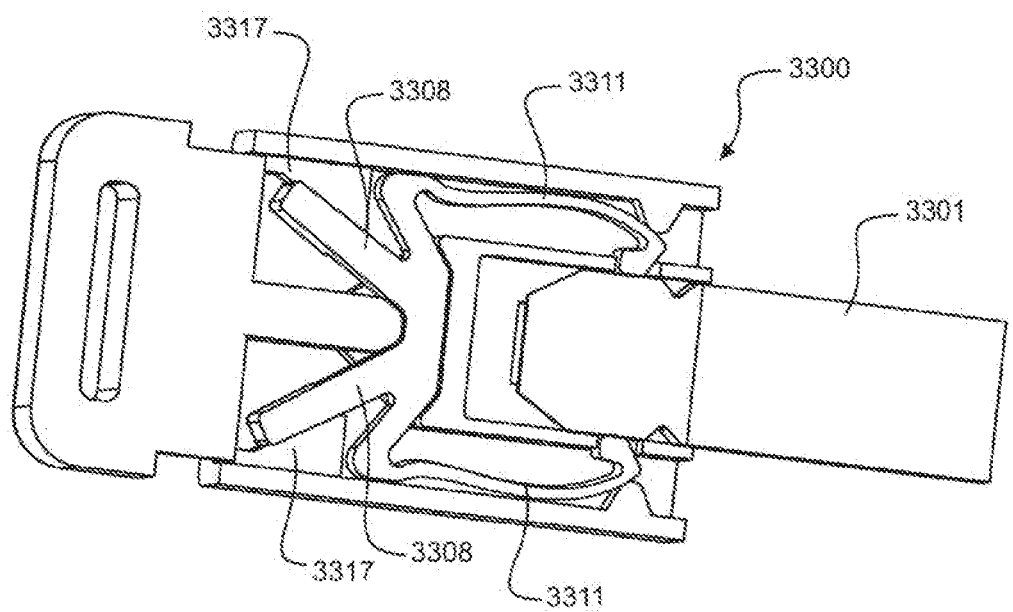

FIG. 134 is a cross sectional view of the connector of FIG. 133, showing the initial stages of the clip being engaged with the detent.

Figure 135:
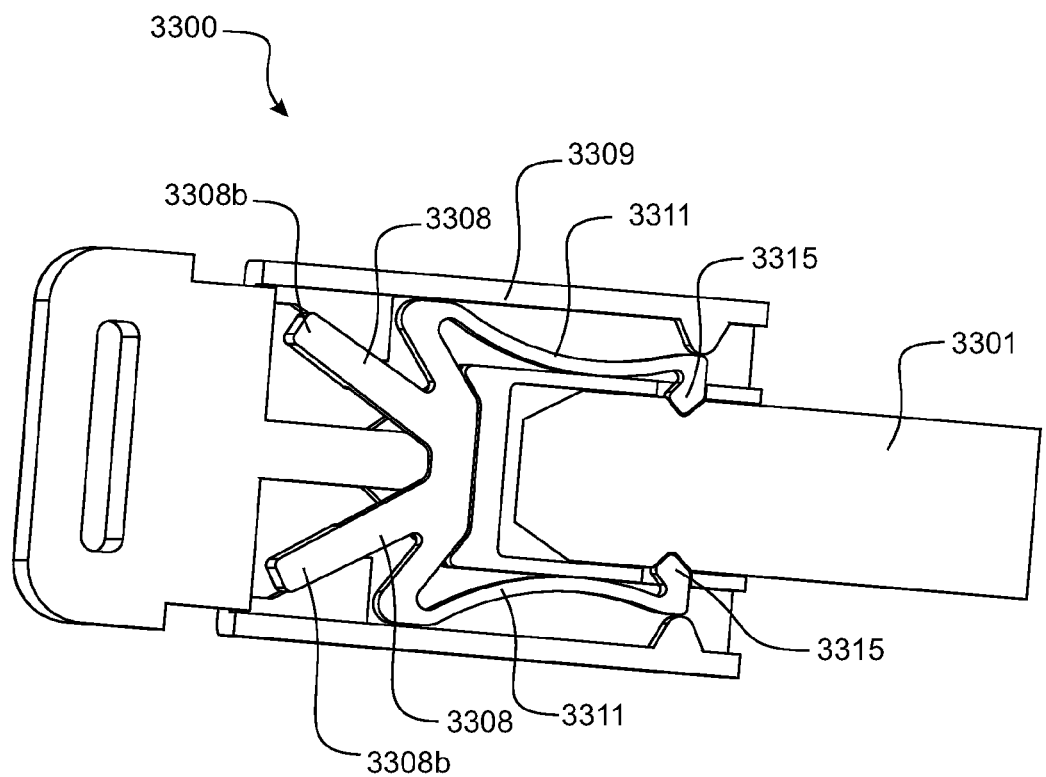

FIG. 135 is a cross sectional view of the connector of FIG. 133 showing the slide in the secured position.

Figure 136:
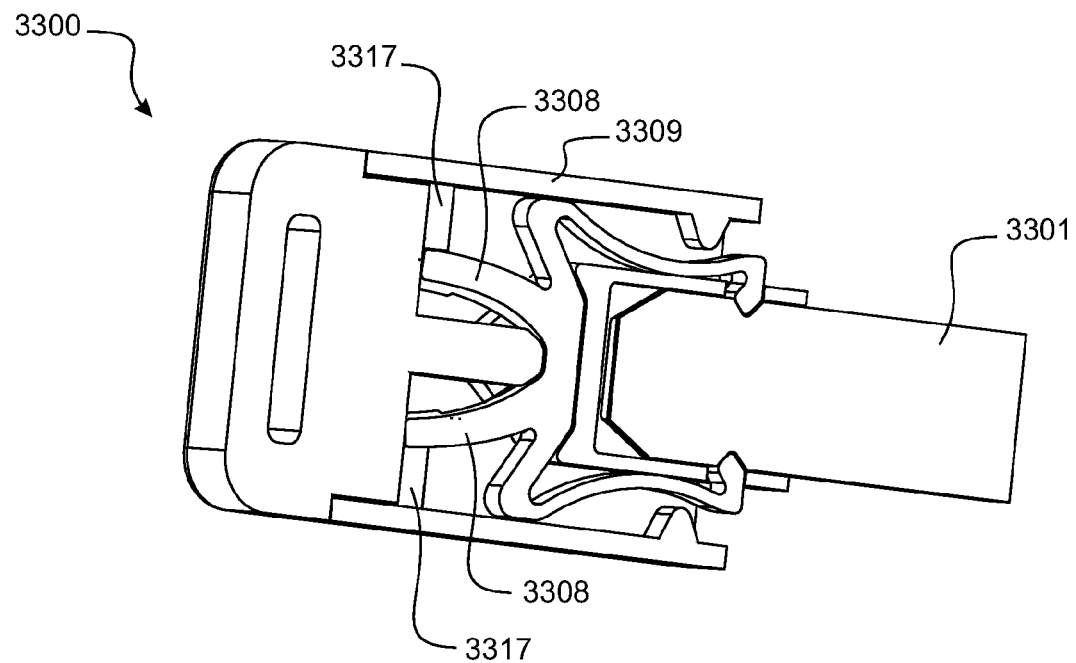

FIG. 136 is a cross sectional view of the connector of FIG. 133 showing the slide in a free position.

Figure 137:
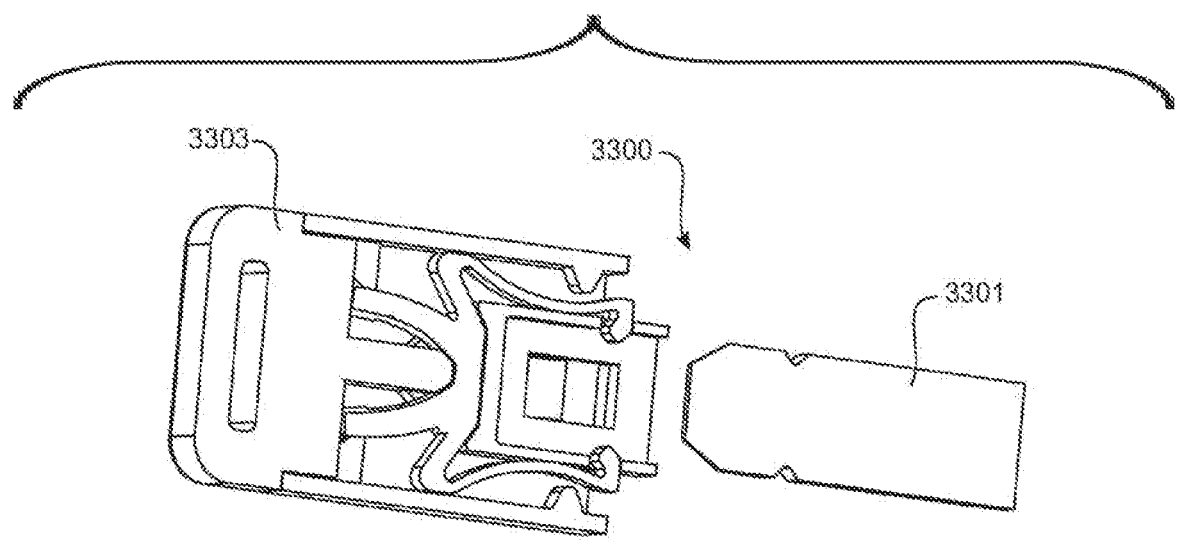

FIG. 137 is a cross sectional view of the connector of FIG. 133 showing the clip removed from the carrier.

Figure 138:
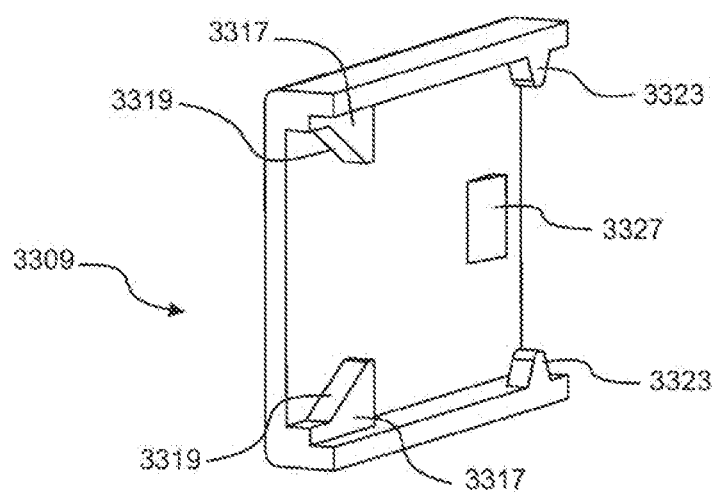

FIG. 138 is a cross sectional view of one half of the slide of the second embodiment.

Figure 139:
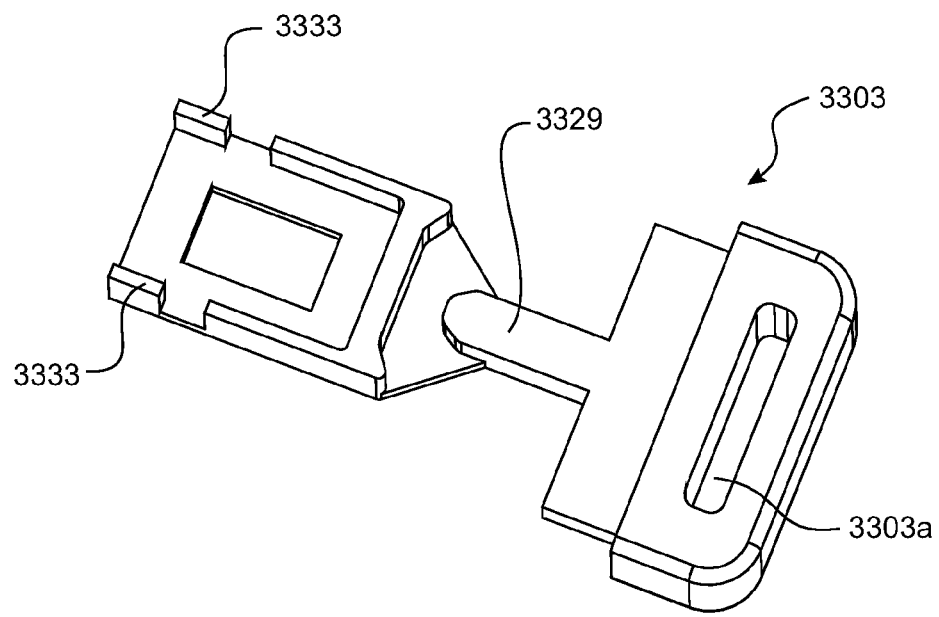

FIG. 139 is a front perspective view of the carrier of the second embodiment.

Figure 140:
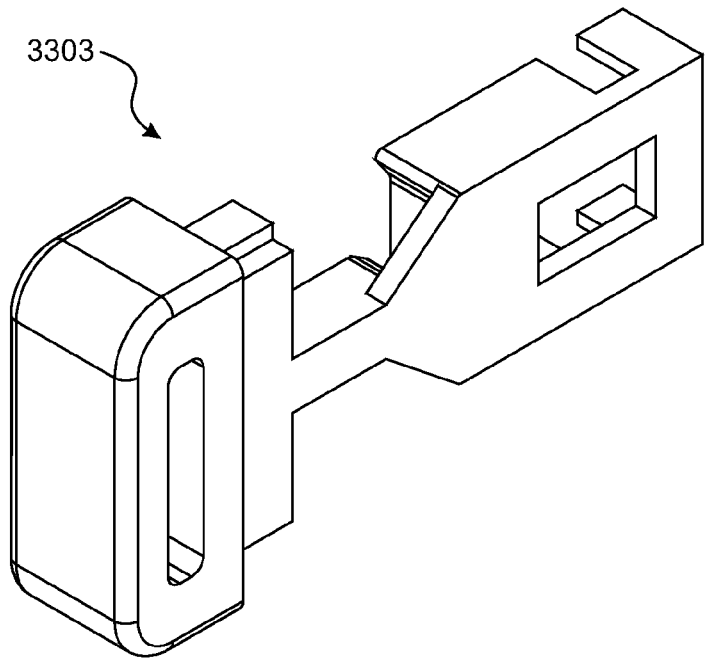

FIG. 140 is a rear perspective view of the carrier of the second embodiment.

Figure 141:
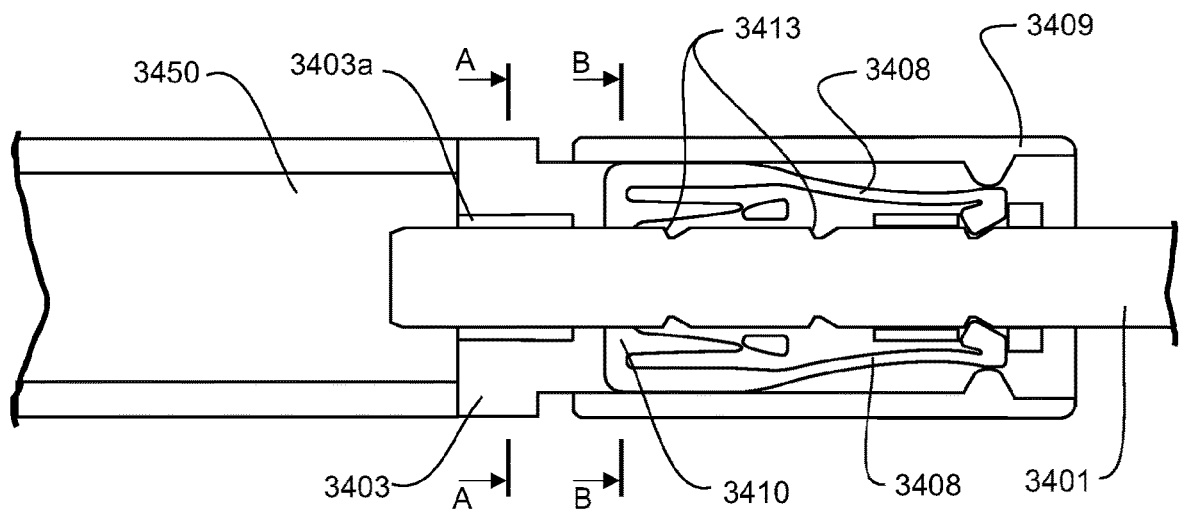

FIG. 141 is a cross sectional view of a third embodiment connector, showing the slide in a secured position.

Figure 142:
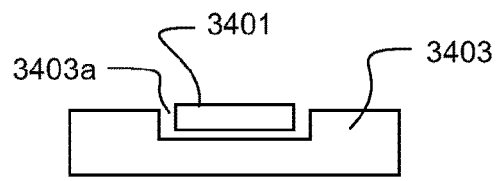

FIG. 142 is a cross sectional view taken through line A-A of FIG. 141.

Figure 143:
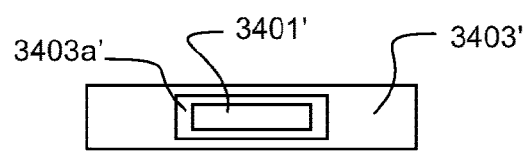

FIG. 143 is a cross sectional view taken through line A-A of FIG. 141 showing an alternative cut out to that of FIG. 142.

Figure 144:
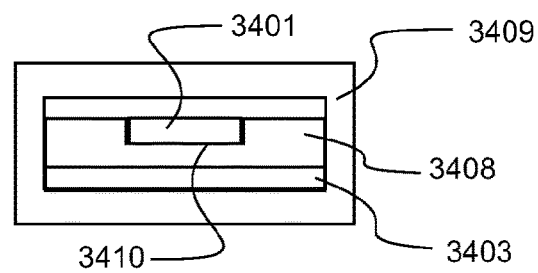

FIG. 144 is a cross sectional view taken through line B-B of FIG. 141.

Figure 145:
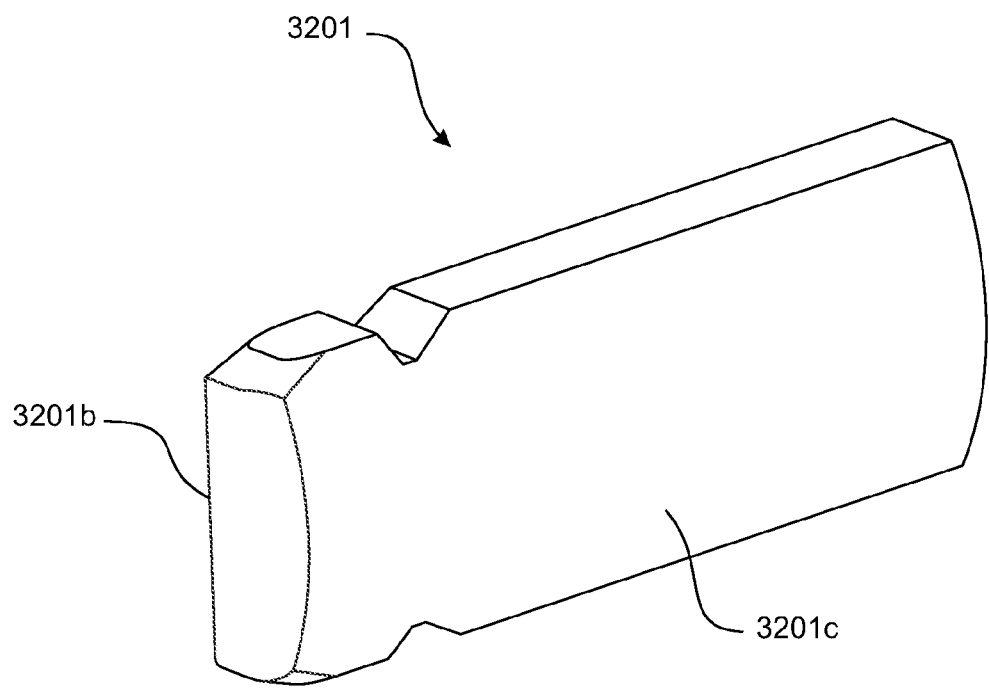

FIG. 145 is a perspective view of an alternative embodiment of the clip.

Figure 146:
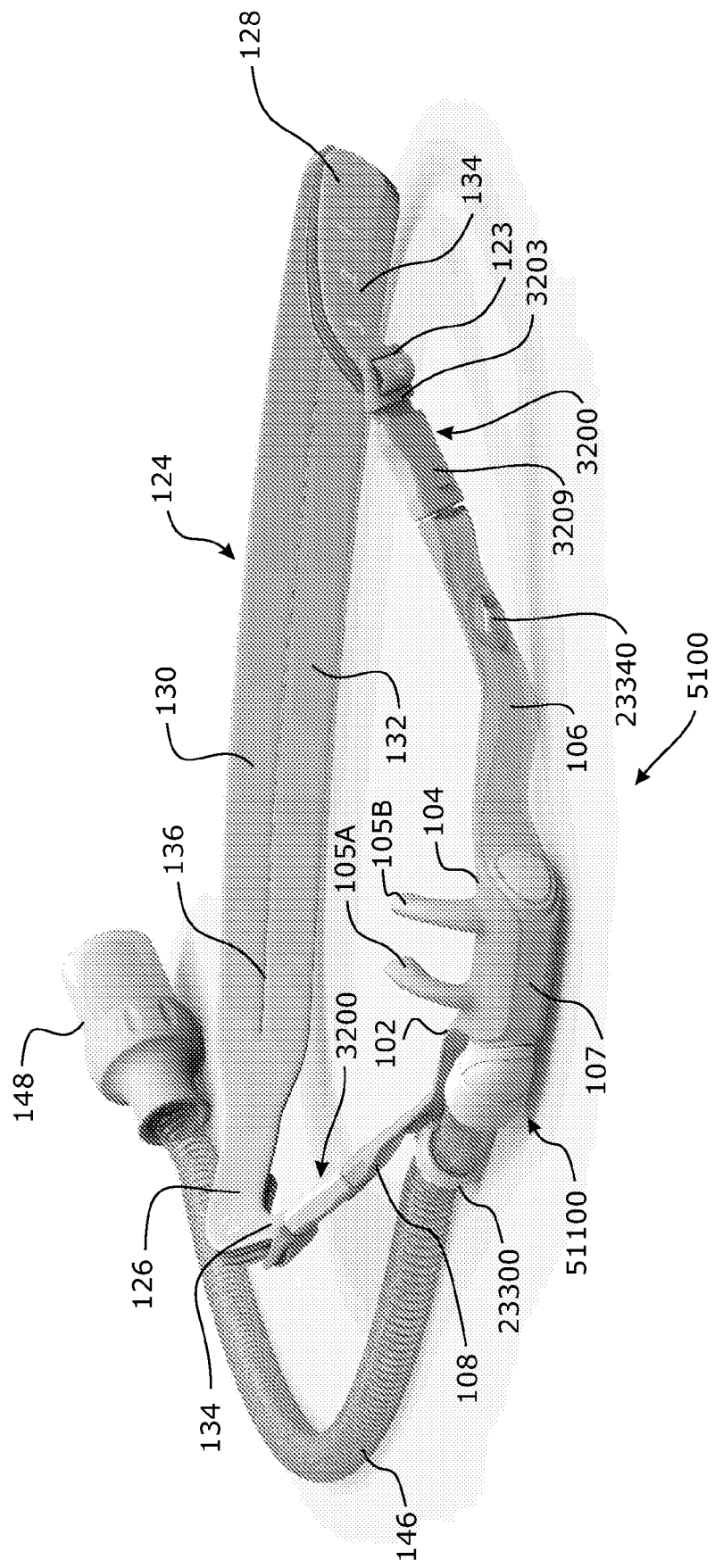

FIG. 146 is a perspective view of a patient interface comprising an assembly and combination of a number of embodiment features described herein.

Figure 147:
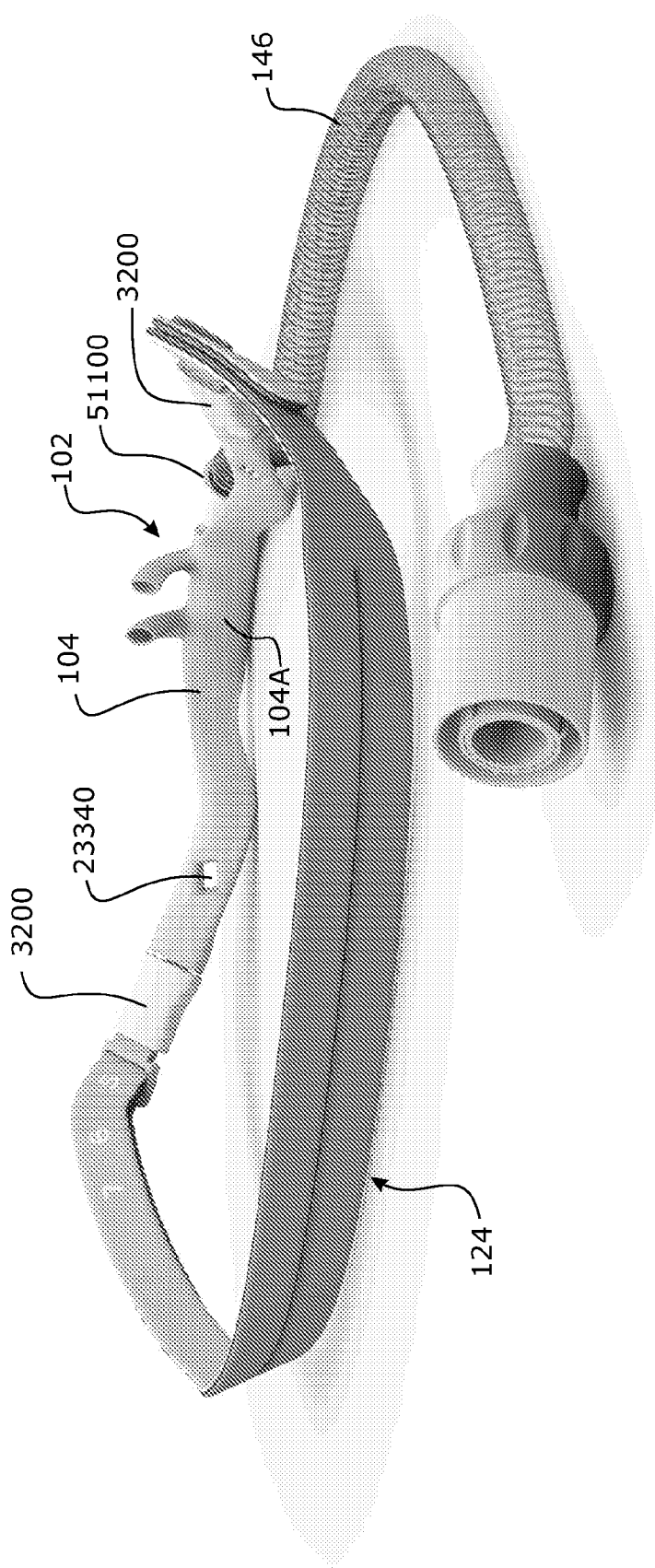

FIG. 147 is a perspective rear view of the patient interface of FIG. 146.

Figure 148:
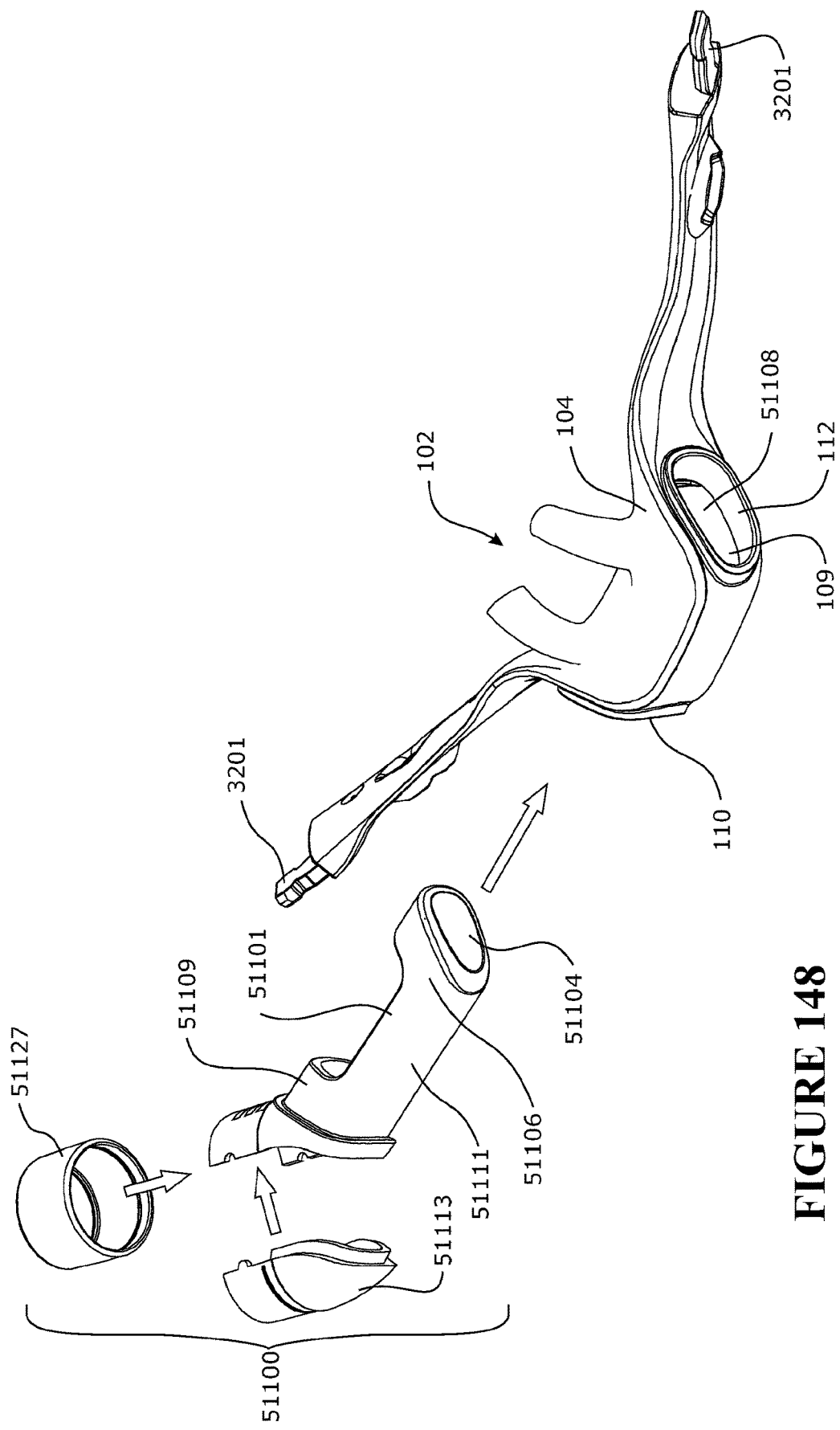

FIG. 148 is an exploded perspective view of a frame portion and a manifold assembly of the patient interface of FIG. 146.

Figure 149:
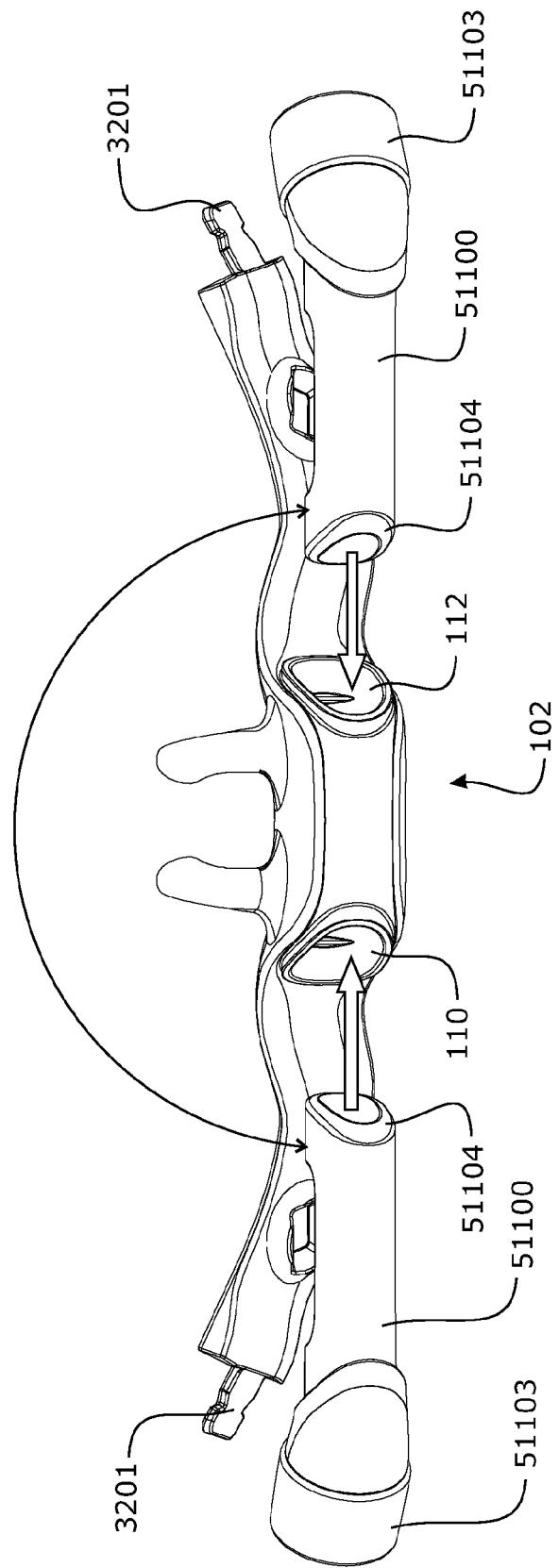

FIG. 149 is a front view of a frame portion of the patient interface of FIG. 146 with a manifold assembly of the patient interface shown positioned for assembly with the frame portion from both a left side and a right side.

Figure 150:
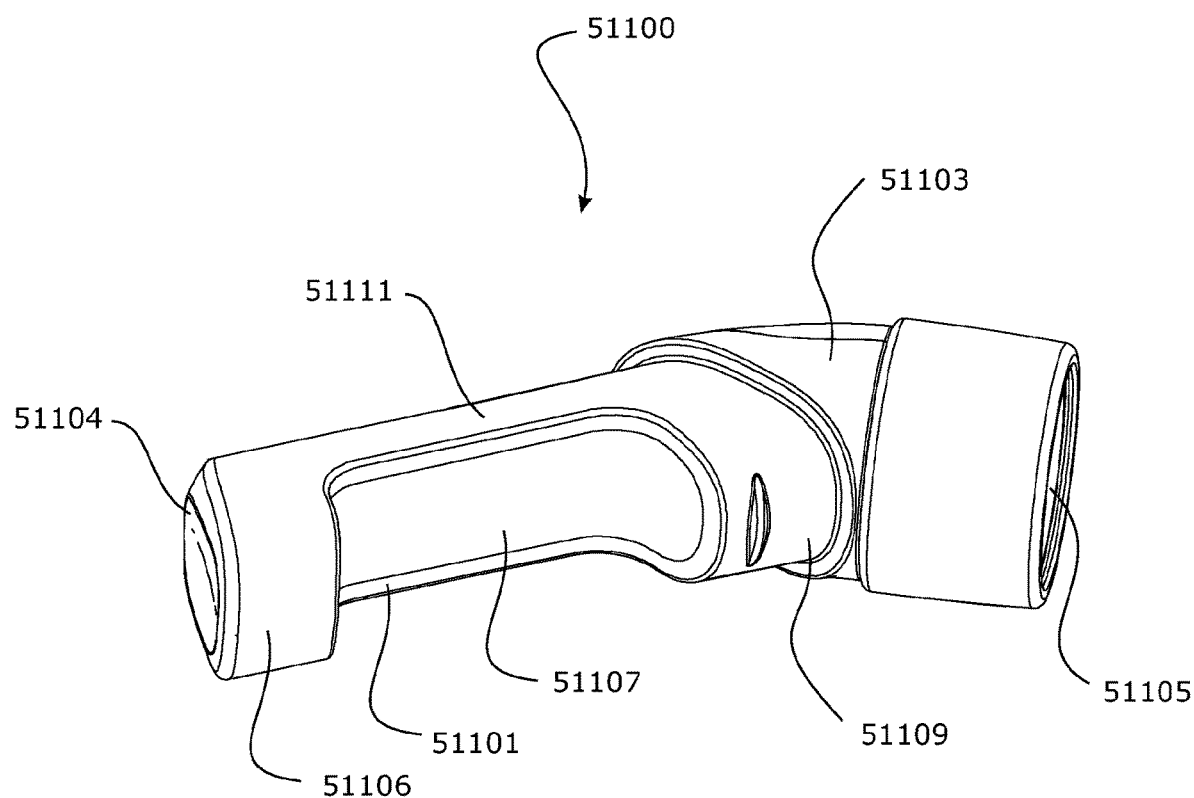

FIG. 150 is a perspective rear view of a manifold assembly of the patient interface of FIG. 146.

Figure 151:
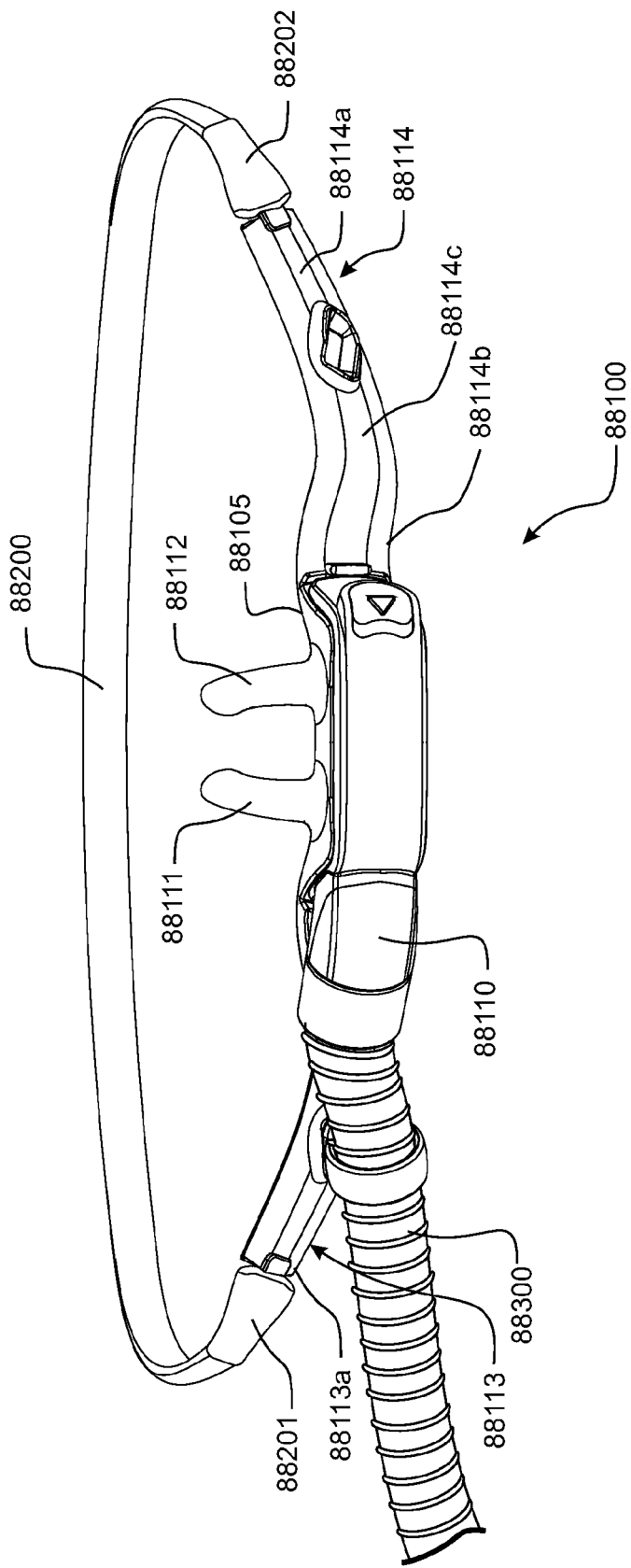
Figure 152:
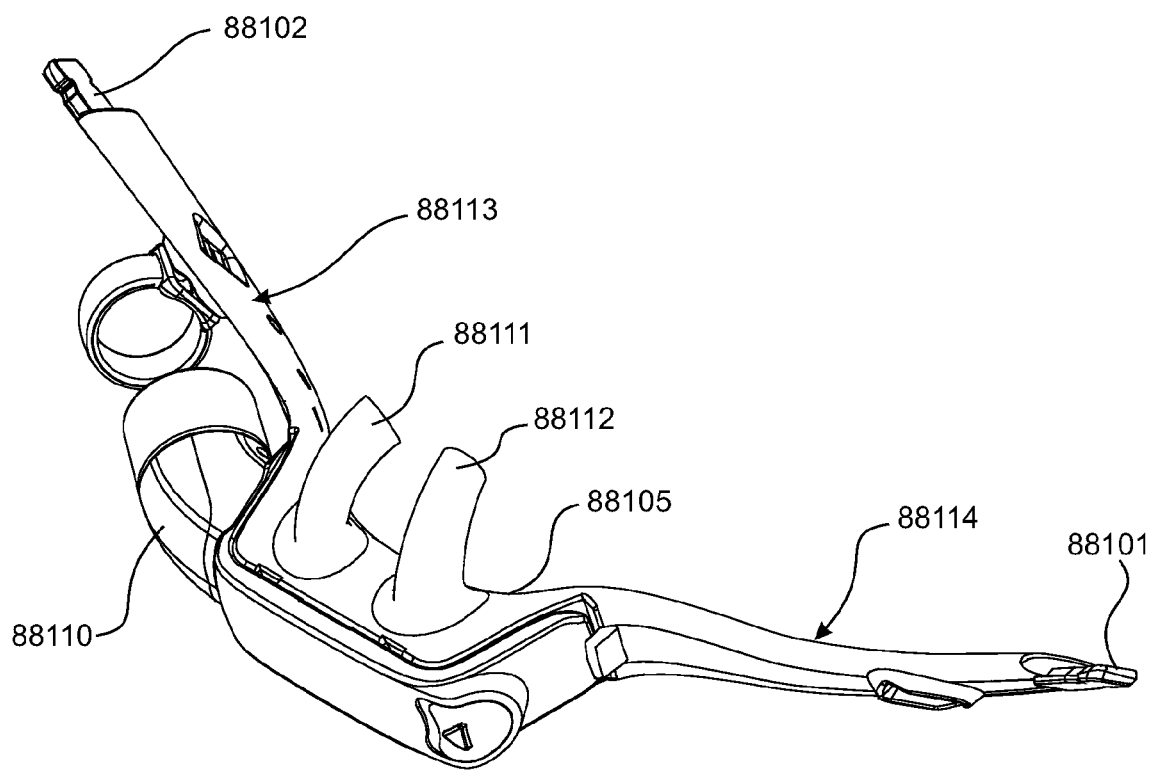
Figure 153:
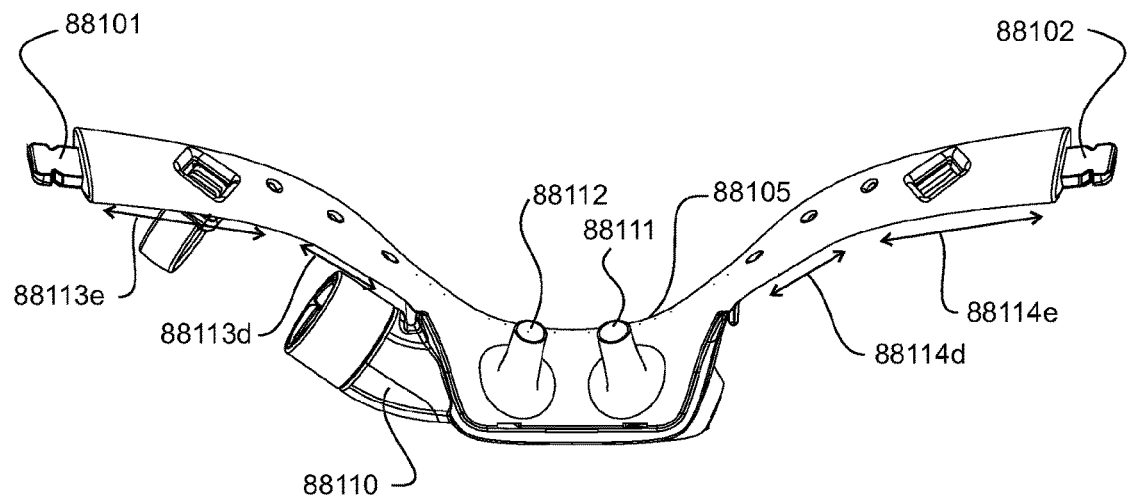
Figure 154:
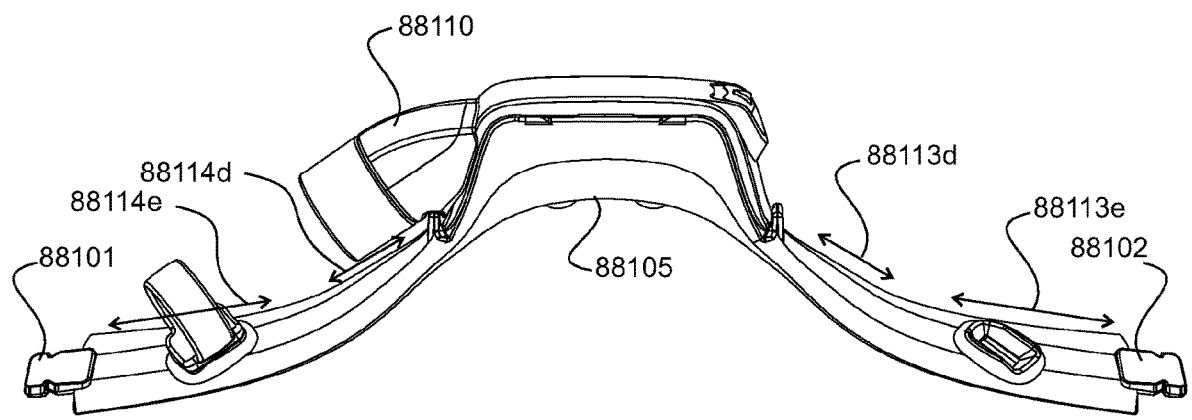

FIG. 151 is a view from the front and slightly above of a preferred embodiment of a patient interface of the invention including a head strap;

FIG. 152 is a view three quarter from above of the embodiment of FIG. 151 but without the head strap;

FIG. 153 is a view from above of the embodiment of FIGS. 151 and 152 without the head strap; and FIG. 154 is a view from below of the embodiment of FIGS. 151 to 153 without the head strap.

FIGS. 155-161 illustrate an embodiment of a patient interface (or frame thereof) having elongate side arms extending from opposite sides of a manifold or central body part and which are, in-use, provided with an inner surface or patient-side surface for contact with a user's face

DETAILED DESCRIPTION

In this specification, the terms "medical circuit" and "breathing circuit" are used to indicate the general field of the disclosure. It is to be understood that a "circuit" is intended to include open circuits, which do not form a complete closed circuit. For example, high flow delivery systems may be provided, and may include but are not limited to, CPAP systems which may typically consist of a single inspiratory breathing tube between the blower and the patient interface, as well as ventilator driven systems. The term "breathing circuit" is intended to include such "open circuits". Similarly, the term "medical circuit" is intended to include both breathing circuits and insufflation circuits, which are also typically "open." Similarly, the term "medical tubing" is intended to be read as flexible tubing suitable for use in the type of medical circuits described above connecting between components of a medical circuit and providing a low resistance gases pathway between components of a medical circuit.

In the field of medical circuits, and in particular breathing circuits, including anaesthetic circuits, condensation or rain-out can be a particular problem where high humidity breathing gases come into contact with the walls of a component at a relatively lower temperature. With reference to FIG. 1B, a humidified ventilation system is shown in which a patient 3100 is receiving humidified and pressurised gases through a patient interface 3102 connected to a humidified gases transportation pathway or inspiratory breathing tube 3103. It will be appreciated the patient interface 3102 may take the form of a nasal mask, oral mask, oronasal mask, nasal cannula, endotracheal tube or full-face mask, for example but without limitation.

It should be understood that delivery systems could also be continuous, variable or bi-level positive airway pressure or numerous other forms of respiratory therapy. The inspiratory tube 3103 is connected to the outlet 3104 of a humidification chamber 3105 which contains a volume of water 3106. The inspiratory tube 3103 may include a heater or heater wires (not shown) which heat the humidified gases within the tube to reduce the formation of condensation. The humidification chamber 3105 is heated by a heater plate 3107 of humidifier base 3108. The humidifier base 3108 is provided with an electronic controller which may comprise a microprocessor based controller executing computer software commands stored in associated memory.

In response to the user set humidity or temperature value input via dial 3110, for example, and/or other inputs, the controller determines when (or to what level) to energize heater plate 3107 to heat the water 3106 within the humidification chamber 3105. As the volume of water is heated, water vapour begins to fill the chamber above the water's surface and is passed out of the humidification chamber outlet 3104. A flow of gases (for example, air) is provided from a gases supply or ventilator 3115, which enters the chamber 3105 through inlet 3116, which may include a fan, blower or the like 3121 for providing a flow of gases. Exhaled gases from the patient's mouth are returned to the ventilator via a return expiratory breathing tube 3130 that may also include a heater or heater wires (not shown), which heat the humidified gases within the expiratory breathing tube to reduce the formation of condensation.

It is preferable that medical tubing (for example the inspiratory and/or expiratory breathing tubes 3103,3130) is: resistant to crushing, resistant to restrictions in flow when bent (e.g., increased resistance to flow<50% when bent around a 1 inch cylinder), resistant to kinking, resistant to changes in length/volume under fluctuating internal pressure (e.g., resistance to compliance), resistant to leaking (e.g., <25 ml/min @6 kPa), have low flow resistance (e.g., increase in pressure @ max. rated flow<0.2 kPa), electrically safe (e.g., resistant to sparks in the tubing) given an operating environment that may be oxygen-rich.

International standard ISO 5367:2000(E) (Fourth edition, Jun. 6, 2000) is one example of how some of these desirable parameters are measured and quantified, and the document is hereby incorporated into this specification in its entirety by reference. It is preferable that components described herein meet or exceed some or all of these standards. Further, reference to medical tubes includes breathing tubes as defined in the above ISO standard.

In accordance with certain features, aspects and advantages of this disclosure, a component is provided as an accessory for use with medical tubing and/or cabling, particularly for use in medical breathing circuits, surgical insufflation systems, medical feeding apparatus, and/or medical monitoring apparatus, or any combination of any two or more thereof.

The component is locatable about the exterior surface of at least one tube and/or at least one cable, such as a breathing tube for use in the inspiratory and/or expiratory limb of a breathing circuit, or tubes associated with surgical insufflation systems, or tubes associated with feeding apparatus, and/or cables associated with such systems and/or cables associated with medical monitoring apparatus, and has particular application for the location, positioning and support of such medical tubing and/or cabling relative to a user or equipment associated with the user (e.g., user interfaces or patient interfaces, such as masks, nasal cannula and the like, briefly described above). The component is an auxiliary component, which may be attached or attachable to a patient interface, optionally an auxiliary part of a patient interface. The component does not itself form a part of a flow path through which gases or nutrition pass.

The ability to locate a medical tube and/or cable relative to a user has certain advantages. Being able to help support the weight of the medical tubing and/or cabling connected to equipment associated with the user has a number of advantages including but not limited to, for example, reducing the weight transferred to a user or equipment associated with the user, which may in turn impact on the efficiency of a treatment being provided to a user, or the overall comfort experienced by a user when using such equipment.

Further, as a user moves or re-positions their body relative to the medical tubing and/or cabling, or associated equipment, strain may be transferred to the tubing and/or cabling or to the user via the associated equipment. A relatively quick and effective re-positioning or re-locating of the tubing and/or cabling to provide support again would be useful. Certain features, aspects and advantages of the present disclosure attempt to provide or go at least some way towards providing at least an alternative component facilitating such advantages. For example, one such example can provide for the use the "clip" to ensure tubing or conduit does not interfere with the side swapping ability of an adjustable or re-orientable manifold to the patient interface. Other combinations of the "clip" with the "buckle" as well as "twisted frame arms", "swivel manifold" and "tapered lead in" may all be provided in combination with each other.

Such a component can be utilised to position or locate inspiratory or expiratory medical tubing, or other tubing associated with such medical circuits, and/or cabling as described above. Particular application may have uses in the obstructive sleep apnoea fields, as well as in hospital situations including but not limited to surgery requiring insufflation, and/or patient feeding, and/or patient monitoring.

Figure 82:
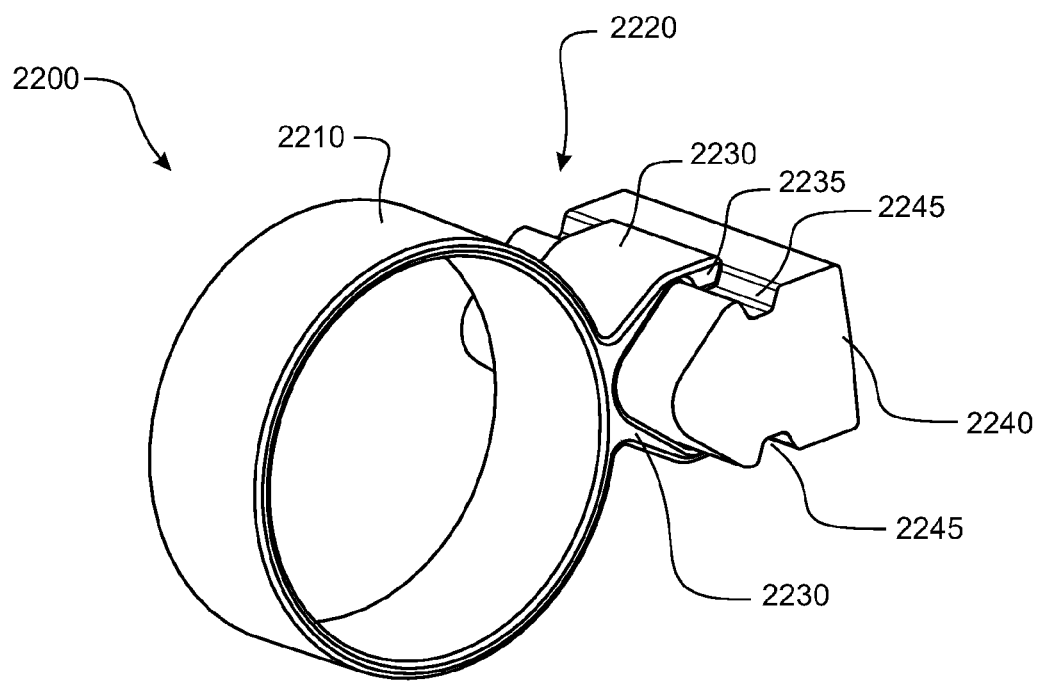
FIG. 82 is a perspective view of one embodiment of a component that is attached to a mounting portion.
Figure 83:
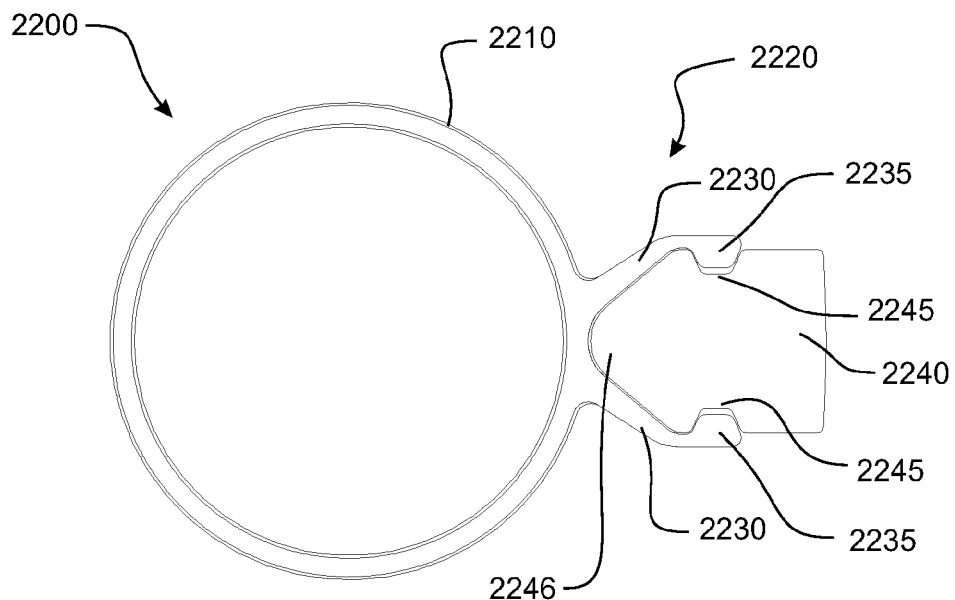
FIG. 83 is a side view of the embodiment of FIG. 82.

In one aspect of the present disclosure, and with reference to FIGS. 82 and 83, a component 2200 is provided for use with at least one tube and/or at least one cable, such as a tube in a medical breathing circuit (not shown). Any reference to a tube below includes reference to a cable. The component 2200 comprises an at least substantially annular body 2210, optionally an annular body, for receiving a tube, where the tube passes through the body 2210 so that the body at least partially surrounds, and may surround a perimeter of the tube. The body 2210 may also be square, substantially square or of another rectilinear configuration, for example (not shown). The tube may lie loosely in body 2210, with the tube bearing only on a portion of the inner surface of the body 2210, or the body 2210 may hold the tube lightly or tightly, such as with a light interference fit or an interference fit. In one embodiment, in use, the body 2210 is generally readily movable along a length of a tube, while holding the tube firmly enough such that there is no undesirable movement of the tube within the body 2210. For example, the body 2210 is slidable along the length of the tube or rotatable about or along the tube. Alternatively, the body 2210 may optionally be fixed in place on the tube. The body 2210 receives the tube by an operator threading the tube through the body 2210 and positioning the body 2210 at the desired location along the length of the tube, relative to an intended mounting portion 2240.

In various embodiments (such as described below), an internal surface of the body may comprise one or more projections (not shown) engageable with one or more corresponding recesses of a tube, such as the recesses of a corrugated tube or a tube with a helically recessed surface region. The internal surface of the body may comprise a first projection engageable with a first recess and a second projection engageable with the same or another recess. In such embodiments, the body 2100 may be wound onto the tube.

Component 2200 includes an attachment 2220 that is integral with or non-moveably fixed to the body 2210. Alternatively, attachment 2220 may be pivotably, rotatably and/or removably fixed to the body 2210 (for example, as described below in relation to FIGS. 89 and 90). Attachment 2220 is arranged to snap fit or snap engage a mounting portion 2240 and removeably hold component 2200 securely in place. In one embodiment, attachment 2200 comprises a pair of arms 2230 that extend from the body 2210 forming a female connector that is shaped to engage the corresponding male connector, mounting portion 2240. Arms 2230 may extend from the body 2210 at the same point or adjacent points, at any suitable angle, for example substantially parallel to a virtual radial line (not shown) extending from the centre of body 2210, or at an angle of about 30 degrees to about 50 degrees from a virtual radial line extending from the centre of body 2210, such that the distal ends of the arms are substantially opposite each other as shown in FIGS. 82 and 83, forming a pair of jaws adapted to engage the mounting portion 2240. Arms 2230 comprise lugs 2235 that engage with corresponding recesses 2245 on the mounting portion 2240. The lugs 2235 and corresponding recesses 2245 are shaped to both retain the attachment 2220 in place on the mounting portion 2240 and also provide sensory feedback to an operator, as described below. The mounting portion 2240 may be shaped to guide the lugs 2235 into the recesses 2245 and to aid engagement of the attachment 2220 with the mounting portion 2240. For example, mounting portion 2240 may comprise a curved projection 2246 extending from the main body of the mounting portion 2240 that is shaped to center the mounting portion 2240 between arms 2230 and also to displace arms 2230 as the attachment 2220 is brought into engagement with mounting portion 2240.

It should be understood that the relative arrangement of the arms 2230, lugs 2235, recesses 2245 and/or projection 2246 can be modified to provide the desired degree of retention. Removal of component 2200 from mounting portion 2240 may be achieved by an operator with a twisting action or sliding action or pulling action to disengage the lugs 2235 from recesses 2245.

Figure 84:
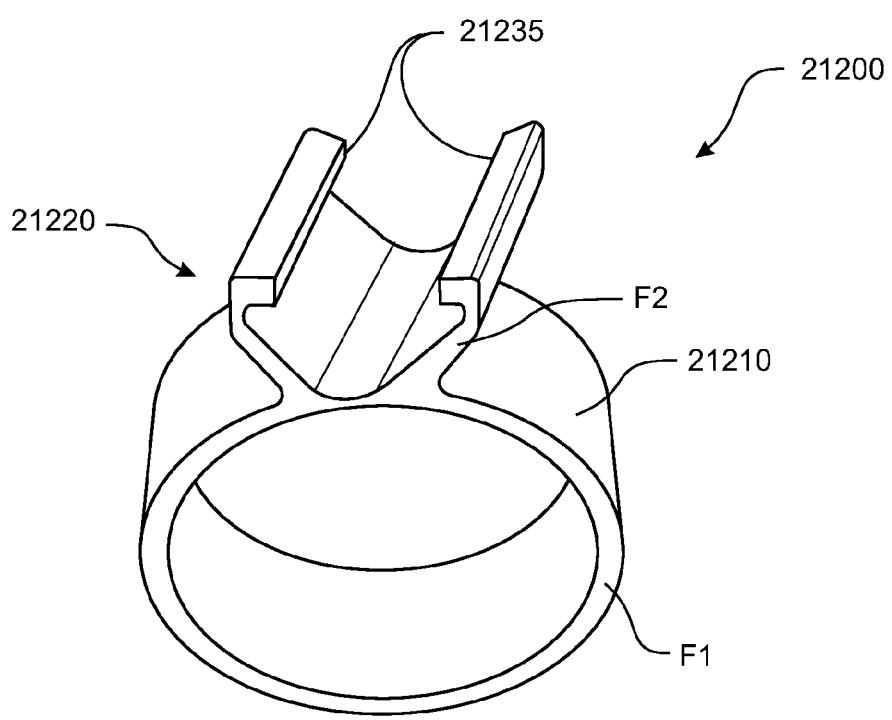
FIG. 84 is a perspective view of another embodiment.

FIG. 84 illustrates an alternative embodiment of a component 2200 of FIGS. 82 and 83 where component 21200 comprises attachment 21220, and attachment 21220 is rotated or skewed relative to the open face or end F1 of body 21210, for example at an angle of about 30 to 70 degrees. That is, a virtual axis (not shown) positioned between and parallel to the lugs 21235 of the attachment 21220 is at a non-parallel angle to an axis extending axially through a centre of the body 21210. As illustrated, although rotated or skewed, the open faces or ends F2 of attachment 21220 may remain in plane with the open faces or ends F1 of body 21210.

In use, an operator such as a patient (for example, in-home or otherwise self-managing), a nurse or a doctor may be desirous of non-visual confirmation that engagement of attachment 2220 with mounting portion 2240 is complete, possibly because visual confirmation is not possible due to light levels, patient positioning, or the speed with which engagement must be completed, for example. Such desired non-visual confirmation may include sensory feedback including audible feedback, tactile feedback, or both, that the attachment has fully and correctly engaged the mounting portion and is retained in place. Accordingly, the attachment 2220 can provide sensory feedback to an operator when the attachment 2220 engages the mounting portion 2240, optionally with a snap fit or snap engagement. The attachment 2220 can provide sensory feedback to an operator when lug 2235 on the attachment 2220 engages a recess 2245 on the mounting portion, optionally with a snap fit or snap engagement. It should be understood that the relative arrangement of the arms 2230, lugs 2235 and recesses 2245 can be modified to provide the desired sensory feedback. It should also be understood that such arrangements to provide non-visual confirmation of engagement may be used with any embodiment described herein, including but not limited to the embodiments of FIGS. 93, 94, 98 to 102, 105 to 110, and 113 to 115.

In use, as the component 2200 is installed, the arms 2230 are deformed apart by the mounting portion 2240 and the lugs 2235 "snap" into engagement into recesses 2245 due to the resilience of the material used to manufacture the attachment 2220 and/or the mounting portion 2240.

The component 2200 may comprise at least one retainer portion, as described below in relation to FIG. 116.

Figure 85:
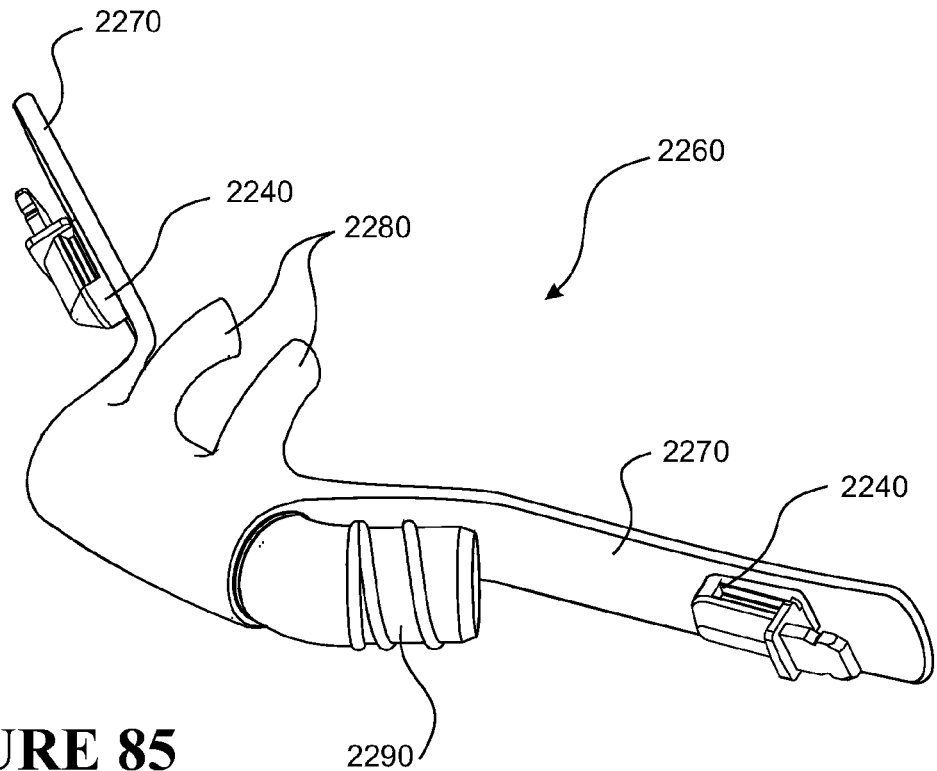
FIG. 85 is a perspective view of another embodiment.
Figure 86:
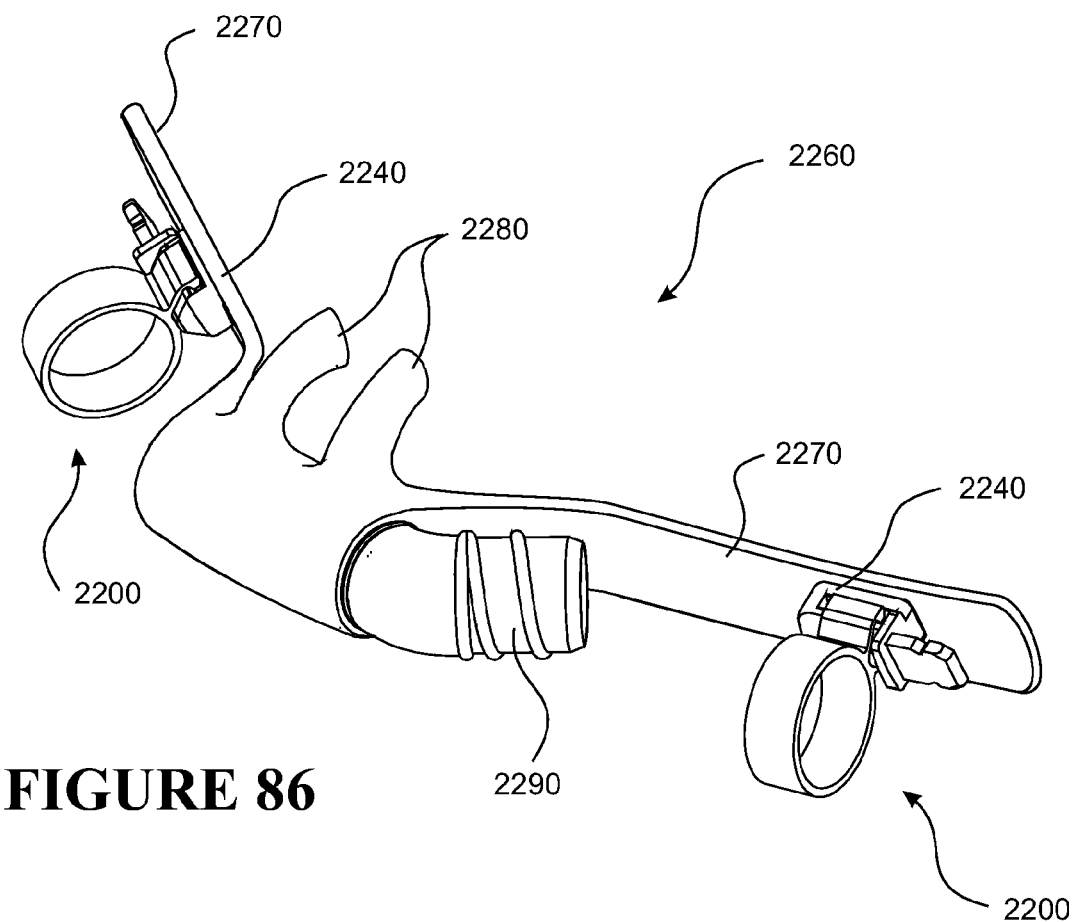
FIG. 86 is a perspective view of another embodiment.

As shown in FIGS. 85 and 86, a plurality of mounting portions 2240 may be present on a patient interface 2260, either integral with, non-removeably attached to, or removeably attached to the patient interface 2260. The one or more mounting portions 2240 can be integral with or removeably attached to an auxiliary part of a patient interface, such as an arm 2270 or wing that forms part of the supporting structure of the patient interface 2240 but is not directly involved in the functioning of the breathing circuit. A patient interface 2260, such as a nasal cannula, has auxiliary left and right sides, such as left and right arms 2270 that generally rest on a patient's face, particularly on the cheeks, with a mounting portion 2240 located on each, on either side of the nostril prongs 2280. This arrangement allows attachment of a component 2200 to either or both mounting portions, and for a tube (not shown) to be attached to manifold 2290, and routed to the left or right side of the patient interface and readily routed to the other side when necessary for treatment, patient positioning, patient comfort, equipment positioning, equipment stability, or the like. In FIGS. 85 and 86, manifold 2290 is shown routed to the operator right side (patient left side) of a bilateral patient interface 2260. Not shown is the alternate configuration on the opposite side but it should be understood that the manifold 2290 can be readily routed to the operator left side (patient right side) of the bilateral patient interface 2260. It should be understood that any embodiment of a component described herein, and any embodiment of a component and mounting portion combination described herein may be used with such a patient interface.

Figure 87:
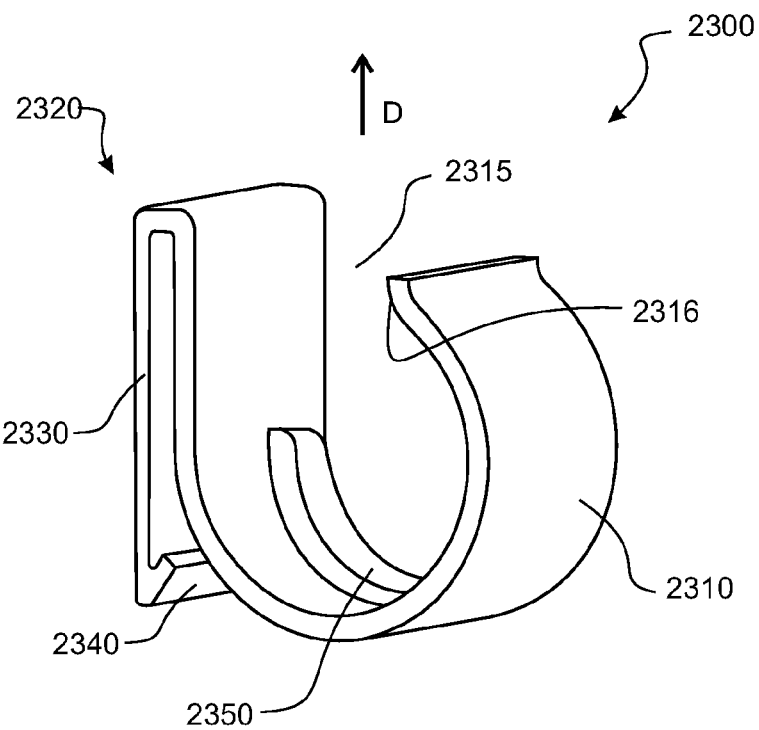
FIG. 87 is a perspective view of another embodiment.
Figure 88:
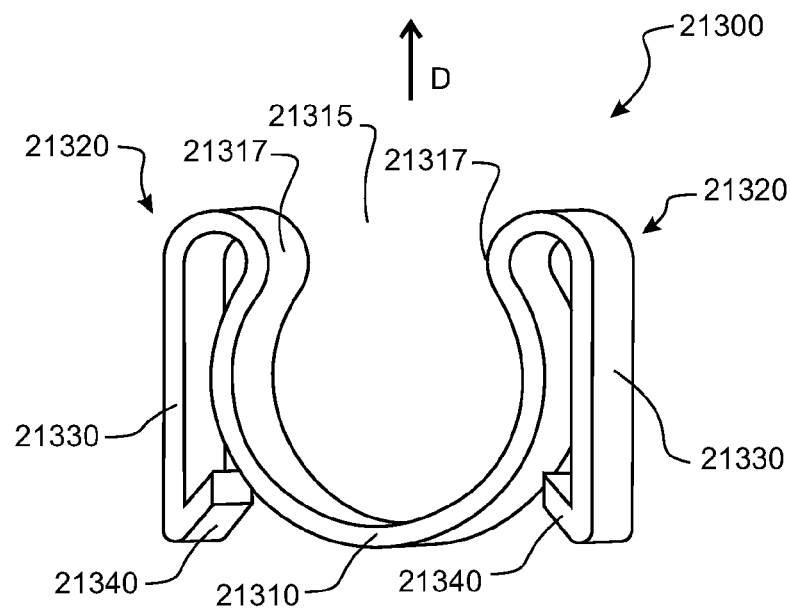
FIG. 88 is a perspective view of another embodiment.
Figure 106:
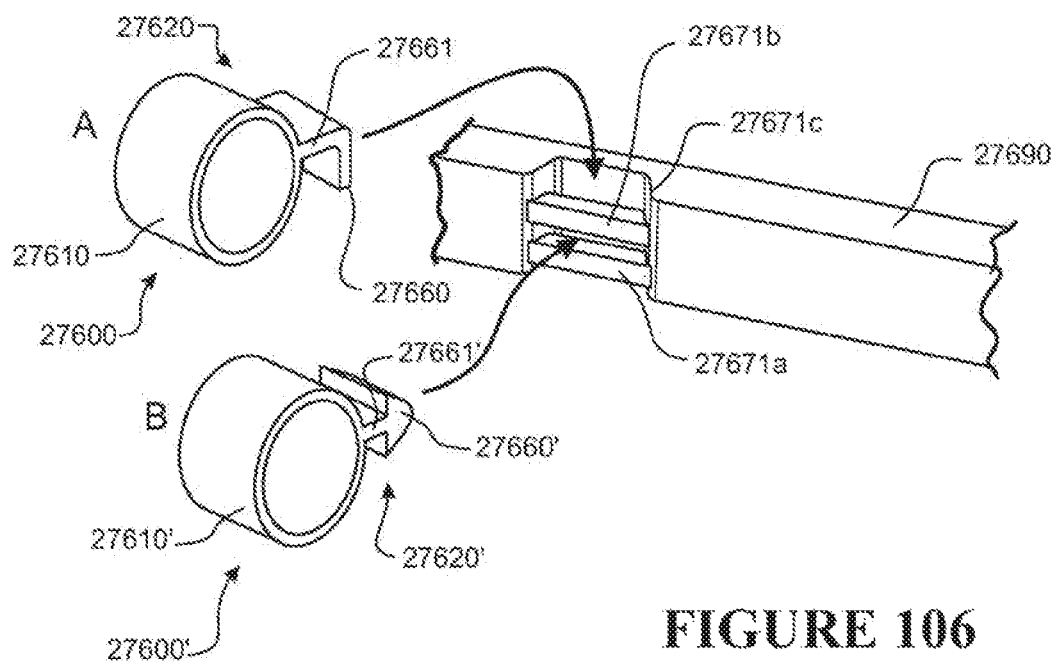
FIG. 106 is a perspective view of another embodiment showing (A) a first component, and (B) an alternative component.
Figure 107:
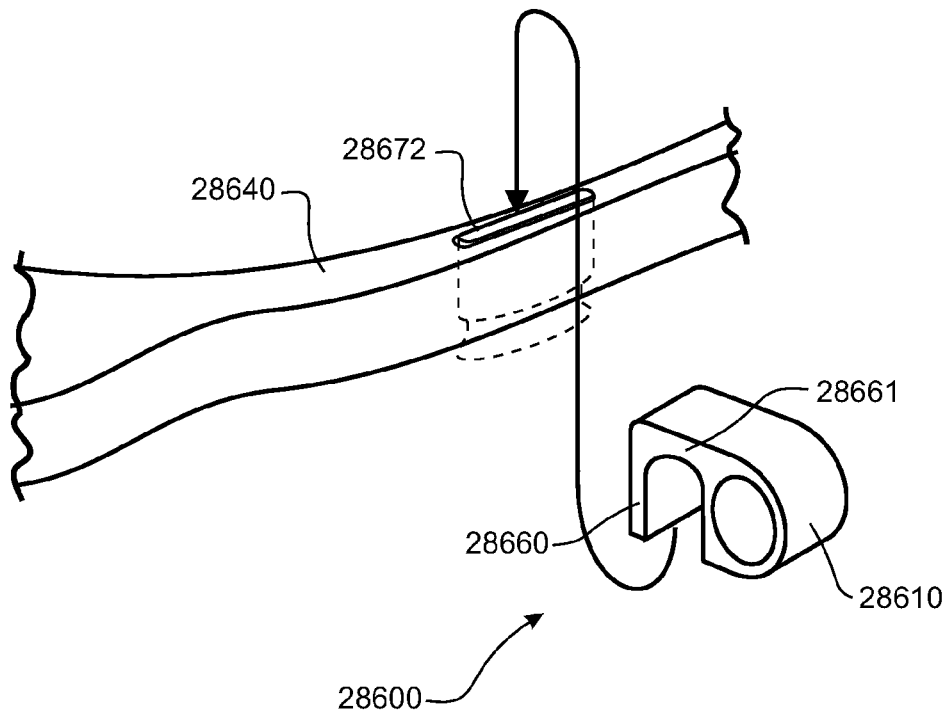
FIG. 107 is a perspective view of another embodiment.
Figure 108:
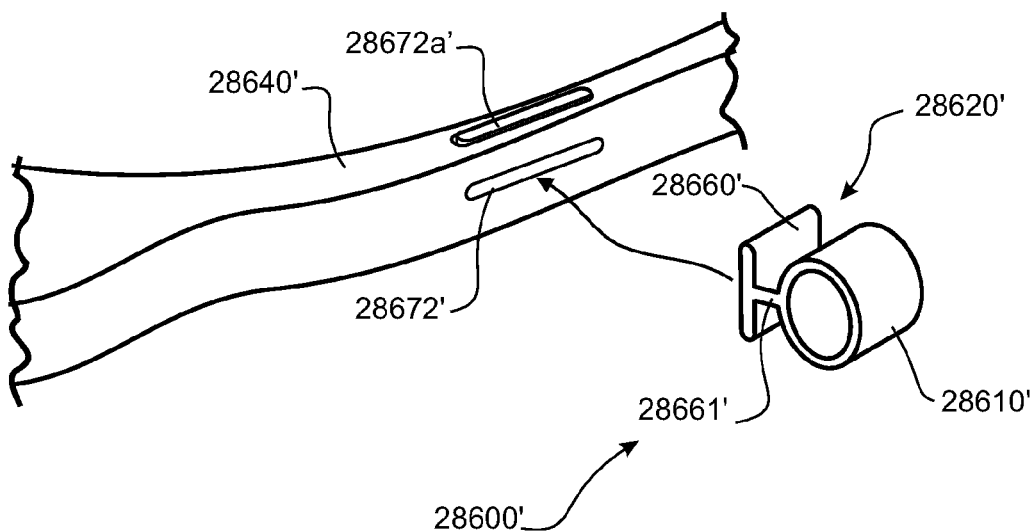
FIG. 108 is a perspective view of another embodiment.

In another embodiment, and with reference to FIGS. 87 and 88, a component 2300,21300 comprises a substantially C-shaped body 2310,21310 having a mouth 2315,21315, and one or two attachments 2320,21320. The body 2310, 21310 receives a tube (not shown) through mouth 2315, 21315 and at least partially surrounds a perimeter of the tube. Body 2310,21310 receives the tube by, for example, pushing body 2310,21310 against a tube in mounting direction D. Body 2310,21310 is substantially C-shaped, such that an arm ending with body portion 2316, or two diverging arms forming shoulders 21317 pass around and at least partially surround a perimeter of a tube, for example to the extent that the body 2310,21310 extends around more than about 50%, and alternatively up to and including 100%, of the perimeter of the tube to retain the tube within the body 2310,21310. For example, as shown in FIG. 87, in use body portion 2316 will extend in one direction, and as shown in FIG. 88, in use shoulders 21317 will extend in both directions, around a perimeter of a tube. Each attachment 2320, 21320 comprises an arm 2330,21330 positioned substantially tangentially to, and spaced apart from the body 2310, 21310. As shown in FIGS. 87 and 88, arm(s) 2330,21330 project initially from the body 2310,21310 adjacent the mouth 2315,21315, in a direction away from the mouth, and then extend substantially tangentially relative to, and spaced apart from, body 2310,21310. Each arm 2330,21330 optionally comprises a return or stop in the form of a projection 2340,21340 that extends from the distal end of the arm 2320,21320 substantially towards the body 2310,21310. In use, the arm(s) 2330,21330 operate in a similar manner to a clip on a pen and receive, for example, a head strap of a patient interface, a lanyard, or removeably engage with, for example, a slot on a patient interface shaped to receive the arm, such as is generally depicted in FIGS. 106 to 108, described below. Projection 2340,21340 serves to minimize unintentional disengagement of the component from the site of engagement. In either embodiment, an internal surface of the body may comprise a locator to locate the component on the tube, such as one or more projections 2350 engageable with one or more corresponding recesses of a tube, such as the recesses of a corrugated tube or a tube with a helically recessed surface region.

Figure 89:
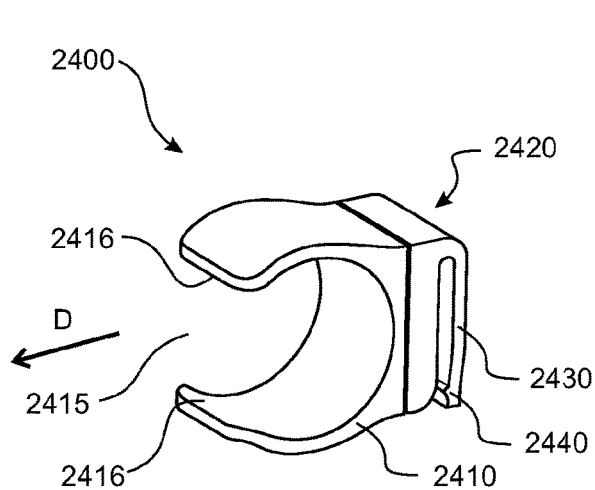
FIG. 89 is a perspective view of another embodiment.
Figure 90:
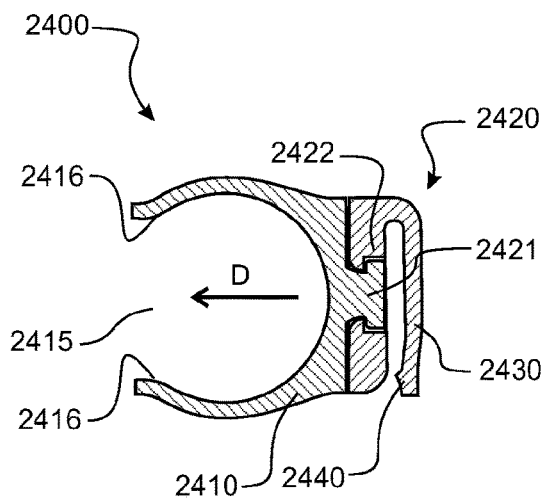
FIG. 90 is a cross-section view of the embodiment of FIG. 89.

In another embodiment, and with reference to FIGS. 89 and 90, a component 2400 comprises a substantially C-shaped body 2410 having a mouth 2415, and an attachment 2420. The body 2410 receives a tube (not shown) through mouth 2415 and at least partially surrounds a perimeter of the tube. Body 2410 receives the tube by, for example, pushing body 2410 against a tube in mounting direction D. Body 2410 is substantially C-shaped, such that diverging arms end with body portions or jaws 2416 that pass around and at least partially surround a perimeter of a tube, for example to the extent that the body 2410 extends around more than about 50%, and alternatively up to and including 100%, of the perimeter of the tube to retain the tube within the body 2410. Attachment 2420 comprises an arm 2430 positioned substantially tangentially to, and spaced apart from the body 2410. As shown in FIGS. 89 and 90, attachment 2420 is attached to body 2410 by a substantially T-shaped lug 2421 that projects from body 2410 and engages with a corresponding aperture 2422 in attachment 2420 such that body 2410 and attachment 2420 are rotatable relative to each other. Arm 2430 projects from attachment 2420 and extends substantially tangentially relative to, and spaced apart from the body 2410. Arm 2430 optionally comprises a return or stop in the form of a projection 2440 that extends from the distal end of the arm 2430 substantially towards the body 2410. Attachment 2420 and thus arm 2430 are positioned on the opposite side of body 2410 relative to mouth 2415. In use, arm 2430 operates in a similar manner to the clip on a pen and receives, for example, a head strap of a patient interface, a lanyard, or removeably engages with, for example, a slot on a patient interface shaped to receive the arm, such as is generally depicted in FIGS. 106 to 108 discussed below. Projection 2440 serves to minimize unintentional disengagement of the component from the site of engagement. It should be understood that the attachment 2420 of this embodiment may be modified to include two or more arms as described in relation to the embodiments described below.

Figure 91:
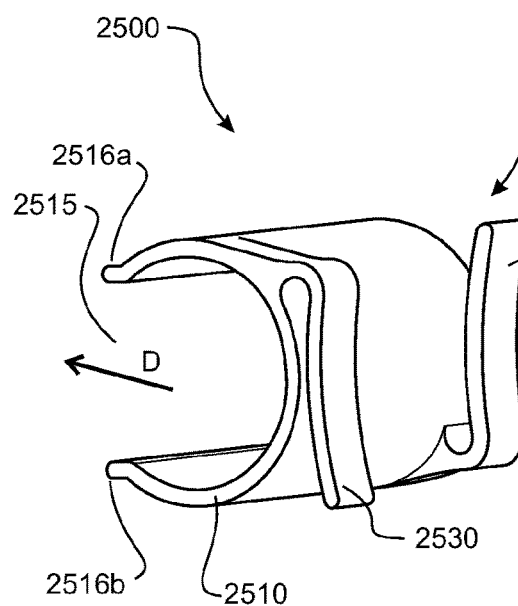
FIG. 91 is a perspective view of another embodiment.
Figure 92:
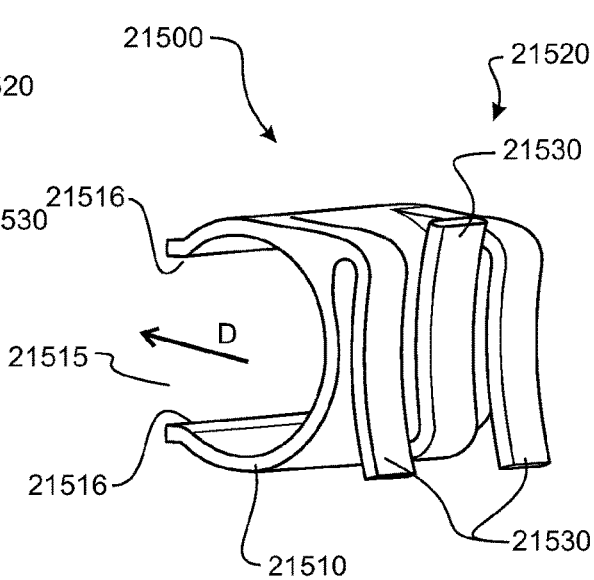
FIG. 92 is a perspective view of another embodiment.

In another embodiment, and with reference to FIGS. 91 and 92, components 2500,21500 are of an arrangement substantially similar to component 2400 of FIGS. 89 and 90, where attachment 2520,21520 may be integral with body 2510,21510 (as shown), non-rotatably fixed (not shown), or rotatably fixed to body 2510,21510 as with the arrangement depicted in FIGS. 89 and 90. Substantially C-shaped body 2510,21510 comprises mouth 2515,21515, diverging arms ending with jaws 2516a,2516b,21516 and attachment 2520, 21520. The body 2510,21510 receives a tube (not shown) through mouth 2515,21515 and at least partially surrounds a perimeter of the tube. Body 2510,21510 receives the tube by, for example, pushing body 2510,21510 against a tube in mounting direction D. Body 2510,21510 is shaped such that diverging arms ending with body portions or jaws 2516a, 2516b,21516 pass around and at least partially surround a perimeter of a tube, for example to the extent that the body 2510,21510 extends around more than about 50%, and alternatively up to and including 100%, of the perimeter of the tube to retain the tube within the body 2510,21510.

Attachment 2520,21520 comprises a plurality arms 2530, 21530 oriented substantially parallel to each other, with one or more arms extending in the same direction or opposite directions relative to each other. Arms 2530,21530 project from body 2510,21510 at a location that does not interfere with access to mouth 2515,21515, typically on the opposite side of body 2510,21510 from mouth 2515,21515. FIG. 91 shows component 2500 with two arms 2530 extending substantially tangentially to body 2510, substantially parallel to each other, and extending in opposite directions to each other, with one arm 2530 projecting from the body 2510 at a point substantially opposite jaw 2516*a* and another arm 2530 projecting from the body at a point substantially opposite jaw 2516*b*. As illustrated, arms 2530 are located on the body 2510 and extend in directions that are transverse or orthogonal to the mounting direction D of the component 2500 on the tube. As shown in FIG. 92, component 21500 may comprise three arms 21530, arranged in an alternating pattern, with a first arm extending in a first direction, a second arm located adjacent and parallel to the first arm extending in the opposite direction, and a third arm located adjacent and parallel to the second arm extending in the same direction as the first arm. In use, a head strap of a patient interface or a lanyard is fed or wound through arms 2530,21530. Alternatively, and particularly in relation to the embodiment of FIG. 91, the component 2500 is placed on a strap or lanyard with the strap or lanyard resting between and parallel to arms 2530, and the component 2500 is then rotated about 90 degrees in a direction such that each arm 2530 engages the strap or lanyard. Arms 2530,21530 may optionally comprise a return or stop in the form of a projection (not shown) that extends from the distal end of each arm 2530,21530 substantially towards the body 2510, 21510.

Figure 93:
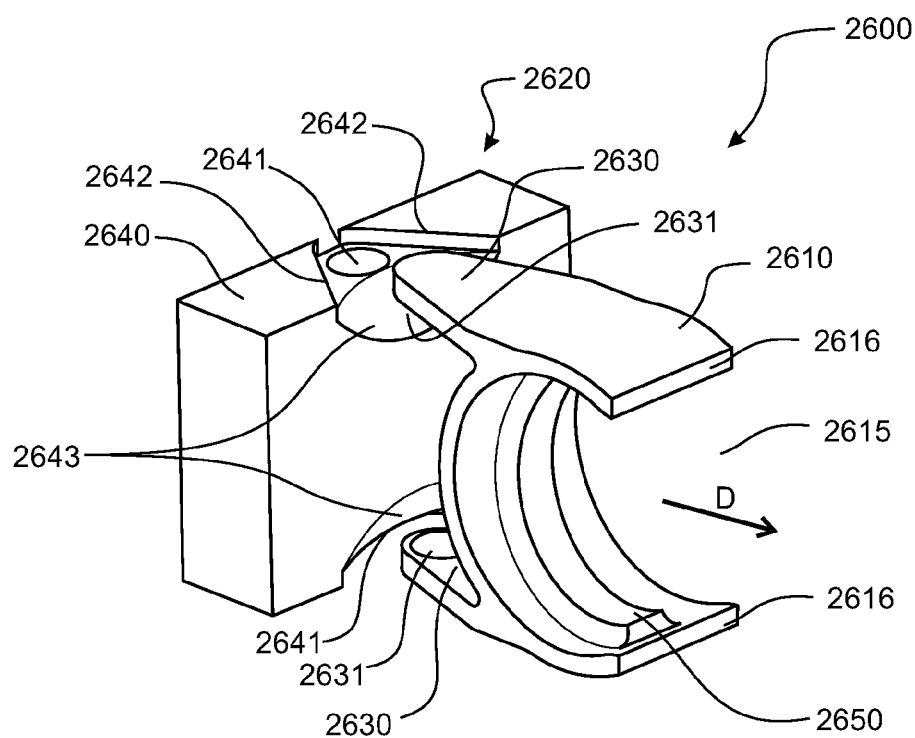
FIG. 93 is a perspective view of another embodiment.

In another embodiment, and with reference to FIG. 93, component 2600 comprises a substantially C-shaped body 2610 having a mouth 2615, and an attachment 2620. The body 2610 receives a tube (not shown) through mouth 2615 and at least partially surrounds a perimeter of the tube. Body 2610 receives the tube by, for example, pushing body 2610 against a tube in mounting direction D. Body 2610 is shaped such that diverging arms ending with body portions or jaws 2616 (or 21616 as shown for example in FIG. 94) pass around and at least partially surround a perimeter of a tube, for example to the extent that the body 2610 extends around more than about 50%, and alternatively up to and including 100%, of the perimeter of the tube to retain the tube within the body 2610. An internal surface of the body may comprise a locator to locate the component on the tube, such as one or more projections 2650 engageable with one or more corresponding recesses of a tube, such as the recesses of a corrugated tube or a tube with a helically recessed surface region. Attachment 2620 comprises two arms 2630 positioned substantially tangentially to and extending from body 2610 in a direction away from the mouth 2615. Each arm 2630 projects from the body 2610 at a point substantially opposite a jaw 2616 and comprises a lug or recess 2631. Each lug or recess 2631 engages with a corresponding lug or recess 2641 on mounting portion 2640. The mounting portion 2640 may be shaped to guide the arms 2630 into place so that lugs or recesses 2631 correctly engage corresponding lugs or recesses 2641, and so that, in use, arms 2630 do not need to be directly lined up with the lugs or recesses 2641 to achieve correct engagement. For example, mounting portion 2640 may comprise walls or projections 2642 that are shaped or located to guide arms 2630 into place. Mounting portion 2640 may further comprise recessed regions 2643 adjacent and between lugs or recesses 2641 that are shaped to guide arms 2630 into place. Mounting portion 2640 is generally a quadrilaterally-faced hexahedra in shape, for example cuboid, with lugs or recesses 2641 formed in opposing faces and recessed regions 2643 formed in the face of the mounting portion that is directly adjacent body 2610 when body 2610 is in place on the mounting portion 2640. Mounting portion 2640 may be integral with a patient interface (not shown), non-removeably attached to, or removeably attachable to a patient interface. Removable attachment of mounting portion 2640 may comprise, for example, an interference fit or snap fit connection, or slots for receiving a head strap (not shown).

Figure 94:
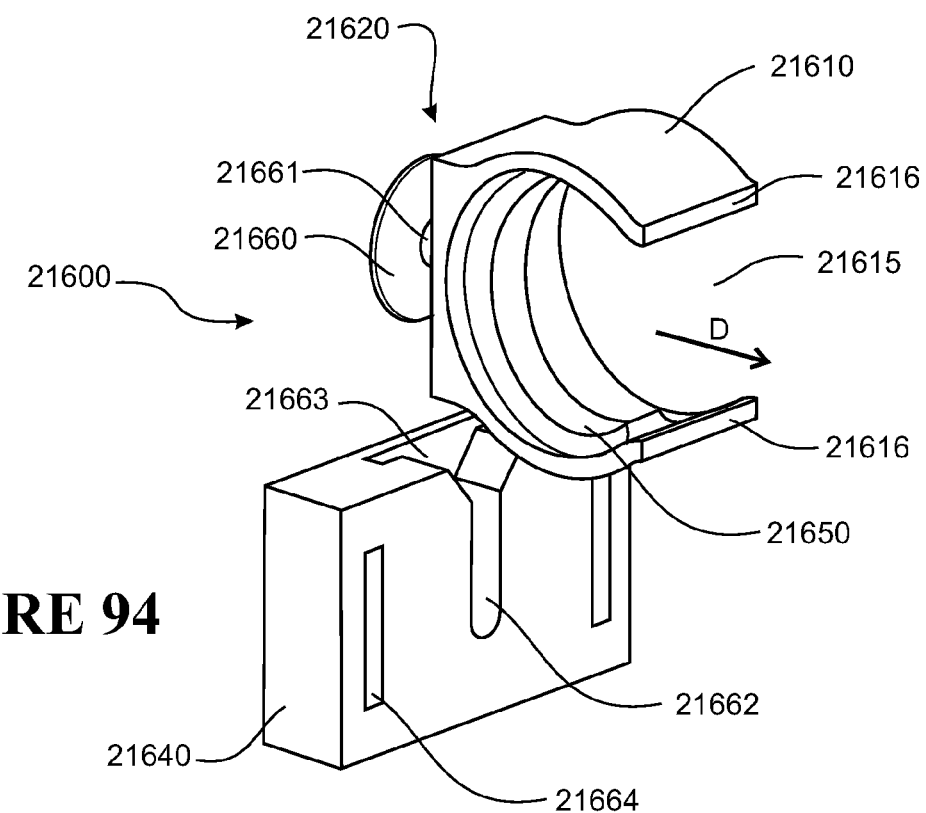
FIG. 94 is a perspective view of another embodiment.

In another embodiment, and with reference to FIG. 94, component 21600 comprises a substantially C-shaped body 21610 as described for the embodiment of FIG. 93. An internal surface of the body 21610 may comprise a locator to locate the component on the tube, such as one or more projections 21650 (or 23650 as is for example shown in FIG. 100) engageable with one or more corresponding recesses of a tube, such as the recesses of a corrugated tube or a tube with a helically recessed surface region. Attachment 21620 (or 27620, or 27620' for example) comprises a lug 21660 (or 27661 or 27661' for example) extending from body 21610 that is optionally substantially T-shaped in cross-section, and, as illustrated, may comprise a disc or other enlarged head connected at its centre to body 21610 by a short projection 21661, for example a cylindrical projection. Lug 21660 projects from the body 21610 at a point substantially opposite mouth 21615 and engages with a corresponding T-shaped slot 21662 in mounting portion 21640. The mounting portion 21640 may be shaped to guide the lug 21660 into place so that lug 21660 correctly engages corresponding slot 21662. For example, mounting portion 21640 may comprise a tapered or V-shaped recess 21663 (interface zone) at the mouth of slot 21662 so that, in use, lug 21660 does not need to be directly lined up with the elongate portion of slot 21662 to achieve correct engagement. As illustrated, mounting portion 21640 is generally a quadrilaterally-faced hexahedra in shape, for example cuboid, with the substantially T-shaped mouth of slot 21662 in one face to accept the lug 21660 that is substantially T-shaped in cross section, and an elongate portion of slot 21662 that receives the projection 21661 extends into a directly adjacent face such that body 21610 projects from that face when the lug 21660 is engaged with the slot 21662. When lug 21660 is disc shaped, lug 21660 will be rotatable within slot 21662 and thus body 21610 will be rotatable about the axis of cylindrical projection 21661. Mounting portion 21640 may be integral with a patient interface (not shown), non-removeably attached to, or removeably attachable to a patient interface. Removable attachment of mounting portion 21640 may comprise, for example, an interference fit or snap fit connection (not shown), or slots 21664 for receiving a head strap. It should be understood that slot 21662 in FIG. 94, and equivalent arrangements 24662,29662 in FIGS. 101 and 109 below, comprise an inner track that slidably receives lug 21660 and an outer track that slidably receives projection 21661 but is narrower than the inner track. In a "locked" or "retained" position, lug 21660 is at or near the end of the inner track that is opposite the mouth of the slot, and projection 21661 extends from the lug through the outer track to support the body 21610 in place. If body 21610 is pulled or pushed in a direction perpendicular to the tracks then it will not substantially move relative to the mounting portion in which the slot 21662 is formed.

Figure 95:
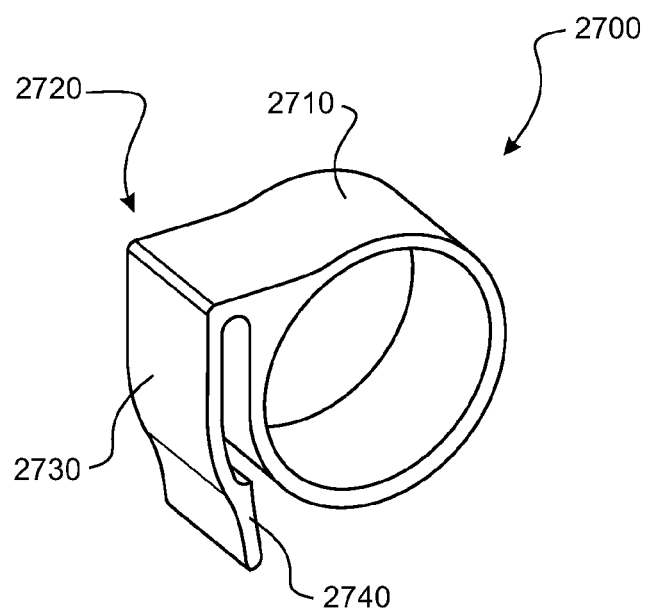
FIG. 95 is a perspective view of another embodiment.
Figure 96:
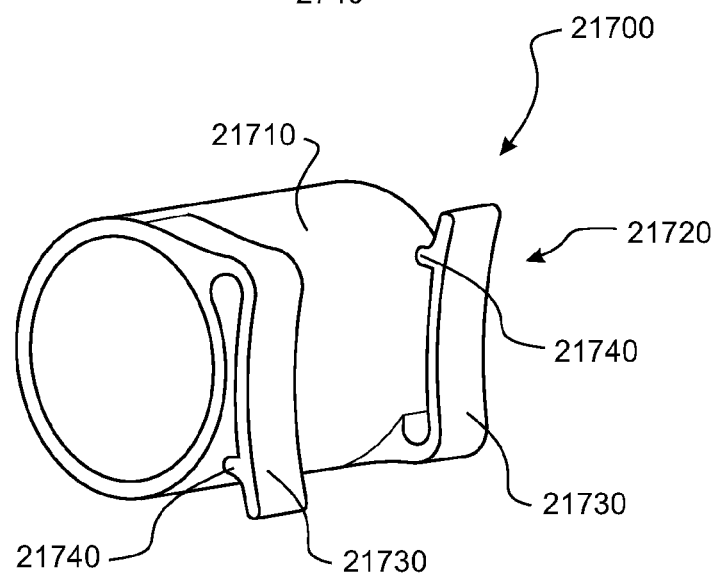
FIG. 96 is a perspective view of another embodiment.
Figure 97:
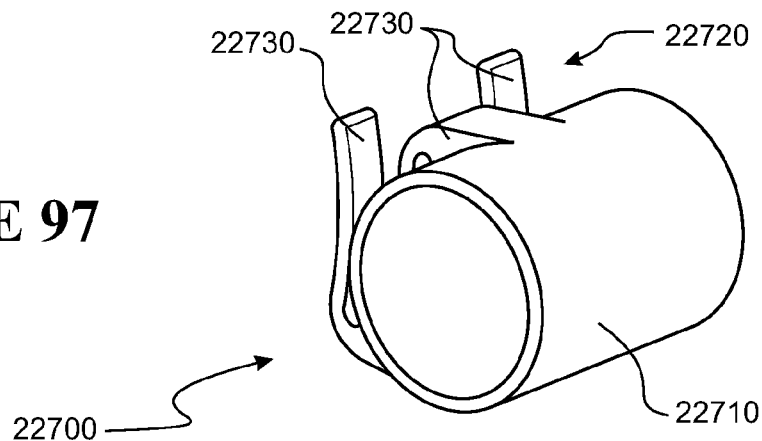
FIG. 97 is a perspective view of another embodiment.

In another embodiment, and with reference to FIGS. 95 to 97, component 2700,21700,22700 is arranged in substantially the same way as the embodiments of FIGS. 87 and 89 to 92, with body 2710,21710,22710, attachment 2720, 21720,22720, one or more arms 2730,21730,22730 and optional projections 2740,21740, except that body 2710, 21710,22710 is substantially annular or annular, as with the embodiment of FIGS. 82 to 84. Arm(s) 2730,21730,22730 project from the body 2710,21710,22710 and then extend substantially tangentially relative to, and spaced apart from, body 2710,21710,22710. Each arm 2730,21730,22730 optionally comprises a return or stop in the form of a projection 2740,21740 that extends from the distal end of the arm 2730,21730,22730 substantially towards the body 2710, 21710,22710. Arm(s) 2730,21730,22730 may otherwise be arranged as described for the embodiments of FIGS. 87 and 89 to 92.

Figure 98:
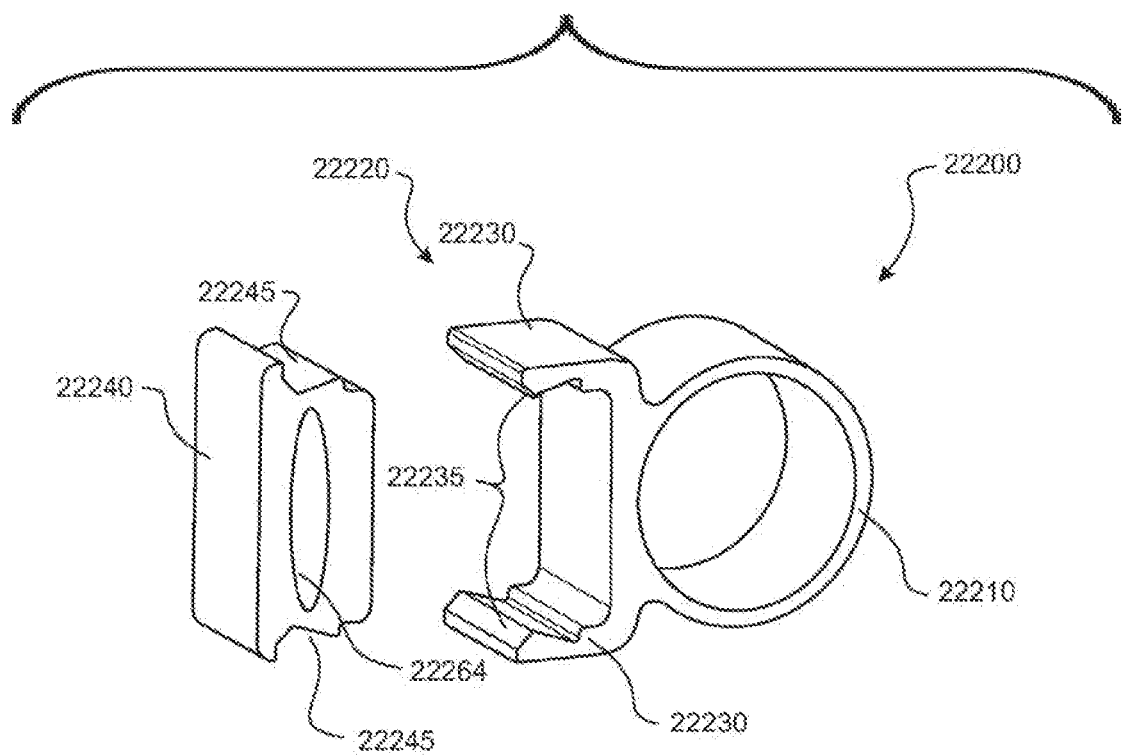
FIG. 98 is a perspective view of another embodiment

In another embodiment, and with reference to FIG. 98 component 22200 includes an attachment 22220 that is integral with or fixed to the body 22210. Attachment 22220 may be non-moveably, pivotably, rotatably and/or removably fixed to the body 22210 (for example, as described above in relation to FIGS. 89 and 90). Attachment 22220 is arranged to snap fit or snap engage a mounting portion 22240 and removeably hold component 22200 securely in place. In one embodiment, attachment 22200 comprises a pair of arms 22230 that extend from the body 22210 forming a female connector that is shaped to engage the corresponding male connector, mounting portion 22240. Arms 22230 may extend from the body 22210 at any suitable angle. The arms 22230 can extend to be substantially parallel to each other and to a virtual radial line (not shown) extending from the centre of body 22210, such that the distal ends of the arms are substantially opposite each other as shown in FIG. 98, forming a pair of jaws adapted to engage the mounting portion 22240. Arms 22230 comprise lugs 22235 that engage with corresponding recesses 22245 on the mounting portion 22240. The lugs 22235 and corresponding recesses 22245 are shaped to both retain the attachment 22220 in place on the mounting portion 22240 and also provide sensory feedback to an operator, as discussed above. The mounting portion 22240 may be shaped as described above. Mounting portion 22240 may be present on a patient interface (not shown), integral with, non-removeably attached to, or removeably attached to the patient interface. Mounting portion 22240 comprises slot 22264 for receiving a head strap.

Figure 99:
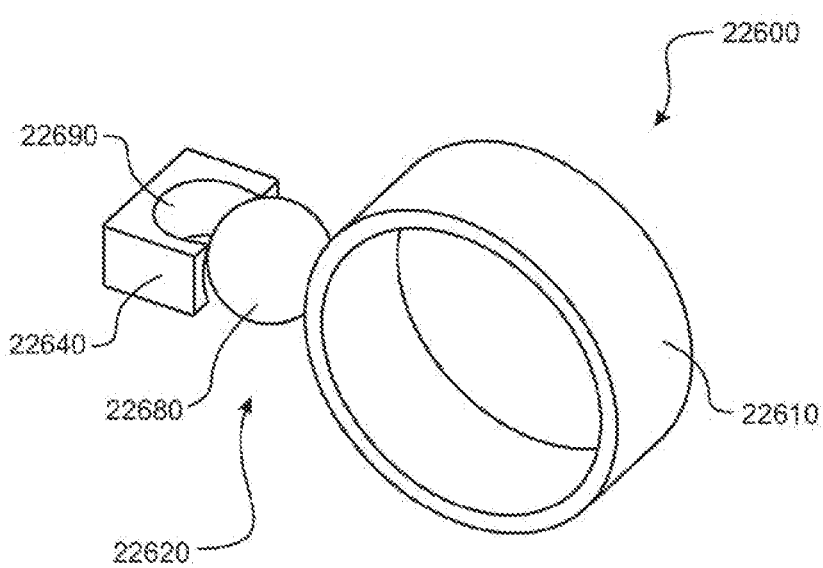
FIG. 99 is a perspective view of another embodiment.

In another embodiment, and with reference to FIG. 99, component 22600 is arranged in substantially the same way as the embodiment of FIG. 94, with body 22610, and attachment 22620 that engages mounting portion 22640, except that body 22610 is at least substantially annular or annular, as with the embodiment of FIGS. 82 to 84. Attachment 22620 comprises a sphere 22680 that may be spaced apart from body 22610 by a projection (not shown) and that engages with a corresponding recess 22690 in mounting portion 22640 to form a ball-joint. Body 22610 will be rotatable relative to the mounting portion 22640 about the ball-joint. Mounting portion 22640 may be integral with a patient interface, non-removeably attached to, or removeably attachable to a patient interface. Removable attachment of mounting portion 22640 may comprise, for example, an interference fit or snap fit connection, or slots for receiving a head strap (not shown).

Figure 100:
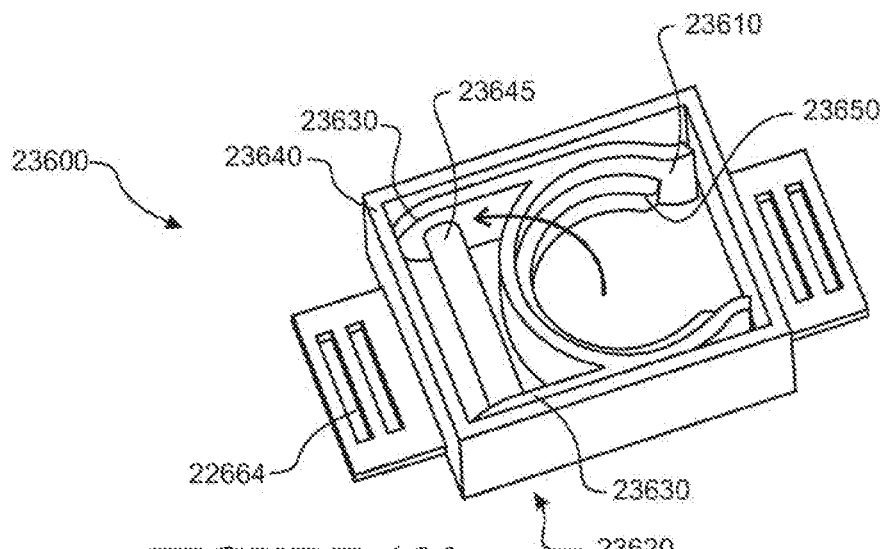
FIG. 100 is a perspective view of another embodiment.

In another embodiment, and with reference to FIG. 100, component 23600 is arranged in substantially the same way as the embodiment of FIG. 93, with body 23610, and attachment 23620 that engages mounting portion 23640 comprising slots 23664, except that body 23610 is pivotably engaged within mounting portion 23640. Mounting portion 23640 is an open box or a frame, within which body 23610 is located by arms 23630 that are pivotably engaged with opposing interior walls of the box or frame. Arms 23630 may be engaged through matched pairs of lugs and recesses on each arm and the corresponding site on an interior wall of mounting portion 23640, as described and illustrated for the embodiment of FIG. 93. Alternatively, arms 23630 may be pivotably attached by way of a pin 23645 that is located between opposing walls of mounting portion 23640. In FIG. 100 body 23610 is depicted in a stowed position. In use, body 23610 is pivoted out of the mounting portion 23640 to receive a tube (not shown).

Figure 101:
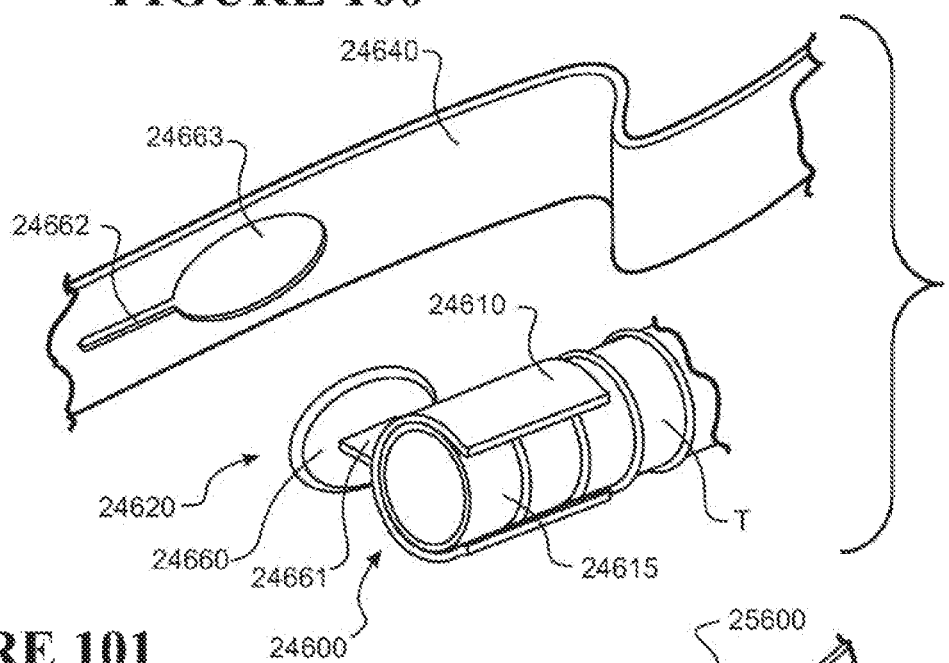
FIG. 101 is a perspective view of another embodiment

In another embodiment, and with reference to FIG. 101, component 24600 is arranged in substantially the same way as the embodiment of FIG. 94, with body 24610, and attachment 24620 that engages mounting portion 24640, except that mounting portion 24640 is, or is integral with, an arm or a head strap of a patient interface. Attachment 24620 comprises a lug 24660 extending from body 24610 that is substantially T-shaped in cross-section, and, as illustrated, may comprise a disc or other enlarged head connected substantially at its centre to body 24610 by a projection 24661. Lug 24660 projects from the body 24610 at a point substantially opposite mouth 24615 and the lug 24660 engages with a corresponding suitably shaped slot 24662 in mounting portion 24640. An interface zone 24663 is adjacent and connected to the slot 24662, and accepts the disc or enlarged head and allows the disc to enter the narrower slot 24662, whereby, when fully inserted, disc 24660 is retained in place within mounting portion 24640 and projection 24661 extends through slot 24662, as described in relation to FIG. 94 above. A tube T is shown engaged within the body 24610.

Figure 102:
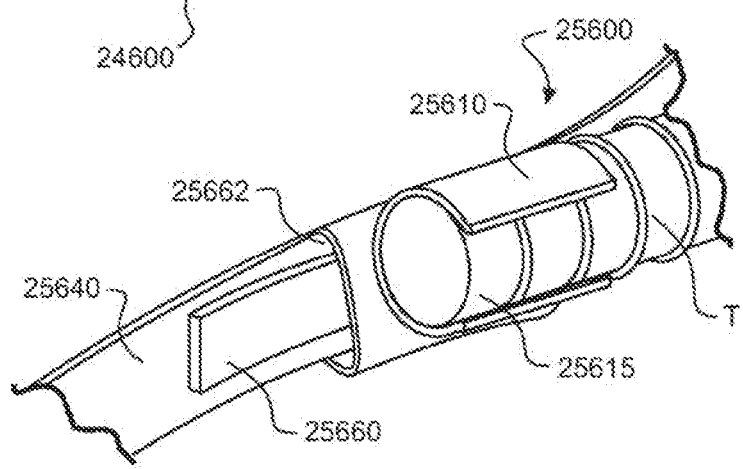
FIG. 102 is a perspective view of another embodiment.

In another embodiment, and with reference to FIG. 102, component 25600 is arranged in substantially the same way as the embodiment of FIG. 101, with body 25610, lug 25660, and mounting portion 25640 that is, or is integral with, an arm or a head strap of a patient interface. Lug 25660 extends from the body 25610 at a point substantially opposite mouth 25615 and engages with a corresponding suitably shaped slot or loop 25662 in or on mounting portion 25640. Tube T is shown engaged within body 25610.

Figure 103:
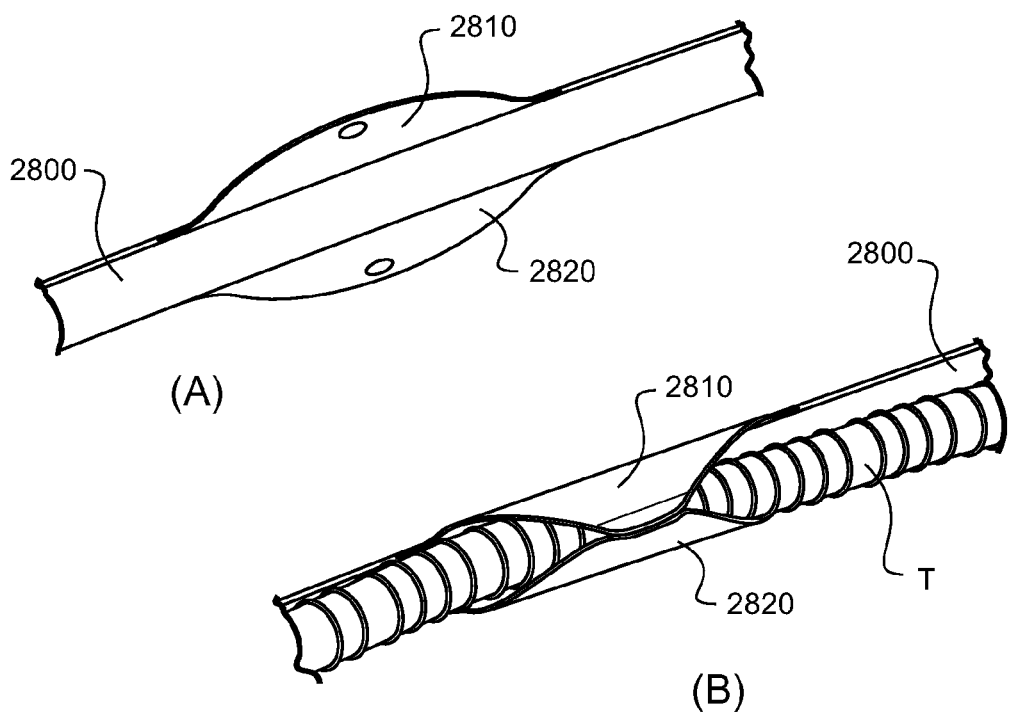
FIG. 103 is a perspective view of additional embodiments of in (A) open configuration, (B) closed configuration, and (C) open configuration.

In another embodiment, and with reference to FIG. 103, an arm or a head strap of a patient interface 2800, comprises first and second projections or wings 2810,2820 that alone or together surround a perimeter of a tube T, and are shown in open (A),(C) and closed (B) positions in relation to a tube T. In one embodiment, first and second projections or wings 2810,2820 are fixed in a closed position (B) using known connectors, such as a loop and hook fastener, press fit or snap fit connectors, or similar connectors known in the art. In another embodiment, first and second projections or wings 2810,2820 comprise a deformable material that will substantially hold its shape after being deformed about the tube T.

Figure 104:
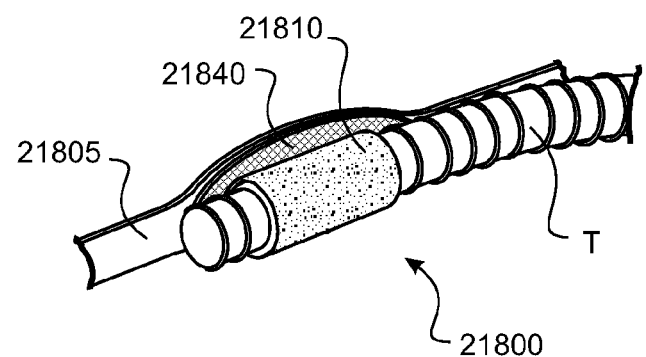
FIG. 104 is a perspective view of another embodiment.

In another embodiment, and with reference to FIG. 104, an arm or a head strap of a patient interface 21805, comprises a mounting portion 21840 that receives a component 21800. The component 21800 comprises an at least substantially annular body 21810, for example an annular body such as a sleeve, for receiving a tube T, where the tube passes through the body 21810 so that the body at least partially surrounds, and may optionally surrounds a perimeter of the tube T. The body 21810 and the mounting portion 21840 each comprise corresponding sections of a loop and hook fastener or equivalent adherent material allowing a releasable connection. In use, the component 21800 encompassing a tube T can be located on mounting portion 21840 by a user pressing the body 21810 against the mounting portion 21840, and can be readily removed and re-located.

Figure 105:
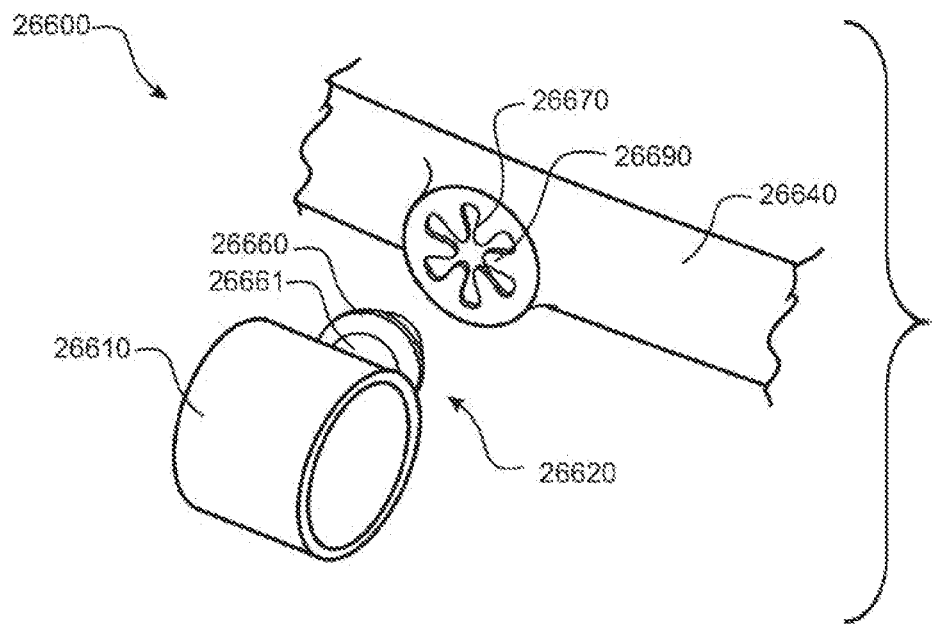
FIG. 105 is a perspective view of another embodiment.

In another embodiment, and with reference to FIG. 105, component 26600 is arranged in substantially the same way as the embodiments of FIGS. 94 and 101, with at least substantially annular, for example annular body 26610, and attachment 26620 that engages mounting portion 26640, except that the mounting portion is integral with an arm or other portion of a patient interface. Attachment 26620 comprises a lug 26660, extending from body 26610 that is shaped to engage a corresponding shaped recess or slot in mounting portion 26640, as described below. It should be understood that as an alternative to depicted body 26610, the body 26610 may instead comprise the features of any alternative body described herein. In relation to FIGS. 106 to 109, alternative embodiments are described below. Unless described below, the features and functioning of the embodiments of FIGS. 106 to 110 should be considered the same as for the embodiment of FIG. 105, and like reference numerals indicate like parts with the addition of 1000, or the addition of 1000 and a prime (') (for example, component 26600 is identified as components 27600 and 27600' in FIG. 106, and 8600 in FIG. 107). The various embodiments of FIGS. 105 to 109 are arranged to provide sensory feedback, as described above.

Referring to FIG. 105, orifice 26670 is shaped to receive conical or frustoconical lug 26660, with the narrowest portion of lug 26660 being the first to engage orifice 26670. Orifice 26670 within mounting portion 26640 comprises a plurality of resiliently flexible flanges 26690 spaced about the periphery of the orifice and projecting into the centre of the orifice 26670. In use, the flanges 26690 deform from a resting position and allow lug 26660 to move into the orifice 26670 to a certain depth. Once lug 26660 has reached that depth, flanges 26690 return to their resting position and retain the lug 26660 in place within orifice 26670, with projection 26661 extending from the orifice between the flanges 26690 and supporting body 26610 in place. In some embodiments, sensory feedback is provided by the flanges 26690 returning to their resting position and retaining the lug 26660 in place within the orifice 26670.

Referring to FIG. 106, elongate bars 27671a,27671b are mounted on or within mounting portion 27690, such as within recess 27671c. Recess 27671c comprises a cut-out or notch within mounting portion 27690 and bars 27671a,27671b span the space defined by the walls of the recess 27671c, each end of bars 27671a,27671b engaging an opposing wall of recess 27671c, with bar 27671a spaced apart from bar 27671b, and bars 27671a,27671b both spaced apart from any additional walls of recess 27671c. Referring to FIG. 106 (A), lug 27660 is shaped to hook behind one or both of bars 27671a,27671b or between bars 27671a, 27671b, such that it is retained in place by bars 27671a, 27671b and projection 27661 extends past or between one or both of bars 27671a,27671b and supports body 27610 in place. Referring to FIG. 106 (B), lug 27660' is triangular in cross-section, or is conical or frustoconical, being shaped to be pushed between bars 27671a,27671b. Either lug 27660' is resiliently deformable from a resting shape or bars 27671a,27671b are resiliently deformable or deflectable from a resting position to allow lug 27660' to be pushed into place between bars 27671a,27671b. Once lug 27660' is in place, either lug 27660' or bars 27671a,27671b return to their resting shape or position and lug 27660' is retained in place between bars 27671a,27671b, with projection 27661' extending between bars 27671a,27671b and supporting body 27610' in place.

Referring to FIG. 107, together, lug 28600 and projection 28661 are substantially L-shaped and projection 28661 extends substantially tangentially from body 28610, such that lug 28600 is also positioned substantially tangentially to, and spaced apart from the body 28610. In use, slot 28672 receives lug 28600 and projection 28661 extends outwards from mounting portion 28640 and supports body 28610 in place.

Referring to FIG. 108, together, lug 28600' and projection 28661' are substantially T-shaped and projection 28661' extends radially from body 28610' extending from the centre of body 28610', such that lug 28600' is positioned transversely to the projection and spaced apart from the body 28610'. In use, slots 28672' or 28672a' receive lug 28600' and projection 28661' extends outwards from mounting portion 28640' and supports body 28610' in place. Optionally mounting portion 28640' surrounding slots 28672', 28672a' is resiliently deformable from a resting position to allow lug 28660' to be moved into place within slots 28672',28672a'.

Figure 109:
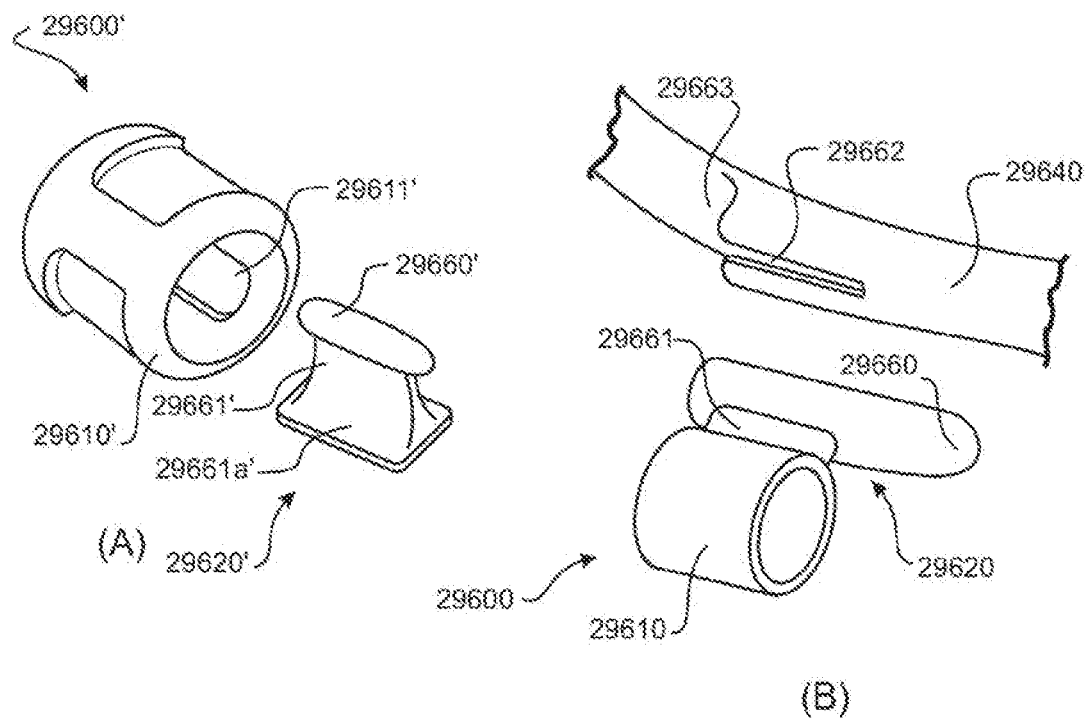
FIG. 109 is a perspective view of another embodiment showing (A) disassembled component body and attachment, and (B) assembled component body and attachment.

Referring to FIG. 109 (B), slot 29662 has an interface zone 29663 that accepts lug 29660 of the attachment 29620 and allows lug 29660 to enter the slot 29662, whereby, when fully inserted, lug 29660 is retained in place within mounting portion 29640 and projection 29661 extends through slot 29662 holding body 29610 in place. Referring to FIG. 109 (A), body 29610' and attachment 29620' comprise separate pieces. Body 29610' includes slot 29611' though which lug 29660' may be inserted from the interior of the body. Attachment 29620' is retained in place in body 29610' by foot 29661a' of projection 29661' that bears against an inner wall of body 29610', so that, in use, when body 29610' receives a tube (not shown), at least the presence of the tube prevents attachment 29620' from disengaging from body 29610'. FIG. 109(A) shows the component configuration 29600', while FIG. 109(B) shows the component configuration 29620.

Figure 110:
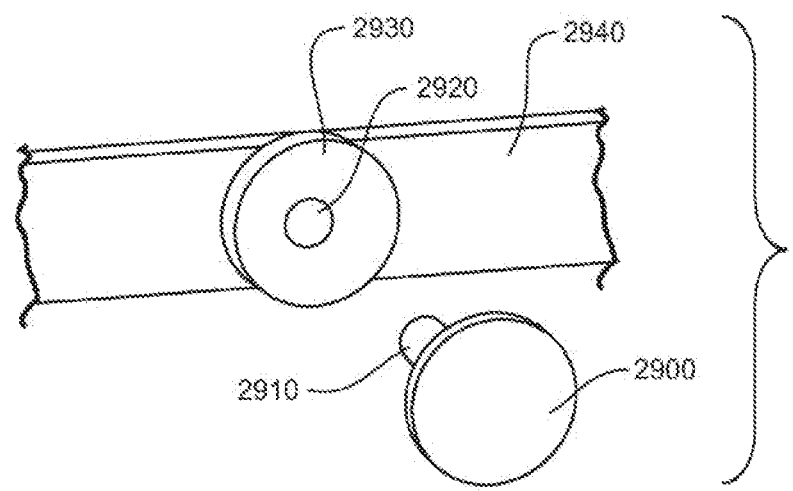
FIG. 110 is a perspective view of another embodiment.

In another embodiment, FIG. 110 illustrates a snap fit or interference fit connector that may be used in any embodiment of the disclosure to, for example, retain a mounting portion in place on a patient interface or head strap 2940. Connector 2900 would be affixed at a suitable point on mounting portion or be integral with mounting portion at a suitable point for attachment of mounting portion to patient interface or head strap 2940. Connector 2900 comprises a projection 2910 that engages with and is removably retained within orifice 2920 by, for example, a snap fit or interference fit connection, as are known in the art. Orifice 2920 may be formed directly in a patient interface 2940 or, as shown, be located in a support 2930 that is affixed to a head strap 2940.

Figure 111:
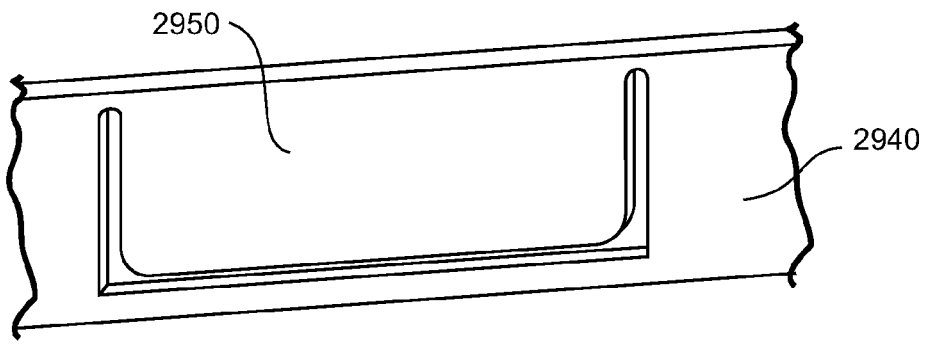
FIG. 111 is a perspective view of another embodiment (A) with no tube in place, and (B) with a tube in place.
Figure 111:
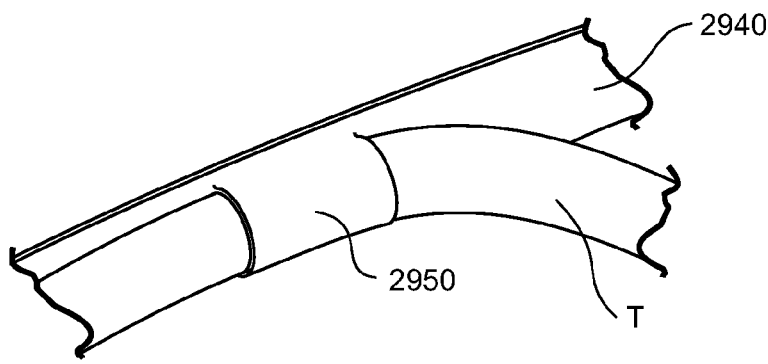

In another embodiment, and with reference to FIG. 111, patient interface or head strap 2940 comprises a flap 2950 of suitable material to retain a tube T. As illustrated in FIG. 111 (A), flap 2950 is formed by cutting or moulding a U-shaped slot in a head strap 2940. Flap 2950 extends transversely from, for example, one edge of a side of an arm of a patient interface 2940, or from one edge of a lay-flat section of a head strap 2940, is wrapped around a perimeter of a tube T as shown in FIG. 111 (B), and is secured in place by known methods, such as a loop and hook fastener, or a snap fit or interference fit connection, to a suitable location on patient interface or head strap 2940. Alternatively, two transverse slits may be made in a lay-flat section of a head strap 2940, passing entirely through the head strap 2940, such that a tube T may be threaded through each slit and retained in place. In another embodiment, the flap 2950 comprises a deformable material that will substantially hold its shape after being deformed about the tube T.

Figure 112:
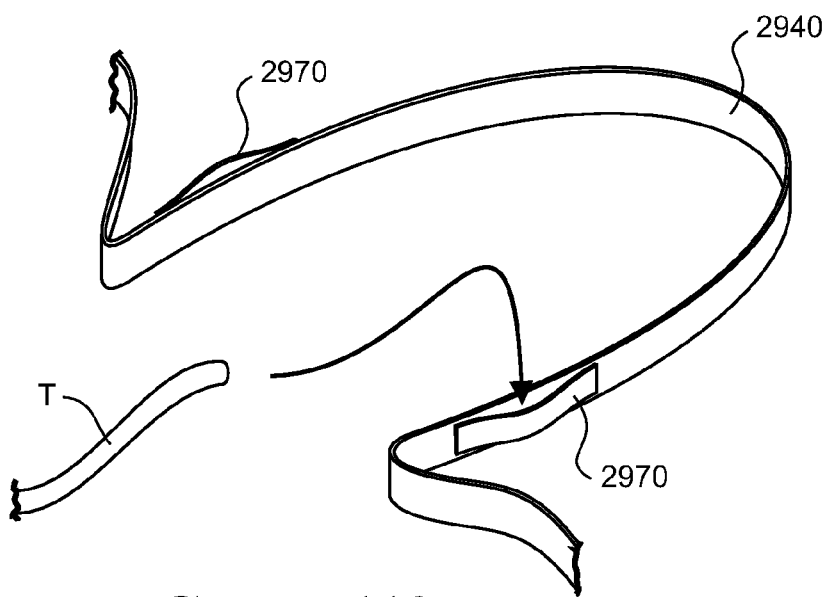
FIG. 112 is a perspective view of another.

In another embodiment, and with reference to FIG. 112, patient interface or head strap 2940 comprises a loop 2970 of suitable material to retain a tube T. Loop 2970 comprises an elongate piece of material that is attached by each end to patient interface or head strap 2940, for example in a longitudinal direction with the loop 2970 accessible from above or below the patient interface or head strap 2940 when in use on a seated patient. Alternatively, loop 2970 is integrally formed in patient interface or head strap 2940, or formed but cutting parallel elongate slits in a longitudinal direction in an arm of a patient interface or a lay-flat section of strap of a head strap 2940.

Figure 113:
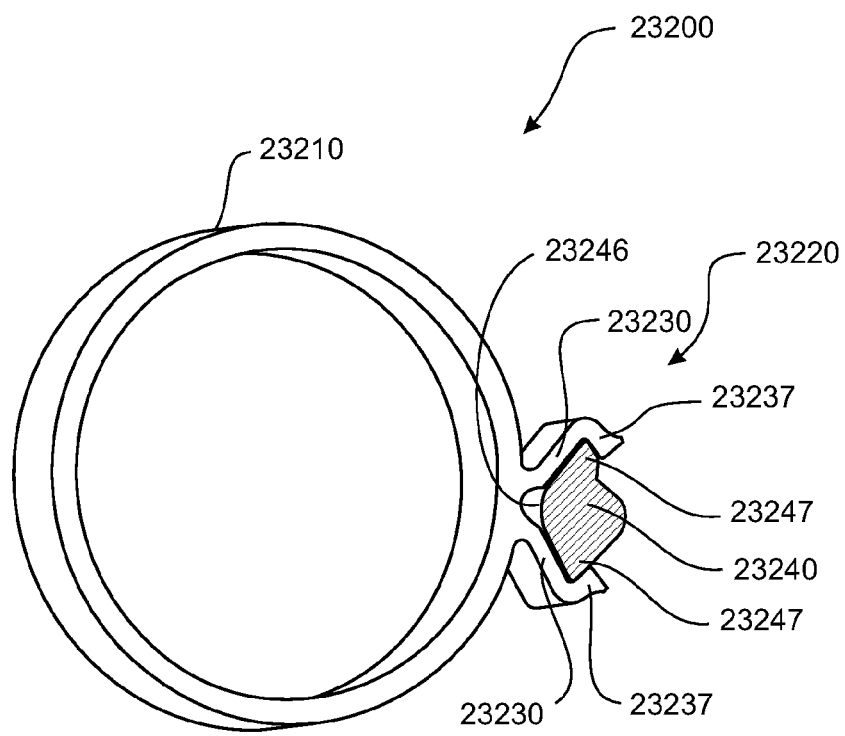
FIG. 113 is a perspective view of another embodiment of a component that is attached to a mounting portion.
Figure 114:
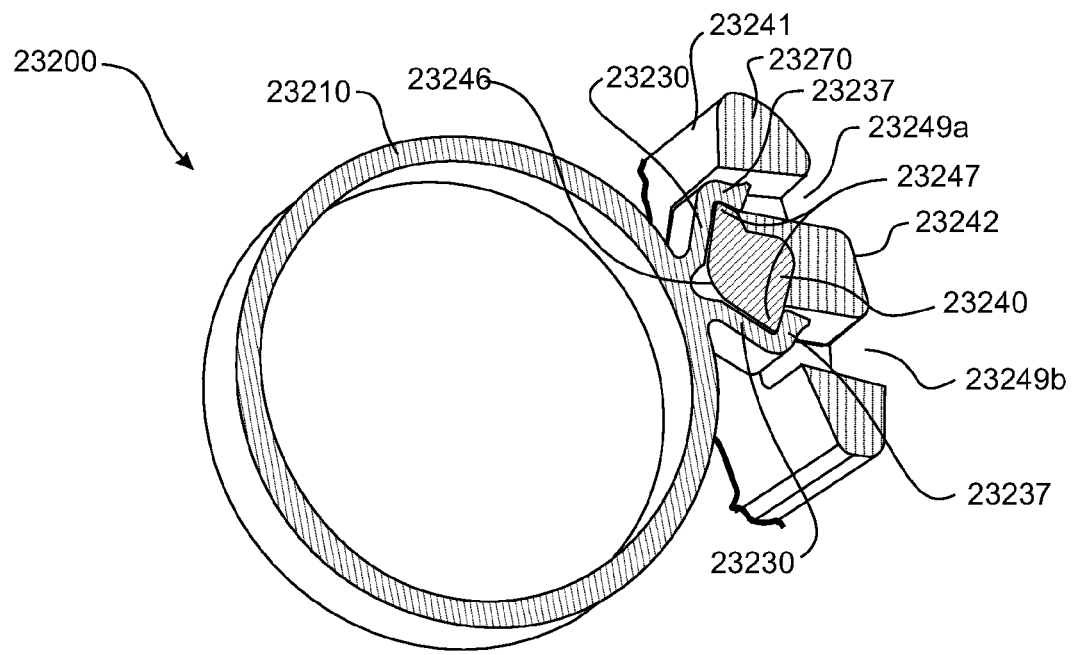
FIG. 114 is a perspective view of the embodiment of FIG. 113 that is attached to a mounting portion integral with an auxiliary portion of patient interface.
Figure 115:
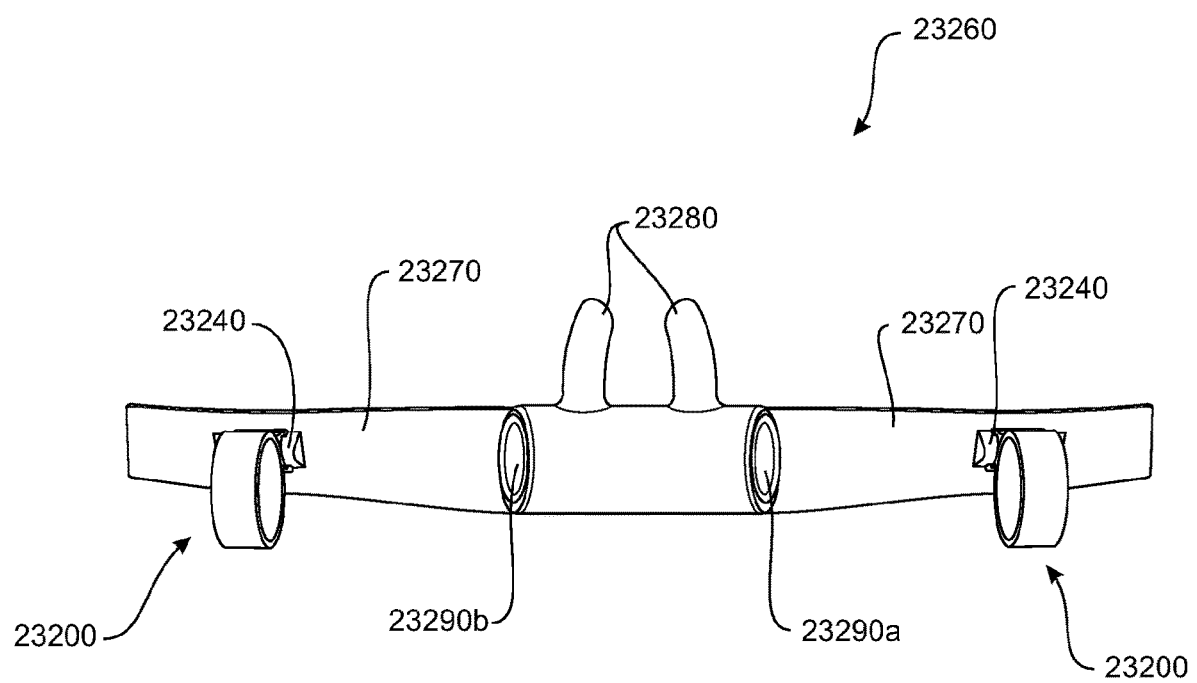
FIG. 115 is a front view of the embodiment of FIG. 113 that is attached to a mounting portion integral with an auxiliary portion of patient interface.

In another embodiment, and with reference to FIGS. 113 to 115, component 23200 is provided for use with a tube (not shown). Component 23200 comprises an at least substantially annular, for example annular body 23210 for receiving a tube as described above. The body 23210 may also be square, substantially square or of another rectilinear configuration, for example (not shown). Component 23200 includes an attachment 23220 that is integral with or fixed to the body 23210. Attachment 23220 may be non-moveably, pivotably, rotatably and/or removably fixed to the body 23210 as described above. Attachment 23220 is arranged to snap fit or snap engage a mounting portion 23240 and removeably hold component 23200 securely in place.

In one embodiment, attachment 23200 comprises a pair of arms 23230 that extend from the body 23210 forming a female connector that is shaped to engage the corresponding male connector, mounting portion 23240. Arms 23230 may extend from the body 23210 at the same point or substantially adjacent points, at any suitable angle, for example substantially parallel to a virtual radial line (not shown) extending from the centre of body 23210 or at an angle of, for example, about 30 degrees to about 50 degrees from a virtual radial line extending from the centre of body 23210, such that the distal ends of the arms are substantially opposite each other as shown in FIGS. 113 and 114, forming a pair of jaws adapted to engage the mounting portion 23240. Arms 23230 comprise angled portions 23237 that engage with corresponding projections 23247 on mounting portion 23240. Angled portions 23237 and corresponding projections 23247 are shaped to both retain the attachment 23220 in place on the mounting portion 23240 and also provide sensory feedback to an operator, as described above. The mounting portion 23240 may be shaped to guide the angled portions 23237 onto the projections 23247 and to aid engagement of the attachment 23220 with the mounting portion 23240. For example, mounting portion 23240 may comprise a shaped upper surface 23246 extending from the main body of the mounting portion 23240 that is shaped to center the mounting portion 23240 between arms 23230 and also to displace arms 23230 and/or angled portions 23237 as the attachment 23220 is brought into engagement with mounting portion 23240.

It should be understood that the relative arrangement of the arms 23230, angled portions 23237, projections 23247 and/or surface 23246 can be modified to provide the desired degree of retention. Removal of component 23200 from mounting portion 23240 may be achieved by an operator with a twisting action or sliding action or pulling action to disengage the angled portions 23237 from projections 23247.

Referring to FIG. 114, the mounting portion 23240 may be integral with a patient interface, such as an auxiliary part or arm 23270 of patient interface comprising an upper surface 23241 and a lower surface 23242. The mounting portion 23240 is formed at or in the upper surface 23241 and slots 23249a, 23249b are formed on either side of mounting portion 23240 to receive arms 23230 and/or angled portions 23237 when the attachment 23220 engages the mounting portion 23240. When attached to the mounting portion 23240, no part of the component 23200 extends past the lower surface 23242.

As shown in FIG. 115, a plurality of mounting portions 23240 may be present on a patient interface 23260, optionally integral with the patient interface 23260. Optionally the one or more mounting portions 23240 are integral with an auxiliary part of a patient interface, such as an arm 23270 or wing that forms part of the supporting structure of the patient interface 23240 but is not directly involved in the functioning of the breathing circuit. A patient interface 23260, such as a nasal cannula, has auxiliary left and right sides, such as left and right arms 23270 that generally rest on a patient's face, particularly on the cheeks, with a mounting portion 23240 located on each, on either side of the nostril prongs 23280. This arrangement allows attachment of a component 23200 to either or both mounting portions, and for a tube (not shown) to be attached to either of ports 23290a, 23290b to be routed to the left or right side of the interface and readily routed to the other side when necessary for treatment, patient positioning, patient comfort, equipment positioning, or the like, as described above in relation to FIGS. 85 and 86.

Figure 116:
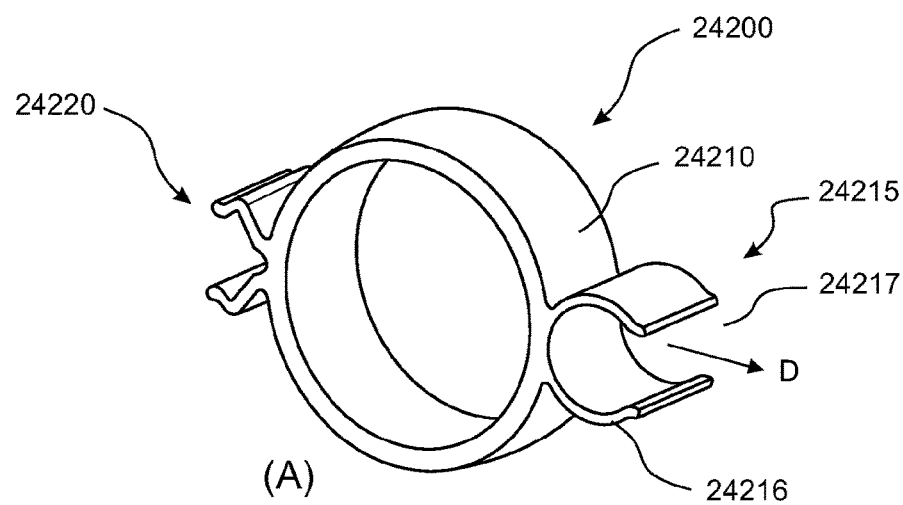
FIG. 116 is a perspective view of three embodiments (A), (B), (C) of a component comprising at least one retainer portion.
Figure 116:
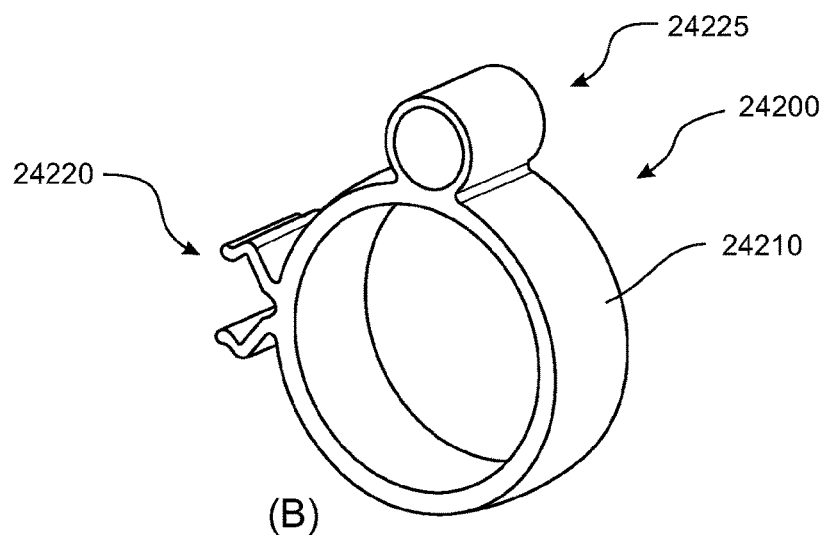
Figure 116:
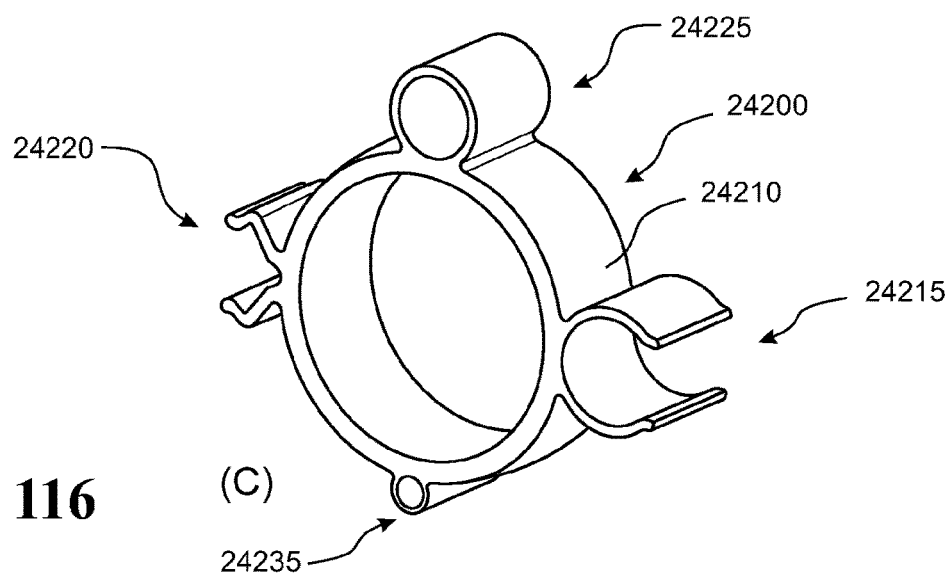

In another embodiment, and with reference to FIGS. 116 (A), (B) and (C), a component 24200 comprises an at least substantially annular body 24210 and an attachment 24220 that is integral with or fixed to the body 24210. Component 24200 is arranged and is for use as described above in relation to component 23200. The body 24210 comprises at least one retainer portion 24215, 24225, 24235 for receiving at least one accessory. The at least one accessory can be at least one tube and/or at least one cable and/or at least one lanyard. For example, the at least one accessory may comprise a gas line, a gas monitoring line including but not limited to a gas sampling line or a line for measuring end tidal volume, a hydration tube, a feeding tube, a nasogastric tube, a cable including but not limited to an electrical cable (for example, to deliver power to a heater) or a sensor cable (such as a temperature probe or pressure sensor cable), or a lanyard, or any combination of any two or more thereof. The at least one retainer portion can be an annular, substantially annular, square, substantially square, or rectilinear portion that receives the at least one accessory. As depicted in FIG. 116 (A), in one embodiment a retainer portion 24215 comprises a substantially C-shaped body 24216 having a mouth 24217. The body 24216 receives a tube or cable (not shown) through mouth 24217 and at least partially surrounds a perimeter of the tube or cable. Body 24216 receives the tube or cable by, for example, pushing body 24216 against a tube or cable in mounting direction D. Body 24216 is substantially C-shaped, such that two diverging arms pass around and at least partially surround a perimeter of a tube or cable, for example to the extent that the body 24216 extends around more than about 50%, and alternatively up to and including 100%, of the perimeter of the tube or cable to retain the tube or cable within the body 24216. The retainer portion 24215 may extend from the body 24210 at a point substantially opposite attachment 24220. Additionally or alternatively, as depicted in FIG. 116 (B), a retainer portion 24225 is a substantially annular portion that receives the at least one accessory. The retainer portion 24225 may extend from the body 24210 at a point substantially opposite attachment 24220 (not shown) or at a point that otherwise does not interfere with operation of attachment 24220. Additionally or alternatively, as depicted in FIG. 116 (C), the body 24210 may comprise a plurality of retainer portions 24215, 24225, 24235, each of which extends from body 24210 at a point that does not interfere with operation of attachment 24220. Additionally or alternatively, a retainer portion may comprise a recessed region of the component 24200, or body 24210 (not shown).

One or more of the retainer portions of component 24200 may be incorporated into any embodiment of a component described herein.

In another embodiment, and with reference to FIGS. 117, 118, 119, 120 and 121(A)-(B), a component 23300 is provided for use with a tube (not shown). Component 23300 comprises an at least substantially annular aperture, optionally an annular body 23310 for receiving a tube as described above. The body 23310 may also be square, substantially square or of another rectilinear configuration, for example (not shown). Different geometries may be provided on an external surface for a user to hold or grip more easily or for particular aesthetics. For example, the outer surface of the body may be of any shape or geometry, whilst the internal surface of the body may be configured for receiving of a tube.

Component 23300 may include an attachment 23320 that is integral with or fixed to the body 23310. Attachment 23320 may be non-moveably, pivotably, rotatably and/or removably fixed to the body 23310 as described above. Attachment 23320 can be arranged to snap fit or snap engage a mounting portion 23340 and removeably hold component 23300 securely in place.

In one embodiment, attachment 23300 comprises a pair of arms 23330 that extend from the body 23310 forming a male connector that is shaped to engage the corresponding female connector, mounting portion 23340. Arms 23330 may extend from the body 23310 at the same point or substantially adjacent points, or spread apart points. The arms can extend from the body in a manner so as to provide for parallel arms or arms which extend towards each other or arms which extend away from each other.

One or more of the arms may comprise tapered sections or angled walls so as to facilitate retention by the mounting portion of the or each arm, optionally retained in a longitudinal direction (i.e. insertion or removal or in and out of the mounting portion) and/or in a lateral direction (i.e. when the arms are moved from side to side with respect to the mounting portion). A combination of tapered sections or angled walls of the arms and/or of features of the mounting portion may provide for retention.

For example, in some embodiments the arms may include lead-in features which may be created or formed by one more bevelled surfaces on the arms instead of an angled portion or a lug portion.

The arms or the angled portions or lug portions of the arms may optionally include chamfered or bevelled portions to create or provide such a lead in. There may be additional angled or chamfered or bevelled faces or surfaces on the mounting portion for receiving or guiding such arms. The arms may also optionally comprise surface relief features for improved retention with the mounting portion or parts of the mounting portion.

Further, the or one or more of the mounting portions may comprise one or more bevels or chamfers or tapered lead-in shaped portions or sections, or angled bosses on the female and male portions. Any one or more of these, or other geometries, may be utilised for the mounting portion to assist with insertion of an arm or arms or orientation of the arm or arms for insertion within the mounting portion and/or may assist in providing for a more securely or more positively retained arm or arms within a mounting portion. For example, the mounting portion may be of a shape which is to be provided in contact with an arm or arms, as well as other parts of the attachment.

Figure 117:
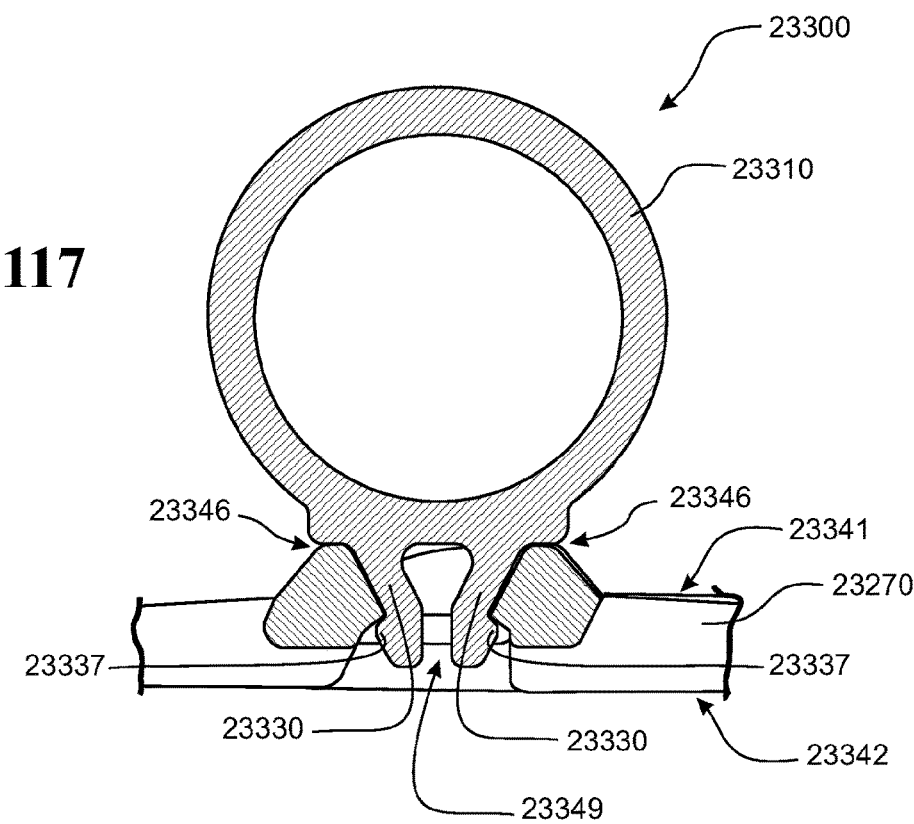
FIG. 117 is a cross-section view of a component attached to a patient interface.
Figure 118:
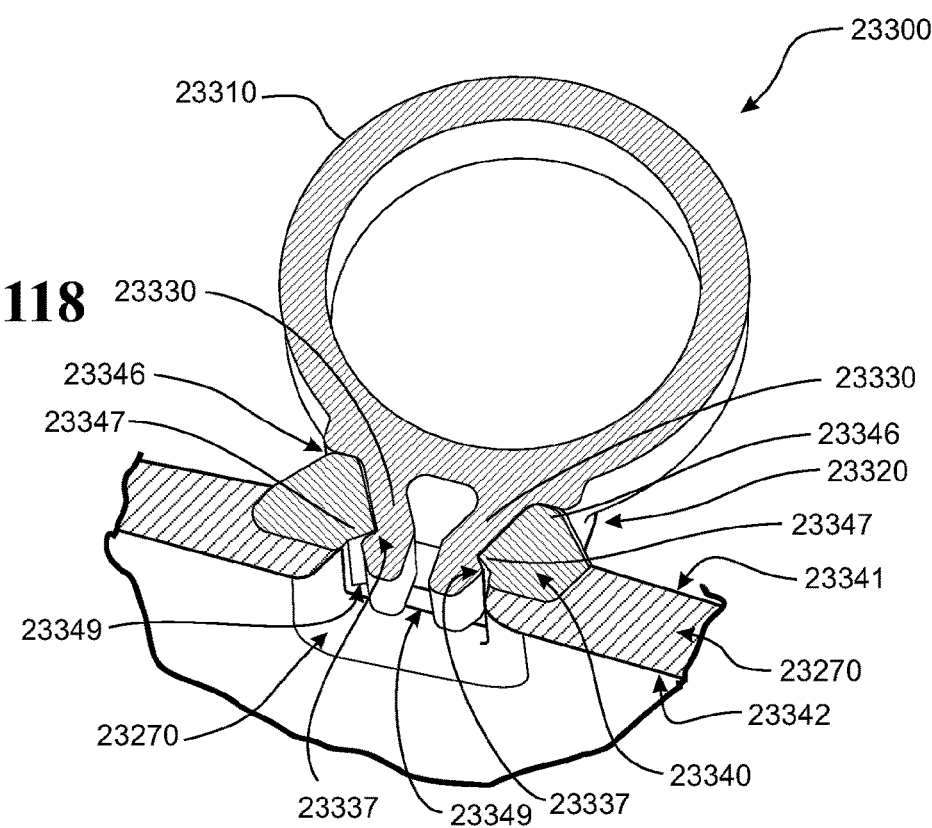
FIG. 118 is a cross-sectional perspective view of the cross-section view of FIG. 117.

FIGS. 117 and 118 show the distal ends of the arms engaged with the mounting portion 23340. It will be appreciated such arms 23330 could extend from the body parallel with each other or at an angle (whether towards each other or away from each other). The arms or at least parts of the arms can be deflected when inserted and retained by the mounting portion.

Arms 23330 can comprise angled portions or lug portions 23337 engageable with corresponding projections 23347 on mounting portion 23340. Angled portions or lug portions 23337 and corresponding projections 23347 can be shaped to both retain the attachment 23320 in place on or within the mounting portion 23340 and which may also provide sensory feedback to an operator, as previously described above. The mounting portion 23340 may be shaped to guide the angled or lug portions 23337 onto and/or into the projections 23347 and to aid engagement of the attachment 23320 with the mounting portion 23340. In some embodiments, the shape or geometry of the arms or angled portions or lug portions may also be used to assist in guiding the arms into the mounting portion for correct insertion and/or retention.

For example, mounting portion 23340 may comprise a shaped upper surface 23346 extending from or about the main body of the mounting portion 23340 that is shaped to effectively center or align or guide the arms 23330 when bringing the arms 23330 into engagement with the mounting portion 23340. The shaped upper surface 23346 for example may be a shaped perimeter region extending about the mounting portion 23340, which in the case of this embodiment provided for an aperture (i.e. the female mounting portion 23340). The upper shaped surface 23349 is configured so as to direct or guide or deflect or displace the arms 23330 and/or angled or lug portions 23337 as the attachment 23320 is brought into engagement with mounting portion 23340. The upper shaped surface 23349 shown in FIGS. 117 and 118 is a surface of the mounting portion which provides for a reactive surface upon which the arms or angled portions or lug portions can become engaged or into contact with.

It should be understood that the relative arrangement of the arms 23330, angled or lug portions 23337, projections 23347 and/or surface 23346 can be modified to provide the desired degree of retention. Removal of component 23300 from mounting portion 23340 may be achieved by an operator with a twisting action or sliding action or pulling action to disengage the angled or lug portions 23337 from projections 23347.

For example, the shape or angles of the arms or angles portions or lug portions can be configured to aide with lead-in of the arms to the mounting portion. The shape or angles of the arms may help guide the arms into the mounting portion when the cannula is in-use. In one embodiment, a user can line up the tube with the arms such that the tube is axially aligned with the arms. The mounting portion can be provided as a part of the patient interface such that it is angled or offset and the shape or angles of the arms can helps to lead-in and guide the arms into the mounting portion—this may assist in making insertion of the attachment/arms to the mounting portion easier and/or quicker.

The arms are shaped to correspond to the mounting portion. This prevents the tube clip from wobbling and moving. The top surface of the mounting portion acts as a stop so that the arms are not pushed in too far.

Referring to FIGS. 117 and 118, the mounting portion 23340 may be integral with a patient interface, optionally an auxiliary part or arm 23270 of a patient interface (such as, but not limited to, a nasal cannula) which may comprise of an upper surface 23341 and a lower surface 23342. The mounting portion 23340 is formed at or in the upper surface 23341 and a slot or aperture 23349 is formed by the mounting portion 23340 to receive arms 23330 and/or angled portion or lug portions 23337 when the attachment 23320 engages the mounting portion 23340. When attached to the mounting portion 23340, optionally no part of the component 23300 extends past the lower surface 23342.

There can be multiple mounting portions spaced or positioned about a patient interface, for example along the length of an arm of a nasal cannula interface. Whilst FIG. 121 A,B shown a single mounting portion on each side arm, it is contemplated that a additional mounting portions, or at least provisions for providing additional mounting portions, can be provided on a patient interface, such as along an arm of a nasal cannula. In this way, customization of the location of the mounting portion and thereby retention of the tube is allowed. In view of such embodiments, the body or tube clip may be mounted or mountable at a plurality of different positions along a patient interface, such as a nasal cannula frame arm. Alternatively, the mounting portion could itself be an auxiliary component which is removably attachable or can be clipped or positioned at different positions on a headgear which may be associated with a patient interface. The mounting portion could be clipped or connected to lanyard, clothes or any other feature around the patient to retain the tube.

In at least some embodiments the mounting portion or aperture of the mounting portion can be oriented or shaped in an off-set manner or is angled relative to the patient interface, such as an arm or a nasal cannula, such that when the attachment of the body is engaged to or with the female mounting portion or aperture, a tube connected to the body is substantially aligned with an arm or frame of the patient interface. In at least some embodiments in this manner the tube follows the shape of a cannula frame arm and provides the visual appearance of the tube entering or being connected with a manifold or fluid connection port of a patient interface in a "straight" orientation or alignment.

Figure 119:
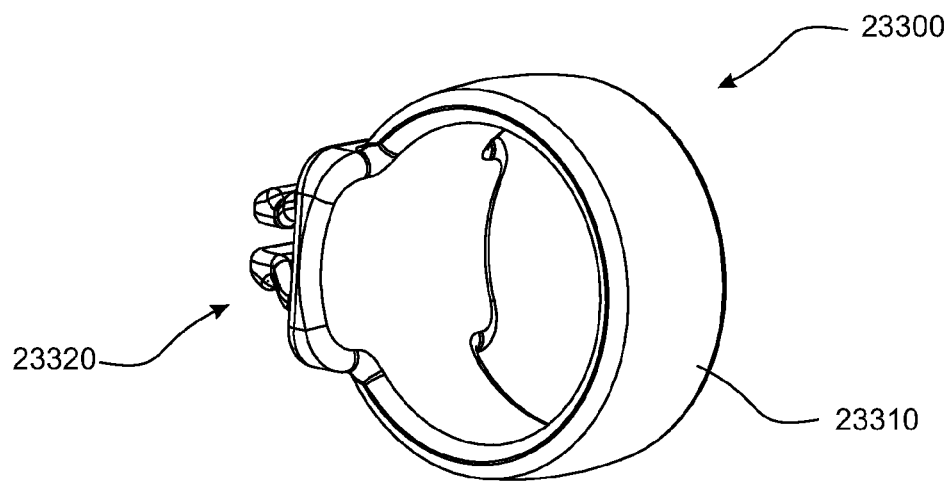
FIG. 119 is a perspective view of the embodiment of FIGS. 117 and 118.
Figure 120:
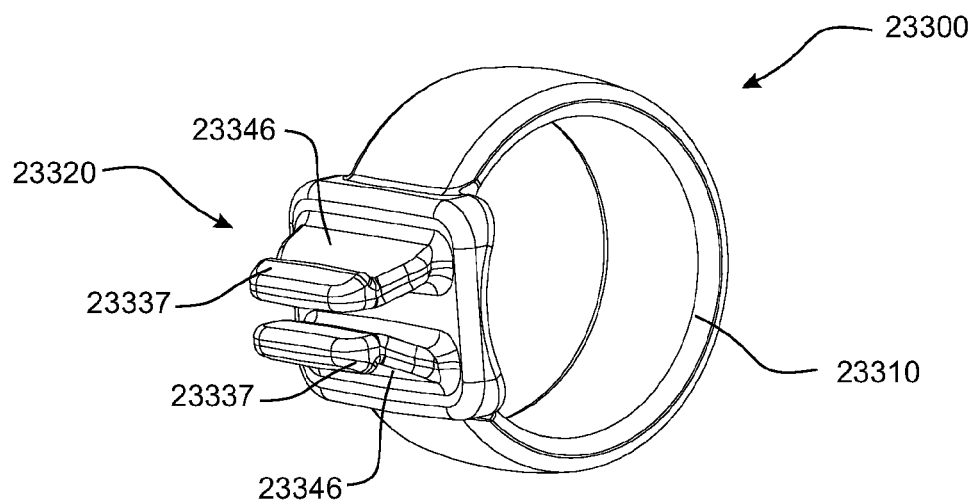
FIG. 120 is another perspective view of the embodiment of FIG. 119.
Figure 121:
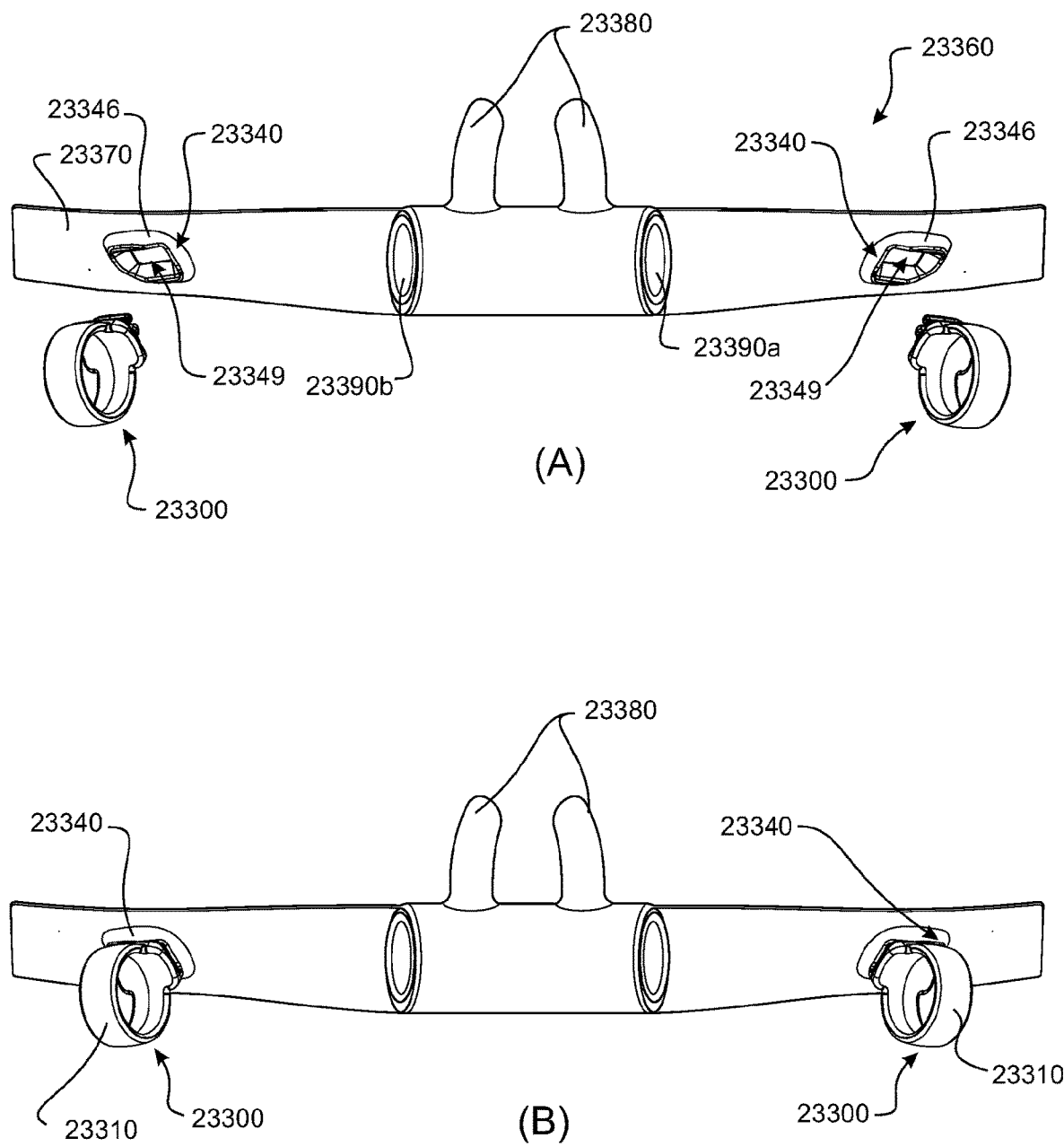
FIG. 121 (A) is a front view of the embodiment of FIGS. 117-120 that is not yet attached to a mounting portion integral with an auxiliary portion of patient interface.

FIGS. 119 and 120 provide for additional perspective views of the component 23300.

As shown in FIGS. 121(A)-(B), a plurality of mounting portions 23340 may be present on a patient interface 23360, optionally integral with, or optionally formed as part of, the patient interface 23360. The one or more mounting portions 23340 may be integral with an auxiliary part of a patient interface, such as an arm 23370 or wing that forms part of the supporting structure of the patient interface 23360 but is not directly involved in the functioning of the breathing circuit. A patient interface 23360, such as a nasal cannula, may have auxiliary left and right sides, such as left and right arms 23370 that generally rest on a patient's face, particularly (but not limited to being) on the cheeks, with a mounting portion 23340 located on each, on either side of the nostril or nasal prongs 23380. This arrangement allows attachment of a component 23300 to either or both mounting portions 23340 (or other mounting portions not shown, but which may be provisioned or spaced along each or both of the side arms 23370), and for a tube (not shown) to be attached to either of ports 23390*a*, 23290*b* to be routed to the left or right side of the interface and readily routed to the other side when necessary for treatment, patient positioning, patient comfort, equipment positioning, or the like, as described above in relation to FIGS. 85 and 86.

FIG. 121(A) shows a patient interface 23360 with a component 23300 not yet positioned in the installed position with the mounting portion 23340. FIG. 121(B) shows a patient interface with a component 23300 in the installed position. It will be appreciated that for the purposes of these figures only, a pair of components 23300 have been shown for connection in each of the optionally positioned or located mounting portions 23340 along each of the left and right side arms 23370. In use, a single component 23300 which retains a tube (not shown) is likely to be utilised, for connection to a single mounting portion 23340. Then, when a patient or user wish to relocate the position or location of the tube from the breathing circuit, the component 23300 may be disengaged from the mounting portion 23340, and moved to the other of the available mounting portions 23340 to then securely re-retain the tube in place.

In some embodiments, more than one component may be utilised to retain or support or secure tubes, for example multiple mounting portions may be provided and multiple components can be used for multiple tubes, such as gas delivery tubs, feeding tubes or other tubes or wires used as part of a patient interface or for patient care or therapy monitoring or control.

It will be appreciated the component 23300 may be re-configured to optionally include at least one retainer portion, such as those labeled as items 24215, 24225, 24235 for receiving at least one accessory in FIGS. 116(A)-(C).

A component of the disclosure may be provided in combination with at least one tube and/or at least one cable. Accordingly, the present disclosure also relates broadly to a tube or cable, such as for use in a medical breathing circuit, the tube or cable (as herein described) comprising a component as herein described, the component being optionally removeably engaged to a mounting portion as herein described, the mounting portion being removably attachable to a patient interface, such as in a medical breathing circuit.

Further, a component of the disclosure may be provided in combination with a patient interface. Accordingly, the present disclosure also relates broadly to a patient interface (as herein described), such as for use in a medical breathing circuit, the patient interface comprising a mounting portion as herein described, integral with, non-removeably attached to, or removably attached to the patient interface, and a component as herein described removeably engaged to the mounting portion.

Still further, a component of the disclosure may be provided in combination with a tube and/or patient interface and/or instructions for use. Accordingly, the present disclosure also relates broadly to a kit comprising a component as herein described and any two or more of a patient interface as herein described, optionally comprising an integral mounting portion as herein described, a mounting portion as herein described, and instructions for assembly and/or use.

The components described herein, and their associated mounting portions (whether separate or integral with the components) may be formed of any suitable material allowing the features described herein including, for example, a medical grade material and/or a suitable polymeric material.

Any one or more features from any embodiment may be combined with any one or more features from any one or more other embodiments.

As discussed previously, in this specification, the terms "medical circuit" and "breathing circuit" are used to indicate the general field of the disclosure.

Figure 122:
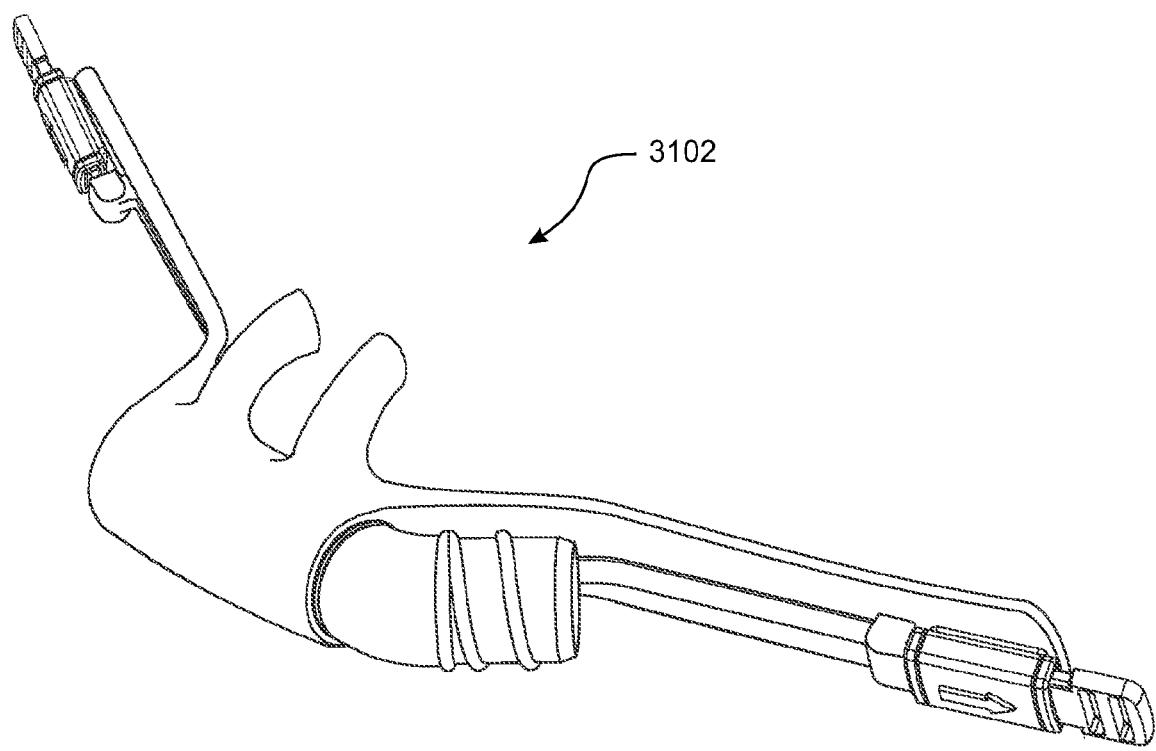

With reference to FIG. 122, patient interface 3102 for use in a medical breathing circuit is shown. The patient interface 3102 comprises a pair of connectors. With reference to FIGS. 123 to 132, a first preferred embodiment connector 3200 will now be described. The connector 3200 has a first connector part in the form of a clip 3201, a second connector part in the form of a carrier 3203, a detent 3205 for securing the clip and the carrier together, a biasing means 3207, and a slide 3209. The slide 3209 is moveable relative to the clip 3201 and/or the carrier 3203 between a secured position and a free position. In the secured position, the detent 3205 is substantially inhibited from moving and releasing the clip 3201 from the carrier 3203. In the free position, the detent 3205 is able to move to release the clip 3201 from the carrier 3203. The biasing means 3207 urges the slide towards the secured position.

In the preferred embodiment shown, the biasing means 3207 and detent 3205 are integrally formed together. The biasing means 3207 comprises a pair of resilient legs 3208 and the detent comprises a pair of resilient arms 3211. The arms and legs are substantially resistant to deformation or are resiliently flexible. The arms 3211 are flexible to allow the clip 3201 to be inserted when the slider 3209 is in the secured position, as described below. The arms and legs extend from a body portion 3210.

As described in more detail below, the resilient legs 3208 urge the slide towards the secured position. The legs extend from the body portion 3210 in the same direction and are the same length as each other. The sides 3208a of each leg are slightly tapered so that a free end 3208b of each leg is narrower than an end 3208c that joins the body portion 3210. The free end 3208b of each leg is rounded. The side surfaces, top surface 3208d and bottom surface 3208e of each leg are substantially planar surfaces.

The resilient arms 3211 are spaced apart and extend from the body portion 3210 in the same direction as the legs 3208. The arms are the same length as each other, and longer than the legs. The arms 3211 are biased towards each other. As described in more detail below, when the clip 3201 is inserted into the carrier 3203, the pair of resilient arms 3211 are biased towards engagement with the notches of the clip.

Each arm has a linear portion closest to the body portion 3210 which extends into an arcuate portion 3212. The arcuate portion 3212 allows the arms 3211 to bend when the clip 3201 is inserted into the carrier 3203 with the slide 3209 in the secured position. The arcuate portion 3212 is concave when viewed from the position of the slide. The arcuate portion 3212 has a narrower width than the linear portion. The side surfaces, top and bottom surfaces of each arm are substantially planar surfaces. The top and bottom surfaces act as bearing surfaces between the slide 3209 and the subassembly of the carrier with the biasing means 3207/detent 3205.

Figure 124:
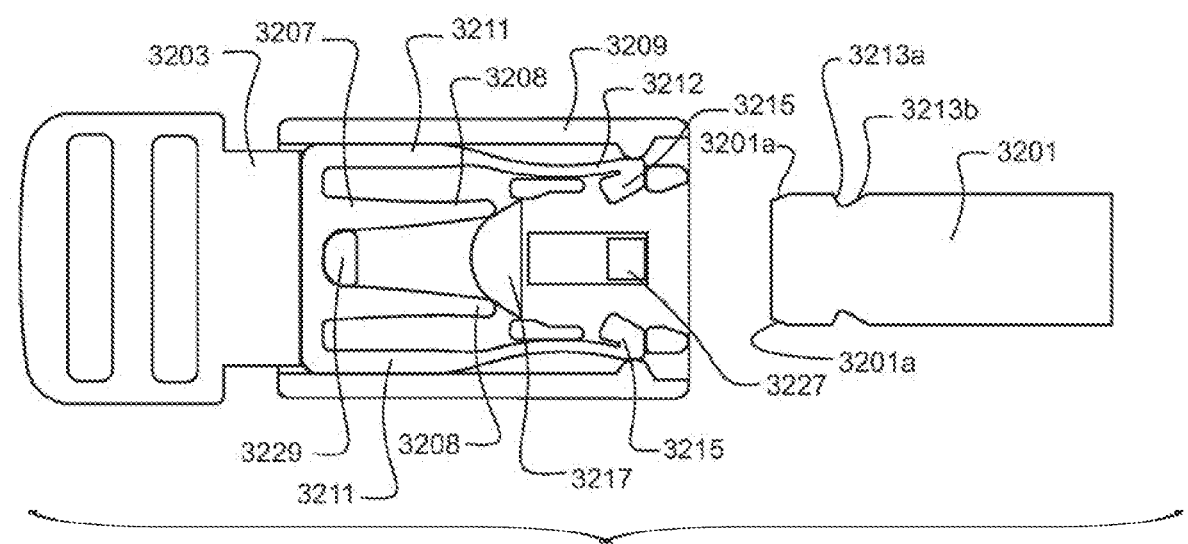

Each resilient arm 3211 comprises a protrusion 3215 for engagement with a complementary notch of the clip 3201. The protrusion 3215 is at the free end of each arm. Each protrusion 3215 has a generally triangular shape, as shown in FIG. 124 and the notch has a complementary triangular shape for positive engagement between the protrusion and the notch. In an alternative embodiment, the notch may be a shoulder.

The slide 3209 has a lug 3217 for engagement with the biasing means and a stop 3227 or 3327 as shown in FIG. 138 for locating the slide and carrier 3203 in the secured configuration. Another stop may be provided near stop 3227 to control the extent of movement of the slider in the free position. There may be an additional stop, or stop 3227 may be extended. In the preferred embodiment shown, the slide 3209 is a sleeve. The sleeve has a first interior surface and a second spaced apart interior surface opposite the first surface. The stop 3227 is formed on the first surface and the lug 3217 is formed on the second surface. In an alternative embodiment, the stop and lug may be formed on the same surface. FIGS. 124 to 128 are cross sectional views through a central plane of the connector. Accordingly, those figures show the lug, the stop, and the biasing means.

As shown in FIGS. 124 to 128, the lug 3217 is centrally positioned within the slide 3309. The lug 3217 has two outwardly tapered surfaces 3219 with a rounded nose 3221.

Figure 130:
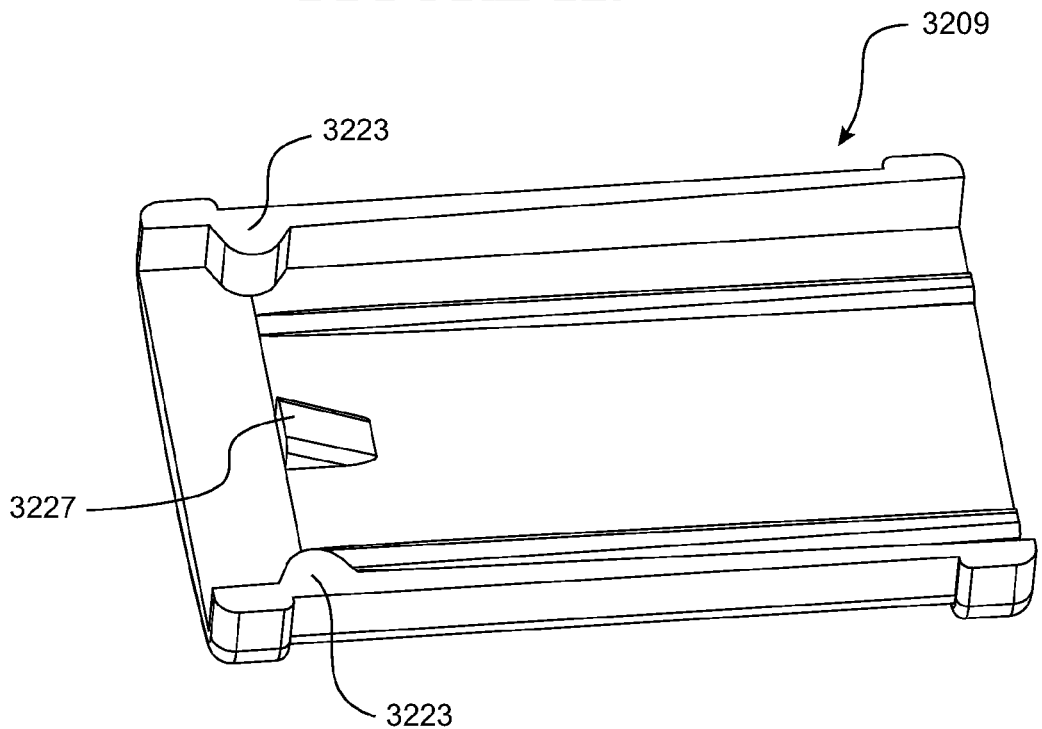
Figure 131:
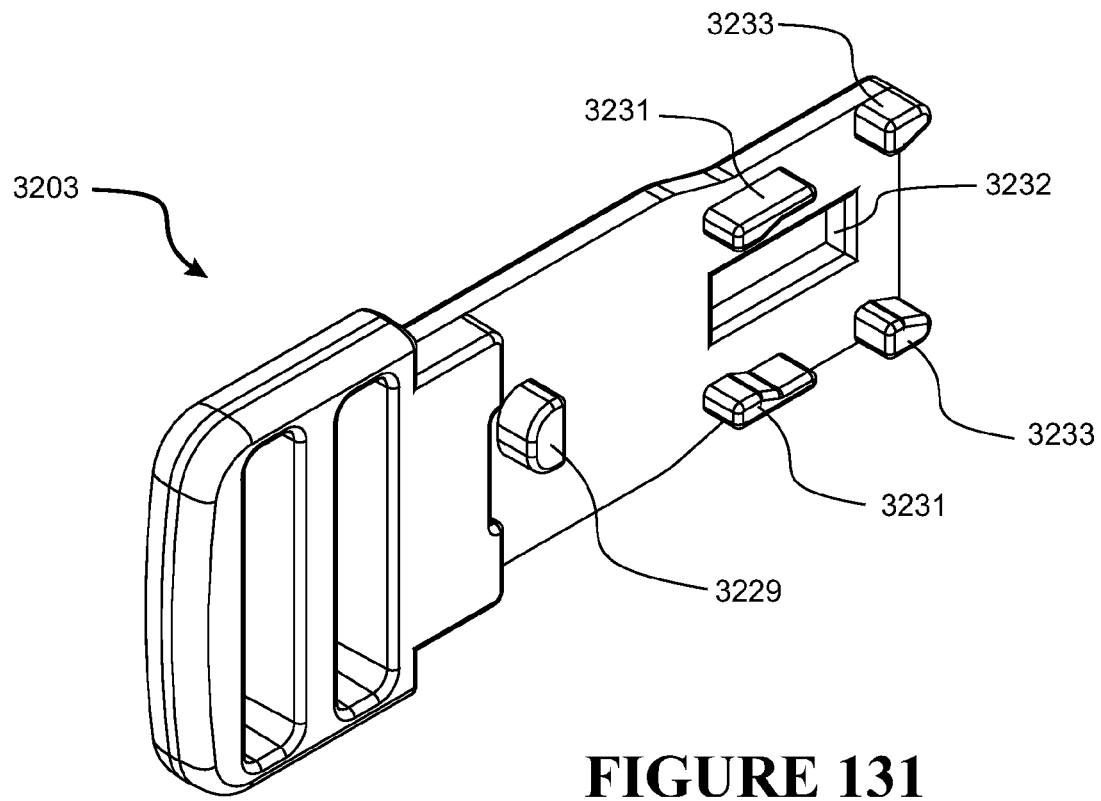
Figure 132:
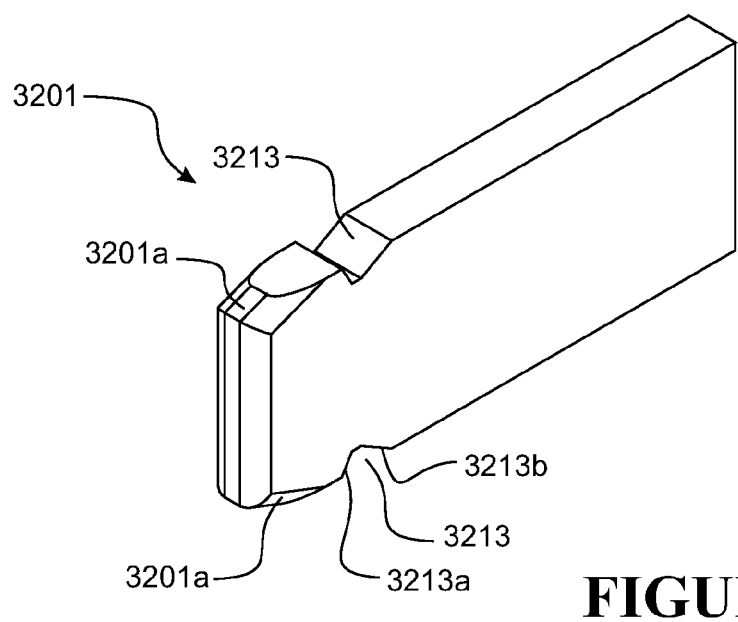

The stop has a wedge-shaped profile when viewed from the side, as shown in FIG. 130. The stop cooperates with a slot in the carrier. When the slide is in the secured position, a surface of the stop engages a surface of the slot, preventing the slide from moving past the secured position. The wedge shape of the stop aids assembly of the slide to the carrier.

The slide 3209 has two protrusions 3223 for engagement with the detent for substantially inhibiting movement and release of the clip 3201 from the carrier 3203. The protrusions are generally semi-circular shaped, as shown in FIGS. 124 to 128. The slide 3209 has a pair of longitudinally extending rails 3225. The slide may have scalloped portions for a user to grasp the slider. The slider may be fitted with a soft sleeve component to provide the user with a better grip to operate the connector, which may also be more comfortable for a patient to have against their skin. The sleeve may be overmoulded or co-moulded with the sleeve or may be a separately formed component that is assembled with the slider.

The clip 3201 is a substantially planar and rigid component. The clip 3201 comprises a pair of notches 3213. The notches 3213 are positioned towards a nose section 3201a of the clip 3201 and are a generally triangular shape. A first side 3213a of the notch 3213 closest to the nose of the clip 3201 is a steeper angle than the second side 3213b of the notch 3213. The first side is relatively steep to assist in preventing the clip 3201 from being removed when the slide is in the secured position.

In an alternative embodiment, shown in FIG. 145, the clip 3201 may be asymmetrical. In particular, one face 3201b is planar and the other face is curved 3201c. When this alternative embodiment is used, the carrier 3203 is orientated relative to the clip 3201 in a specific direction to ensure graphics on the carrier 3203 are always visible to a user and/or a soft material/shape is always positioned toward the patient.

The clip 3201 is either attachable to, or integrally formed with a mask frame of a patient interface 3102 or other portion of a patient interface, such as for example an arm or both arms of a nasal cannula patient interface configuration.

The carrier has one or more apertures 3303a for attachment of a strap of headgear, as shown in FIG. 139 and is adapted for carrying the combined detent/biasing means. The carrier 3203 has a location feature for locating the biasing means. In particular, the carrier has a lug 3229 spaced apart from a planar surface 3230. When assembled with the combined detent/biasing means the body portion 3210 fits snugly in the space between the lug and the planar surface.

The carrier 3203 also has a pair of guide features 3231 for guiding the clip 3201.

The carrier 3203 further has a pair of guide feature 3233 for guiding the clip 3201. Each guide feature 3233 inhibits the clip 3201 from releasing when the slide 3209 is in the secured position. The detent cams between the guide features 3233 and the protrusions 3223 on the slide 3209, preventing the clip 3201 from being removed without first releasing the slide 3209. In addition, the angled surface of the entrance of guide feature 3233 aids inserting clip 3201 into the assembly by guiding/aligning the clip to the correct location.

The carrier may be advantageously provisioned at the terminal end of a part of a headgear or strap for headgear or other associated portion used for securing or retaining headgear or a head strap upon a user's head. In this manner, the clip 3201 as a male part is provisioned on or as part of a patient interface, while the carrier 3203 is provisioned on or as part of a headgear or head strap part or component. Such a set up allows for the slide 3209 to be pulled by a user away from the interface to allow the slide and associated detent to move from the secured position to the free position.

With reference to FIGS. 124 to 128, a method of connecting the clip 3201 and carrier 3203 will now be described. FIG. 124 is a cross sectional view of the connector of FIG. 123, before the clip 3201 is engaged with the detent 3205. The slide 3209 is biased to the secured position.

Figure 125:
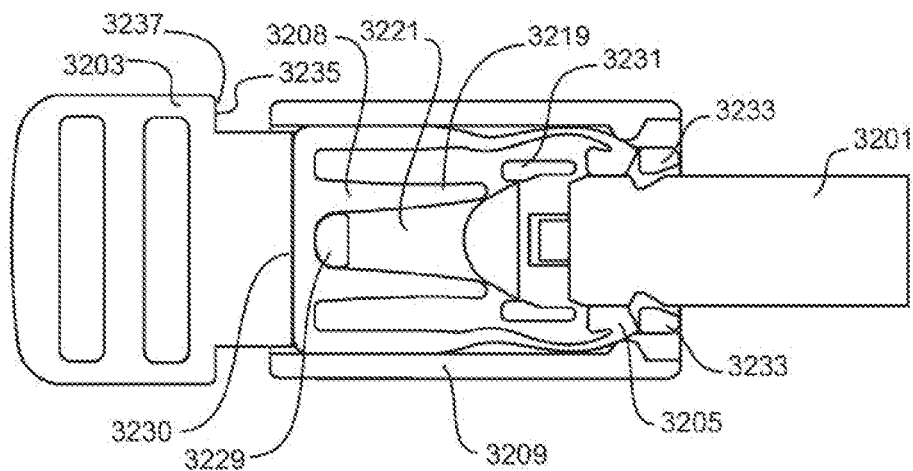

With reference to FIG. 125, an initial stage of the clip 3201 being engaged with the detent 3205 is shown. The clip 3201 is inserted into carrier between the guide features 3233. The clip 3201 is guided/aligned into the correct location by the angled surface of each of the guide feature 3233.

The arcuate portion 3212 allows the arms 3211 to bend when the clip 3201 is inserted into the carrier 3203 with the slide 3209 in the secured position. In particular, the arms 3211 bend laterally away from the clip 3201. The arms may bend into a curved shape as shown in which the arcuate portion 3212 is convex when viewed from the position of the slide. Alternatively, the arms may flex or bend into a less curved position or a position in which the arcuate portion 3212 is still concave, but less concave than shown in FIG. 127.

Figure 123:
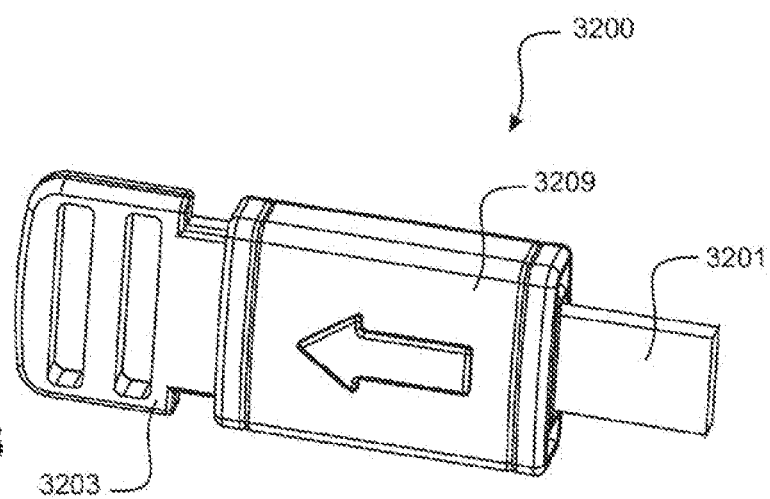
Figure 126:
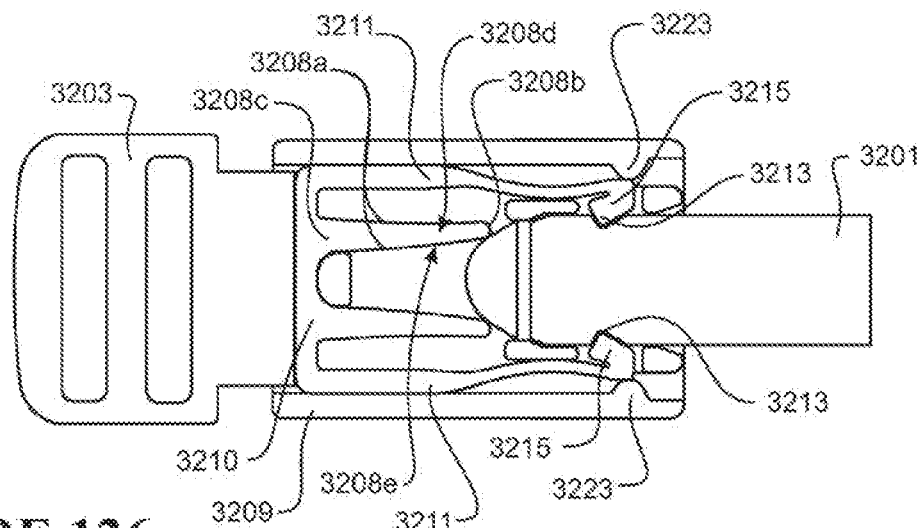

FIG. 126 is a cross sectional view of the connector of FIG. 123 showing the slide in the secured position. In this position, the protrusions 3215 of the arms 3211 engage the notches 3213 of the clip 3201. The arms 3211 are prevented from moving when in the position shown in FIG. 126 unless the slide 3209 is moved. In particular, the arms 3211 cannot move towards each other because the clip 3201 is positioned between them. The arms 3211 cannot move away from each other because the protrusions 3223 of the slide 3209 prevent outwardly lateral movement of the arms. The protrusions 3233 also prevent the protrusions 3215 on the arm 3211 from flexing backwards and disengaging from the clip 3201.

Figure 127:
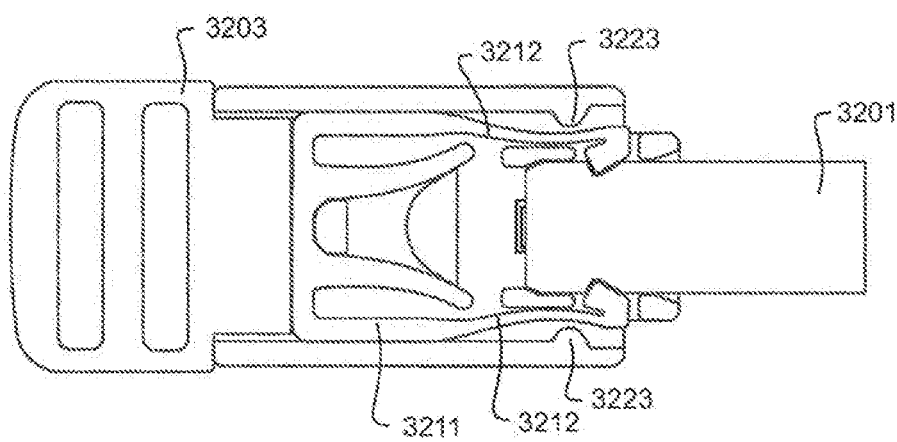

FIG. 127 is a cross sectional view of the connector of FIG. 123 showing the slide 3209 in a free position, allowing the clip 3201 to be removed. The slide 3209 is moved to a free position in which the detent 3205 is able to move. In the free position, an end 3235 of the slide 3209 closest to the carrier 3203 abuts a shoulder 3237 of the carrier to prevent the slide 3209 moving back too far. The arcuate portion of the resilient arms provides a clearance space into which the protrusions of the slide may move when the slide moves to the free position. The legs 3208 (as also shown for example by 3408, such as in FIG. 141) of the biasing means are moved away from each other by the lug and the arms 3211 are also moved away from each other by the clip 3201. The legs 3208 are substantially resistant to deformation or are resiliently flexible and are biased towards each other and will act on the tapered surfaces of the lug, urging the slider back to the secured position. After moving the slide, the protrusions 3223 have moved into the free space provided by the arcuate portions 3212 of the arms 3211 and the arms are free to move. Pulling on the clip 3201 causes the arms 3211 to flex away from each other, releasing the clip 3201 from the carrier 3203.

Figure 128:
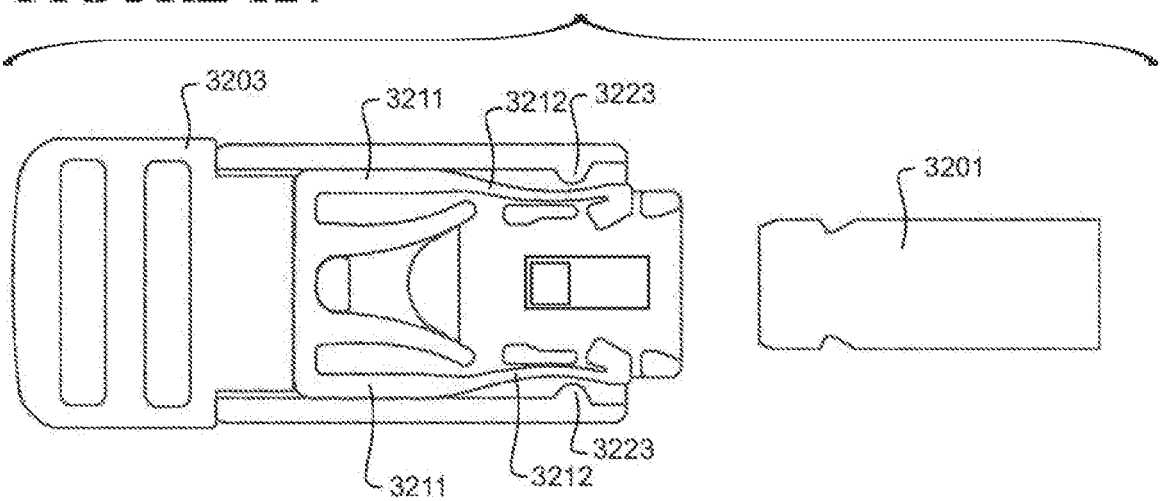
Figure 129:
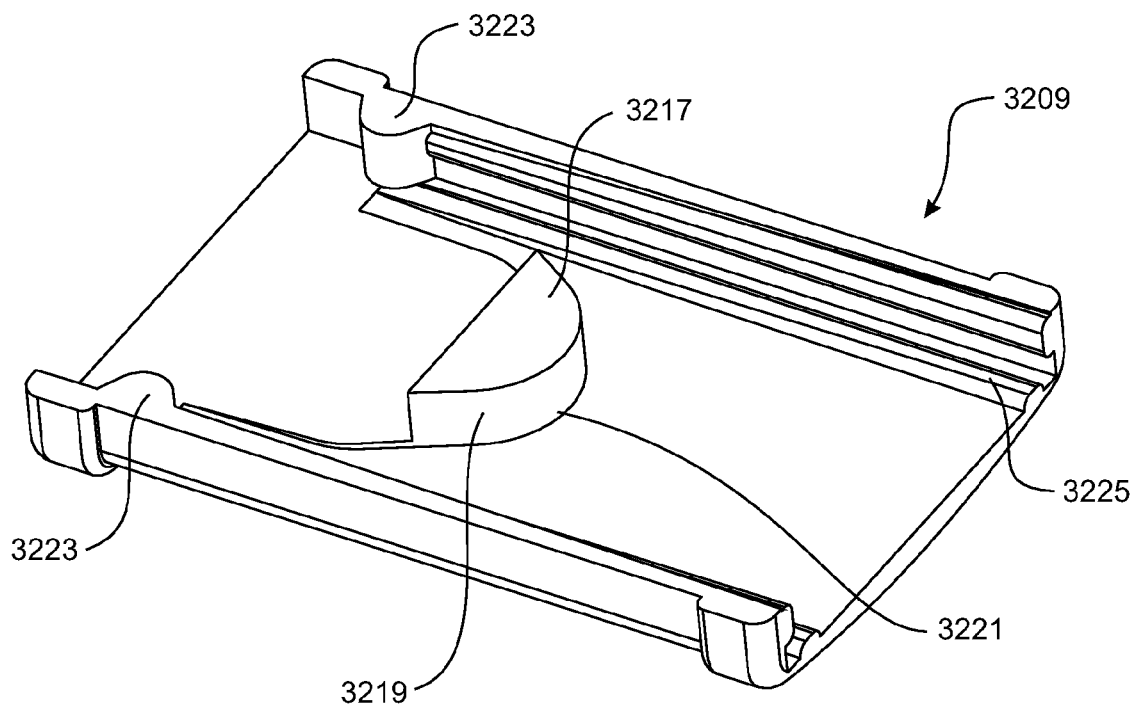

FIG. 128 is a cross sectional view of the connector of FIG. 123 showing the clip 3201 removed from the carrier 3203.

A connector of the disclosure may be provided in combination with a patient interface. Accordingly, the present disclosure also relates broadly to a patient interface (as herein described) for use in a medical breathing circuit, the patient interface 3102 comprising a connector as herein described, integral with, non-removeably attached to, or removably attached to the patient interface 3102 for connecting the patient interface with headgear.

The connectors 3200, 3300 may be formed of any suitable material allowing the features described herein including, for example, a medical grade material and/or a suitable polymeric material.

With reference to FIGS. 133 to 140 a second embodiment of the connector will now be described. Unless described as otherwise below, the features and functioning of the connector should be considered the same as described for the first embodiment above, and like reference numerals indicate like parts with the addition of 100.

The connector 3300 has a first connector part in the form of a clip 3301, a second connector part in the form of a carrier 3303, a detent 3305 for securing the clip and the carrier together, a biasing means 3307, and a slide 3309. The slide 3309 is moveable relative to the clip 3301 and/or the carrier 3303 between a secured position and a free position. In the secured position, the detent 3305 is substantially inhibited from moving and releasing the clip 3301 from the carrier 3303. In the free position, the detent 3305 is able to move to release the clip 3301 from the carrier 3303. The biasing means 3307 urges the slide towards the secured position.

In the second embodiment, the biasing means 3307 and detent 3305 are integrally formed together. The biasing means 3307 comprises a pair of resilient legs 3308 and the detent 3305 comprises a pair of resilient arms 3311. The legs 3308 extend from the body portion 3310 (or 3410 as for example shown in FIGS. 141, 144) generally in the opposite direction to the direction of the arms. The legs 3308 are the same length as each other. The free ends 3308*b* of each leg 3308 is enlarged compared to the remainder of each leg. The free end 3308*b* of each leg 3308 is rectangular.

The slide 3309 has a pair of lugs 3317 for engagement with the biasing means 3307. As shown in FIG. 138, the lugs 3317 are positioned near the periphery of the slide. The lugs 3317 each have a tapered surface 3319.

The carrier 3303 has a single aperture for attachment of a strap, as shown in FIG. 122 and is adapted for carrying the combined detent 3305/biasing means 3307. The carrier 3303 has a location feature for locating the biasing means. In particular, the carrier 3303 has a leg 3329. When assembled with the combined detent 3305/biasing means 3307 the free end of the leg fits snugly in the space between the lug and a planar surface.

With reference to FIGS. 133 to 138, a method of connecting the clip 3301 and carrier 3303 of the second embodiment will now be described. FIG. 133 is a cross sectional view of the connector of FIG. 123, before the clip 3301 is engaged with the detent 3305. The slide 3309 is biased to the secured position.

FIG. 134 is a cross sectional view of the connector of FIG. 133, showing the initial stages of the clip 3301 being engaged with the detent 3305.

FIG. 135 is a cross sectional view of the connector of FIG. 133 showing the slide 3309 in the secured position. In this position, the protrusions 3315 of the arms engage the notches of the clip 3301. The arms 3311 are prevented from moving when in the position shown in FIG. 135 unless the slide 3309 is moved. In particular, the arms 3311 cannot move towards each other because the clip 3301 is positioned between them. The arms 3311 cannot move away from each other because the protrusions 3323 of the slide 3309 prevent outwardly lateral movement of the arms 3311. Each arm is prevented from flexing by engaging with protrusions 3333.

FIG. 136 is a cross sectional view of the connector of FIG. 133 showing the slide 3309 in a free position, allowing the clip 3301 to be removed. The legs 3308 are moved towards each other by the lugs 3317 and the arms 3311 are also moved away from each other by the clip 3301. The legs 3308 are substantially resistant to deformation or are resiliently flexible and are biased away from each other and will act on the tapered surfaces of the lugs, urging the slide 3309 back to the secured position.

FIG. 137 is a cross sectional view of the connector of FIG. 133 showing the clip 3301 removed from the carrier 3303.

With reference to FIGS. 141 to 144 a third embodiment of the connector will now be described. Unless described as otherwise below, the features and functioning of the connector should be considered the same as described for the first embodiment above, and like reference numerals indicate like parts with the addition of 200.

FIG. 141 is a cross sectional view of a third embodiment connector, showing the slide 3409 in a secured position. In this embodiment, the clip 3401 has a plurality of notches 3413. The notches 3413 may be evenly or unevenly spaced along the length of the clip. The carrier 3403 and head strap 3450 have spaces through which the clip may extend, if necessary. The carrier 3403 is formed with a slot 3403a and the head strap may be a hollow component or a component having an opening for receiving the clip 3401. The plurality of notches 3413, together with the slot 3403a formed in the carrier and the hollow head strap, allow the connector to provide some adjustability of the connector.

FIG. 142 is a cross sectional view taken through line A-A of FIG. 141. FIG. 143 is a cross sectional view taken through line A-A of FIG. 141 having the same the features and functioning of the connector of FIG. 142 with the addition of '. FIG. 143 shows a slot 3403a' formed in the carriage 3403'.

FIG. 144 is a cross sectional view taken through line B-B of FIG. 141 showing the relative position of the components using this alternative embodiment in the secured position.

Any one or more features from any embodiment may be combined with any one or more features from any one or more other embodiments.

The carrier has been described as a separate component to the combined detent/biasing means component. Alternatively, the carrier may be integrally formed with the detent/biasing means component.

The biasing means has been described as comprising a pair of resilient legs. Alternatively, the biasing means may comprise a single leg or more than two legs. In further alternatives, the leg biasing means may comprise any other type of spring element to act as a return mechanism for the slider.

The detent has been described as comprising a pair of resilient arms. Alternatively, the detent may comprise a single arm or more than two arms. The clip has been described as having a pair of notches. Alternatively, the clip may have a single notch or more than one notch. The number and position of the notches will correspond to the number and position of the complementary protrusions on the resilient arms.

The biasing means has been described as having two legs that move away from each other and are biased towards each other to urge the slider to the secured position. Alternatively, the legs may be deformed in another direction to provide a similar return action. For example, the legs may twist or bend along their length.

The features and characteristics of the legs may be modified to suit the application; that is, they can be modified to tune the force of on the slide as it moves between the secured and free position. The features and characteristics that may be chosen or designed to be modified include the angle of the legs, the thickness of the legs, and the angle of the lug.

In a further alternative embodiment, the combined detent/biasing means component may be formed in two parts. Each part would have an arm and a leg and would be held in place relative to the carrier by location features. In a further alternative embodiment, the detent/biasing means may be a single leg and arm combination that act on one side of the clip only. In this embodiment, the connector will have location features for securing the detent/biasing means in place together with guides and/or abutment features to ensure the components of the connector are correctly located relative to each other in view of the forces acting on the components by the arm/leg.

The biasing means and detent have been described as being integrally formed together. Alternatively, they may be separately formed components that may or may not be connected together.

The embodiments of the connector have been described as having a biasing means for urging the slide towards the secured position. In an alternative embodiment, the connector may not have a biasing means, but the slider could be held in the free and/or secured positions by other suitable mechanisms. For example, the connector may have one or more catches that hold the slider in the free and/or secured positions. Such catches may automatically engage the slider and/or carrier or may be features that are controlled by a user.

The carrier of the first embodiment is shown with two apertures for receiving a strap and the second embodiment is shown with a single aperture. Either embodiment may have one or two apertures. Alternatively, in either or both of embodiments the carrier may be integrally formed with the strap.

Figure 2:
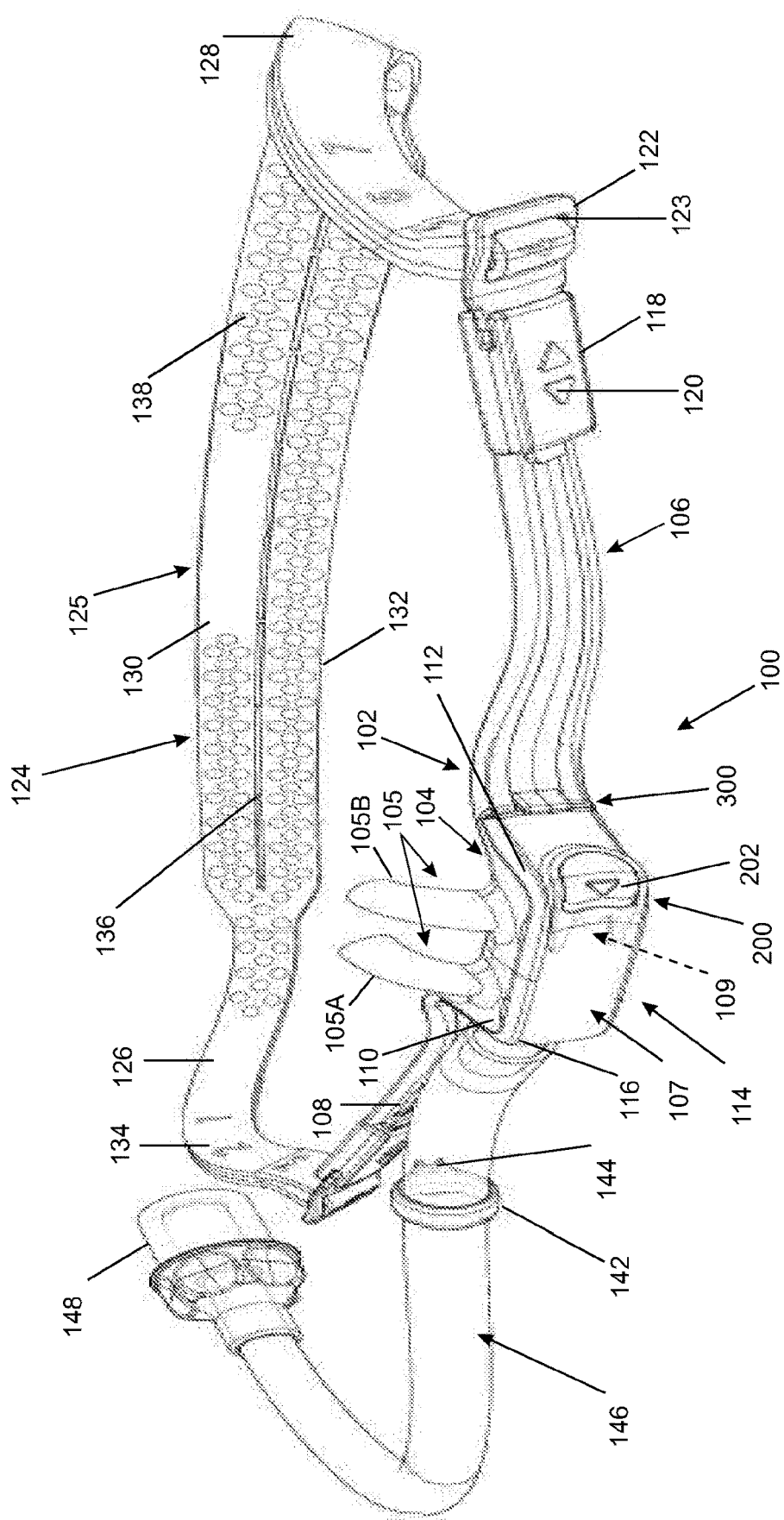
FIG. 2 shows a perspective view of a patient interface.

With reference to the non-limiting exemplary embodiment illustrated in FIG. 2, a patient interface 100 is shown. As illustrated the patient interface 100 comprises a nasal cannula. In some alternative configurations the patient interface 100 may comprise a sealing or non-sealing interface. For example, the patient interface 100 may comprise a nasal mask, an oral mask, an oro-nasal mask, a full face mask, a nasal pillows mask, an endotracheal tube, a combination of the above or some other gas conveying system or apparatus.

Figure 9:
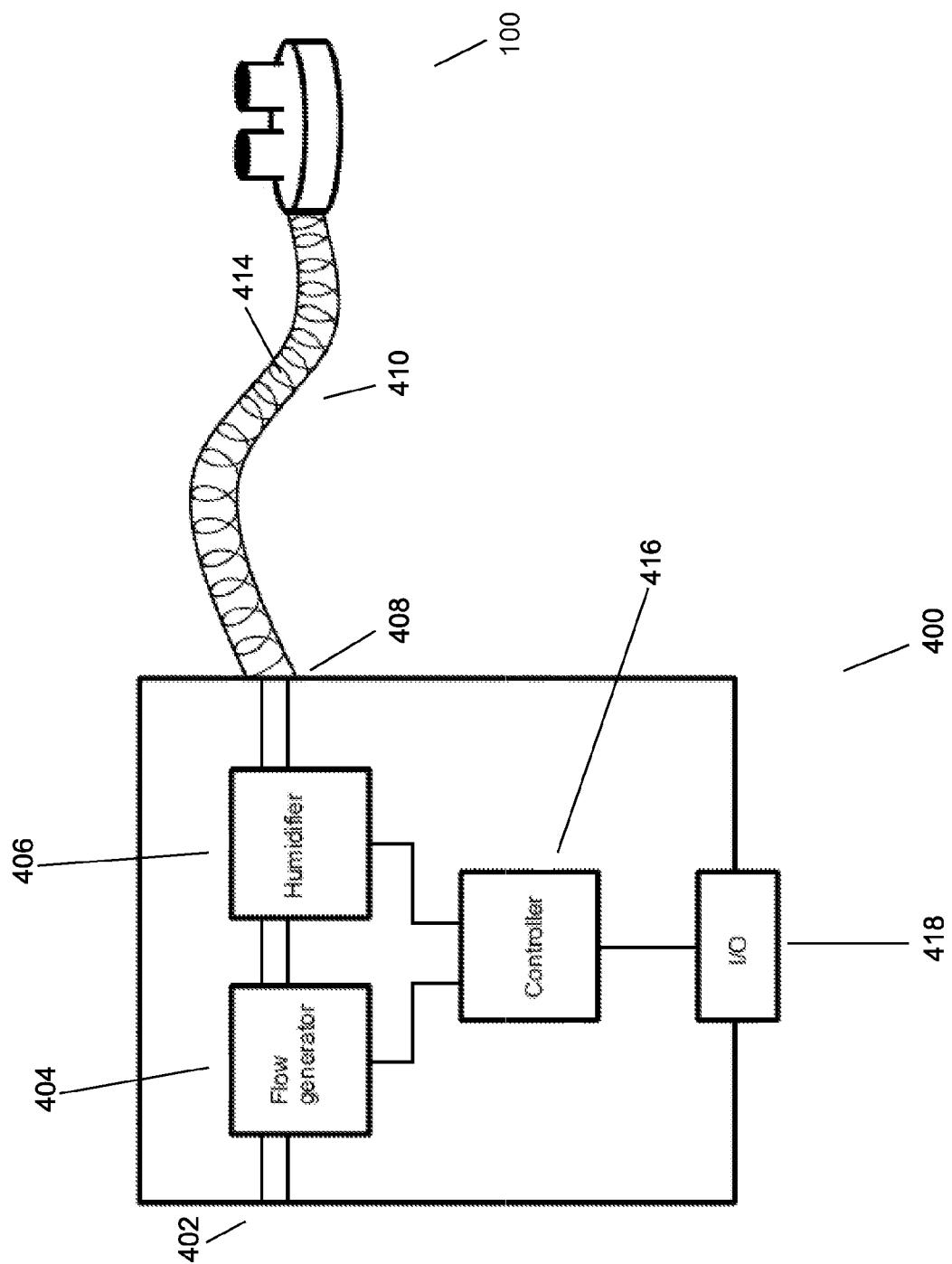
FIG. 9 illustrates the use of the patient interface in a respiratory therapy system.
Figure 10A:
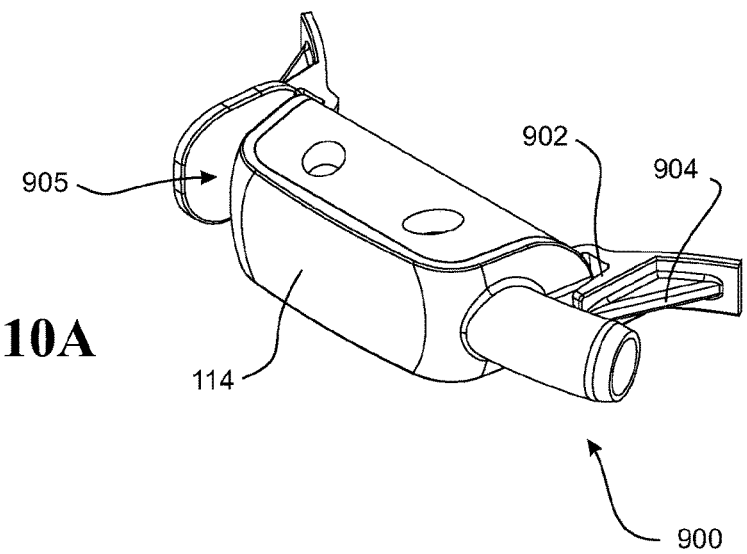
Figure 10B:
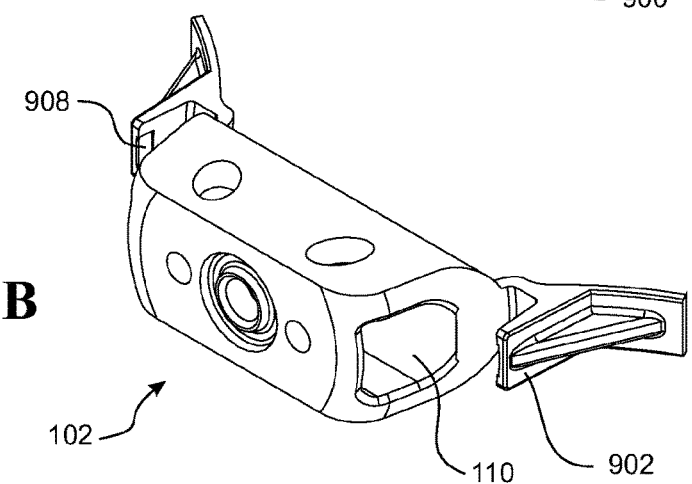
Figure 10C:
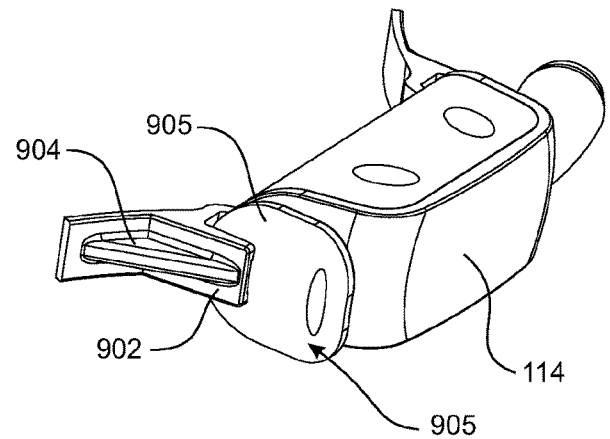
Figure 10D:
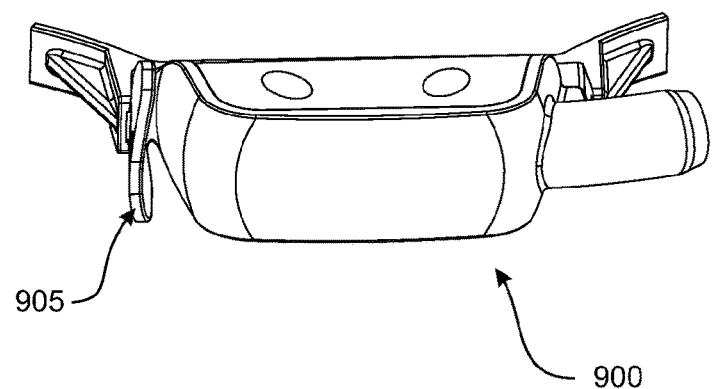
Figure 10E:
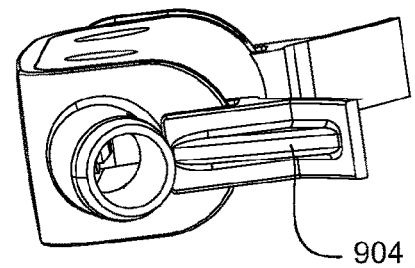
Figure 10F:
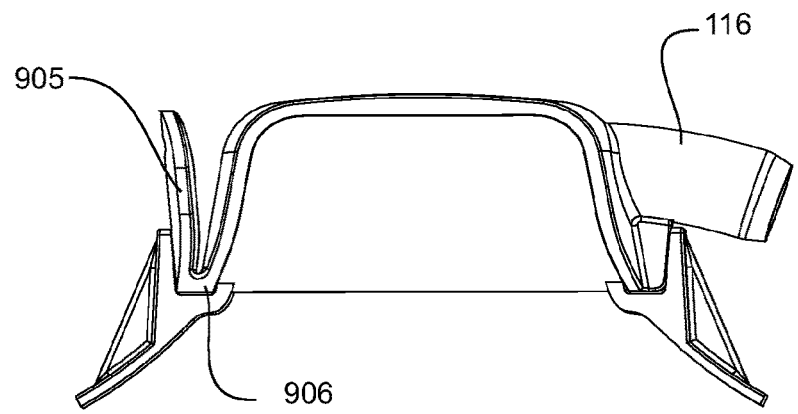
Figure 11A:
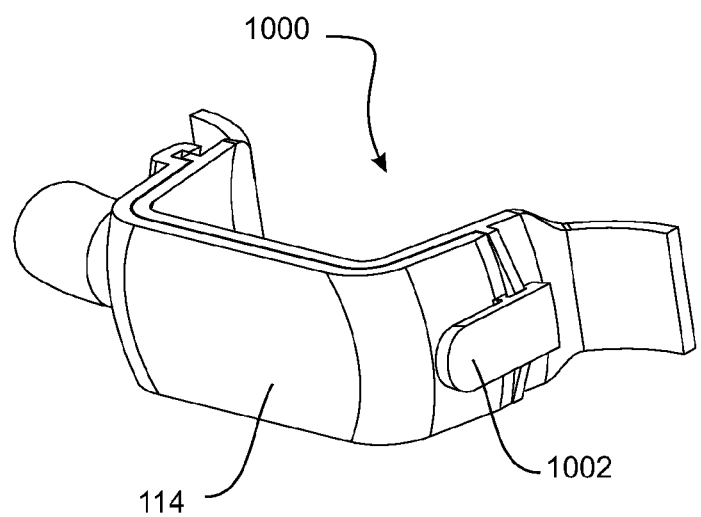
FIGS. 11A-11F show an alternative embodiment of components for the patient interface.
Figure 11B:
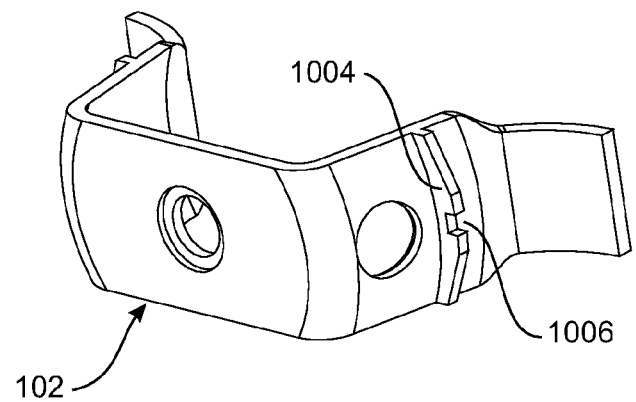
Figure 11C:
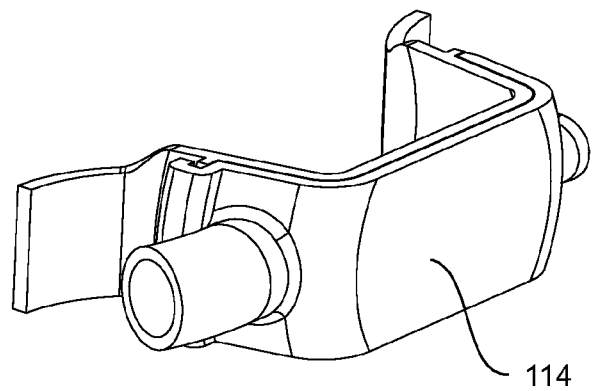
Figure 11D:
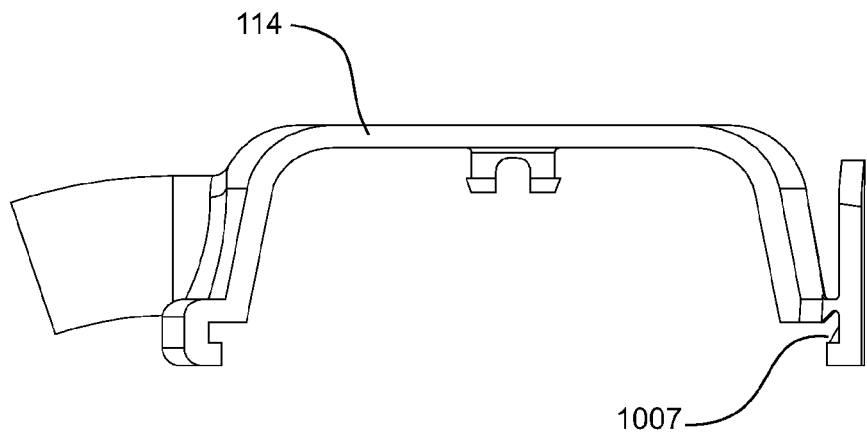
Figure 11E:
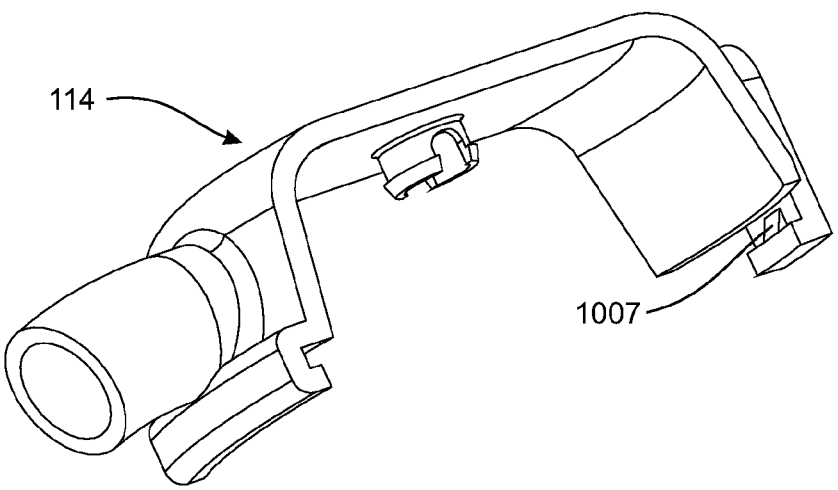
Figure 11F:
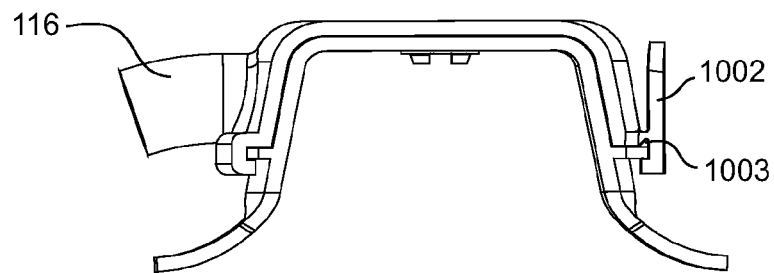
Figure 12A:
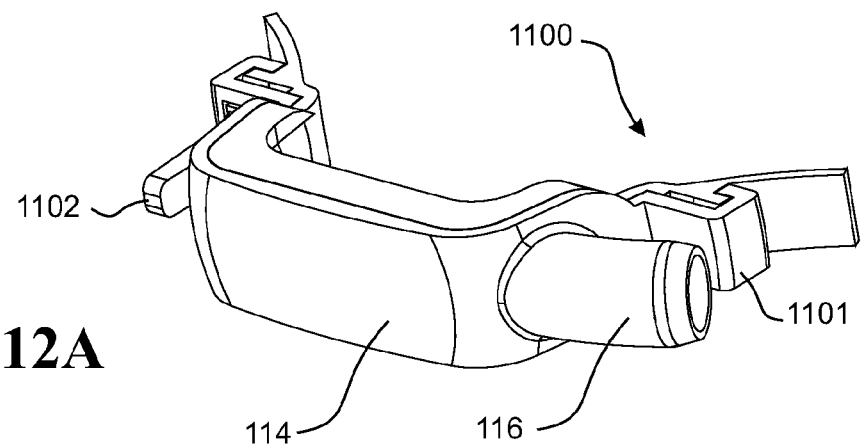
FIGS. 12A-12E show an alternative embodiment of components for the patient interface.
Figure 12B:
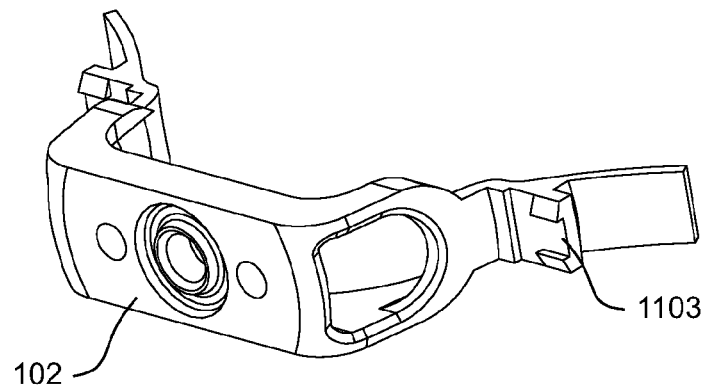
Figure 12C:
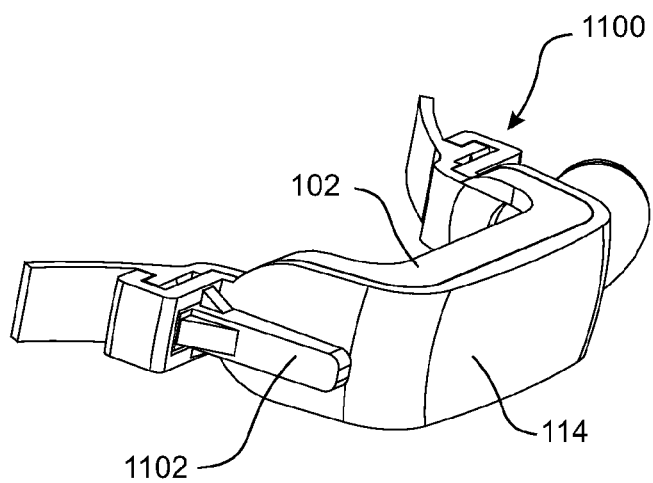
Figure 12D:
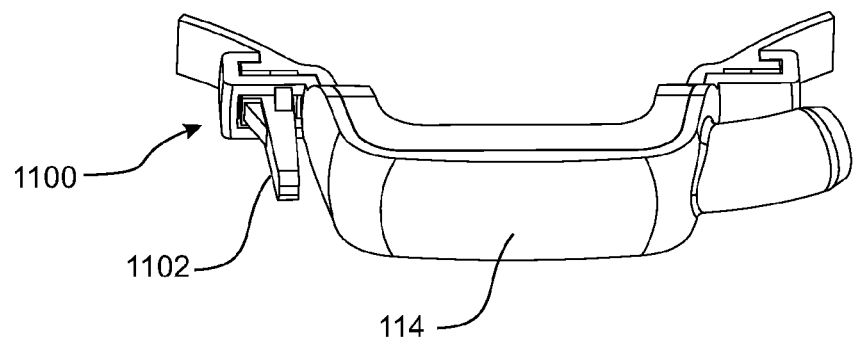
Figure 12E:
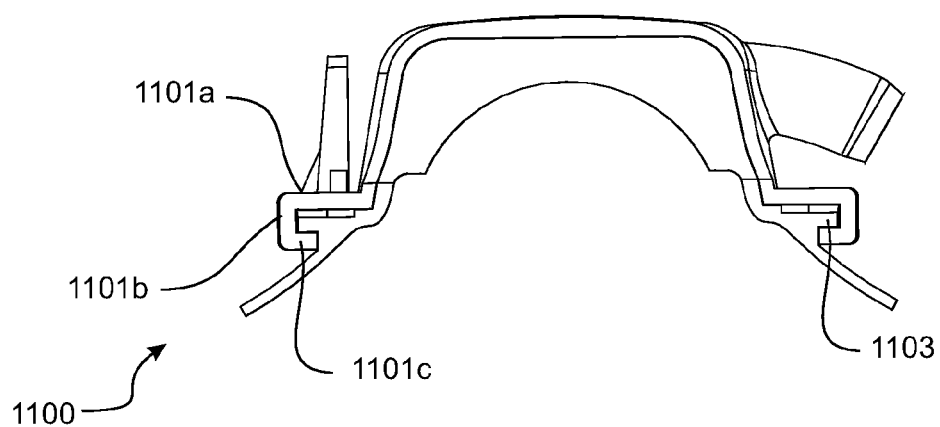
Figure 13A:
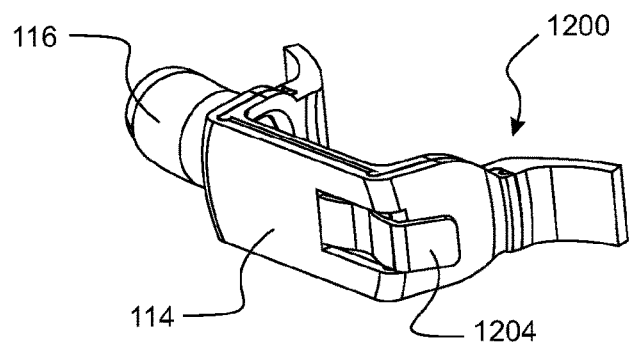
FIGS. 13A-13D show an alternative embodiment of components for the patient interface.
Figure 13B:
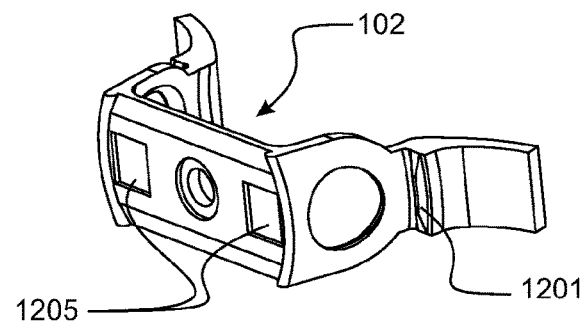
Figure 13C:
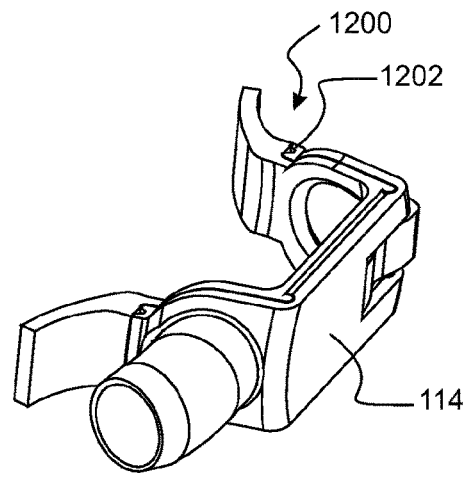
Figure 13D:
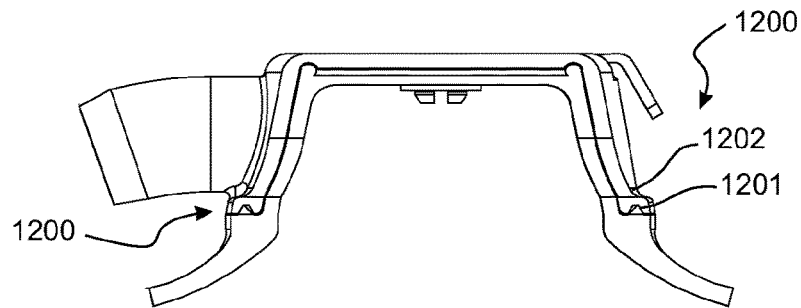

FIG. 9 illustrates the use of the patient interface 100 in a respiratory therapy system 400. The respiratory therapy system 400 comprises a flow generator 404. The flow generator 404 receives gases from a gases inlet 402 and propels them to a humidifier 406. The humidifier 406 heats and humidifies gases. Heated and humidified gases are passed through a gases outlet 408. Gases move from the gas outlet 408 to a gas conduit 410. The gas conduit 410 comprises a heater 414 that reduces or prevents the condensation of moisture along the walls of the gas conduit 410. The heater 414 can comprise a resistive heating wire. The respiratory therapy system 400 comprises a controller 416 that controls the operation of the flow generator 404. The controller 416 also controls the operation of the humidifier 406. The respiratory therapy system 400 comprises an input/output module 418. The input/output module (I/O) 418 allows a user to interact with and set parameters for the flow generator 404 and/or humidifier 406, as well as receive information regarding the operation of respiratory therapy system 400 and its components. The I/O module 418 may comprise, for example, buttons, knobs, dials, switches, levers, touch screens, speakers, displays and/or other input or output elements. In some configurations, the humidifier 406 may not be present. In some configurations, the gas conduit 410 may not have a heater 414.

With further reference to FIG. 2, the patient interface 100 comprises a frame portion 102. The frame portion 102 comprises a contact region 104 that contacts a user in use. At least a part of the contact region 104 sits under a nose or under nares of a user in use (for example, on the lip superior). The frame portion 102 also comprises a non-contact region 107 that faces away from the user in use. In the illustrated configuration, the non-contact region 107 is formed from a relatively hard or rigid material (for example polycarbonates and/or polypropylene) that provides support to the frame portion 102. The contact region 104 comprises a relatively soft, flexible or pliable material (including but not limited to foams, gel-based materials, silicones and/or thermoplastic elastomers) that can be positioned against the face of a user. The contact region 104 is overmoulded or co-moulded onto the non-contact region 107. Soft or flexible materials used in the contact region 104 to increase comfort to the user and may form a soft pillow-like structure that rests in contact with the patient. In some configurations, the contact region 104 may be secured to the non-contact region 107 by other means, including but not limited to adhesives, ultrasonic welding, and/or mechanical fasteners. In some configurations, the frame portion 102 may only comprise a single material.

The frame portion 102 also comprises a gases chamber 109 within the frame portion 102 that can receive gas from a gas source. Gas received into the gases chamber 109 can be channeled to the user through a gas delivery element 105. The gas delivery element 105 delivers gases to the user substantially or completely through the nose, and comprises first and second nasal delivery elements 105A, 105B, such as nasal prongs that are adapted to be fitted into the nares of the user. In the illustrated configuration, the nasal delivery elements 105A, 105B engage with the nares to form an unsealed engagement. In some alternative configurations, the nasal delivery elements 105A, 105B may seal with the nares, or the nasal delivery elements 105A, 105B may have different sealing qualities (for example, the first nasal delivery element 105A may be adapted to sealingly engage with one nare and the second nasal delivery element 105B may not sealingly engage with another nare). In further alternative configurations, the gas delivery element 105 may only comprise a single nasal delivery element, or may only comprise one or more apertures that communicate gases to a nasal, oral, and/or tracheal airway of a user.

The frame portion 102 comprises a first side arm 106 and a second side arm 108. The first and second side arms 106, 108 extend laterally from the frame portion 102 on substantially opposing sides of the frame portion 102, although in some configurations they may extend in other directions or from other sides. The first and second side arms 106, 108 help to support the frame portion 102 and generally rest on a patient's face (e.g. on the cheeks or adjacent the cheeks). The side arms 106, 108 comprise headgear retaining mechanisms 118 adapted to hold headgear 124. As shown, the headgear retaining mechanisms 118 comprise buckles 120. The buckles 120 are adapted to retain buckle carriers 122 each comprising a pair of slots 123 through which sections of headgear 124 can be looped and secured through the use of, for example, hook-and-loop fasteners present on the sections of the headgear 124. In some configurations, the buckle 120 can be made from a relatively hard or rigid material, and the buckle 120 can comprise an overmoulded layer of a relatively soft material. The relatively soft material may be present on a side of the buckle 120 that contacts the face of the user in use. The headgear retaining mechanisms 118, buckles 120 and corresponding features on the patient interface 100 can be the same as or similar to those described in commonly-owned U.S. 62/013,912, which is hereby incorporated by reference in its entirety. In some configurations, no side arms could be present, or only the first side arm 106 or second side arm 108 could be present, and the headgear 124 could interface with the frame portion 102 at other parts of the frame portion 102.

In some configurations, headgear 124 can be secured to the frame section 102 in other manners, for example, the headgear 124 can be overmoulded, co-moulded, or ultrasonically, or RF (radio-frequency) welded onto the frame section 102, stitched to the frame section 102, or adhered through the use of an adhesive substance. In some configurations, other retaining structures such as for example hook-and-loop fasteners, zip fasteners, domes, hooks, or clips could be used. In further alternative configurations, the headgear 124 could be integrally formed with the frame section 102.

As shown, the headgear 124 comprises a central strap portion 125 adapted to be located generally around the back of the head of a user (for example, over parietal and/or occipital portions of the head) and first and second side strap portions 126, 128 generally laterally extending from the central strap portion 125 and adapted to be located generally on the sides of the head of a user (for example, over cheek, zygomatic, temporal, and/or sphenoid portions of the head). The central strap portion 125 comprises a pair of straps 130, 132 linked by one or more bridging sections 136. The bridging sections 136 are adapted to be breakable or cleavable by a user, such that the straps are bifurcatable. For example, the bridging sections 136 may be thin or structurally weak (e.g. the bridging sections 136 may comprise a lower thickness, material strength, and/or structural integrity than the straps 130, 132) such that if the straps 130, 132 are forced apart with a force greater than a threshold level of force, the bridging sections 136 can be divided and the straps 130, 132 can be moved farther apart (e.g. the straps 130, 132 may become capable of a greater level of movement apart from one another). The greater level of movement may allow the straps 130, 132 to support different regions of the head. For example, the first strap 130 may be used to support a mid-parietal section of the head and the second strap 132 may be used to support a mid-occipital section of the head.

Bifurcatable straps may allow for a greater level of adaptability to different user anatomies or for a greater level of user comfort. Bifurcatable straps may also promote improved stability of the headgear 124 (e.g. by preventing excessive movement of the patient interface 100 away from the head). In some configurations, the central strap portion 125 may comprise more than two straps. For example, the central strap portion 125 can comprise three or four straps. In some such configurations, some or all of adjacent pairs of the more than two straps can be joined by bridging sections. In some configurations, the central strap portion 125 may only comprise a single strap, and there may be no bifurcatable component. In some configurations, the bridging sections 136 can be formed from different materials than the rest of the central strap portion 125 (e.g. softer, weaker, or less durable materials than the straps 130, 132). In some configurations, the bridging sections 136 may serve to support the rest of the central strap portion 125. In some configurations, the bridging sections 136 may be more rigid, more durable, or stronger than the straps 130, 132. In some configurations, the first and/or second side strap portions 126, 128 may also be bifurcatable, either separately from the central strap portion 125 or together with the central strap portion 125, or the first and/or second side strap portions 126, 128 may comprise more than one strap. Optionally, an upper and lower rear strap portions of a headgear can be moveable relative to each other and may be configured to allow for auto or a self-adjustment of fitting to the head, the headgear fitting in a position to minimize forces on the septum of the nose while maintaining prongs in nose.

In the illustrated configuration, the headgear 124 comprises guides or markings 134. In the illustrated configuration the markings 134 are present on the first and second section side strap portions 126, 128, and can help to indicate to a user the tightness or looseness of a headgear fit (for example, when used in conjunction with the buckle carrier 122). After looping the side strap portions 126, 128 through the slots 123 of the buckle carriers 122, the side strap portions 126, 128 may be drawn through the buckle carrier 122 until the desired markings 134 are viewable at the buckle carriers 122 or along the surface of the side strap portions 126, 128. The markings 134 help to guide a user to adequately tighten the headgear. In particular the markings 134 help to guide the user to evenly distribute the headgear 124 between the buckles 120 such that the central and side strap portions 125, 126, 128 are positioned correctly or optimally on the head on the user, and can likewise help the user to understand that the portions 125, 126, 128 are in the correct or optimal position. For example, if the same marking 134 is shown at the buckle carriers 122 securing each side strap portion 126, 128, the correct or optimal position for the portions 125, 126, 128 is communicated to the user. The markings 134 comprise numbers 1 through 7 in series, where viewing '1' at a buckle carrier 122 indicates a 'tight' fit and viewing '7' at a buckle carrier 122 indicates a 'loose' fit.

If the fit is not comfortable or desired, the user can draw or push the side strap portions 126, 128 through the buckle carriers 122 (after first unsecuring the strap portion previously secured using hook-and-loop fasteners, for example) until a comfortable or desired fit is achieved (which can be designated by a different marking 134). The looped straps can then be secured again using, for example, the hook-and-loop fasteners described above or elsewhere in this disclosure. In alternative configurations, the markings 134 may comprise printed alphanumeric characters (e.g. 'S' for small, 'M' for medium, for large, 'T' for tight, etc), symbols (e.g. !, ?, %, \*, \*\*, \*\*\*), images, indentations, protrusions, or other information-conveying elements. The markings 134 are present on the outer surface of the side strap portions 126, 128. Alternatively the marking 134 may be covered with a transparent layer (e.g. an overmoulded or adhered resin) to keep the surface covered with markings 134 substantially smooth or to maintain a single texture along the surface. In further alternative configurations the markings 134 can be present on other sections of the headgear 124.

In the illustrated configuration, the headgear 124 comprises frictional elements 138. The frictional elements 138 help to prevent undesired sliding of the headgear 124 around the head of the user (for example, sliding due to oily or smooth hair, or due to oil or perspiration on the head of the user). When the headgear 124 is positioned correctly on the head of the user, the frictional elements 138 can help to prevent undesired re-positioning of the headgear 124 in use. As shown, the frictional elements 138 comprise printed circular shapes or dots present on both straps 130, 132 of the central strap region 125 and present on portions of the side strap sections 126, 128, although the frictional elements 138 could alternatively or additionally be present elsewhere on the headgear. In some configurations, the frictional elements 138 could have printed shapes of other geometries, such as triangles or rectangles. In some configurations, the frictional elements 138 could have patterns or grids of line. In some configurations, the frictional elements 138 can comprise other structures, including but not limited to protrusions, recesses, bumps, or channels, instead of or together with printed shapes.

The patient interface 100 also comprises a manifold 114 that receives gas from a gas source through a manifold inlet 116. The manifold inlet 116 is, at least in some orientations or configurations, in pneumatic communication with the gases chamber 109 of the frame portion 102. The manifold inlet 116 communicates with the gas source through a gas conduit 146 that interfaces with the gas source via a gas source connector 148. The gas source connector 148 may be adapted to swivel or engage in rotary motion relative to the conduit 146 and/or to the gas source. In some alternative configurations, the gas source connector 148 may interface with a gas humidifier or other respiratory therapy device that may be in pneumatic communication with the gas source. A conduit clip 142 can be present on the gas conduit 146. FIG. 2 shows an example of the conduit clip 142. The conduit clip 142 comprises protrusions 144 that can engage with recesses or apertures present on one or both of the first and second side arms 106, 108 of the frame portion 102. The conduit clip 142 supports the gas conduit 146 by retaining it in a set position relative to the frame portion 102, and can help to prevent undesired forces from being exerted on the manifold 114. The conduit clip 142 and corresponding features on the patient interface can be the same or similar to clips disclosed in commonly owned U.S. 62/013,957, which is hereby incorporated by reference in its entirety. The patient interface 100 also comprises a release mechanism 200 comprising a button 202 and a retention mechanism 300, each of which are described in further detail below or elsewhere in this disclosure with reference to the accompanying figures.

Several components of the patient interface 100, including the buckle 120, buckle carrier 122, gas source connector 148 and button 202 are contact points that are manipulatable by the user. Surfaces of the contact points may comprise the same colour, colour pattern, texture or symbol (e.g. red, green, blue, yellow, stripes, polka dots, bumps, hand icon) or may have colours, colour patterns, textures or symbols that stand out relative to colours, colour patterns, textures or symbols used for other parts of the patient interface 100 (e.g. safety orange, hot pink, bright yellow, zigzags, rippled surface). Indicating the contact points using similar or distinctive colours, colour patterns, textures or symbols can help a user to understand the locations and uses of various configurable parts of the patient interface 100.

Figure 3A:
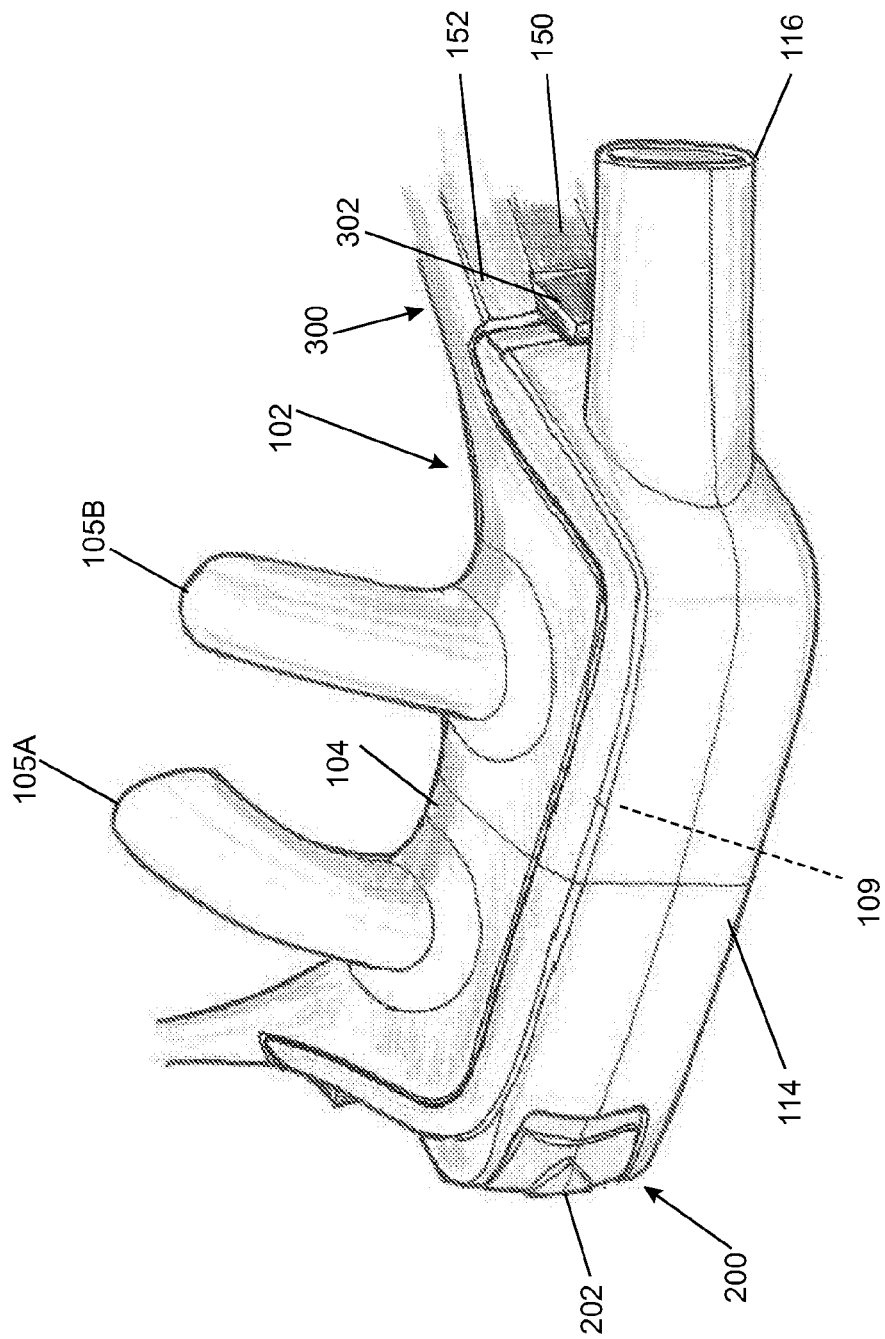
FIG. 3A shows a perspective view of a portion of a patient interface.
Figure 3B:
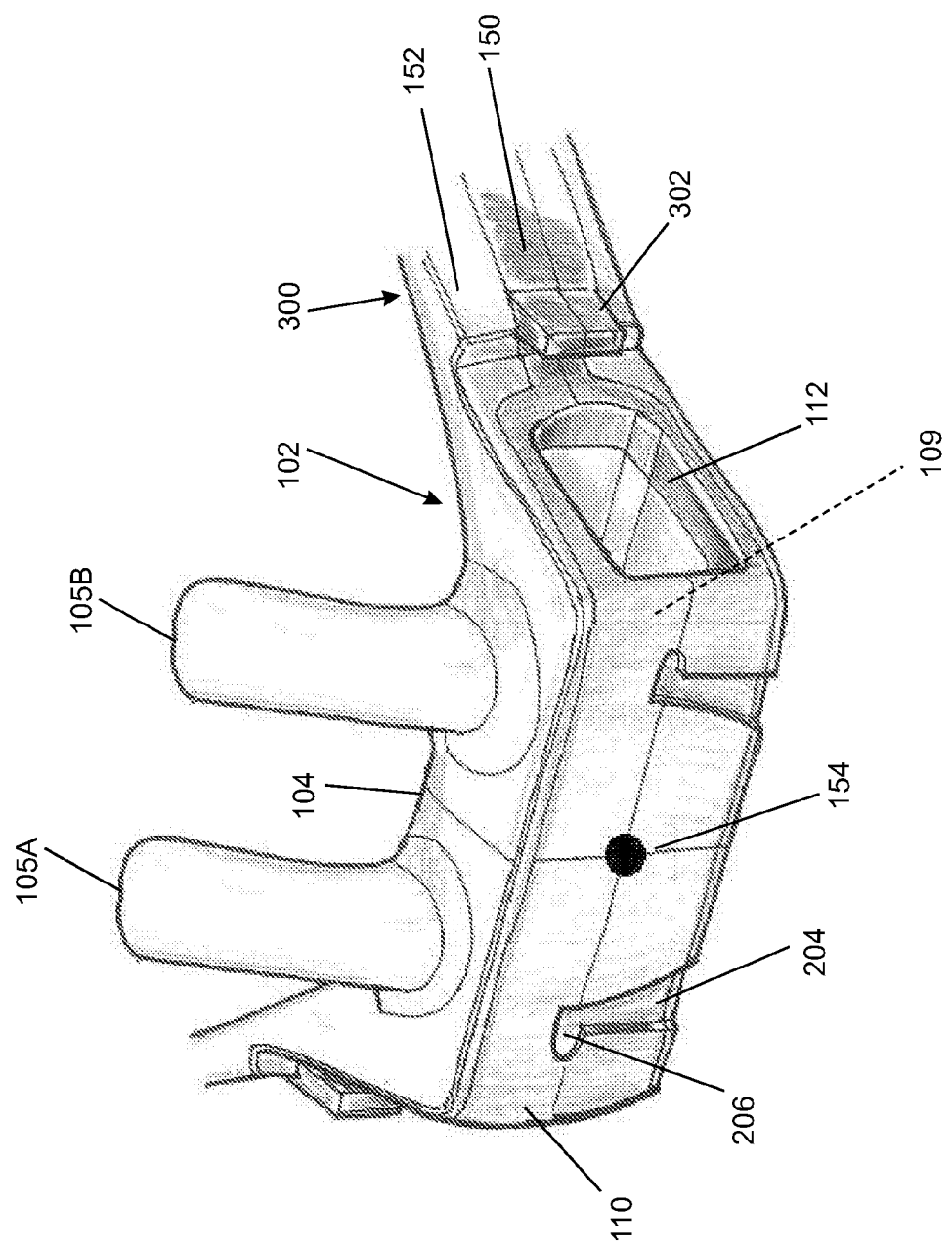
FIG. 3B shows a perspective view of the portion shown in FIG. 3A wherein the manifold has been removed.

FIGS. 3A-3B show an exemplary non-limiting embodiment of a central section of the patient interface 100. As shown and described elsewhere in this disclosure, the frame portion 102 comprises a relatively hard or rigid section 150 and a relatively soft or flexible section 152. The manifold 114 is relative to the frame portion 102, for example rotatably secured to the frame portion 102, or secured in such a way that the manifold 114 can rotate or swivel relative to the frame portion 102, or vice versa, such that the frame portion 102 can rotate or swivel relative to the manifold 114. The manifold 114 may be rotatably secured such that the range of rotary motion between the manifold 114 and the frame portion 102 can be a full 360 degrees. In other embodiments the range of rotary motion may be limited to less than 360 degrees.

For example, the range of rotary motion between the manifold 114 and the frame portion 102 may be limited to 90 degrees or approximately 90 degrees, 100 degrees or approximately 100 degrees, 110 degrees or approximately 110 degrees, 120 degrees or approximately 120 degrees, 130 degrees or approximately 130 degrees, 140 degrees or approximately 140 degrees, 150 degrees or approximately 150 degrees, 160 degrees or approximately 160 degrees, 170 degrees or approximately 170 degrees 180 degrees or approximately 180 degrees, 190 degrees or approximately 190 degrees, 200 degrees or approximately 200 degrees, 210 degrees or approximately 210 degrees, 220 degrees or approximately 220 degrees, 230 degrees or approximately 230 degrees, 240 degrees or approximately 240 degrees, 250 degrees or approximately 250 degrees, 260 degrees or approximately 260 degrees, 270 degrees or approximately 270 degrees. 180 degrees or approximately 180 degrees.

In the illustrated configuration, the manifold inlet 116 is only in substantial pneumatic communication with the gases chamber 109 when the manifold inlet 116 is positioned over or near first or second frame gas inlets 110, 112 of the frame portion 102, although in some configurations the manifold inlet 116 may be in substantial pneumatic communication with the gases chamber 109 of the frame portion 102 in more or less than two orientations.

As shown most clearly in FIG. 3B, the rigid section 150 of the frame portion 102 comprises an axle structure 154 that facilitates rotary motion between the manifold 114 and the frame portion 102. The axle structure 154 comprises a protrusion that can be forced through a complementary aperture of the manifold 114. In a preferred configuration, the axle structure 154 is used to permanently rotatably couple the manifold 114 and the frame portion 102. In some alternative configurations the axle structure 154 may allow for separation of the manifold 114 and the frame portion 102. In some such configurations, the manifold 114 and the frame portion 102 may only be separated when the axle structure 154 is oriented in a certain position, or when manifold 114 is rotationally oriented in certain positions relative to the frame portion 102. In some configurations, the axle structure 154 may comprise other mechanisms that allow for rotary motion between the manifold 114 and the frame portion 102.

As shown in the non-limiting exemplary embodiment illustrated in FIGS. 4A-4C, the axle structure 154 is secured to the frame portion 102. The axle structure 154 may be integrally formed with the frame section 102. Alternatively the axle structure 154 may be attached in other ways including but not limited to one or more of adhesives, and hook-and-loop fasteners, complementary channels and ridges, or hooks.

The axle structure 154 comprises a protrusion section 154A and a base 154B, although in some configurations the base 154B may not be present. The protrusion section 154A comprises a first leg 154A1 and a second leg 154A2. The legs 154A1, 154A2 comprise heads 154A3, 154A4 comprising a bevelled top section and a flattened bottom section. As shown in the continuum illustrated in FIGS. 4A-4C, as the protrusion section 154A is forced through an aperture 156 in the manifold 114, the heads 154A3, 154A4 of the legs 154A1, 154A2 are urged inwardly towards one another as walls of the manifold 114 defining the aperture 156 pass along the bevelled top section of the heads 154A3, 154A4 (see FIG. 4B). After the heads 154A3, 154A4 clear the aperture 156, the heads 154A3, 154A4 outwardly move or snap back into their default positions (see FIG. 4C). The axle structure 154 is then set in place and is made difficult to detach (e.g. permanent) due to the flattened bottom section of the heads 154A3, 154A4. It should be understood that in some configurations the manifold 114 may instead comprise the axle structure 154 and the frame portion 102 may comprise the aperture 156. In some configurations, each of the manifold 114 and the frame portion 102 may comprise both an aperture and an axle structure. It should also be understood that in some configurations that the protrusion section 154A may only comprise a single leg, or that the protrusion section 154A may not comprise any legs. The protrusion section 154A may simply comprise a unitary structure that is flexible or pliable enough to be forced through the aperture 156.

With further reference to FIGS. 3A-3B, and as previously described, the frame portion 102 comprises a retention mechanism 300. The retention mechanism 300 helps to prevent undesired non-rotational motion of the manifold 114 (for example, bending) relative to the frame portion 102, which can arise in use due to forces generated by, for example, the conduit 146 described elsewhere in this disclosure with reference to FIG. 2. In the illustrated configuration, the retention mechanism 300 comprises posts 302 that substantially prevent lateral movement of the manifold 114 with respect to the frame portion 102 when the manifold 114 substantially covers the frame inlets 110, 112 (i.e. when the manifold is in an operative position to supply gases). In some alternative configurations, structures aside from posts 302 may be used, and other movements of the manifold with respect to the frame portion could be prevented. Those alternative configurations are described in more detail below. Additionally, the retention mechanism 300 helps to maintain a sealed gas passageway (e.g. a gas passageway not substantially directly exposed to the ambient environment outside of the patient interface 100) between the gases chamber 109 of the frame portion 102 and the manifold inlet 116 by urging the manifold 114 towards the frame inlets 110, 112 or at least by ensuring that the manifold 114 does not substantially move away from the frame inlets 110, 112 in certain rotational orientations.

Further the retention mechanism 300 preventing movement of the manifold 114, once the manifold 114 is in the operative position, helps to maintain a sealed gases passageway between the gases chamber 109 and the manifold 116. The retention mechanism 300 further prevents rotational motion, in certain rotational orientations of the manifold 114 relative to the frame portion 102. Specifically the retention mechanism 300 is configured to retain the manifold 114 between the frame 102 and the post 302. The manifold is retained by a friction fit to retain the manifold in the operational position. The friction fit retaining the manifold 114 is high enough to retain the manifold in the operational position when the interface 100 is in use, but the friction fit can be overcome by a user when the user is attempting to rotate the manifold. The retention mechanism 300 as shown is a part of the rigid section 150 of the frame portion 102, although in some configurations other sections of the frame portion 102 may comprise the retention mechanism 300.

Figure 5:
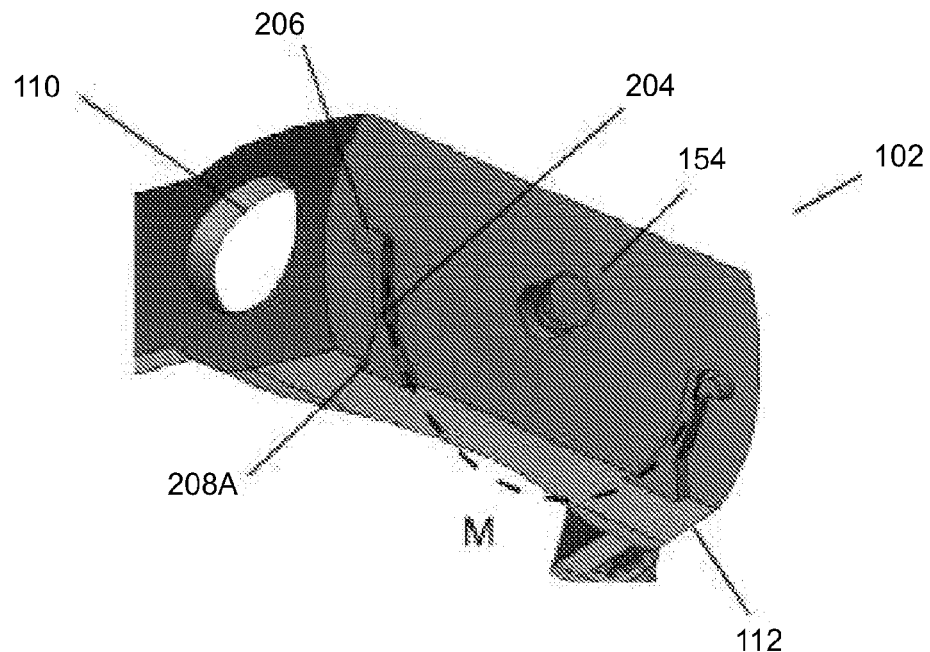
FIG. 5 shows a portion of a frame of a patient interface.
Figure 6:
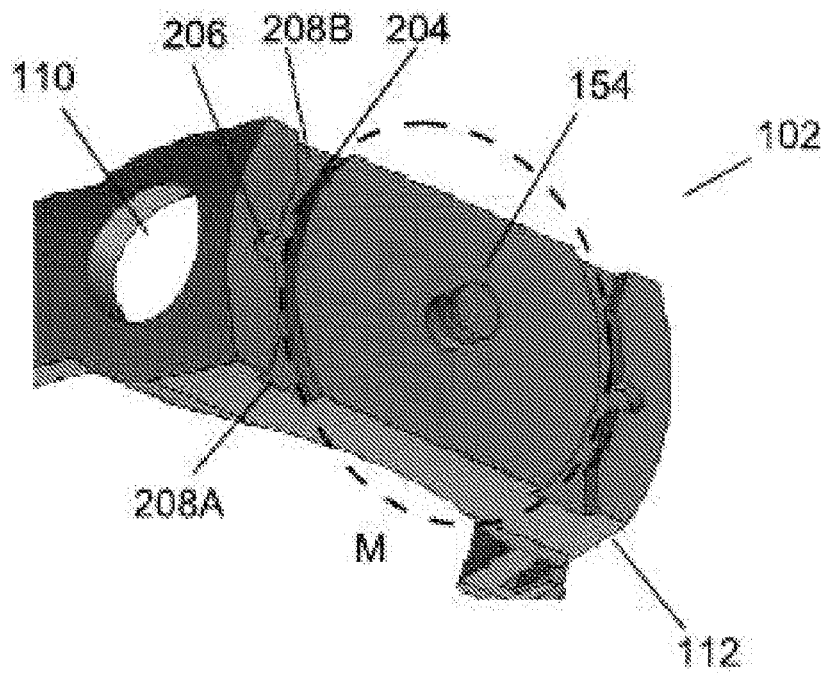
FIG. 6 shows a portion of a frame of a patient interface.

Referring again to FIG. 3B and to the non-limiting exemplary embodiments shown in FIGS. 5 and 6, the frame portion 102 also comprises recessed tracks 204 adjacent to the frame inlets 110, 112. The tracks 204 comprise detention regions 206. The tracks 204 act as channels through which a complementary boss 226 (see FIG. 7B) of the release mechanism 200 of the manifold 114 can move, thereby facilitating rotation of the manifold 114 with respect to the frame portion 102. The boss 226 has a range of motion indicated by dotted line M as shown in FIGS. 5 and 6, showing approximately 180 degrees of freedom of rotation (in FIG. 5) or approximately 360 degrees of freedom of rotation (in FIG. 6). In use, when entering a track 204, the boss 226 is urged to enter the track 204 from lead-in sections 208A (in FIG. 5) or 208B (in FIG. 6). In some alternative configurations the lead-in sections 208A, 208B may not be present. The boss 226 then passes along the track 204 and enters a detention region 206. The boss 226, naturally biased outwardly, moves into the detention region 206. Further rotational motion of the manifold 114 relative to the frame portion 102 is resisted due to the retainment of the boss 226 in the detention region 206.

Figure 7A:
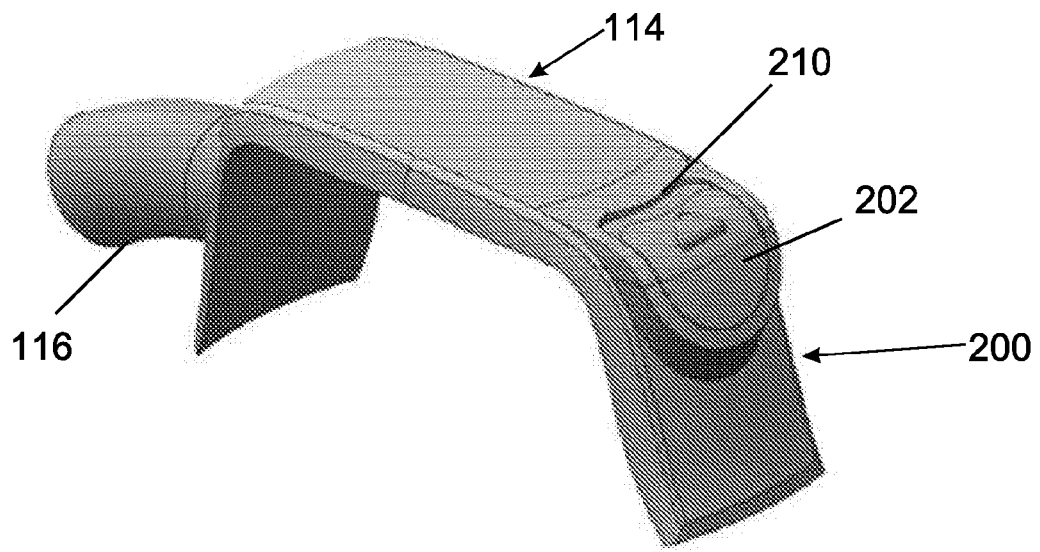
FIG. 7A shows a top-side perspective view of a manifold.
Figure 7B:
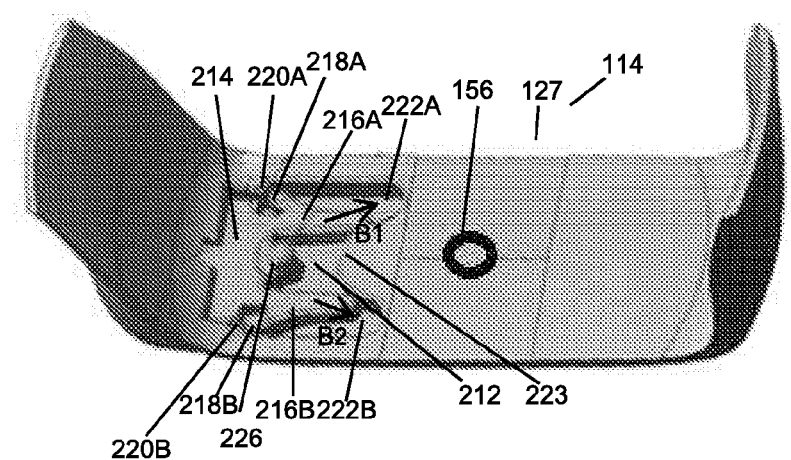
FIG. 7B shows a bottom perspective view of the manifold shown in FIG. 9A.

The non-limiting exemplary embodiment illustrated in FIGS. 7A-7B demonstrates further aspects of the release mechanism 200 of the manifold 114. The release mechanism 200 comprises a manually actuatable button 202. The button 202 can be depressed by sliding in a direction substantially parallel with a longitudinal axis of the manifold. The button is depressed until it hits a button stop 210. The button stop 210 is integrally formed with the manifold 114. Alternatively the button 202 can be a separate piece secured to the manifold 114.

FIG. 7B illustrates the underside 127 of the manifold 114 (manifold inlet 116 not shown). The underside 127 comprises a recess 212 in which a release body 214 sits. The release body 214 is inset in the recess 212 and connected to the button 202.

In the preferred embodiment shown, the release mechanism comprises a pair of resilient side arms 216A, 216B. The side arms 216A, 216B are substantially resistant to deformation or are resiliently flexible. As described in more detail below, the resilient side arms 216A, 216B urge the button towards the locked position. The side arms 216A, 216B extend from the release body 214 in the same direction and are the same length as each other. The sides of each side arm 216A, 216B are slightly tapered so that a free end of each side arm is narrower than an end that joins the release body 214. The free end of each side arm is rounded. The side surfaces, top surface and bottom surface of each side arm are substantially planar surfaces.

The wall of the underside 127 of the manifold 114 defining the recess 212 comprises side stops 220A, 220B against which elbows 218A, 218B of side arms 216A, 216B of the release body 214 rest for locating the release body in the locked configuration. The recess 212 comprises end regions 222A, 222B separated by a lug or bump section 223 of the underside 127 of the manifold 114. As shown in FIG. 7B, the lug 223 is centrally positioned within the recess 212. The lug 223 has two outwardly tapered surfaces with a rounded nose.

As shown, when the button 202 is depressed, the release body 214 is urged forward or towards the lug 223 and the side arms 216A, 216B splay outwardly into the end regions 222A, 222B (as indicated using arrows B1 and B2 shown in FIG. 7B) as they pass along the outwardly tapered surfaces of the lug or bump section 223. The lug or bump section 223 helps to bias the release body 214 back such that when the button 202 is released, the side arms 216A, 216B are compelled to fall back until the elbows 218A, 218B again rest against the side stops 220A, 220B.

The release body 214 also comprises the boss 226 described above or elsewhere in this disclosure with reference to FIGS. 5 and 6. The boss 226 can also help to bias the side arms 216A, 216B outwardly into the end regions 222A, 222B as it moves along the track 208 (comprising of tracks 280A and 208B). This is further demonstrated with reference to FIGS. 8A-8E.

Figure 8A:
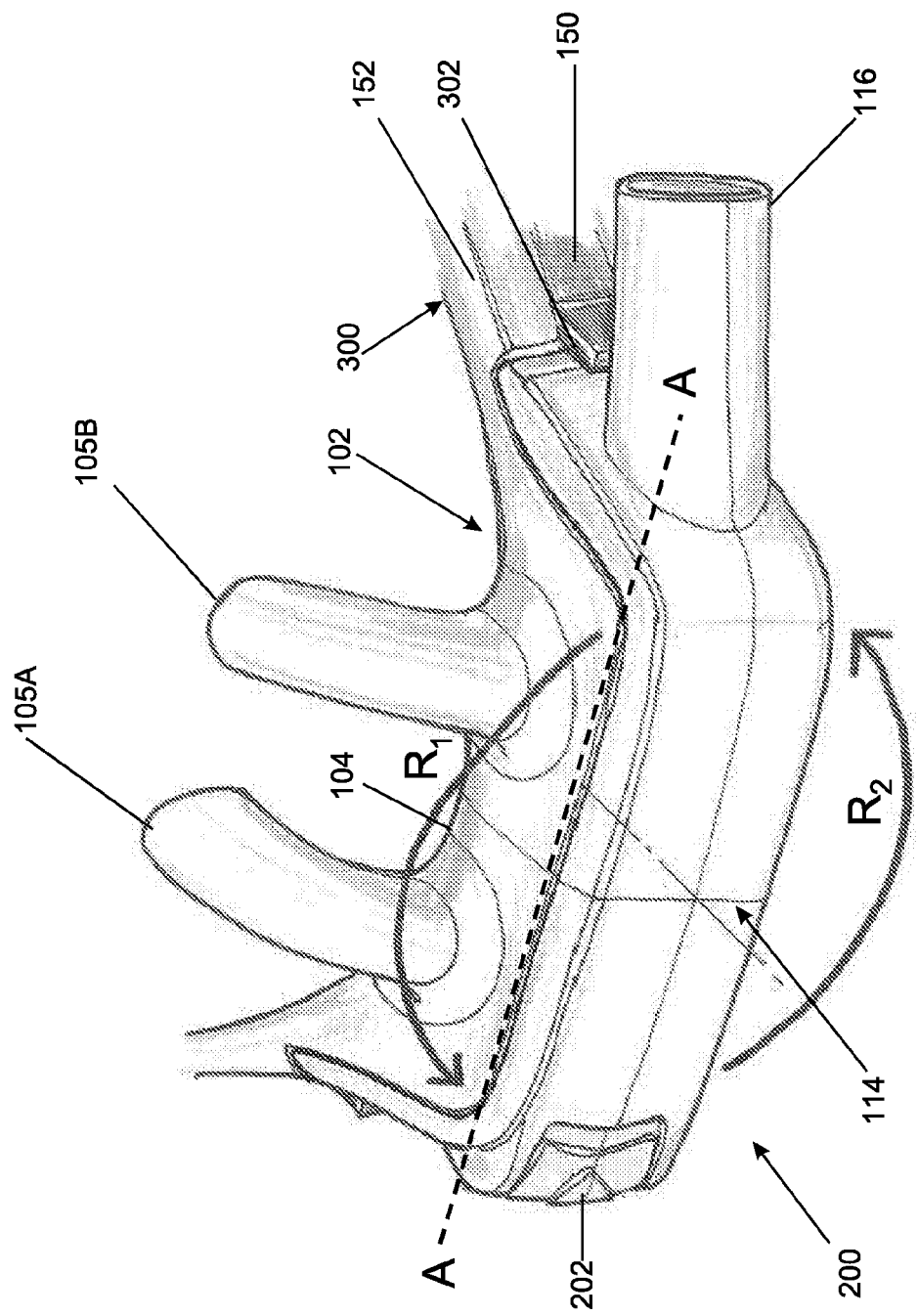
FIGS. 8A-8E show a method of usage of a rotating assembly of a patient interface.

With reference to the non-limiting exemplary embodiment shown in FIGS. 8A-8E, the operation of the release mechanism 200 is shown. FIG. 8A shows an operational position or default state of the patient interface 100 where the manifold inlet 116 is positioned over the frame inlet 112. In the illustrated position, the manifold inlet 116 is positioned to be in fluid communication with the gases chamber 109. In the illustrated position, as per FIG. 8B, the manifold 114 is retained in the operational position by a friction fit with the retention mechanism 300 and the release mechanism 200 being in a locked position. The locked position is described above and is the achieved when the boss 226 is positioned in the detention region 206. Curved arrows R1 and R2 demonstrate a rotary torque force applied to the manifold 114.

During operation of the release mechanism 200 and/or retention mechanism 300, movement of the button 202 or other components may provide sensory feedback to an operator about whether the retention mechanism 300 and the release mechanism 200 are locked or secured. The sensory feedback is audible feedback, tactile feedback, visual feedback, or a combination of two or more types of feedback. For example, the release mechanism 200 may provide feedback by a lug on the button 202 or release body 214 engaging a recess, aperture, or abutment surface on the manifold 114. The boss 226 described above may provide the sensory feedback. The button 202 or release body 214 may have more than one lug engaging with more than one recess, aperture, or abutment surface. The retention mechanism 300 may provide feedback by a lug on the manifold 114 engaging a recess, aperture, or abutment surface on the frame portion 102. For example, the manifold 114 may have the lug and the button 202 or release body 214 may have the recess, aperture, or abutment surface. In other alternative embodiments, complementary lugs and recesses may be on other combinations of components of the manifold 114 assembly, such as the manifold 114 and frame portion 102. In alternative embodiments, the button 202 or release body 214 may have the lug and the manifold 114 may have the recess, aperture, or abutment surface. In addition, the position of the components provides visual feedback to an operator.

Figure 8B:
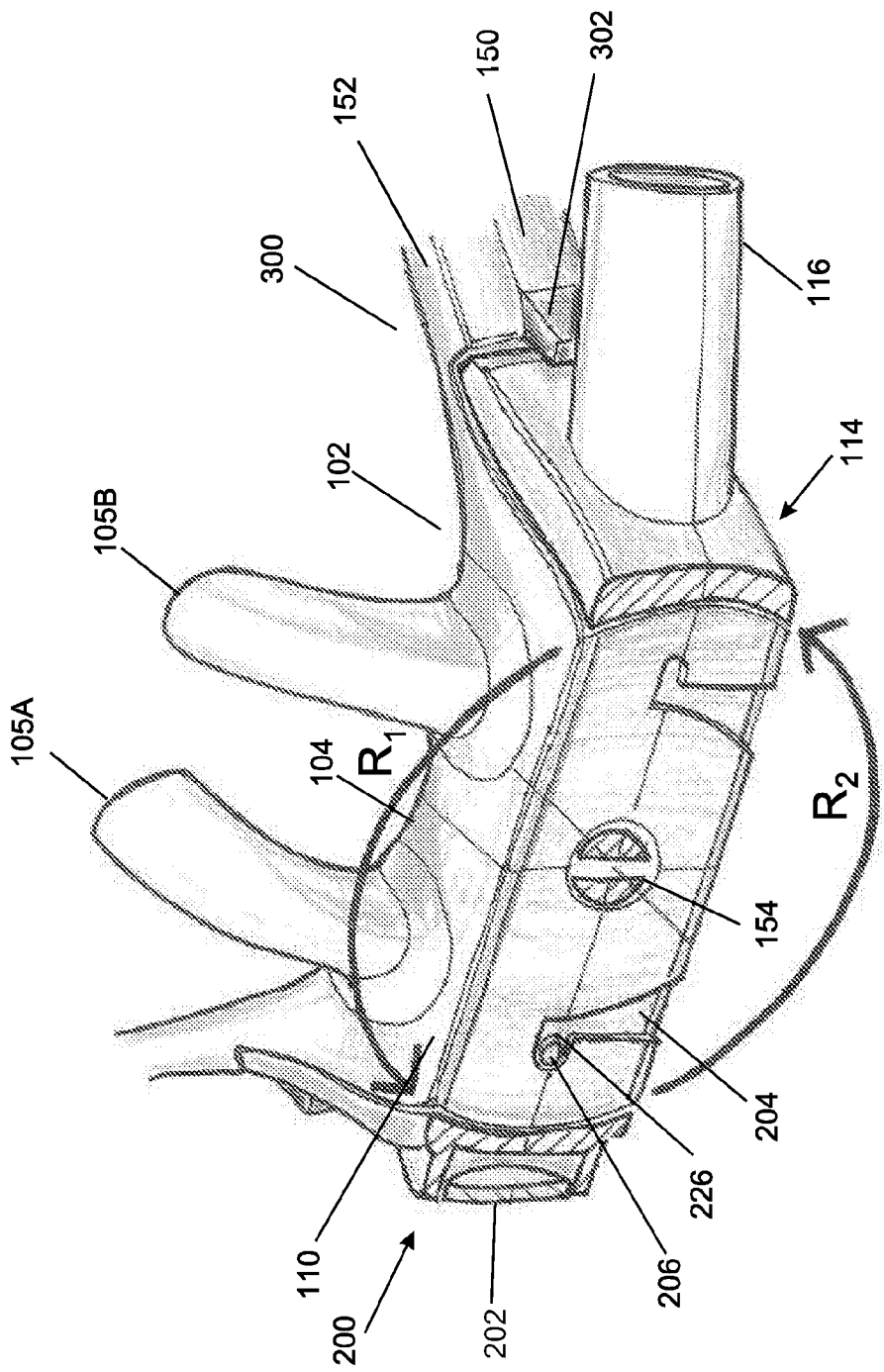
Figure 8C:
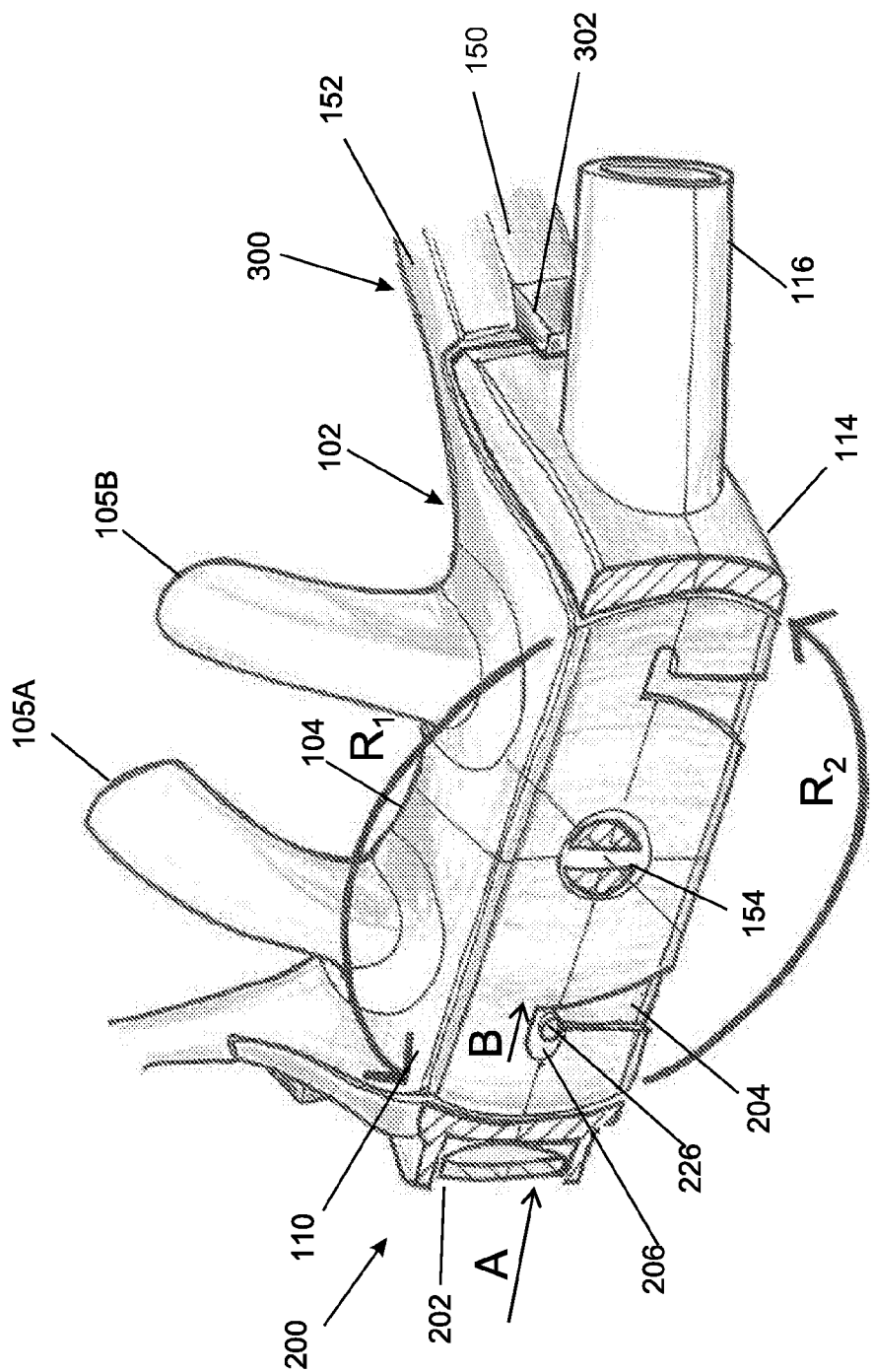
Figure 8D:
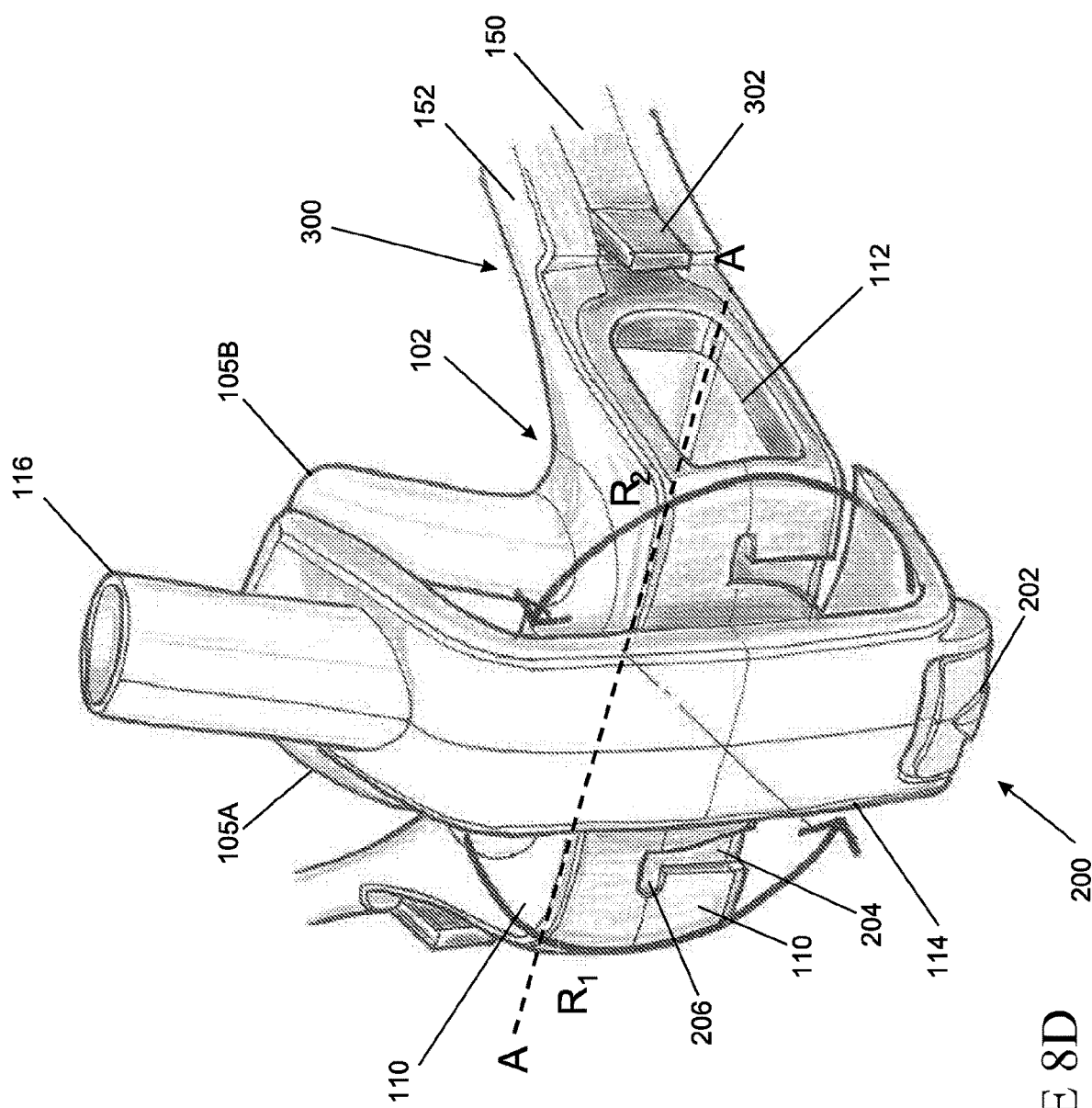
Figure 8E:
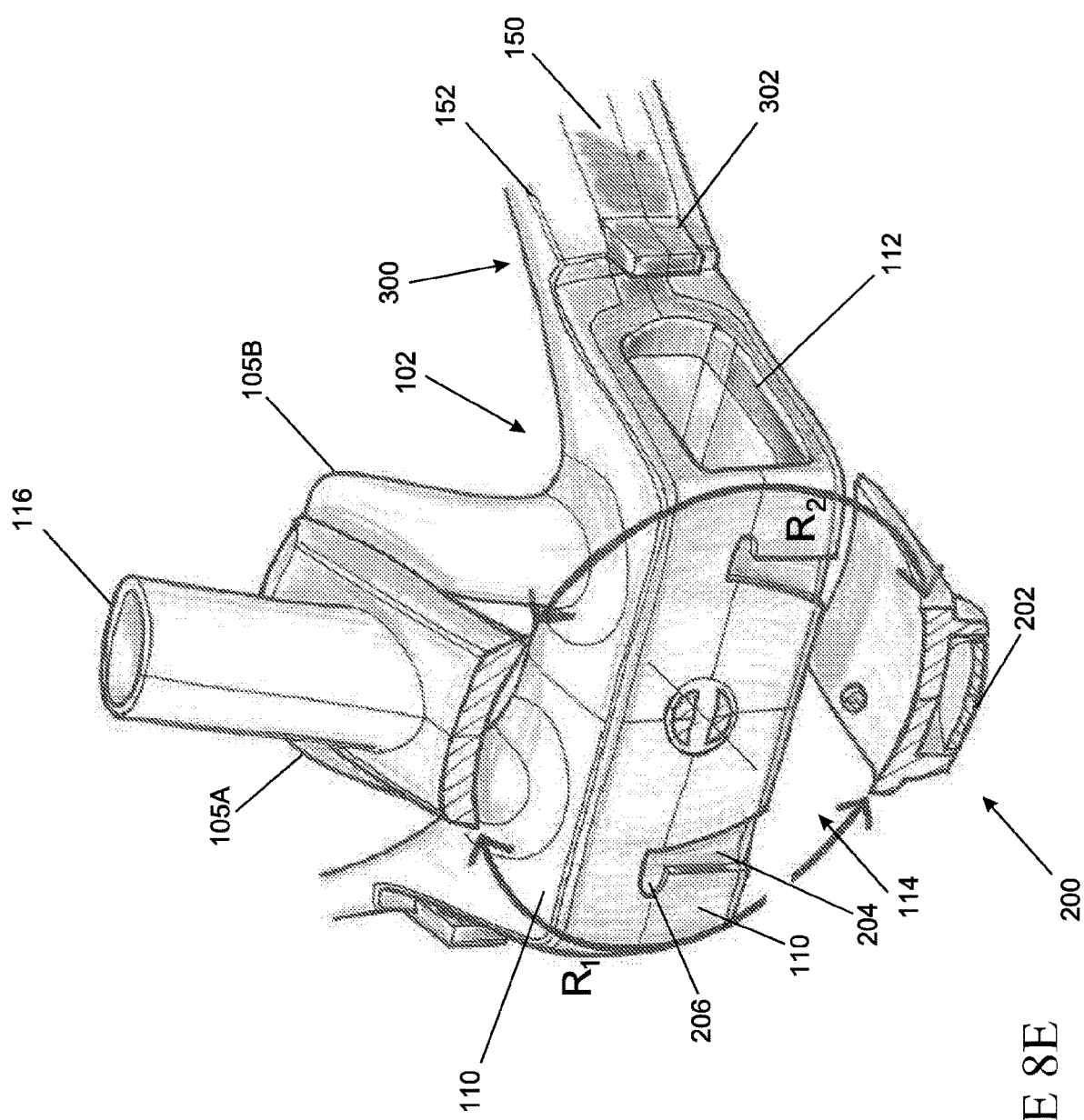

FIG. 8B shows a cross-section of the patient interface 100 along section A-A as shown using a dotted line in FIG. 8A. As shown, the boss 226 is held within the detention region 206 of the track 204 and the torque force applied to the manifold 114 along arrows R1 and R1 does not promote rotary motion between the manifold 114 and the frame section 102. As shown in FIG. 8C, as the button 202 is depressed (e.g. along arrow A), the boss 226 is forced outwardly out of the detention region 206 of the track 204 (e.g. along arrow B) as the side arms 216A, 216B of the release body 214 are splayed around the lug or bump section 223 and into the end regions 222A, 222B (see FIG. 7B). As demonstrated in FIGS. 8D-8E, because the boss 226 is permitted to exit the detention region 206 due to the depression of the button 202, the torque force along arrows R1 and R2 then causes rotational motion between the manifold 114 and the frame section 102 around the axle structure 154. The configuration illustrated in FIGS. 8A-8E allows a 180 degree range of rotational motion between the manifold 114 and the frame section 102. In some alternative configurations, the manifold illustrated in FIG. 6 may be used to allow a 360 degree range of rotational motion between the manifold 114 and the frame section 102.

The manifold has been described as a separate component to the combined release body/side arms component. Alternatively, the manifold may be integrally formed with the release body/side arms component.

The release mechanism has been described as comprising a pair of resilient side arms. Alternatively, the biasing means may comprise a single arm or more than two arms. In further alternatives, the biasing means may comprise any other type of spring element to act as a return mechanism for the slider.

Figure 27:
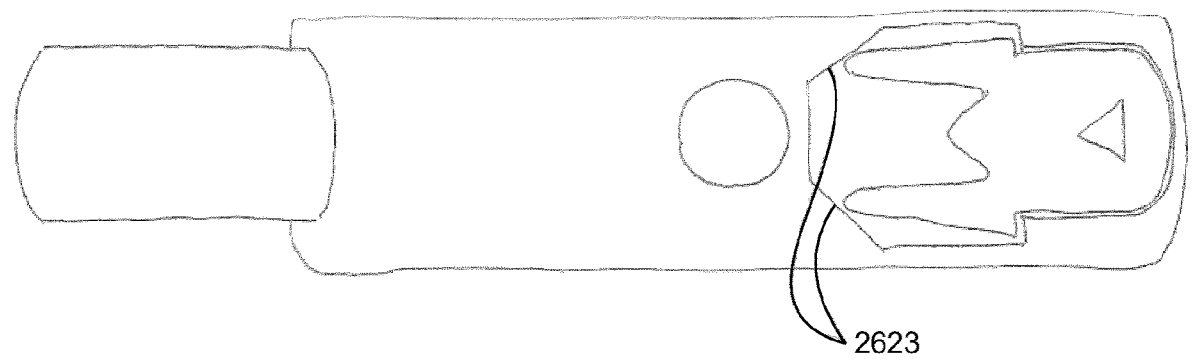
FIG. 27 shows an alternative embodiment of the components for the patient interface

The biasing means has been described as having two side arms that move away from each other and are biased towards each other to urge the button to the locked position. Alternatively, the side arms may be deformed in another direction to provide a similar return action. For example, the side arms may twist or bend along their length. FIG. 27 is a schematic drawing showing an alternative embodiment in which the arms move towards each other and are biased away from each other to urge the button to the locked position. Rather than being splayed around the lug or bump section, the arms are urged inwards by two converging surfaces 2623.

The features and characteristics of the side arms may be modified to suit the application; that is, they can be modified to tune the force of on the slide as it moves between the locked and free position. The features and characteristics that may be chosen or designed to be modified include the angle of the side arms, the thickness of the side arms, and the angle of the lug.

The release body and side arms have been described as being integrally formed together. Alternatively, they may be separately formed components that may or may not be connected together.

The embodiments of the patient interface have been described as having a biasing means for urging the button towards the locked position. In an alternative embodiment, the patient interface may not have a biasing means, but the button could be held in each of the positions by other suitable mechanisms. For example, the patient interface may have one or more catches that hold the button in the required position(s). Such catches may automatically engage the button and/or manifold or may be features that are controlled by a user.

FIGS. 10A-10I show an alternative embodiment of the manifold assembly, in particular, an alternative release and retention mechanism. This configuration is a combined release and retention mechanism 900. The retention mechanism 900 comprises posts 902 that substantially prevent lateral movement of the manifold 114 with respect to the frame portion 102 when the manifold 114 substantially covers the frame inlets 110, 112. Each of the posts has a strengthening rib or gusset 904 to increase the stiffness of the post to reduce or inhibit non-rotational movement between the manifold 114 and the frame section 102. This alternative retention mechanism may comprise more than one rib or gusset associated with each of the posts. Each rib or gusset may be wider or thinner than the gusset shown in the accompanying drawings and/or have a different shape. The release mechanism comprises a lever 905 that is separated from the manifold by a web section 906. The lever 905 has a protuberance 907 shaped to engage a complementary groove, recess, slot, or aperture 908 in the frame portion 1122. The complementary groove, recess, slot, or aperture is formed in the post 902. The manifold 114 is released by a user squeezing the lever towards the centre of the manifold, causing the protuberance of each the lever 905 to disengage from the recess, slot, or aperture and allowing the manifold to rotate.

FIGS. 11A-11F show an alternative embodiment of the manifold assembly, in particular, an alternative retention mechanism. The retention mechanism 1000 comprises an arm 1002 that substantially prevents lateral movement of the manifold 114 with respect to the frame portion 102 when the manifold 114 substantially covers the frame inlets 110, 112. The arm substantially prevents lateral movement by engaging with other features of the patient interface, which are described below. The arm 1002 is attached to the frame portion 102, for example, by a flexible integrally formed hinge. The arm 1002 has a slot 1003 that is shaped to engage a complementary outwardly extending flange 1004. The arm further comprises a protuberance 1007 extending towards the manifold 114. The manifold 114 has a complementary recess, slot, or aperture 1006 for receiving the protuberance. The recess, slot, or aperture 1006 is preferably formed in the flange, but may be formed in another part of the frame portion. The manifold is released by a user pressing an upper portion of the arm 1002 towards the manifold, causing the protuberance 1007 to disengage from the recess, slot, or aperture and allowing the manifold to rotate.

FIGS. 12A-12E show an alternative embodiment of the manifold assembly, in particular, an alternative release and retention mechanism. This configuration is a combined release and retention mechanism. The retention mechanism 1100 comprises a shaped flange 1101 that substantially prevents lateral movement of the manifold 114 with respect to the frame portion 112 when the manifold 114 substantially covers the frame inlets 110, 112. The flange 1101 substantially prevents lateral movement by engaging with a recess, described in detail below. The flange 1101 has a first horizontally extending portion 1101a, followed by a vertically extending portion 1101b, which is followed by another horizontally extending section 1101c. The sections of the flange form a generally C-shaped flange 1101 that surrounds an outwardly extending flange 1103 of the frame portion 102. This configuration further comprises an arm 1102 with a lower portion that is shaped to engage a complementary groove recess, slot, or aperture (not visible) in the frame portion 102. Either a portion of the arm, or the entire arm, is flexible to allow the arm to move as required. The recess, slot, or aperture is preferably formed in the flange, but may be formed in the manifold 114. The manifold 114 is released by a user pressing an upper portion of the arm towards the manifold, causing the lower portion of the lever to disengage from the recess, slot, or aperture and allowing the manifold to rotate.

FIGS. 13A-13D show an alternative embodiment of the manifold assembly, in particular, an alternative release and retention mechanism. This configuration has separate release and retention mechanisms. The retention mechanism 1200 comprises a triangular shaped ridge 1201 on the frame portion that engages a complementary triangular shaped channel 1202 on the manifold. When engaged, the channel and ridge act to substantially prevent lateral movement of the manifold 114 with respect to the frame portion 1122 when the manifold 114 substantially covers the frame inlets 110, 112. The release mechanism comprises an arm 1204 with a lower portion that is shaped to engage a complementary groove recess, slot, or aperture 1205 in the frame portion 1122. The arm further comprises a protuberance extending towards the manifold 114. The manifold 114 is released by a user pressing the free end of the arm towards the manifold, causing the lower portion of the lever to disengage from the recess, slot, or aperture and allowing the manifold to rotate. Either a portion of each arm, or the entire arm, is flexible to allow the arm to move as required.

Figure 14A:
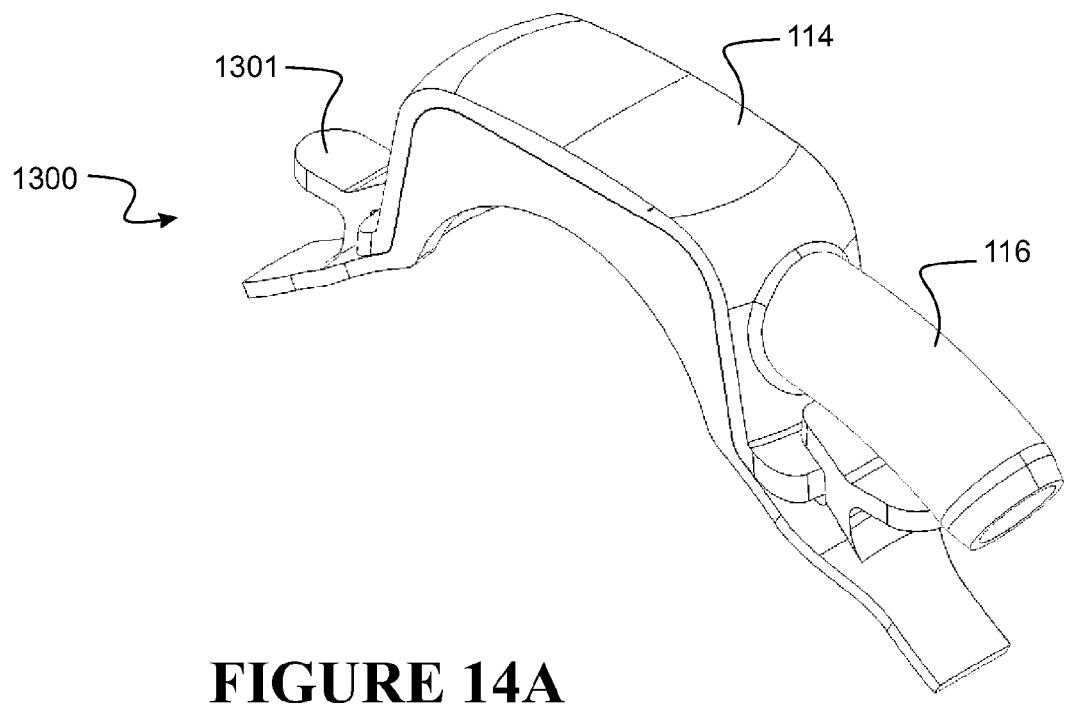
FIGS. 14A-14C show an alternative embodiment of components for the patient interface.
Figure 14B:
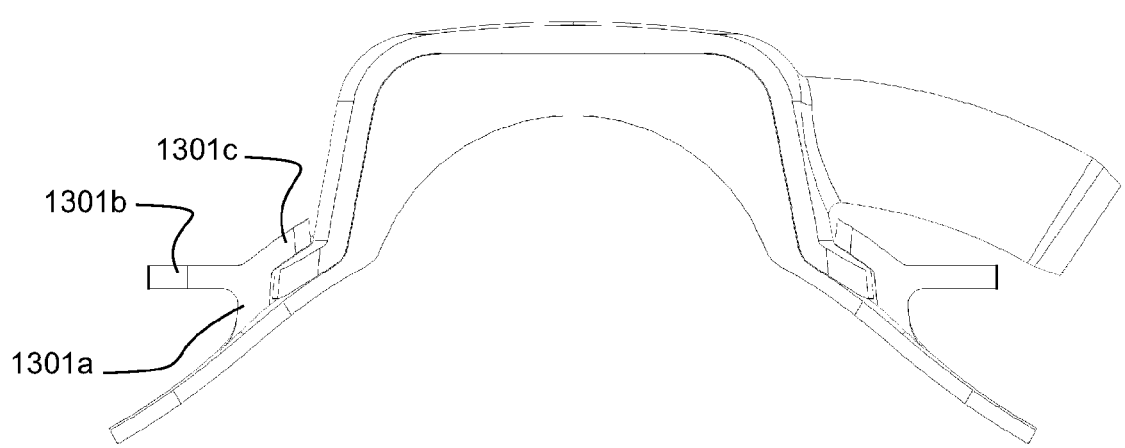
Figure 14C:
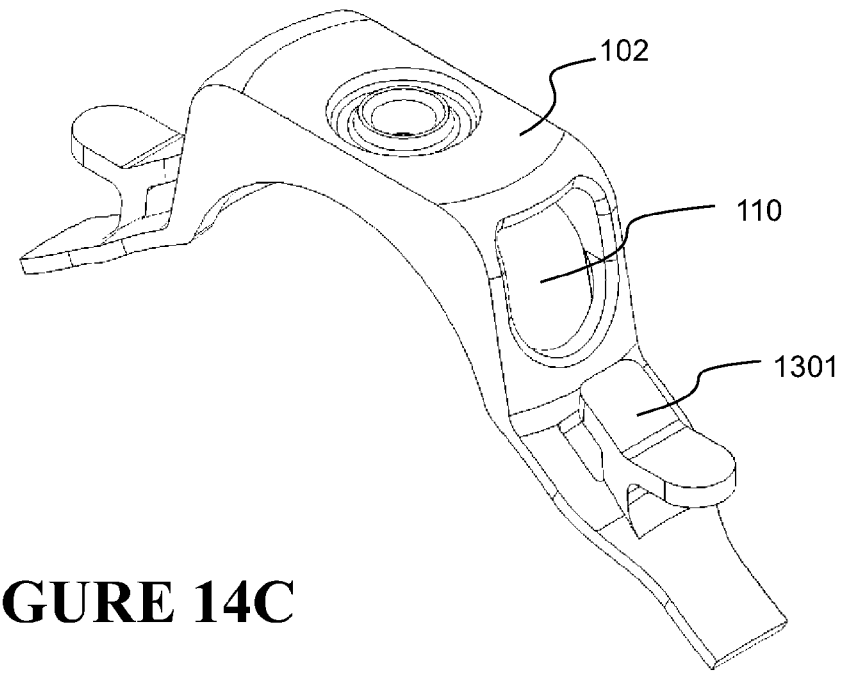
Figure 15A:
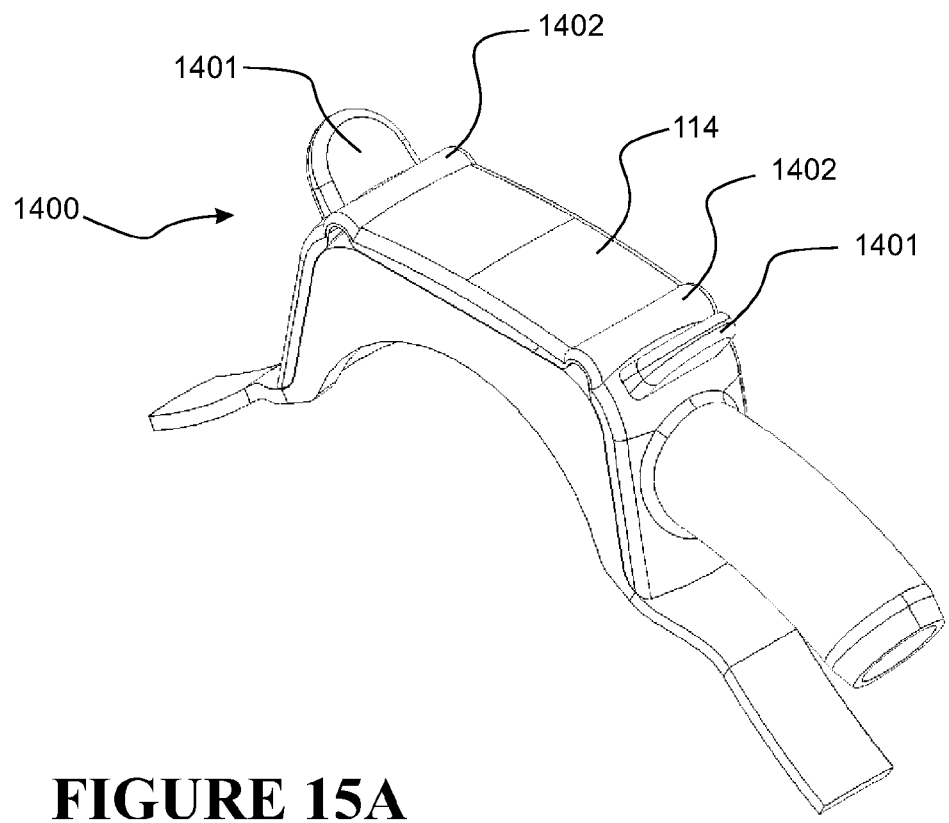
FIGS. 15A-15D show an alternative embodiment of components for the patient interface of the manifold assembly.
Figure 15B:
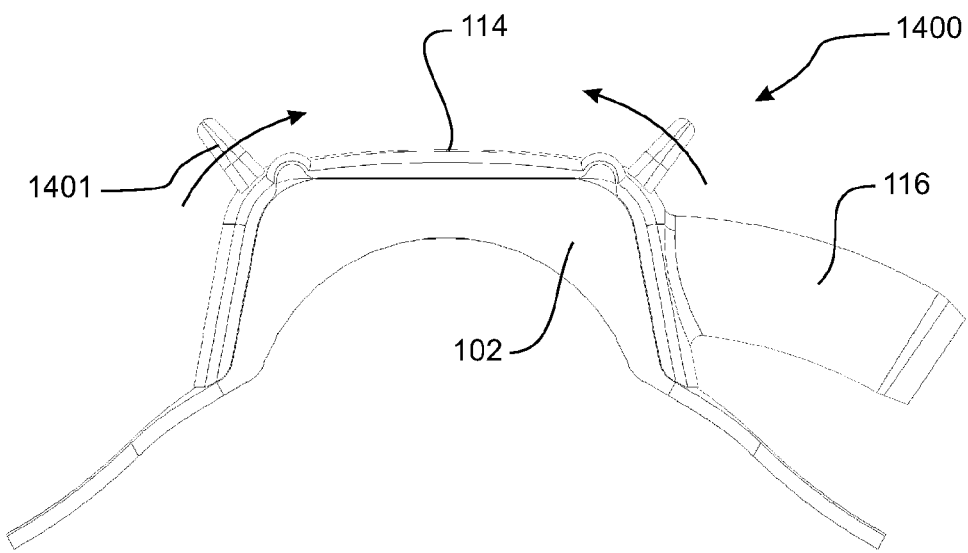
Figure 15C:
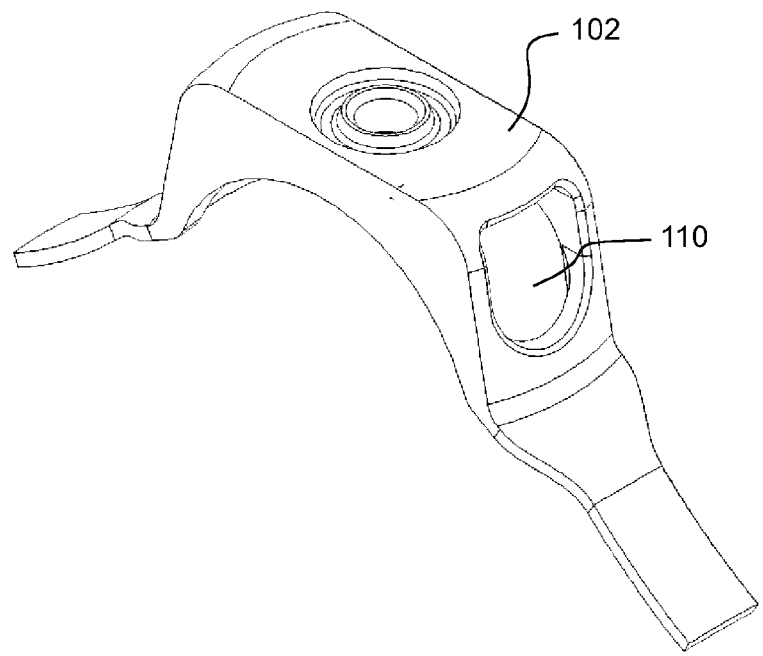
Figure 15D:
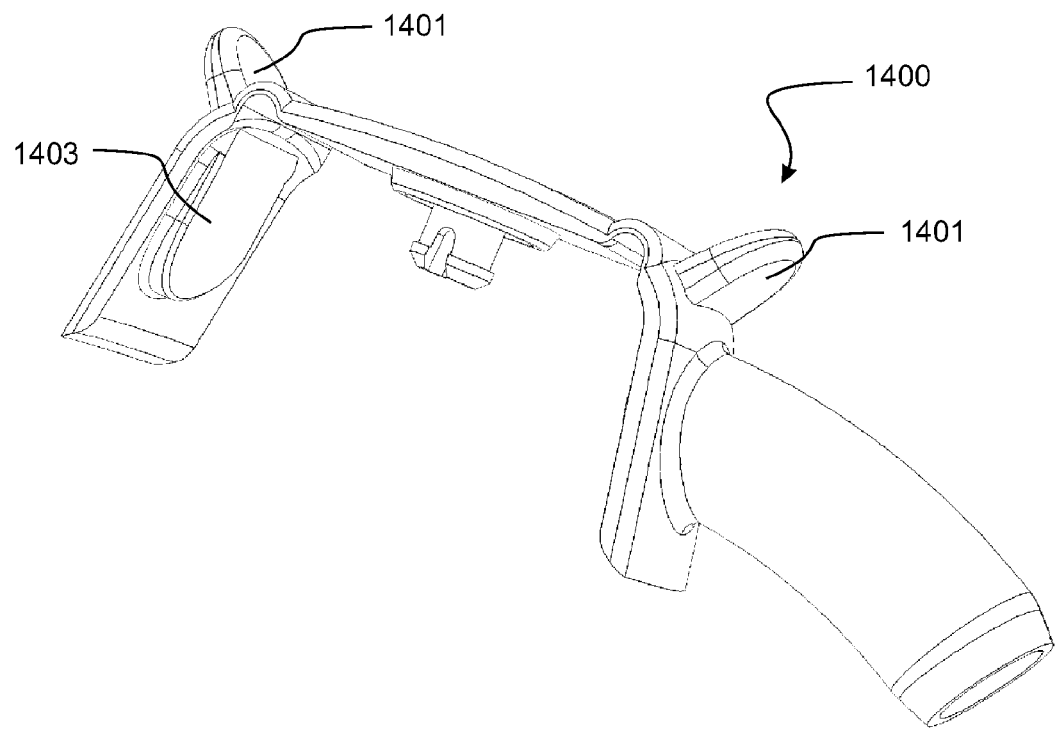

FIGS. 14A-14C show an alternative embodiment of the manifold assembly, in particular, an alternative release and retention mechanism. This configuration is a combined release and retention mechanism 1300. The retention mechanism comprises a shaped lever 1301 that substantially prevents lateral movement of the manifold 114 with respect to the frame portion 1122 when the manifold 114 substantially covers the frame inlets 110, 112. The lever 1301 has a vertically extending portion 1301a, with two generally oppositely extending arms 1301b, 1301c. One of the arms extends towards the manifold and the other arm extends away from the manifold. One of the arms 1301b extends substantially perpendicularly to the vertically extending portion 1301a, while the other arm 1301c extends generally parallel to the part of the frame portion from which the vertically extending portion extends. The sections of the lever form a generally T-shaped feature. Either a portion of each lever, or the entire lever, is flexible to allow the arm to move as required. The first arm is shaped to engage a complementary flange of the manifold 114. The manifold 114 is released by a user pressing the second arm 1301b towards the frame portion 1122, causing the arm to disengage from the manifold and allowing the manifold to rotate.

FIGS. 15A-15D show an alternative embodiment of the manifold assembly, in particular, an alternative release and retention mechanism. This configuration is a combined release and retention mechanism. The combined mechanism 1400 comprises a pair of levers 1401 that substantially prevent lateral movement of the manifold 114 with respect to the frame portion 1122 when the manifold 114 substantially covers the frame inlets 110, 112. Each lever 1401 extends at an angle of about 45 degrees from a top of manifold 112. Each lever is positioned near a flexible section or hinge 1402 of the manifold. One or preferably both sides of the manifold has a protuberance shaped to engage a complementary groove, recess, slot, or aperture in the frame portion 1122. In the embodiment shown, the non-inlet end of the manifold has the protuberance 1403 and the inlet end of the manifold is free of protuberances. The protuberance 1403 engages one of the frame inlets 110, 112 that is not in communication with the manifold inlet. The manifold 114 is released by a user squeezing the levers towards each other as for example in the directions of the arrows in FIG. 15B, causing the protuberances of each arm to disengage from the recess, slot, or aperture and allowing the manifold to rotate.

Figure 16A:
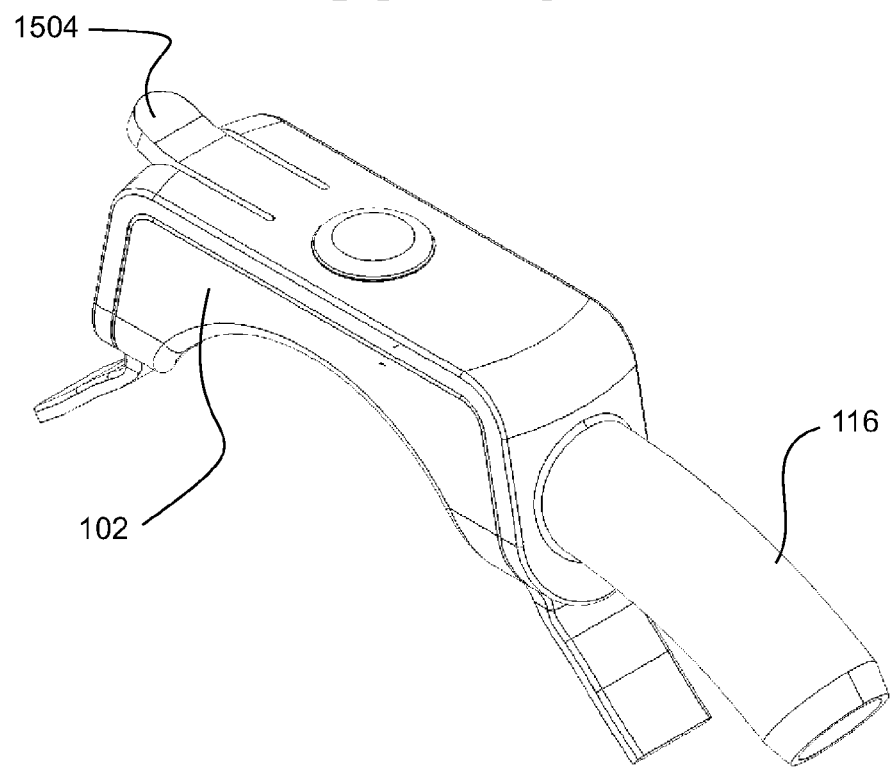
FIGS. 16A-16C show an alternative embodiment of components for the patient interface.
Figure 16B:
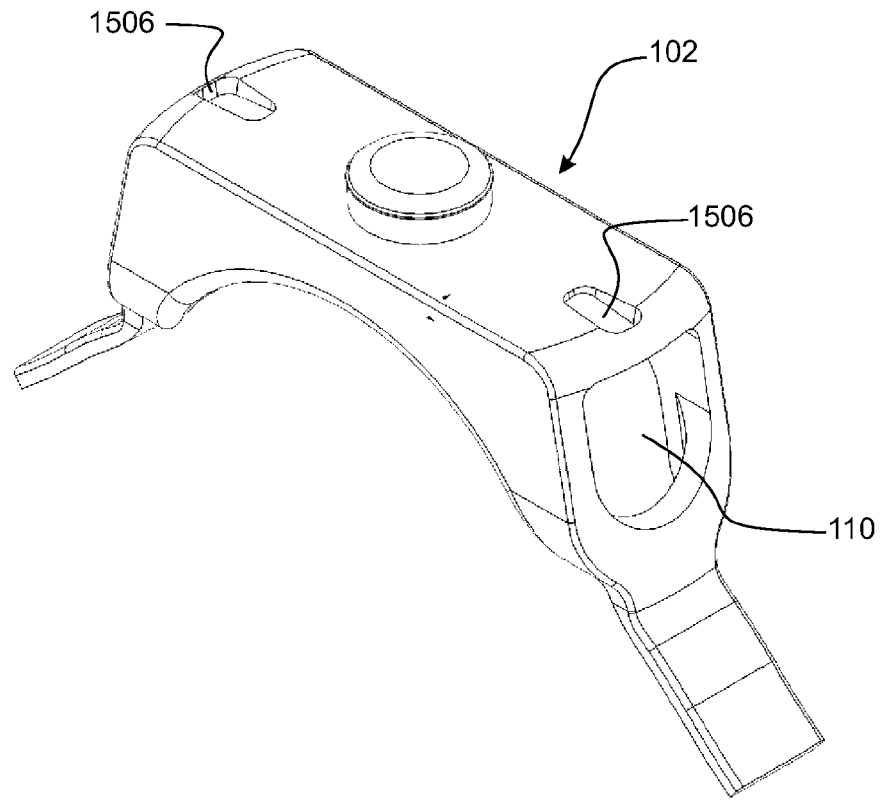
Figure 16C:
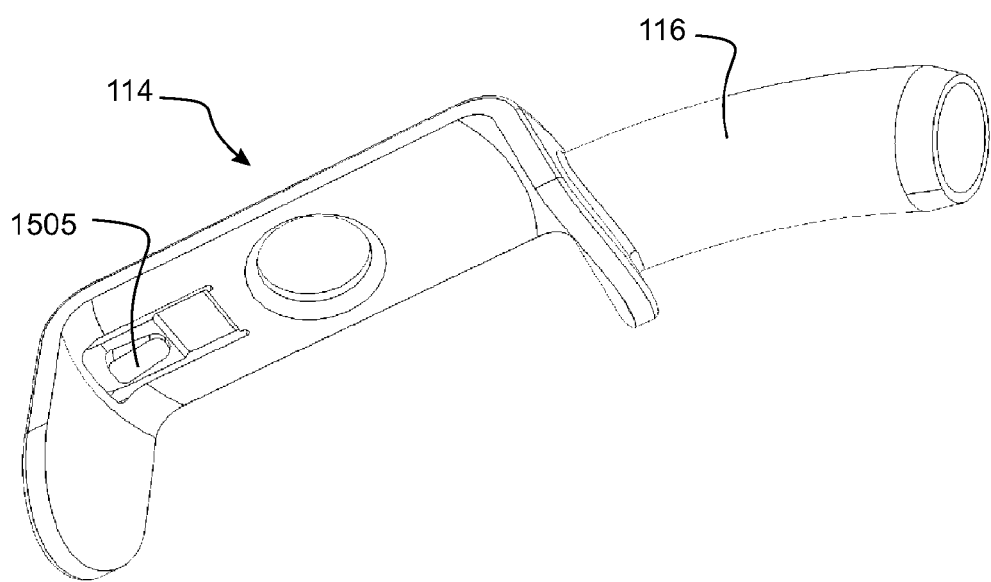

FIGS. 16A-16C show an alternative embodiment of the manifold assembly, in particular, an alternative release mechanism. The release mechanism comprises an arm 1504 with a protuberance 1505 or shaped portion to engage a complementary groove recess, slot, or aperture 1506 in the frame portion 1122. The manifold 114 is released by a user pulling the free end of the arm towards the manifold, causing the protuberance 1505 of the arm 1504 to disengage from the recess, slot, or aperture and allowing the manifold to rotate. Either a portion of each arm, or the entire arm, is flexible to allow the arm to move as required.

Figure 17A:
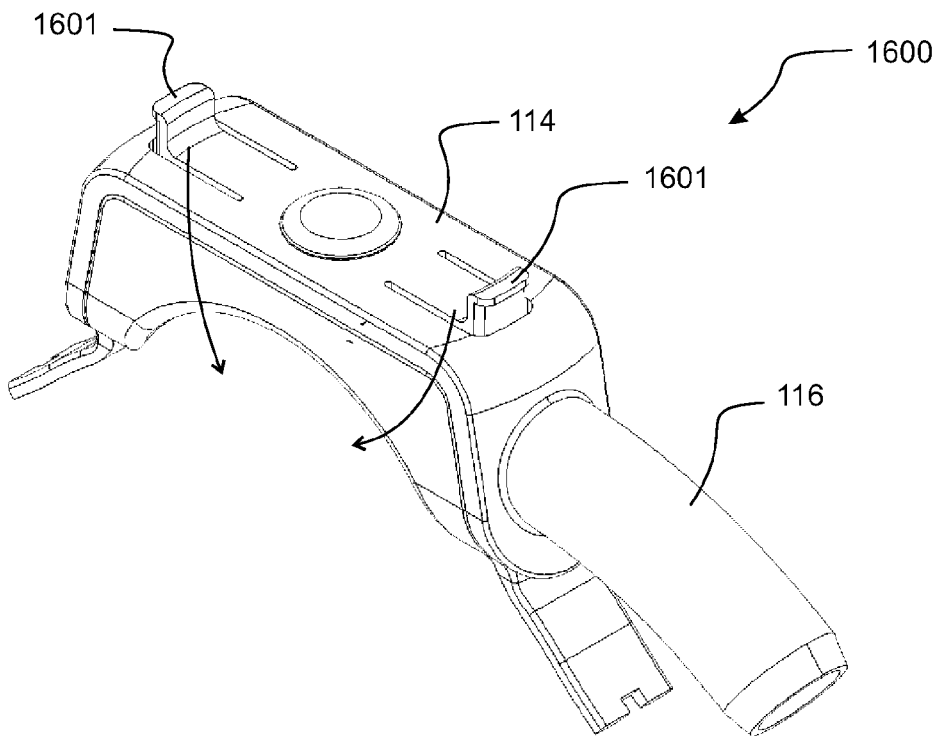
FIGS. 17A-17C show an alternative embodiment of components for the patient interface.
Figure 17B:
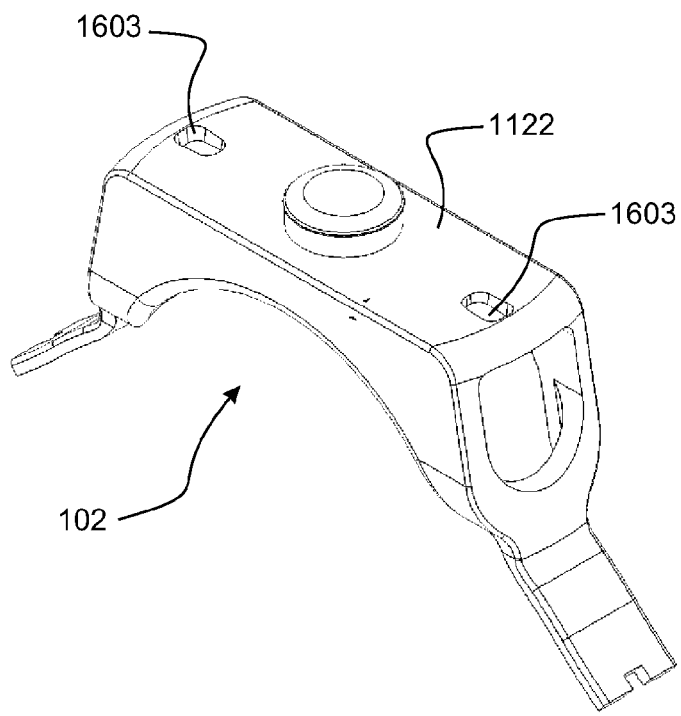
Figure 17C:
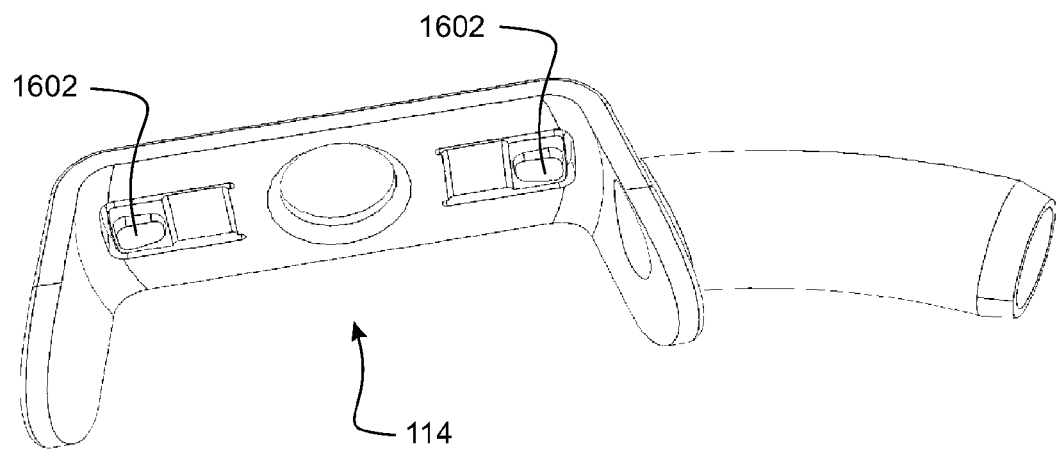

FIGS. 17A-17C show an alternative embodiment of the manifold assembly, in particular, an alternative release mechanism. The release mechanism 1600 comprises a pair of arms 1601 that are separated from the manifold by a C-shaped slot. Each arm 1601 has a tab extending vertically from the manifold 114. Each arm is flexible in at least a rotational direction. Either a portion of each arm, or the entire arm, is flexible to allow the arm to move as required. One or preferably both arms of the manifold has a protuberance 1602 shaped to engage a complementary groove, recess, slot, or aperture 1603 in the frame portion 1122. The manifold 114 is released by a user squeezing the arm towards each other in a rotational type movement as for example in the directions of the arrows in FIG. 17A, causing the protuberances of each arm to disengage from the recess, slot, or aperture and allowing the manifold to rotate.

Figure 18A:
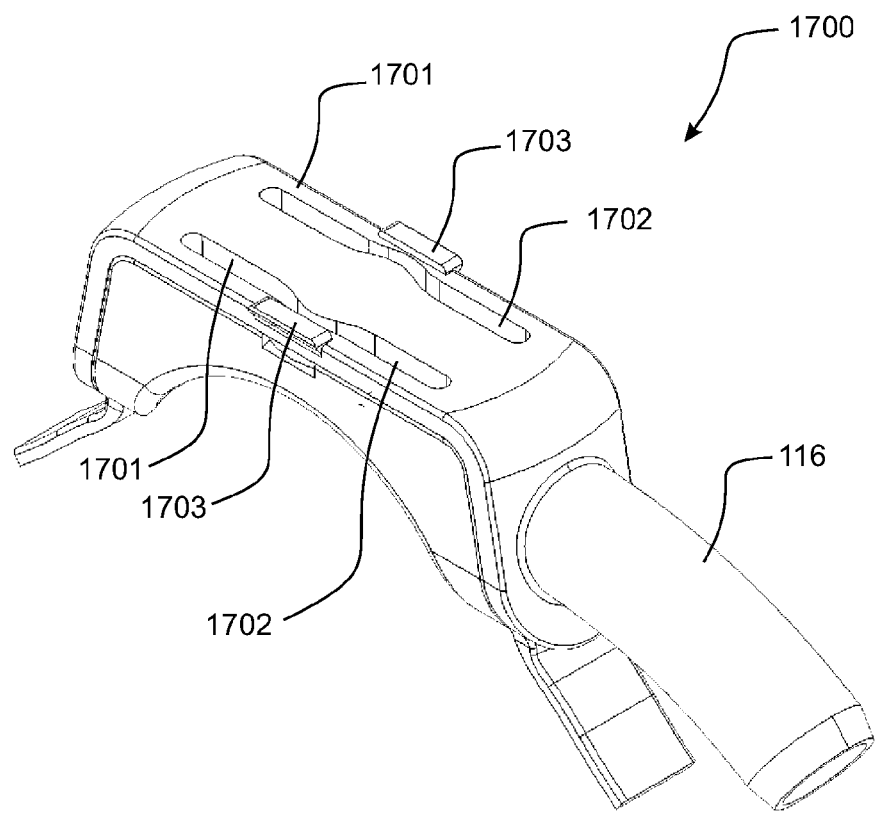
FIGS. 18A-18C show an alternative embodiment of components for the patient interface.
Figure 18B:
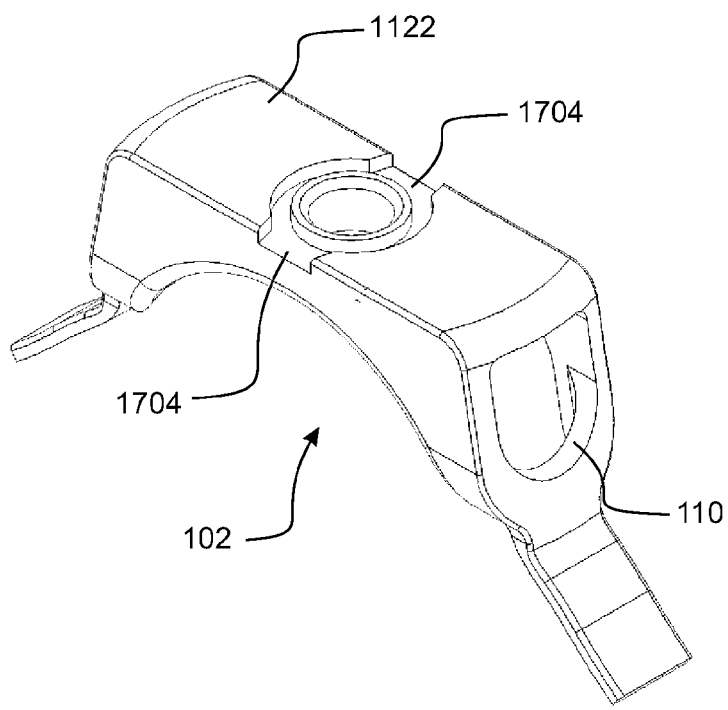
Figure 18C:
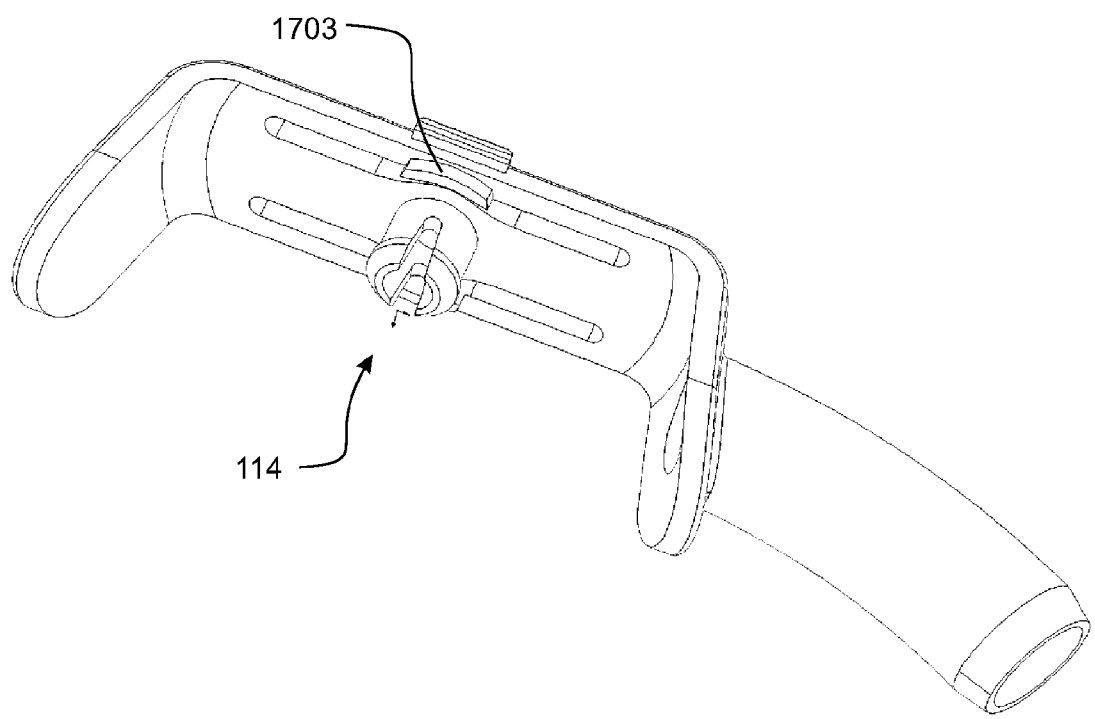

FIGS. 18A-18C show an alternative embodiment of the manifold assembly, in particular, an alternative release mechanism. The release mechanism 1700 (or 2000 as for example shown in FIGS. 21A-21C), comprises a pair of arms 1701 that are separated from the manifold by laterally extending slots 1702. Each arm 1701 has a tab 1703. One or preferably both tabs 1703 of the manifold has a protuberance shaped to engage a complementary groove, recess, slot, or aperture 1704 in the frame portion 1122. The manifold 114 is released by a user squeezing the tabs towards each other and towards the centre of the manifold, causing the protuberances of each tab to disengage from the recess, slot, or aperture and allowing the manifold to rotate.

Figure 19A:
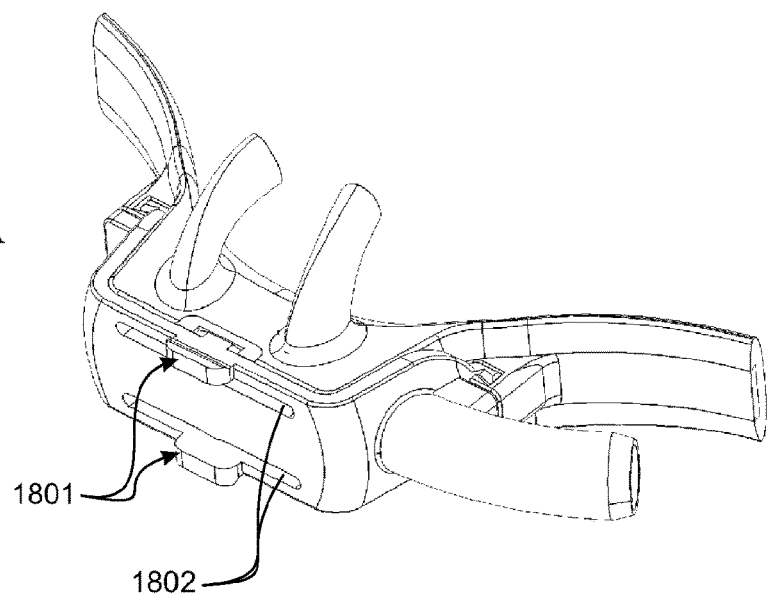
FIGS. 19A-19C show an alternative embodiment of the components for the patient interface.
Figure 19B:
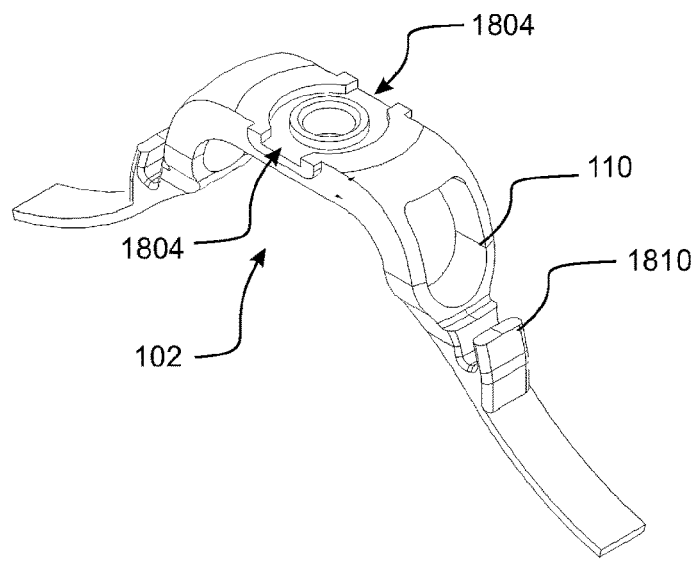
Figure 19C:
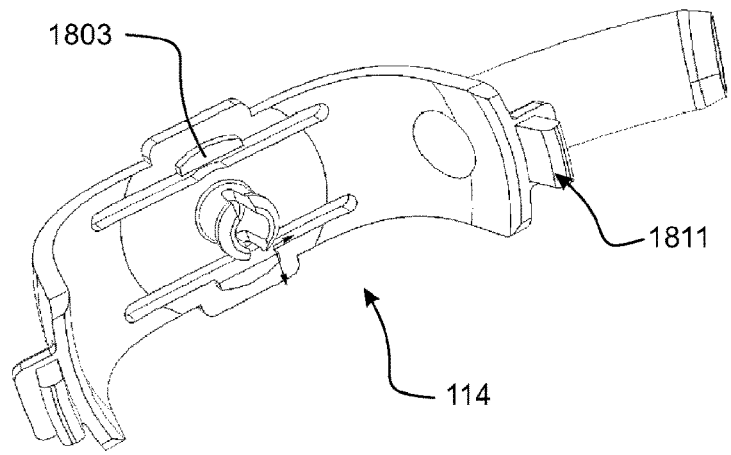

FIGS. 19A-19C show an alternative embodiment of the manifold assembly, in particular, another alternative retention mechanism. FIGS. 19A-C also show a release mechanism that is similar to the release mechanism of FIGS. 18A-18C. This retention mechanism encapsulates the manifold from all four sides. In particular, the frame portion has a leg 1810 on each side and the manifold has a corresponding leg 1811. Provided is a pair of arms 1801 (or 2001 as for example shown in FIGS. 21A-21C), each arm having an associated tab 1803 (or 2003 as for example shown in FIGS. 21A-21C). The arms and tabs being separated from each other by a pair of laterally extending slots 1802 (or 2002 as for example shown in FIGS. 21A-21C). In a similar operation to the embodiment of FIGS. 18A-C, that of FIGS. 19A-C is operated such that preferably both tabs 1803 of the manifold has a protuberance shaped to engage a complementary groove, recess, slot, or aperture 1804 (or 2004 as for example shown in FIGS. 21A-21C), in the portion shown as 102. The manifold 114 is released by a user squeezing the tabs towards each other and towards the centre of the manifold, causing the protuberances of each tab to disengage from the recess, slot, or aperture and allowing the manifold to rotate.

Figure 21A:
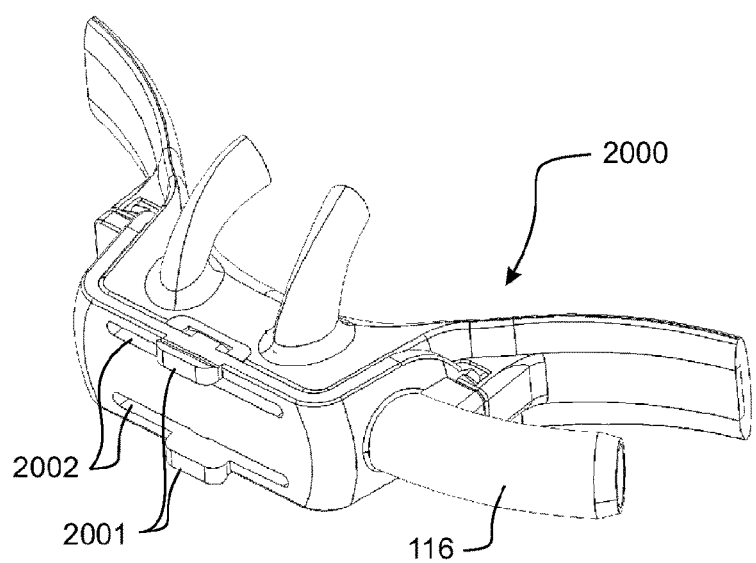
FIGS. 21A-21C show an alternative embodiment of the components for the patient interface.
Figure 21B:
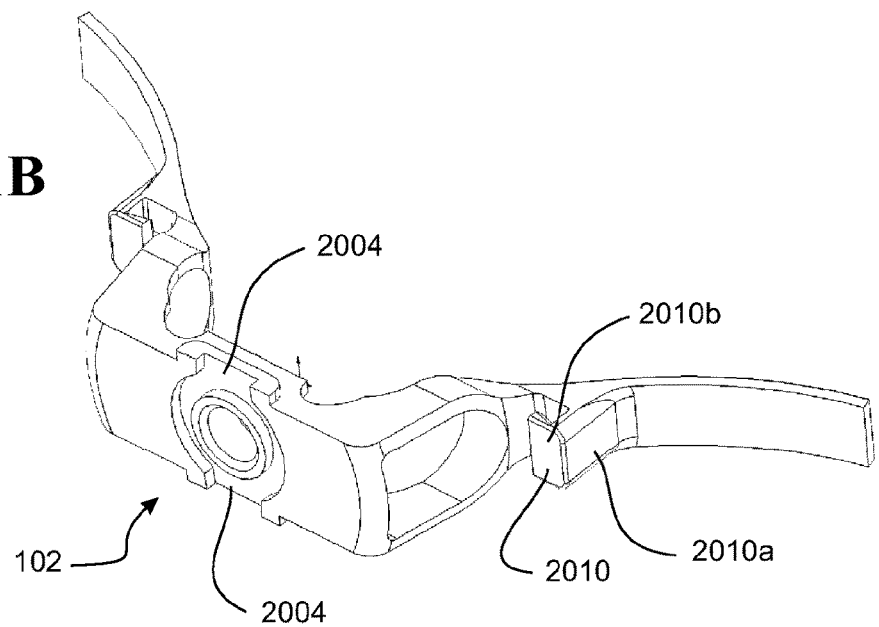
Figure 21C:
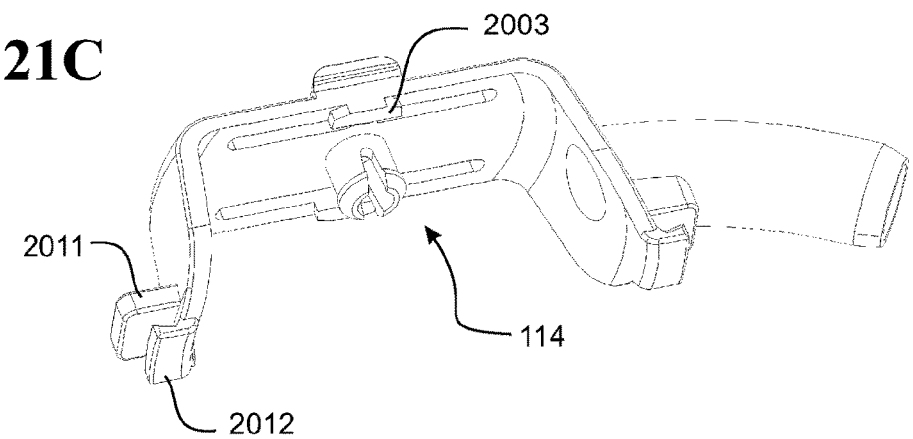

FIGS. 21A-21C show an alternative embodiment of the manifold assembly, in particular, another alternative retention mechanism. FIGS. 21A-21C also shows a release mechanism that is similar to the release mechanism of FIGS. 18A-18C and FIGS. 19A-19C. In particular, the manifold has a pair of generally parallel legs 2011, 2012 on each side and the frame portion has a corresponding leg 2010. Each leg 2010 has a first vertically extending portion 2010a, followed by a horizontally extending portion 2010b.

FIGS. 20A to 20G embodiments in which the manifold and manifold inlet are formed by a first component and a second component together with a fastening component.

Figure 20A:
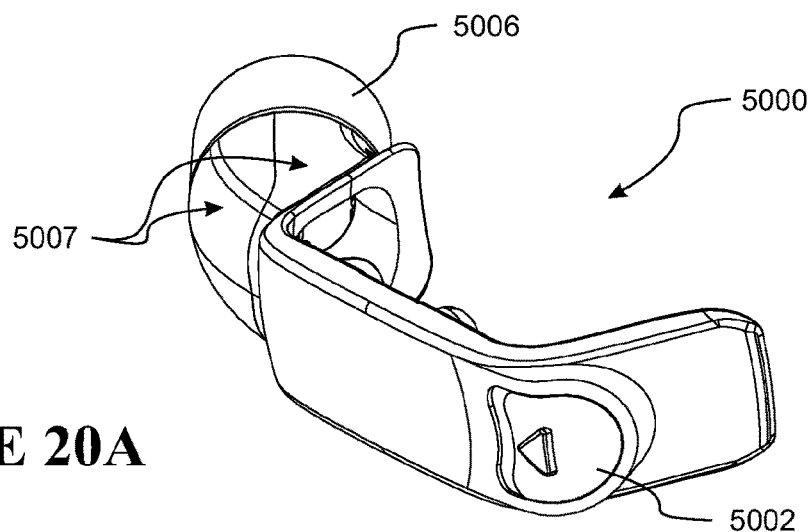
FIGS. 20A-20G show an alternative embodiment of the components for the patient interface.

More particularly, FIG. 20A shows a manifold part 5000 comprising a release mechanism 5002 in the form of a button which may be actuated by a user, as well as a tapered lead-in portion for delivering of gases to the manifold part, the tapered lead-in portion defined by an assembly of first and second components 5007 and a fastening collar 5006.

Figure 20B:
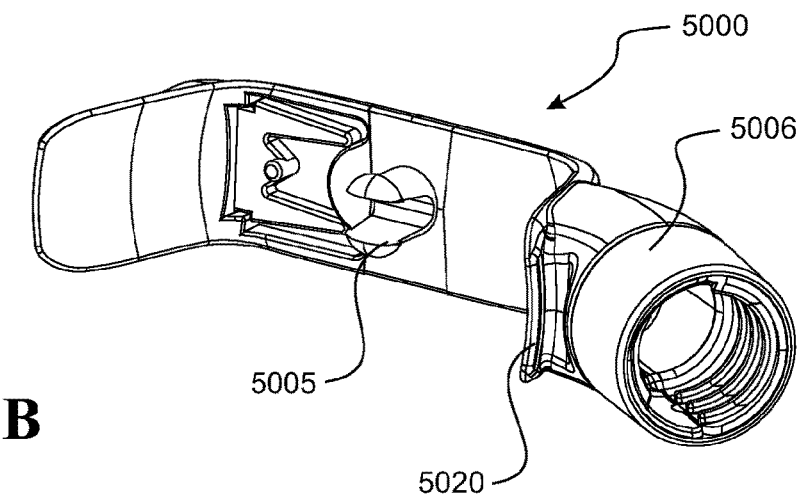

FIG. 20B illustrates a rear perspective view of FIG. 20A, in particular note the axle structure identified as item 5005.

Figure 20C:
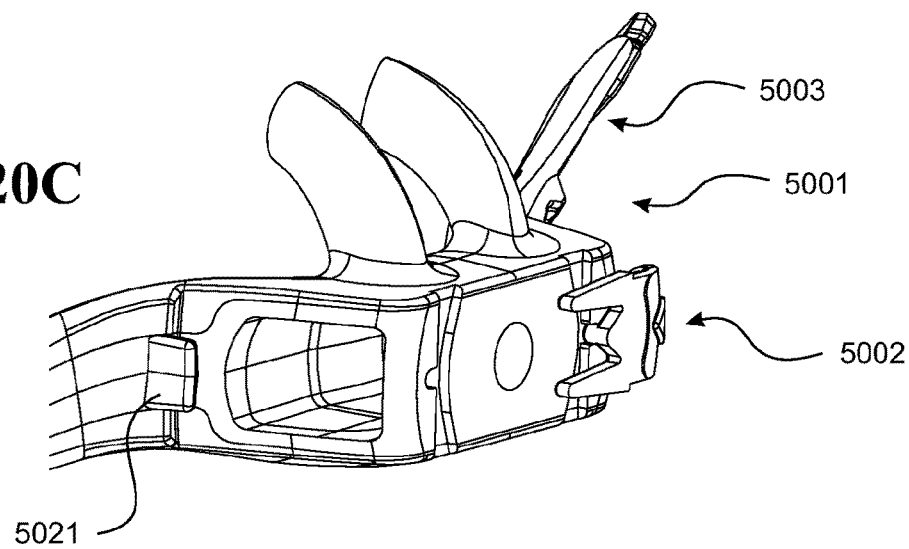

FIG. 20C shows a part of a nasal cannula interface 5001 having nasal prongs 5004 which are utilised for conveying or directing a flow of gas to the nares of a user's nose. Shown in this broken-apart view is some detail of the release mechanism 5002 and one of a pair of side arms 5003 (the other side arm is not shown).

A first part of a retention mechanism 5020 is shown in FIG. 20B, whilst the other part 5021 is shown in FIG. 20C. Each of these parts may be bought into co-operation or engagement such that their engagement facilitates a more secured location of a manifold part 5000 with a frame 5009 of a patient interface.

Figure 20D:
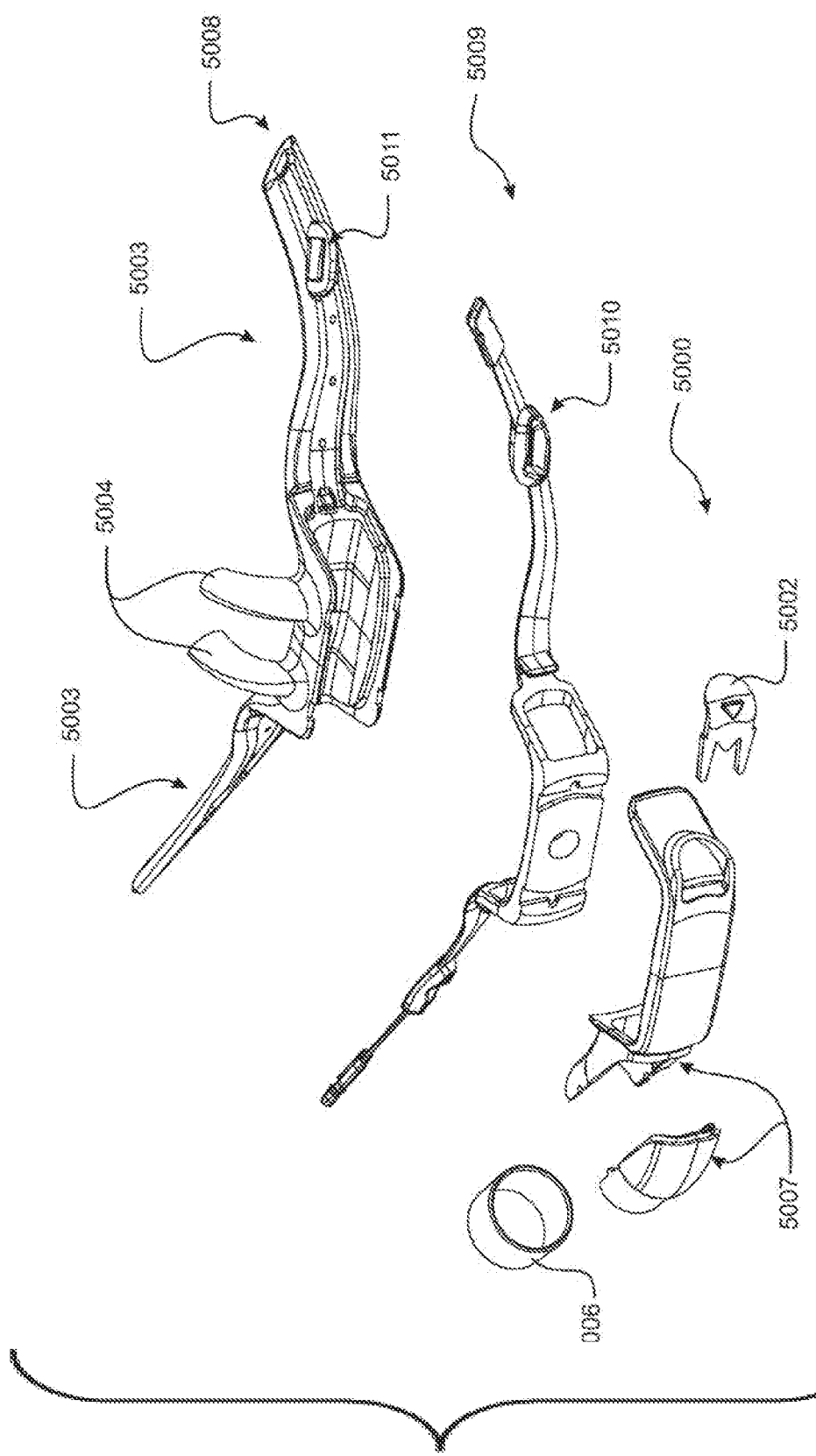

FIG. 20D is an exploded view of the various parts and components which may be assembled together to form one embodiment of a patient interface in which a swivel manifold may be provided and allowed to swivel relative to the frame, yet also be secured in place. Secured in place may be achieved by one or a combination of a retention mechanism and an operable release mechanism which can be actuated by a user or a carer.

FIG. 20D illustrates a relatively soft or pliable or flexible part or a part or material which is of more comfort for contact with the skin of a user, that identified as item 5008. Such a part 5008 may comprise of at least pair of side arms 5003, a pair of nasal prongs 5004, and a mounting portion receiver or locator 5011 provisioned for receiving or locating of a mounting portion 5010. A relatively more rigid or less flexible or more structural element, such as a frame, item 5009 may be combined with the part 5008. Part 5008 can be overmoulded or otherwise received or connected or attached or combined with the frame part 5009—such a combination providing for at least a patient interface of particular dimensional or shape stability, yet with comfort features for a user from the soft or pliable or otherwise more flexible material part 5008. A manifold part 5000 can be combined or attached to the frame part 5009 in such a way as to facilitate swiveling. The manifold part 5000 can be assembled from a plurality of parts or components.

Figure 20E:
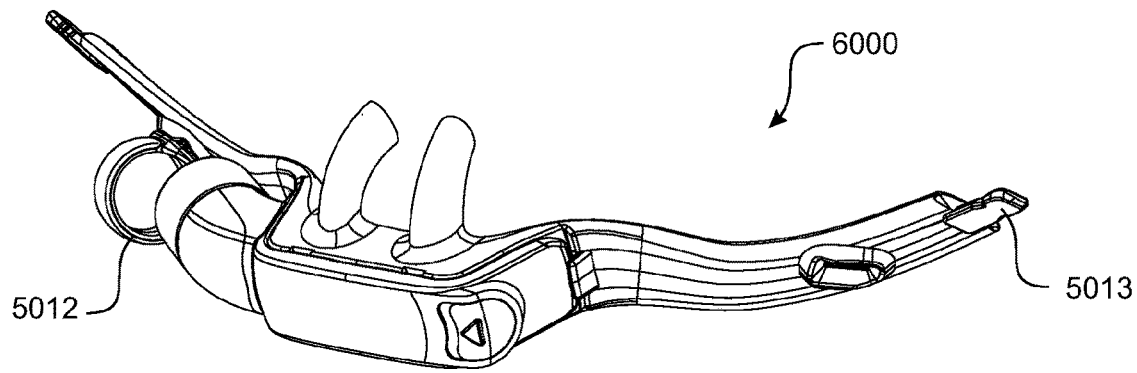

FIG. 20E illustrates a patient interface 6000 in which a manifold part provided for a gas tube connection on a first side of the interface. Note the provision of a tube clip or tube securement system labeled as item 5012 which is retained or secured in place with or by the mounting portion 5010. A gas delivery tube is not shown in-situ, however it will be appreciated in FIG. 20E the gas tube would extend out to one side of the manifold and patient interface, through the tube clip 5012. Each end of the side arms may include a clip or other connection system 5013 for engagement or facility to engage with a headgear system or other securement system for securing a patient interface in position on a user's face. The headgear is not shown, but may be suitable headgear for operation with a nasal cannula.

Figure 20F:
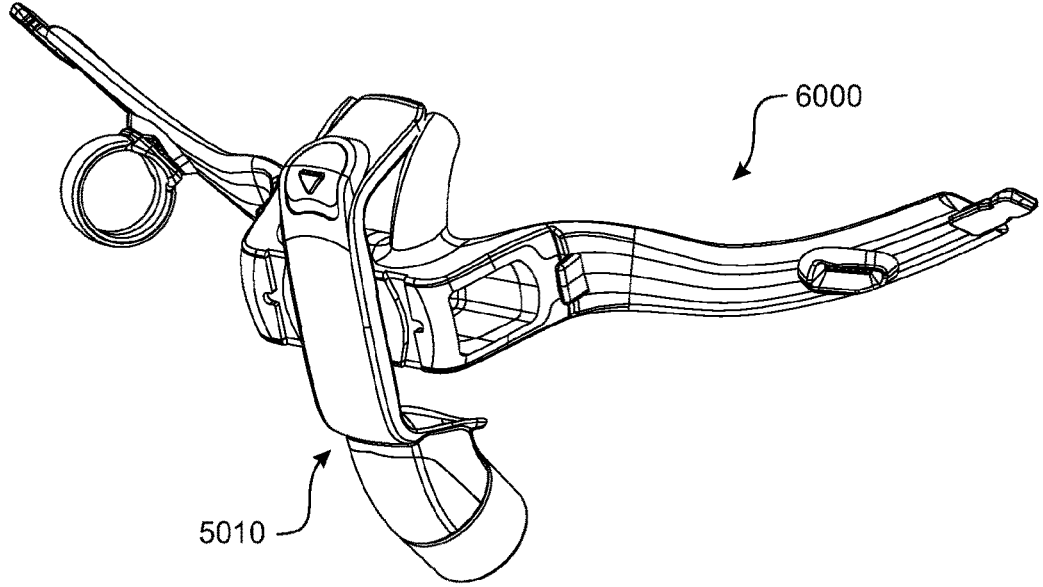
Figure 20G:
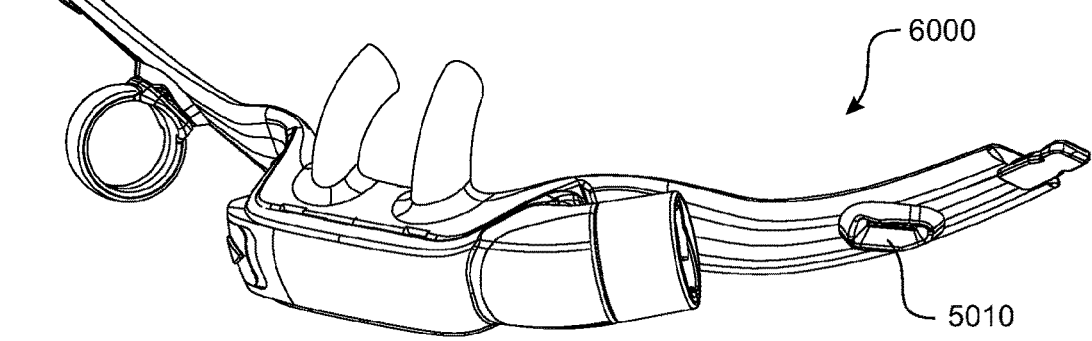

FIG. 20F illustrates the manifold part 5000 in part rotation or partial swivel as the manifold is being rotated or swiveled about an axle structure. FIG. 20G illustrates the manifold part in the re-orientated position after a swivel or rotation through 180°. Note the port available for gas tube connection has been re-located from one side of the interface to the other side. Such relocation of the gas connection port provides particular advantage s, both in terms of patient comfort and user operability, as well as the improved situation of potentially being able to deliver more consistent therapy to a patient.

FIG. 20A shows a front perspective view of a manifold component comprising a release mechanism. In the embodiment shown in FIG. 24A-24E, the fastening component comprises a collar 2305. The collar 2305 is a substantially annular component having a tapered internal surface for engaging with an exterior surface of the manifold inlet portion of the first component and an exterior surface of the manifold inlet portion of the second component. The retention mechanism and release mechanism are similar to that shown and described in relation to FIGS. 2 to 8E.

Many of the embodiments described above have been described as having a single protuberance shaped to engage a complementary groove, recess, slot, or aperture. Alternatively, the manifold assembly may have more than one protuberance.

In addition to the retention mechanism, the components of the patient interface can be modified to increase movement of some of the components while decreasing movement of other components. With reference to FIGS. 22*a* to 23*b*, a variety of modification will now be described.

Figure 22A:
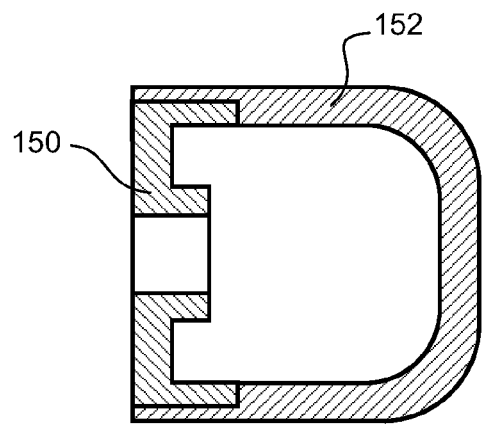
FIGS. 22A-22C show an alternative embodiment of the components for the patient interface.
Figure 22B:
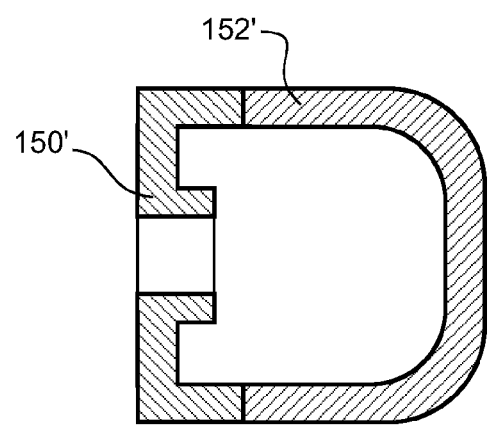
Figure 22C:
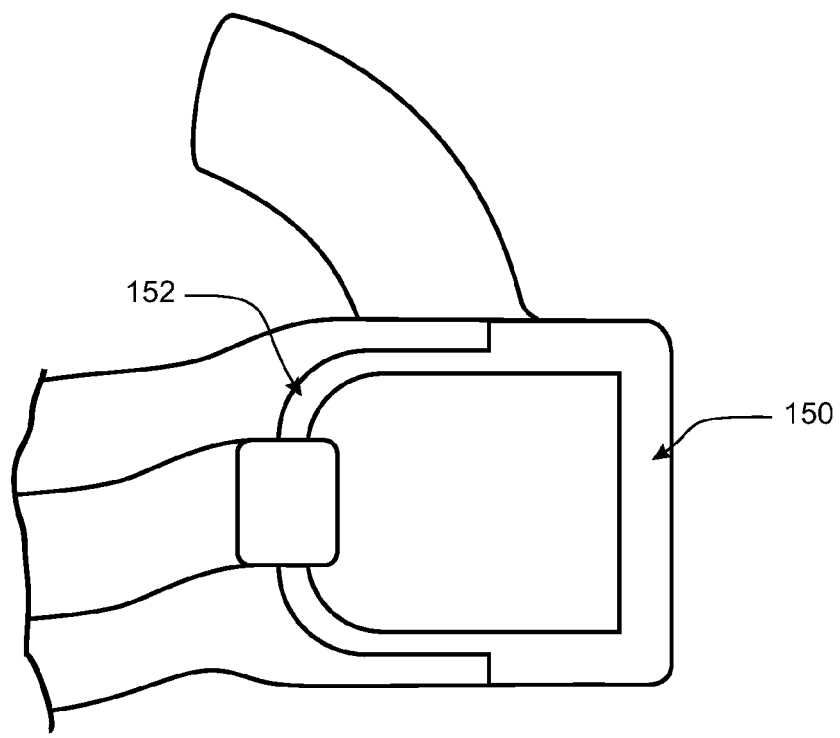

FIGS. 22*a* and 22*b* show alternative arrangements of the relatively hard or rigid section 150, 150' and a relatively soft or flexible section 152, 152'. FIG. 22*b* has a greater section of the relatively hard or rigid section 150 compared to FIG. 22*a*, which increases the torsional stiffness of the frame to resist unwanted movement between the manifold and the frame. With reference to FIGS. 22*a* and 22*b*, the manifold may include one or more gussets or ribs. The frame portion with a variety of ribs and/or gussets provides additional torsional resistance to the frame portion that prevent, or at least substantially inhibit, unwanted movement of the manifold relative to the frame portion. Preventing relative movement prevents, or at least substantially inhibits, gas leaking from the join between the manifold 114 and the frame inlets 110, 112. FIG. 22 shows the relatively hard or rigid section 150 and relatively soft or flexible section 152 implemented as part of a patient interface such as a nasal cannula.

Figure 23A:
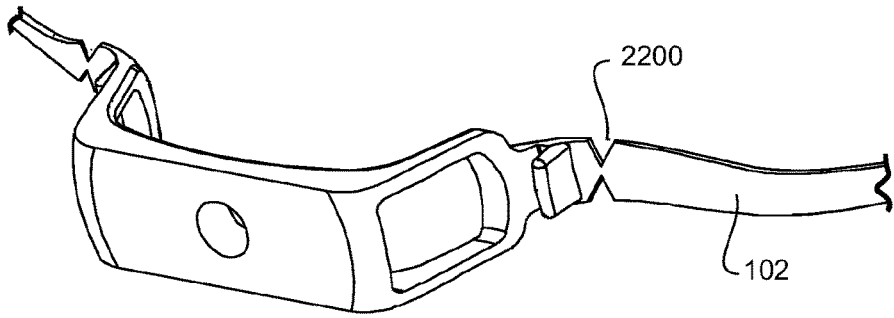
FIGS. 23A-23B show an alternative embodiment of the components for the patient interface.
Figure 23B:
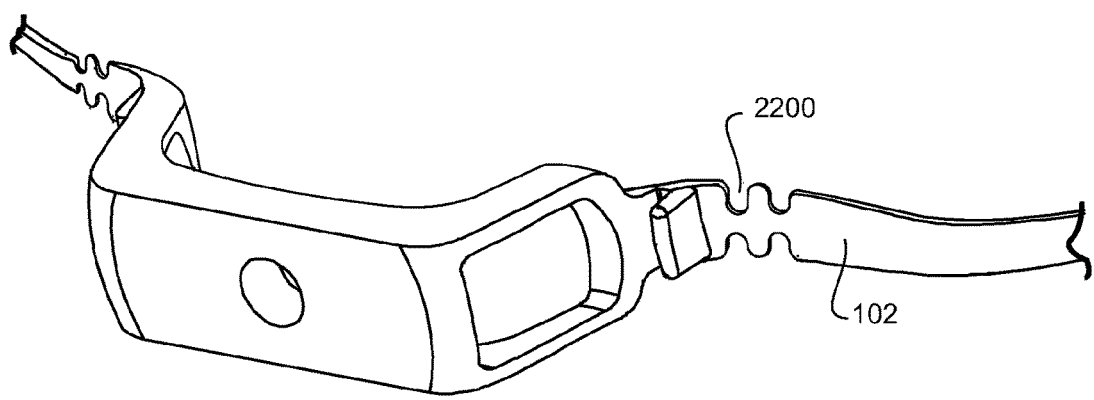
Figure 24A:
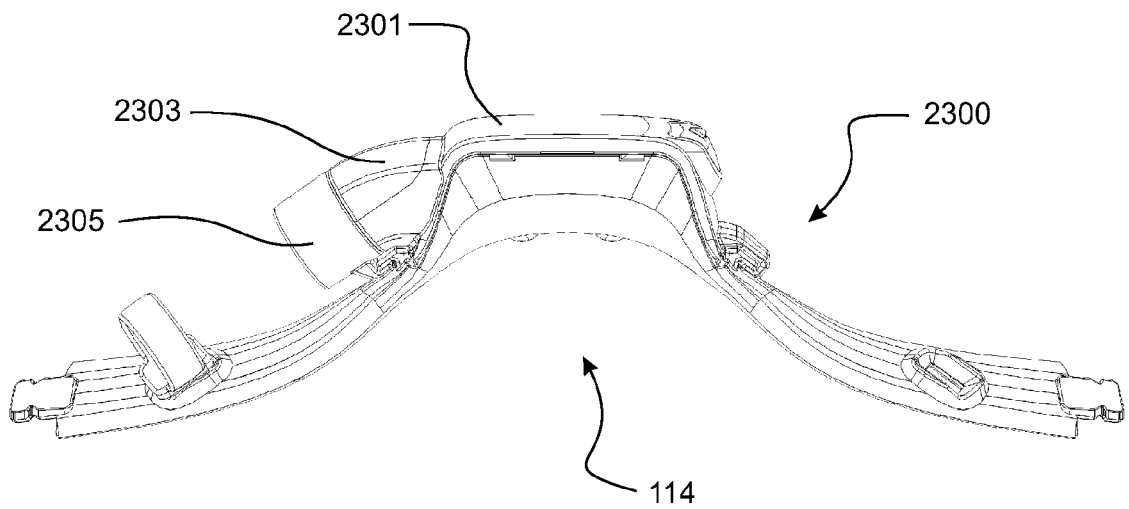
FIGS. 24A-24E show an alternative embodiment of the components for the patient interface.
Figure 24B:
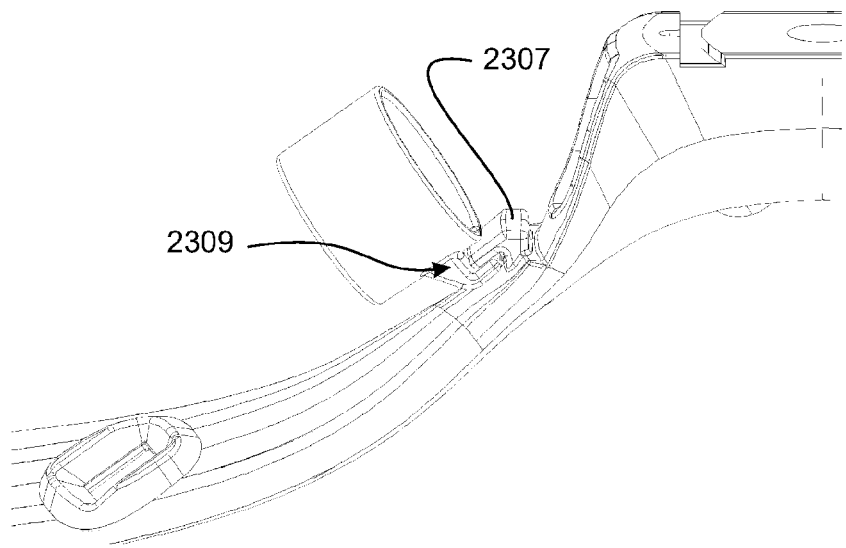
Figure 24C:
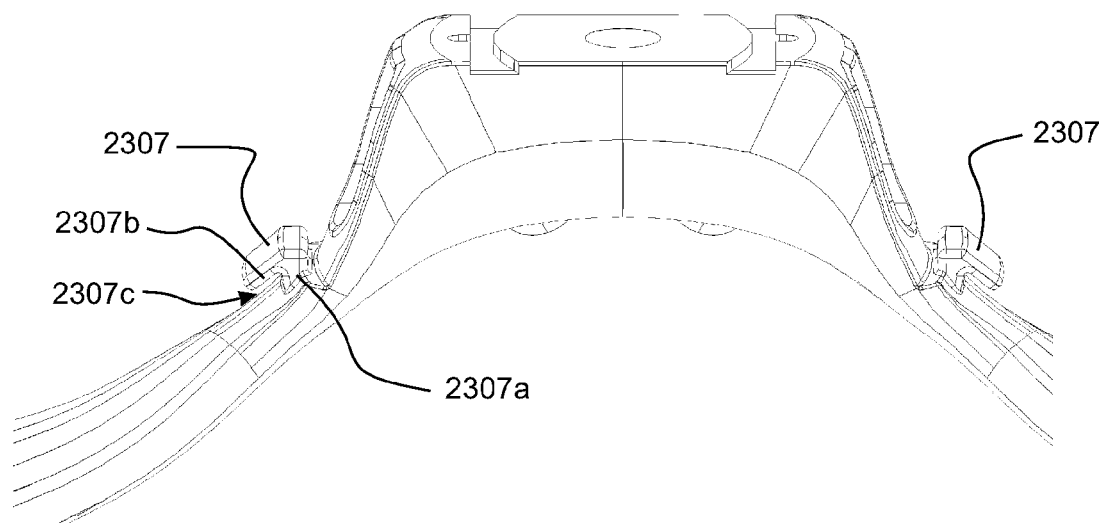
Figure 24D:
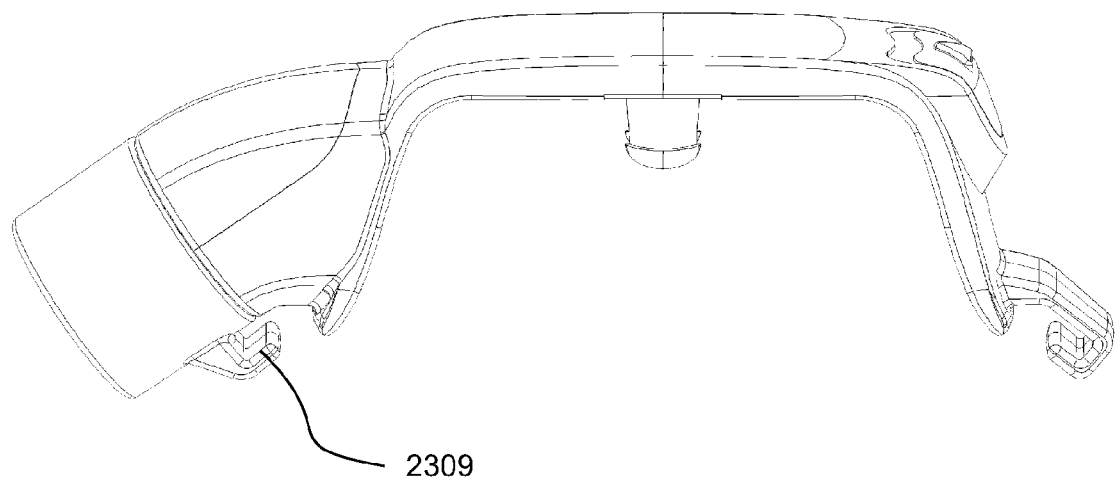
Figure 24E:
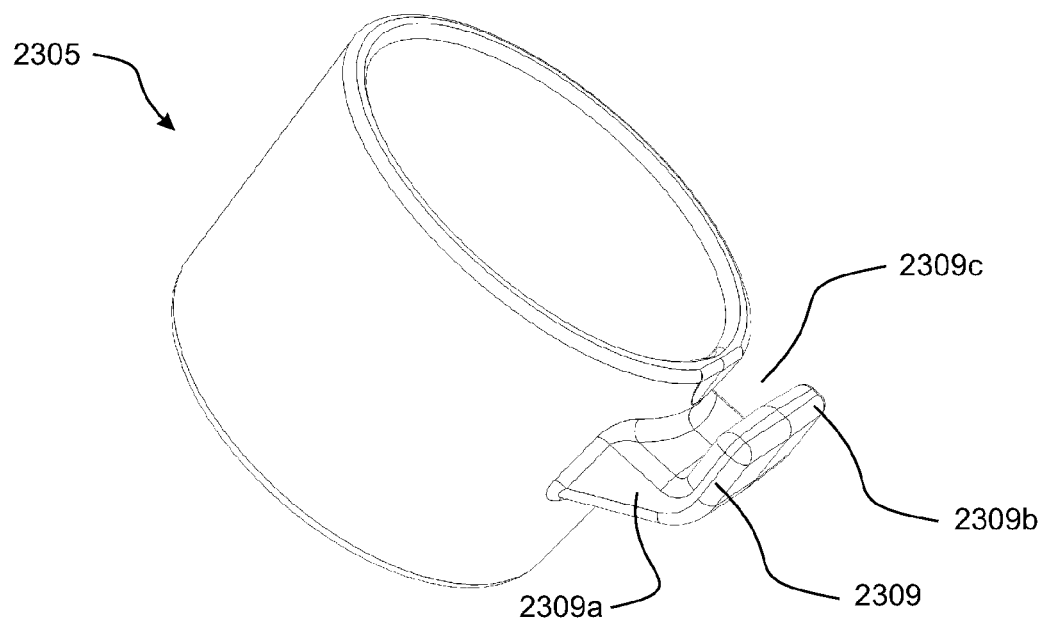
Figure 25A:
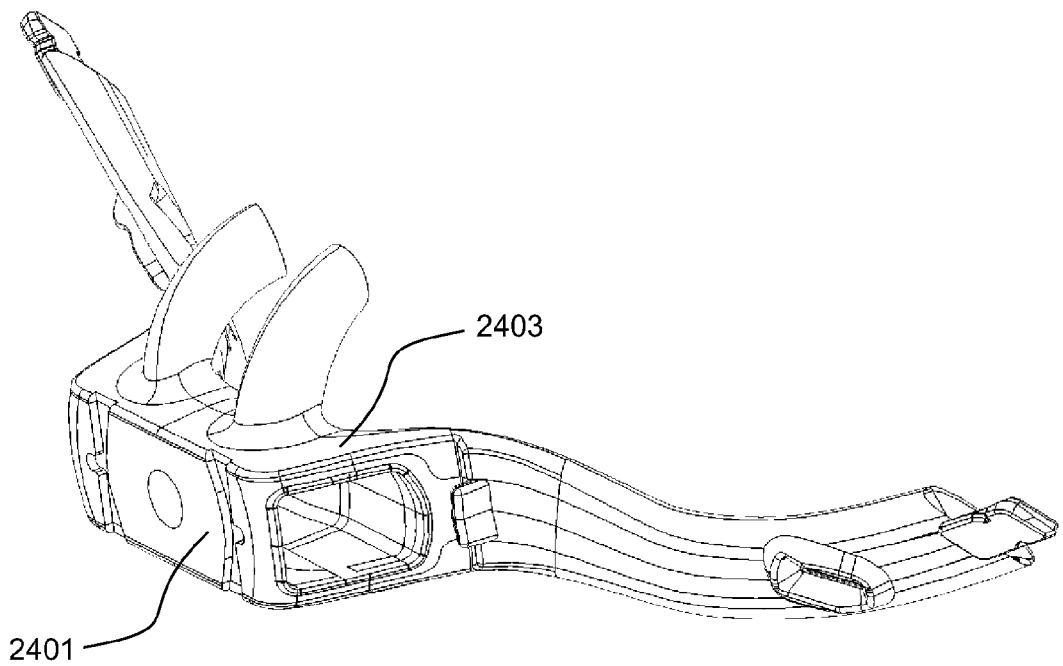
FIGS. 25A-25E show an alternative embodiment of the components for the patient interface.
Figure 25B:
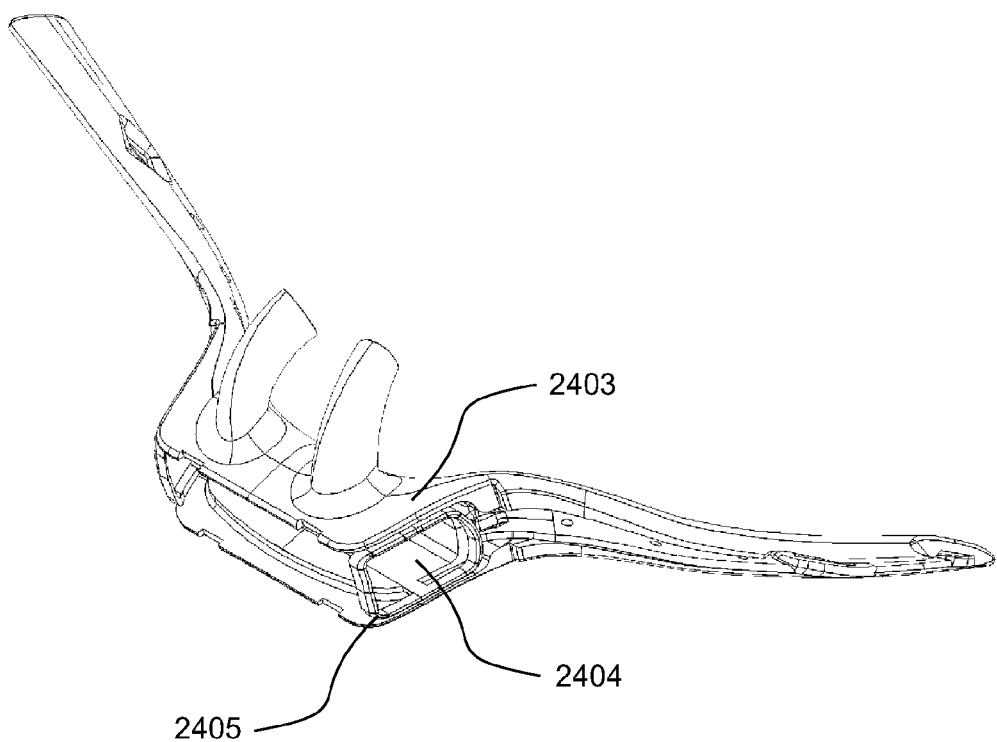
Figure 25C:
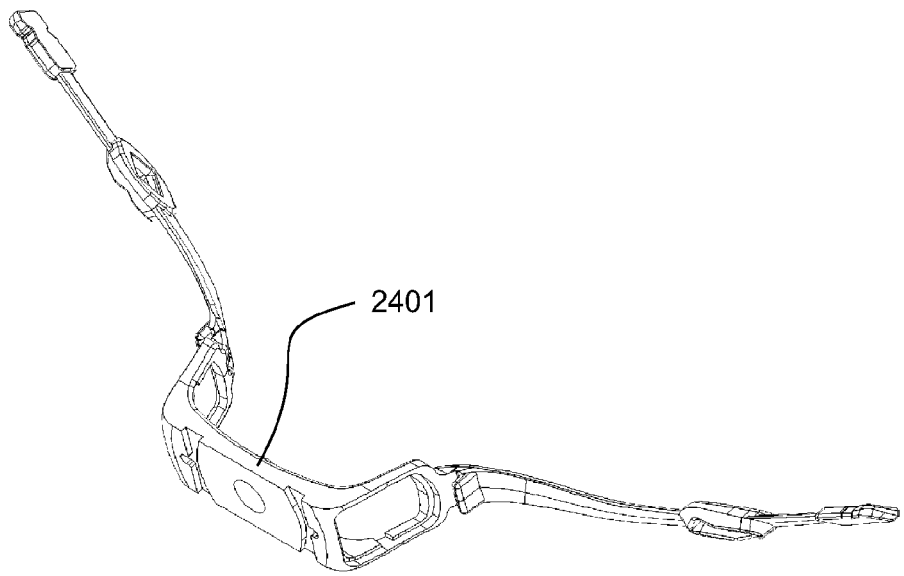
Figure 25D:
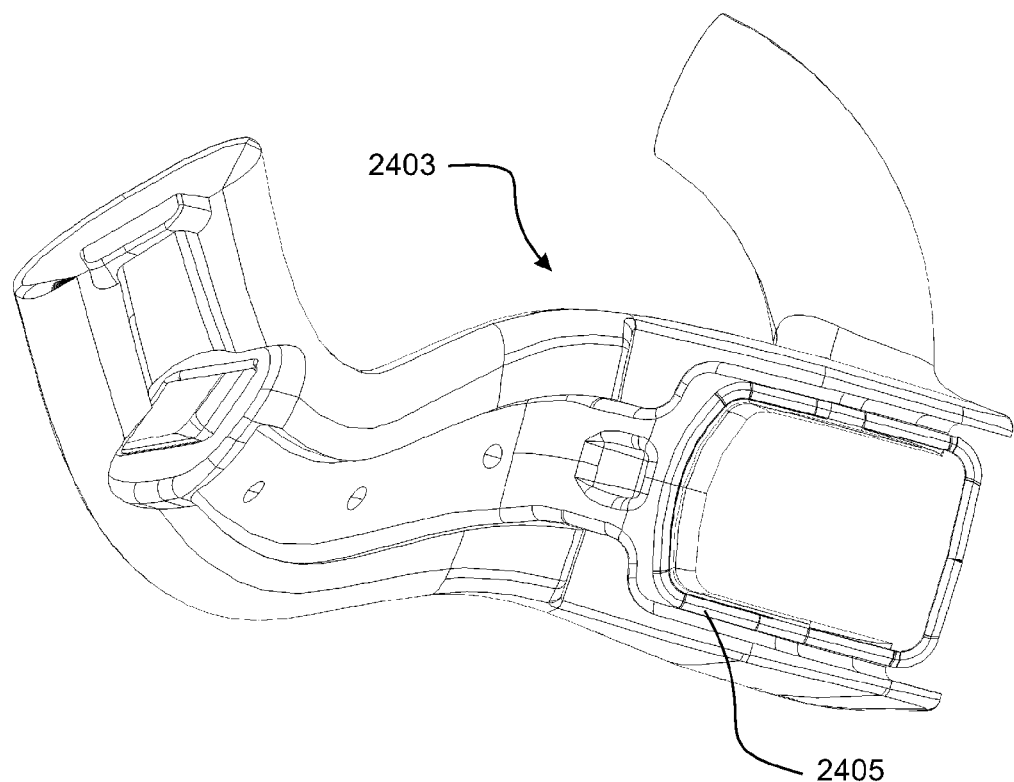
Figure 25E:
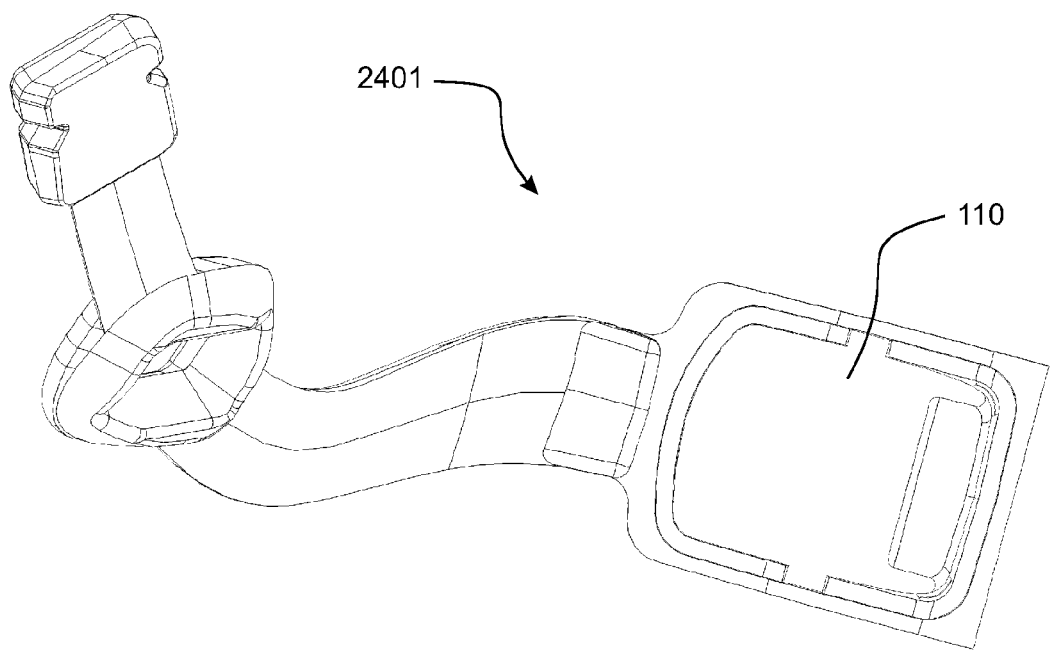
Figure 26A:
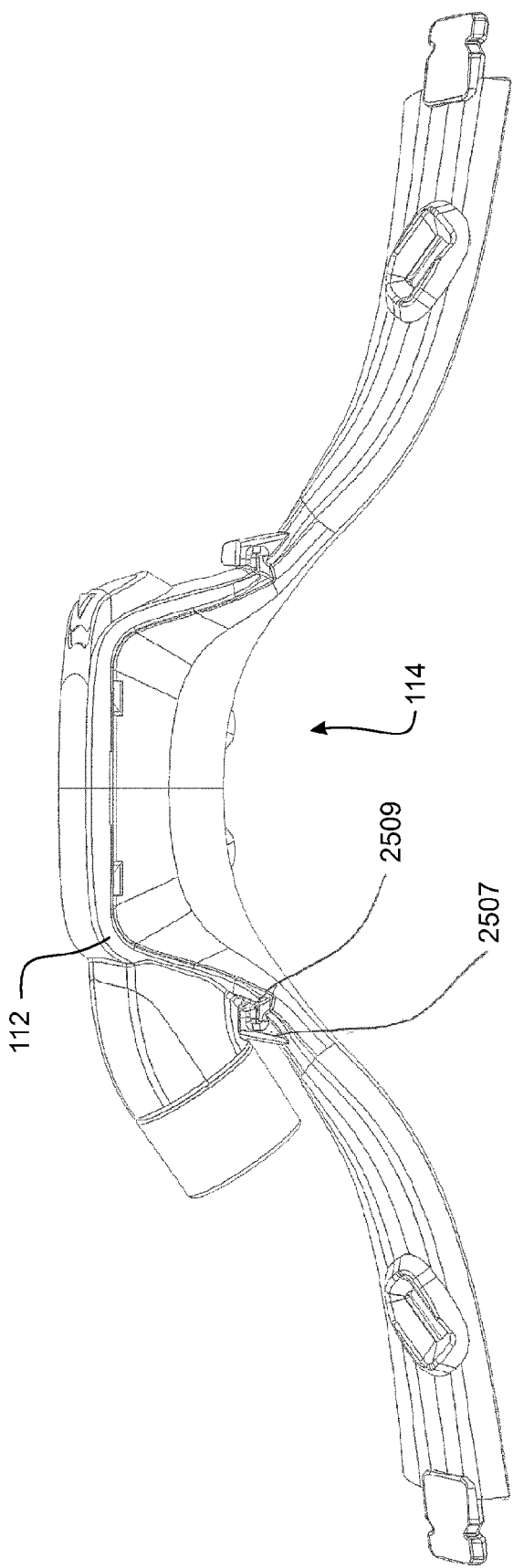
Figure 26C:
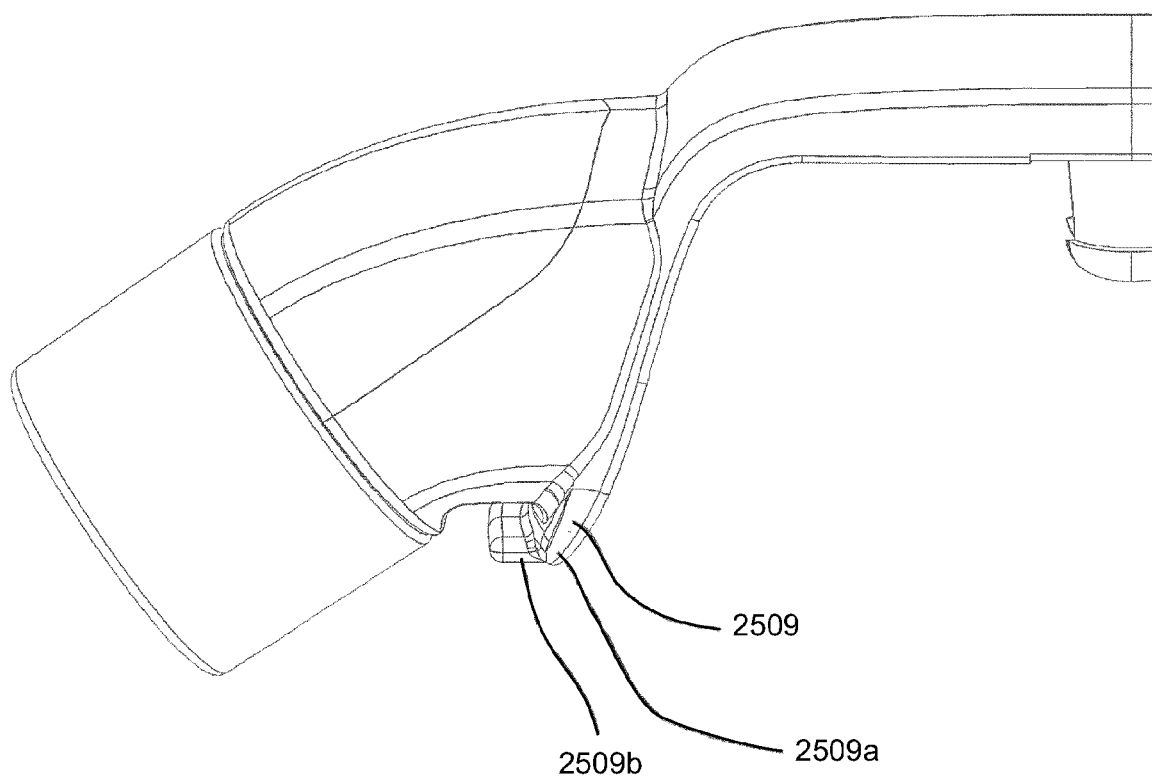
Figure 26D:
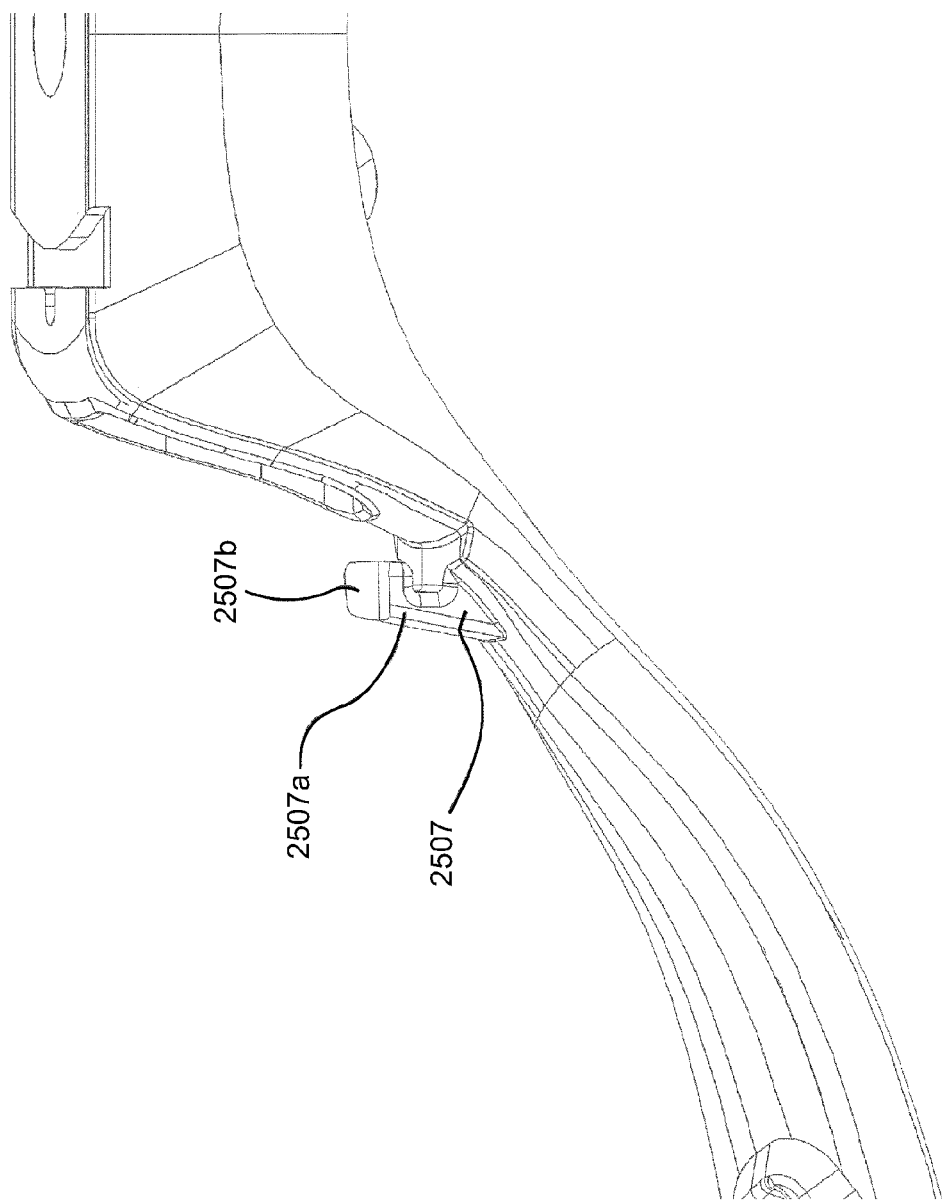

With reference to FIGS. 23A,B, the frame may have one or more notches 2200 or sections removed from the frame to encourage the frame, or a portion of the frame, to hinge or pivot, rather than causing movement between the frame and the manifold. The notches may be triangular, rectangular, or semi-circular notches.

With reference to FIGS. 24*a* to 24*e*, a further retention mechanism is shown. In this embodiment, the manifold 2301 and manifold inlet 2303 are formed by a first component and a second component together with a fastening component. In the preferred embodiment shown in FIGS. 24*a* to 24*e*, the fastening component comprises a collar 2305. The collar 2305 is a substantially annular component having a tapered internal surface for engaging with an exterior surface of the manifold inlet portion of the first component and an exterior surface of the manifold inlet portion of the second component.

The retention mechanism 2300 comprises a shaped hook 2307 on the frame that substantially prevents lateral movement of the manifold 114 with respect to the frame portion 112 when the manifold 114 substantially covers the frame inlets 110, 112. The hook 2307 substantially prevents lateral movement when engaged with a complementary hook 2309 on the collar 2305. The hook 2307 has a first generally vertically extending portion 2307a, followed by a generally horizontally extending portion 2307b. The hook 2307 shown in FIGS. 24a to 24e faces away from the manifold 114, that is, the generally horizontally extending portion 2307b extends from the generally vertically extending portion 2307a away from the manifold 114. However, it will be appreciated that the hook may extend towards the manifold, that is, the generally horizontally extending portion 2307b extends from the generally vertically extending portion 2307a towards the manifold 114.

The collar has a shaped hook 2309 with a first generally vertically extending portion 2309a, followed by a generally horizontally extending portion 2309b. One of the collar hook and the frame hook engages with the other of the collar hook and frame hook. In particular, the horizontal portion of each hook is received in a space (2307c and 2309c) of the complementary hook so that the surfaces of each horizontal portion abut each other. The hook 2309 shown in FIGS. 24a to 24e faces towards the manifold 114, that is, the generally horizontally extending portion 2309b extends from the generally vertically extending portion 2309a towards the manifold 114 when assembled. However, it will be appreciated that the hook may extend away from the manifold, that is, the generally horizontally extending portion 2309b extends from the generally vertically extending portion 2309a away from the manifold 114. It will further be appreciated that the direction in which the hook 2309 of the collar faces will depend upon the direction in which the hook 2307 of the frame faces.

With reference to FIGS. 26a to 26d, a further retention mechanism is shown. This mechanism is similar to the retention mechanism shown in FIGS. 24a to 24e and like numbers are used to indicate like parts with the addition of 200. One difference is that the shaped hook 2507 on the frame portion 112 faces towards the manifold with the generally horizontally extending portion 2507b extending from the generally vertically extending portion 2507a towards the manifold 114. However, it will be appreciated that the hook may extend away from the manifold, that is, the generally horizontally extending portion 2507b extends from the generally vertically extending portion 2507a away from the manifold 114.

The manifold has a shaped hook 2509 with a first generally vertically extending portion 2509a, followed by a generally horizontally extending portion 2509b. One of the manifold hook and the frame hook engages with the other of the manifold hook and frame hook. The frame portion 112 includes two hooks 2507, one on each side of the frame. The hooks are identical to each other but face toward each other, that is, the hooks are mirror images. The manifold 114 also has two hooks, that are identical and face away from each other, which allows the manifold to swivel relative to the frame. In particular, the horizontal portion of each hook is received in a space of the complementary hook so that the surfaces of each horizontal portion abut each other. The hook 2509 shown in FIGS. 26a to 26d faces away from a centre of the manifold 114, that is, the generally horizontally extending portion 2509b extends from the generally vertically extending portion 2509a towards the manifold 114 when assembled. However, it will be appreciated that the hook may extend towards the centre of the manifold, that is, the generally horizontally extending portion 2509b extends from the generally vertically extending portion 2509a towards the manifold 114. It will further be appreciated that the direction in which the hook 2509 of the manifold faces will depend upon the direction in which the hook 2507 of the frame faces.

Any one or more of the embodiments described above may have one or more legs, flanges, tabs, ridges, or hooks on the manifold 114 that positively engage with complementary legs, flanges, tabs, ridges, hooks, recesses, channels, apertures, or slots on the frame. Additionally or alternatively, those features may be on the frame and positively engage with complementary features of the manifold. The positive engagement of those features prevents, or at least substantially inhibits, gas leaking from the join between the manifold 114 and the frame inlets 110, 112.

With reference to FIGS. 25A to 25E, a further embodiment of the patient interface is shown. In this embodiment, the frame has a relatively rigid section 2401 and a relatively flexible section 2403. The relatively flexible section of the frame may be overmoulded onto the relatively rigid section. Alternatively, the relatively flexible section may be a separately formed component that is assembled with the relatively rigid section. The relatively flexible section has a shape and configuration that follows the shape and configuration of the relatively rigid section of the frame. The relatively flexible section has a pair of openings 2404 that correspond to the frame inlets 110, 112.

The relatively flexible section has a raised section 2405 around the periphery of each of the openings 2404 forming a deformable lip seal. The lip seal forms a seal between the manifold 114 and the frame portion 112 when the manifold substantially covers the frame inlets 110, 112. The seal prevents, or at least substantially inhibits, gas leaking from the join between the manifold 114 and the frame inlets 110, 112.

The features and functions of the embodiment shown in FIGS. 24a to 24e may be combined with the features and functions of the embodiment shown in FIGS. 25a to 25e to provide a patient interface with a seal at the inlets together with a positive retention mechanism. In addition, the features and functions of the embodiment shown in FIGS. 26a to 26d may be combined with the features and functions of the embodiment shown in FIGS. 25a to 25e.

The patient interface may be formed of any suitable material allowing the features described herein including, for example, a medical grade material and/or a suitable polymeric material.

Any one or more features from any embodiment may be combined with any one or more features from any one or more other embodiments.

For example, embodiments in which some areas or components are strengthened to reduce movement may be combined with embodiments in which other areas or components are weakened to increase movement. Notwithstanding this, the embodiments described above may be provided as integrated parts or portions or portions or parts which can be assembled to form a part of a patient interface, particularly but not limited to a nasal cannula.

Figure 28A:
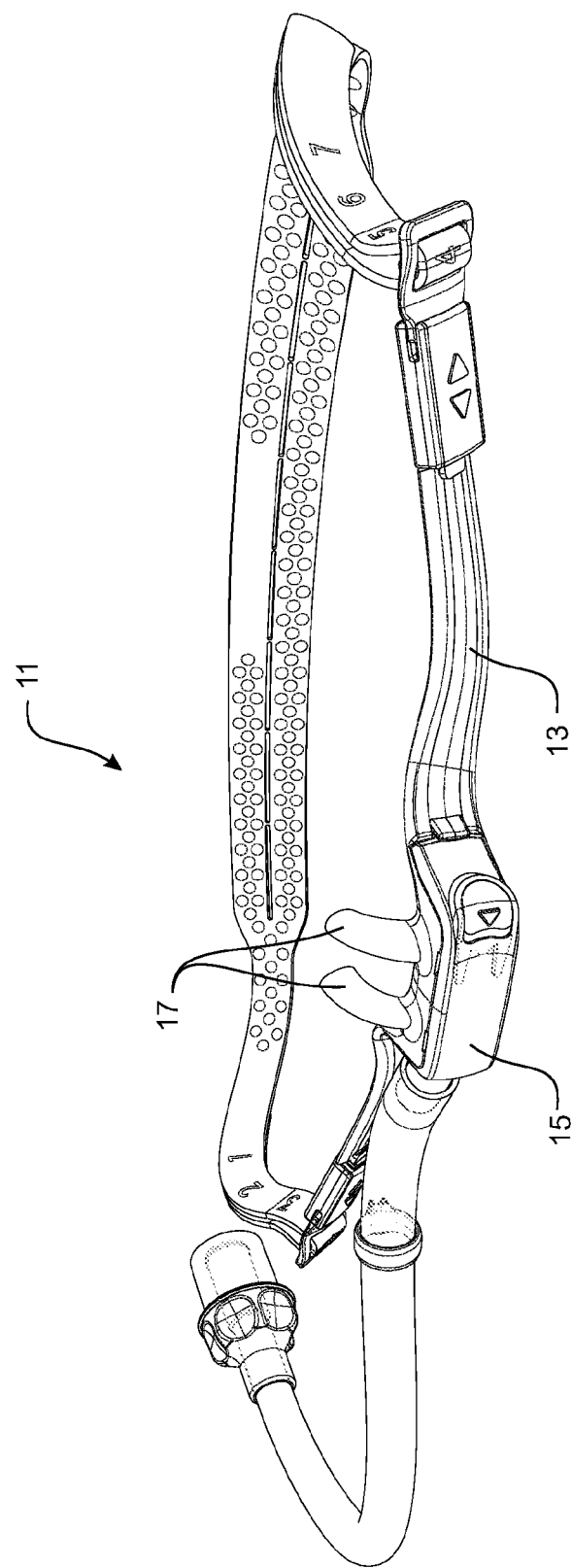
FIG. 28a is a perspective view of a patient interface.
Figure 29:
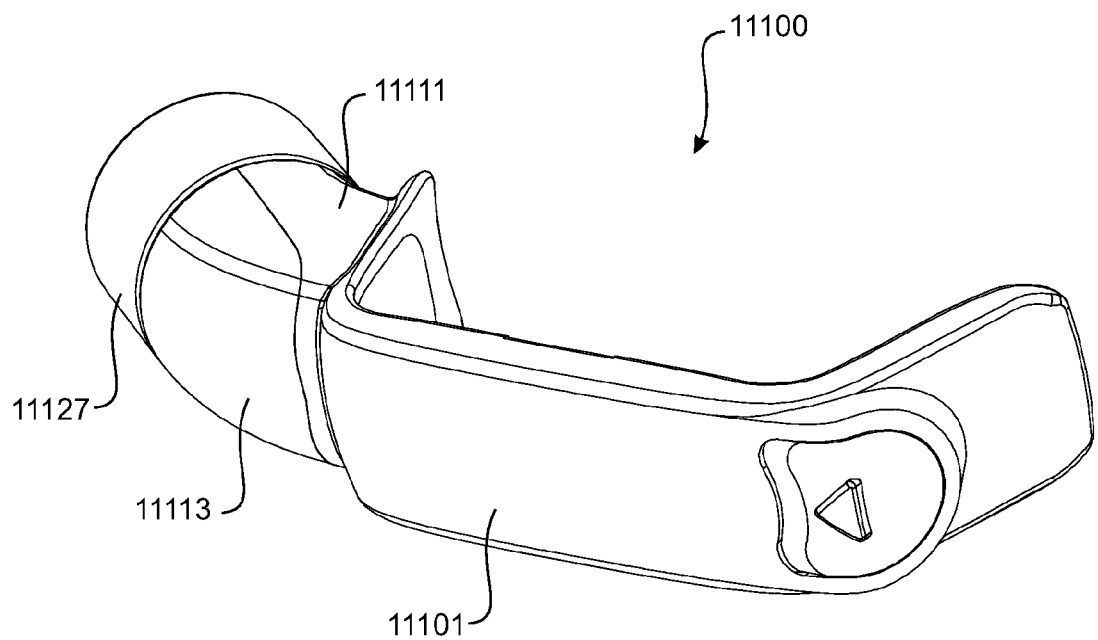
FIG. 29 is a side top perspective view of a first embodiment manifold assembly.
Figure 30:
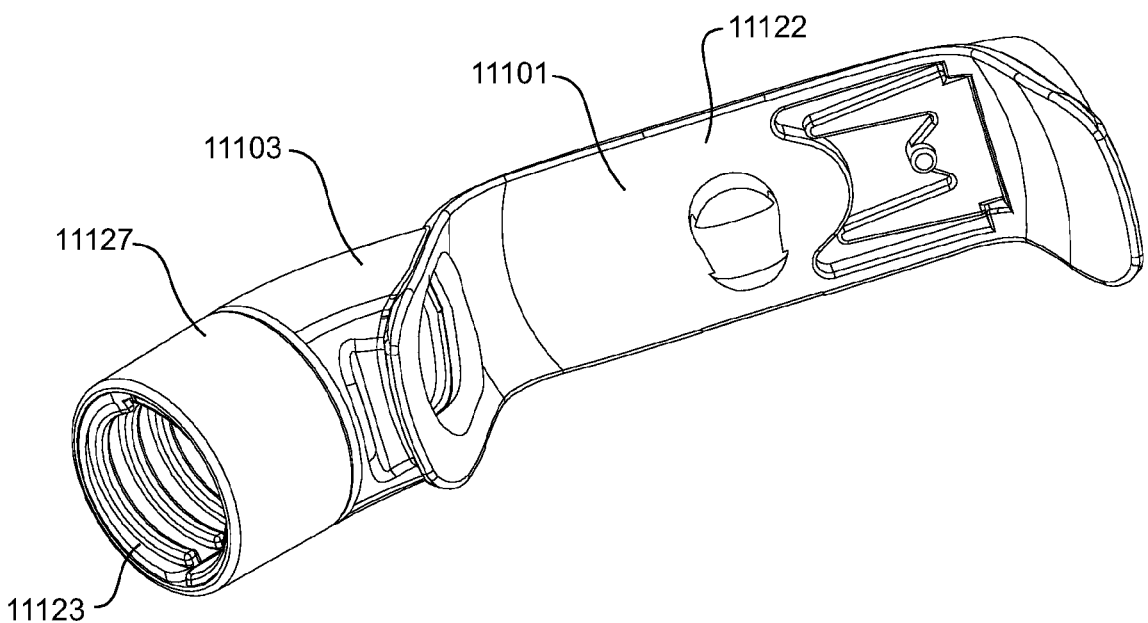
FIG. 30 is a side bottom perspective view of the manifold assembly of FIG. 29.
Figure 31:
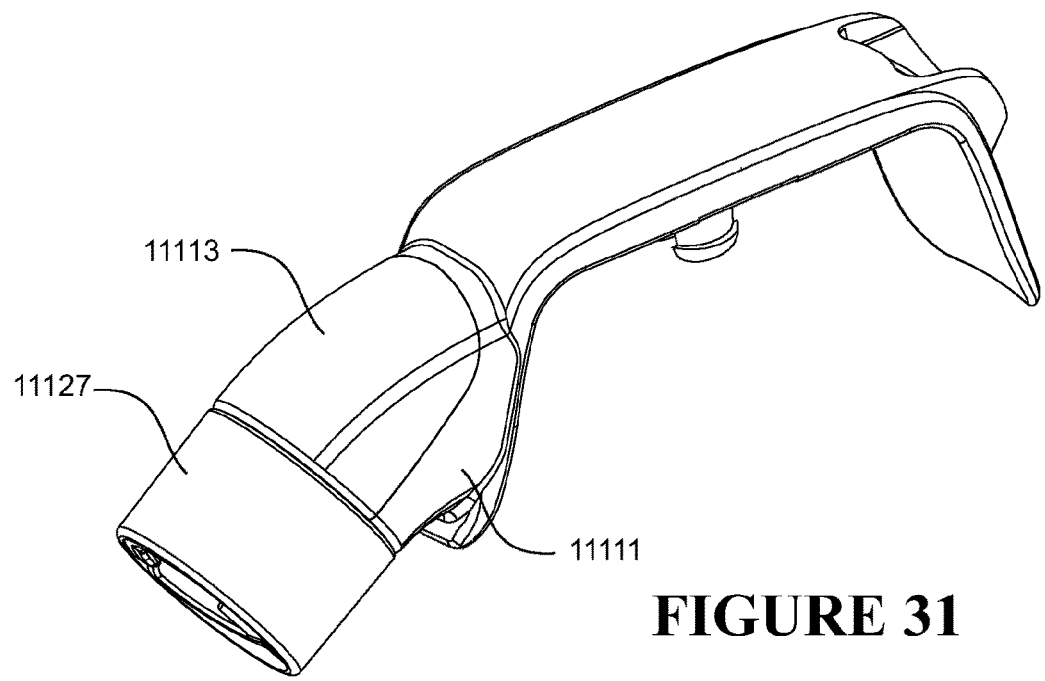
FIG. 31 is a side top perspective view of the manifold assembly of FIG. 29, showing the other side to that shown in FIG. 29.
Figure 32:
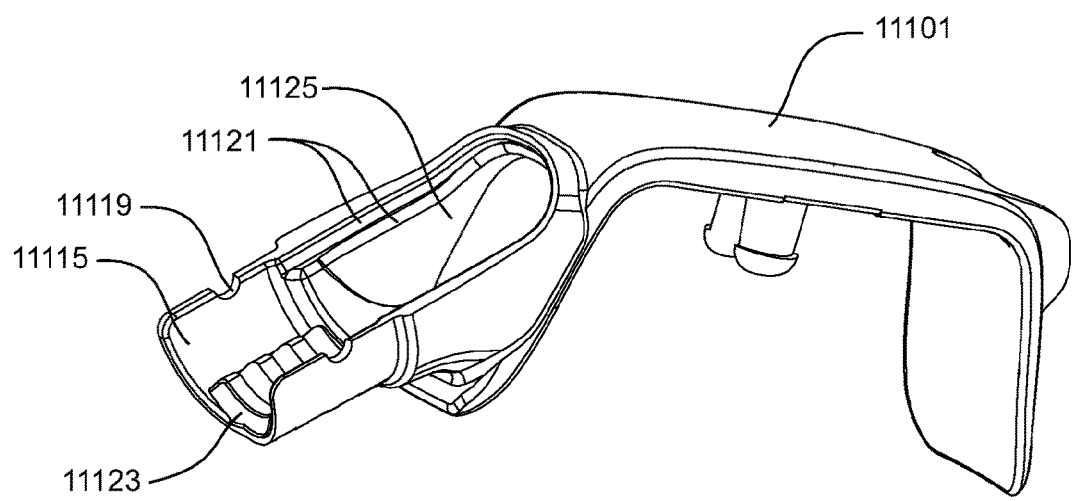
FIG. 32 is a side top perspective view of a first component of the manifold assembly of FIG. 29.
Figure 33:
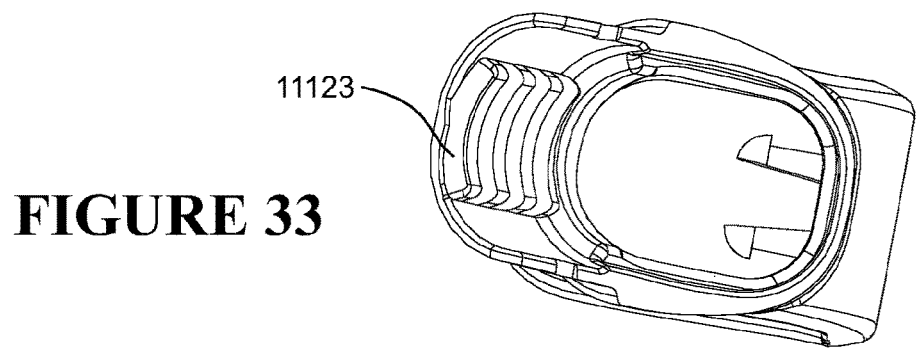
FIG. 33 is an end perspective view of the first component of FIG. 32.

With reference to FIG. 28a, a patient interface 11 for use in a medical breathing circuit is shown. The patient interface 11 comprises a frame section 13 adapted to be positioned on the face of a user and a manifold assembly 15 operatively securable to the frame section. The frame section 13 comprises a gases chamber, which is not visible in FIG. 28a, adapted to channel gases to the user and a pair of nasal delivery elements 17 extending from the gases chamber adapted to be located in a nare of the user.

Figure 46:
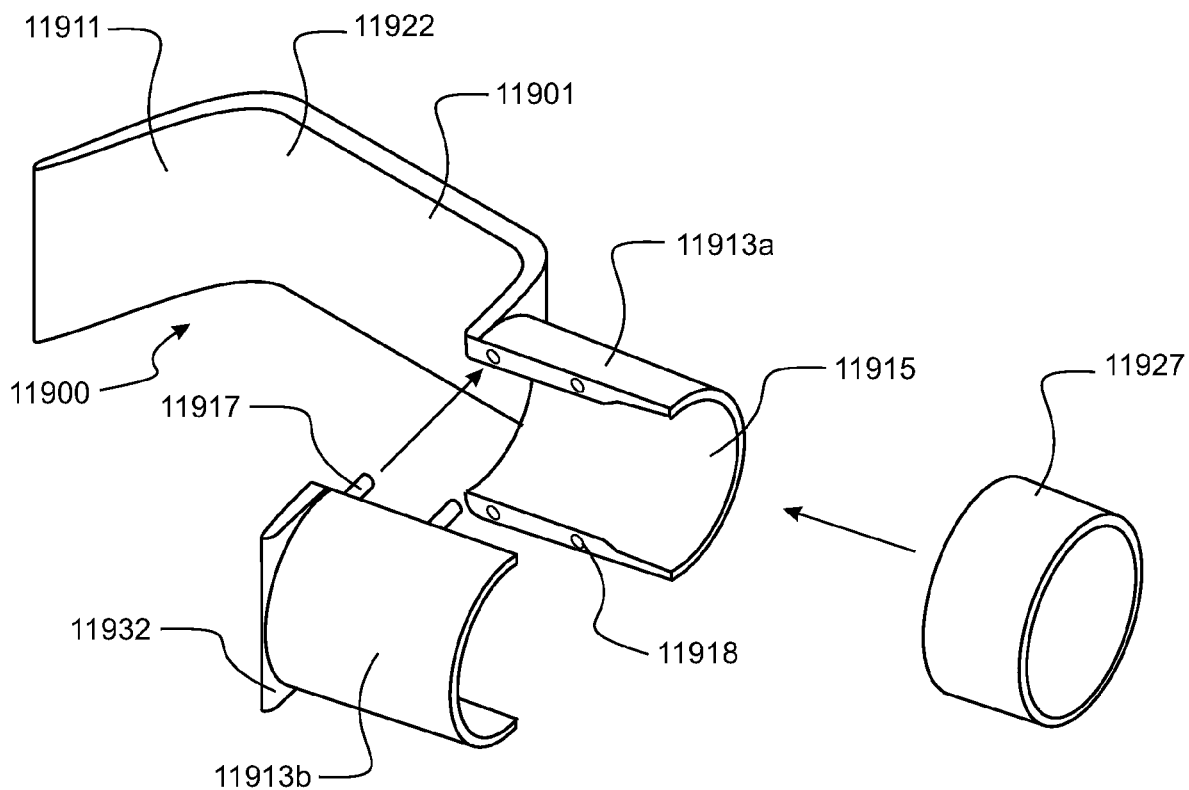
FIG. 46 is a partial exploded view of a ninth embodiment manifold assembly.

With reference to the embodiment shown in FIGS. 29 to 38, the manifold assembly 11100 (or 11900 as for example shown in FIG. 46, or 13400 shown in FIG. 61) has a manifold 11101 and a manifold inlet 11103. The manifold inlet has a tapered lumen 11105 in which an end 11107 proximal the manifold 11101 has an area greater than an area of an end 11109 of the lumen distal the manifold. With reference to FIG. 38, the lumen is gradually tapered from the end 11107 proximal the manifold 11101 to end 11109 of the lumen distal the manifold. In an alternative embodiment, the taper may be non-gradual; that is, it may have sections that have a taper that is different to the taper of an adjacent section. In that alternative embodiment, the non-gradual taper will preferably be relatively smooth where it transitions between taper angles. The transition of the lumen into the manifold cavity is relatively smooth to assist a smooth flow of gas from the conduit, through the lumen of the inlet to the manifold cavity. In the illustrated embodiment, this will reduce the noise of the gas flow from the manifold inlet to the manifold. With reference to FIG. 38, a smooth transition reduces resistance to flow of the gases and reduces the drop in pressure and/or flow velocity.

Figure 57:
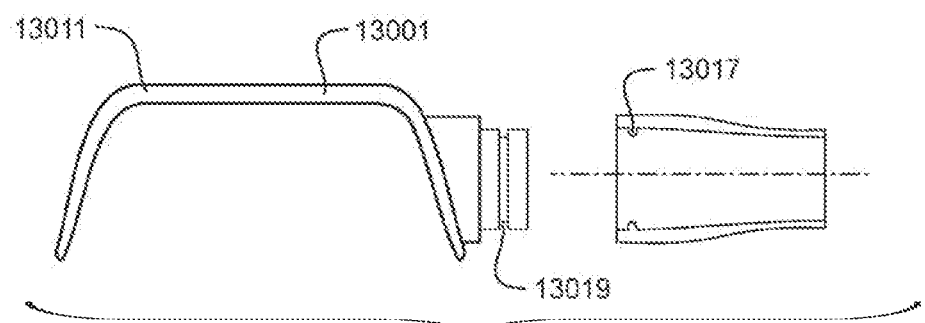
FIG. 57 is an exploded cross sectional view of a nineteenth embodiment manifold assembly.

The manifold assembly 11100 comprises a first component 11111 (or 12211 as for example shown in FIG. 49-50, or 13011 as shown in FIG. 57) and a second component 11113 (or 12213 as for example shown in FIGS. 49-50) engageable with the first component. The manifold assembly is formed from a series of modular components that allow for relatively simple tool designs to be used to create the smooth transition between the manifold inlet and the manifold. In particular, using a modular design allows a combination of relatively simple components to be assembled together to form a more complex shape. The components are engageable such that the first component 11111 forms at least part of the manifold 11101 (or 12201 as for example shown in FIGS. 49-50 or, 13011 as shown in FIG. 57), at least part of the manifold inlet 11103 (or 12203 as for example shown in FIGS. 49-50), or at least part of the manifold 11101 and at least part of the manifold inlet 11103. In addition, the components are engageable such that the second component forms at least part of the manifold 11101, at least part of the manifold inlet 11103, or at least part of the manifold 11101 and at least part of the manifold inlet 11103. That is, there are a number of different embodiments of the first component 11101 and second component 11113 such that each component forms part of, or all of, the manifold 11101 or manifold inlet 11103. The manifold assembly 11100 may comprise further components to either form the manifold 11101 or manifold inlet 11103, fasten the first component and second component together, and/or provide seals between the first component and second component. Each of those variations will be described in more detail below with reference to the accompanying drawings.

With reference to the embodiment shown in FIGS. 29 to 38, the first component 11111 has a first manifold inlet portion 11115, and the second component 11113 is or has a second manifold inlet portion. In the embodiment shown in FIG. 29, the second component 11113 is the second manifold inlet portion. The manifold inlet portion 11115 of the first component 11111 and the manifold inlet portion of the second component 11113 are engageable to form the manifold inlet 11103.

The first component 11111 comprises at least one location feature and the second component comprises at least one complementary location feature. In the embodiment shown in FIG. 29, the location features of the second component comprise protrusions 11117 and the at least one location feature of the first component comprises complementary recesses 11119. In addition, the first and second components comprise complementary abutment surfaces 11121 that extend around a portion of the periphery of each of the components.

The first component 11111 has a manifold portion 11122 forming the manifold 11101. In the embodiment shown, the manifold portion 11122 forms the entire manifold 11101.

The first component has an internally threaded portion 11123 corresponding to an externally threaded portion of a conduit or tube (not shown). The first component also has a smooth, non-threaded portion 11125. The second component 11113 has an internally threaded portion 11126 corresponding to an externally threaded portion of the conduit. The second component has a smooth, non-threaded portion 11129.

The manifold assembly 11100 further comprises a third component that acts as a fastening component. In the embodiment shown in FIG. 29, the fastening component comprises a collar 11127. The collar 11127 is a substantially annular component having a tapered internal surface for engaging with an exterior surface of the manifold inlet portion of the first component and an exterior surface of the manifold inlet portion of the second component. The internal surface is tapered so that it is easier to assemble to collar in one direction than the other direction. In addition, during assembly, as the collar is urged over the manifold inlet portions of the first and second components, the tapered surface has a wedge-type action so the force applied by the collar on the manifold inlet portion increases as the collar moves towards its assembled position.

During assembly, engagement of the collar 11127 with the manifold inlet portion of the first component and/or second component may provide sensory feedback to an operator. For example, a lug on the collar 11127 may engage a recess, aperture, or abutment surface on the first component or the second component, preferably with a snap engagement. The collar 11127 may have more than one lug engaging with more than one recess, aperture, or abutment surface. In alternative embodiments, the first and/or second component may have the lug and the collar may have the recess, aperture, or abutment surface.

The sensory feedback is audible feedback, tactile feedback, visual feedback, or a combination of two or three types of feedback. The manifold assembly is arranged to emit a readily audible sound when the collar engages the manifold inlet portion of the first component and/or second component, preferably with a snap engagement. In the illustrated embodiment, the collar is arranged to undergo a readily tactile movement or emit a readily tactile vibration when the collar(s) engage(s) the first and/or second component, preferably with a snap engagement.

A number of alternative embodiments of the manifold assembly are shown in FIGS. 39 to 46. In these embodiments, the first component has a manifold inlet portion and a manifold portion, and the second component is a manifold inlet portion. Unless described as otherwise below, the features and functioning of the manifold assembly should be considered the same as described for the first embodiment above, and like reference numerals indicate like parts with the addition of 100 or 200 to the previously described embodiment.

Figure 39:
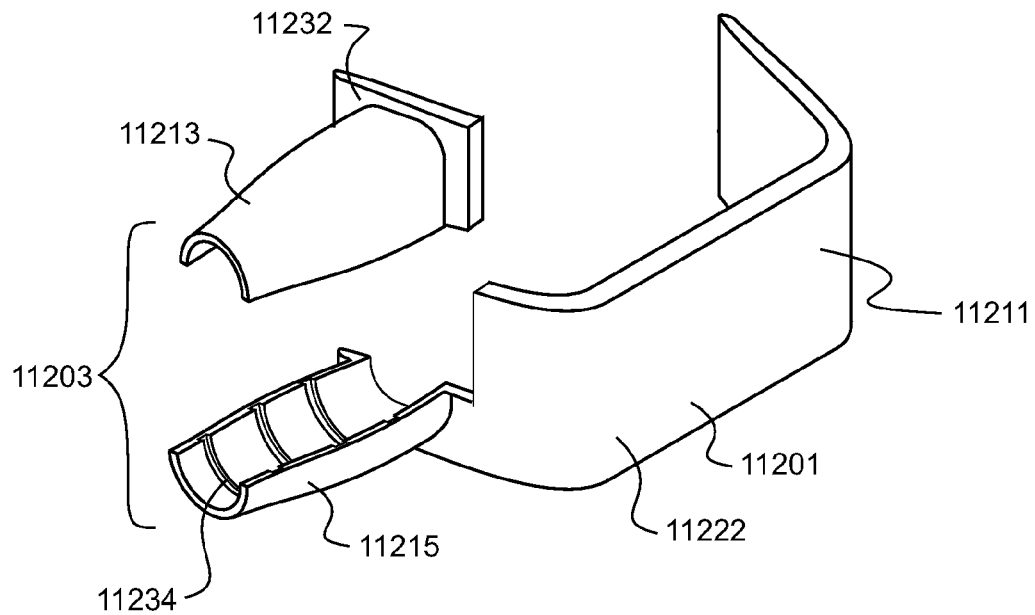
FIG. 39 is an exploded view of a second embodiment manifold assembly.

The embodiment of FIG. 39 has a first component 11211 with a manifold portion 11222 forming the manifold 11201 and a manifold inlet portion 11215. The second component is a manifold inlet portion 11213. The manifold inlet 11203 (or as for example 11303 as shown in FIG. 40, 11403 as shown in FIG. 41 or 11503 as shown in FIG. 42) is formed by the second component and the manifold inlet portion

11215 of the first component 11211. The manifold inlet portion 11213 has an integrally formed flange 11232. The flange 11232 engages the manifold portion 11222 of the first component 11211 to form the manifold. This embodiment includes surface relief features in the form of channels 11234 that may be engageable with the corrugations of an associated conduit or tube (not shown). The surface relief features locate and/or also seal or couple the components and conduit together. The surface relief features created a sealed pneumatic path and pneumatic connection between the conduit and the manifold 11201. Other suitable features include pins and/or bosses together with complementary recesses.

Figure 40:
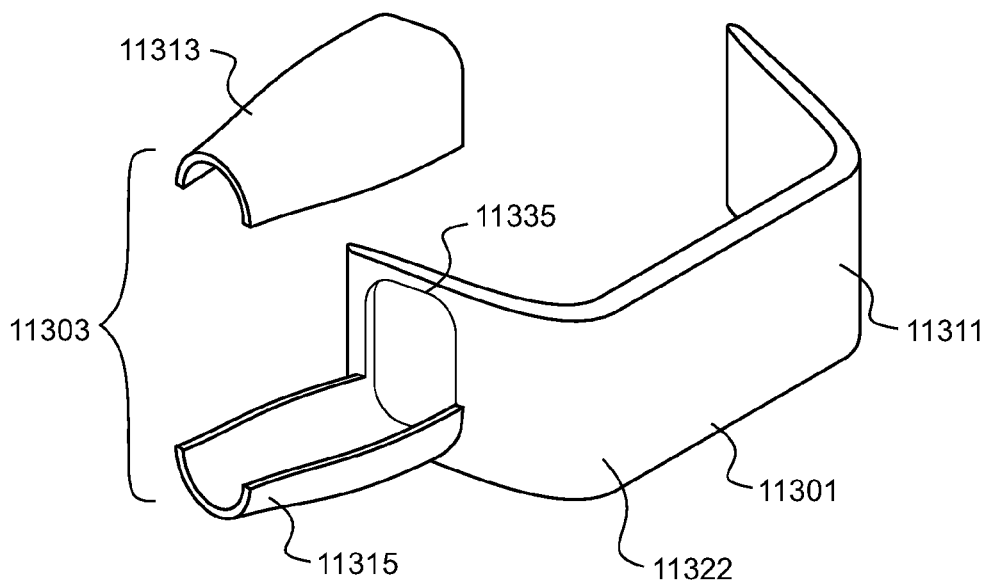
FIG. 40 is an exploded view of a third embodiment manifold assembly.

The embodiment of FIG. 40 has a first component 11311 with a manifold portion 11322 forming the manifold 11301, and a manifold inlet portion 11315; that is, the first portion forms the manifold and a portion of the manifold inlet. The second component 11313 is a manifold inlet portion without a manifold portion. The manifold inlet portion 11313 has a surface (not visible) that engages a surface 11335 of the manifold portion 11322.

Figure 41:
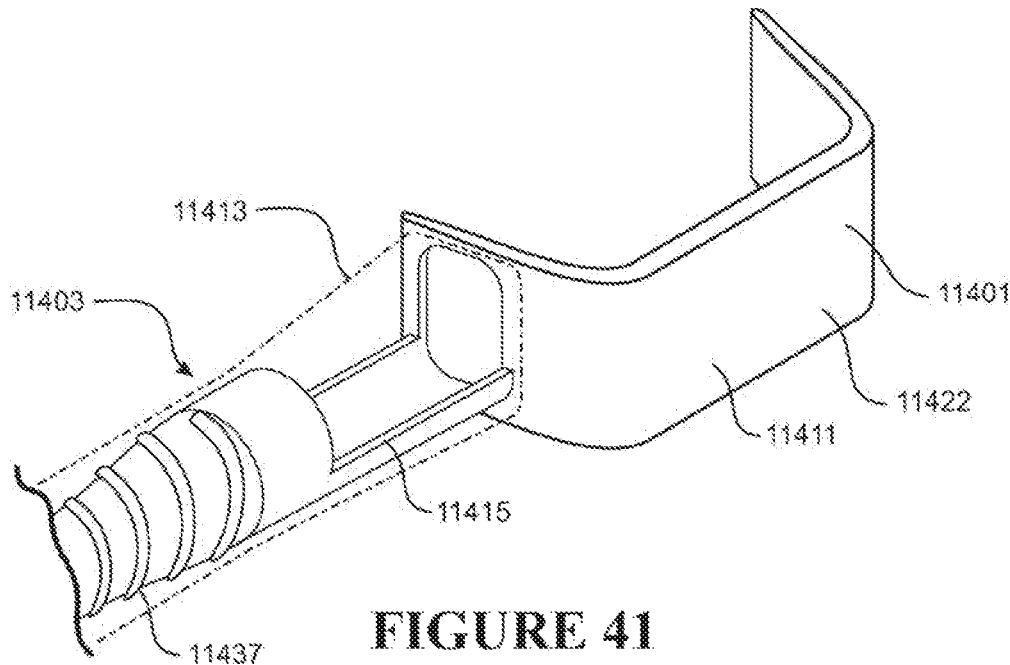
FIG. 41 is an exploded view of a fourth embodiment manifold assembly.
Figure 42:
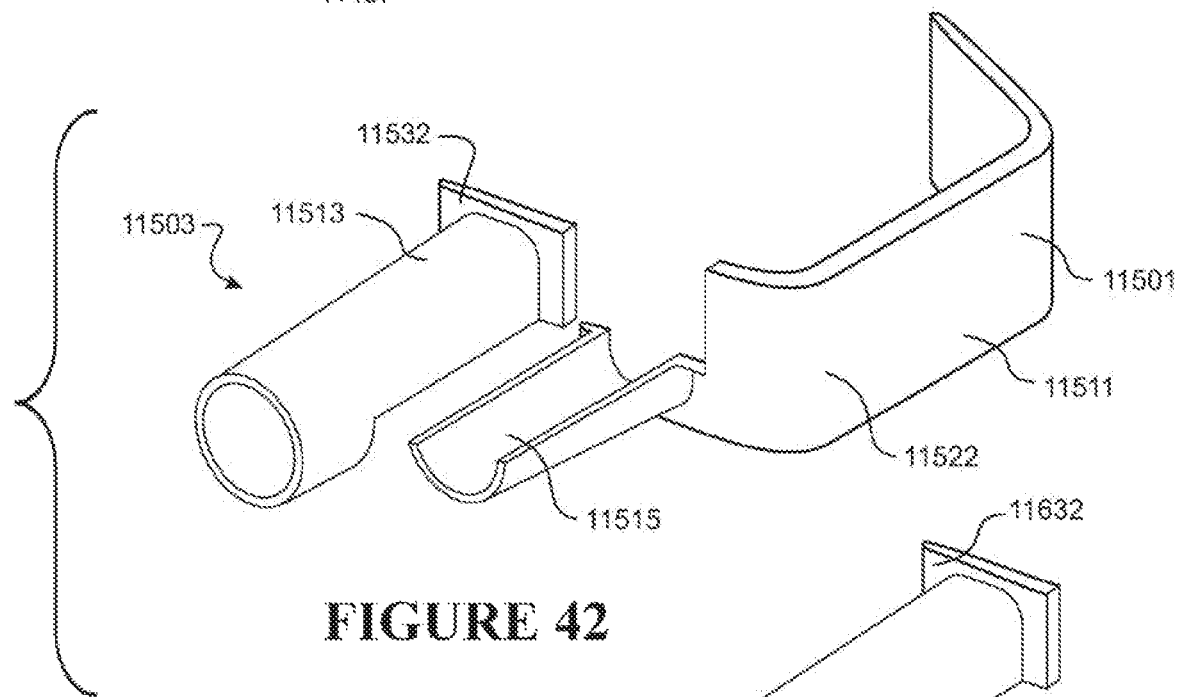
FIG. 42 is an exploded view of a fifth embodiment manifold assembly.

The embodiment of FIG. 41 has a first component 11411 with a manifold portion 11422 forming the manifold 11401 and a manifold inlet portion 11415. The second component 11413 is relatively soft material, preferably TPE, which forms a manifold inlet with the manifold inlet portion 11415 of the first component 11411. The second component 11413 covers and joins the conduit or tube 11437 to the first component.

The embodiment of FIG. 42 has a first component 11511 with a manifold portion 11522 forming the manifold 11501 and a manifold inlet portion 11515; that is, the first portion forms the manifold and a portion of the manifold inlet. The second component is a manifold inlet portion 11513. The manifold inlet portion 11513 has an integrally formed flange 11532 (or 11632 as for example shown in FIG. 43). The flange 11532 engages the manifold portion 11522 of the first component 11511 to form the manifold 11501.

Figure 43:
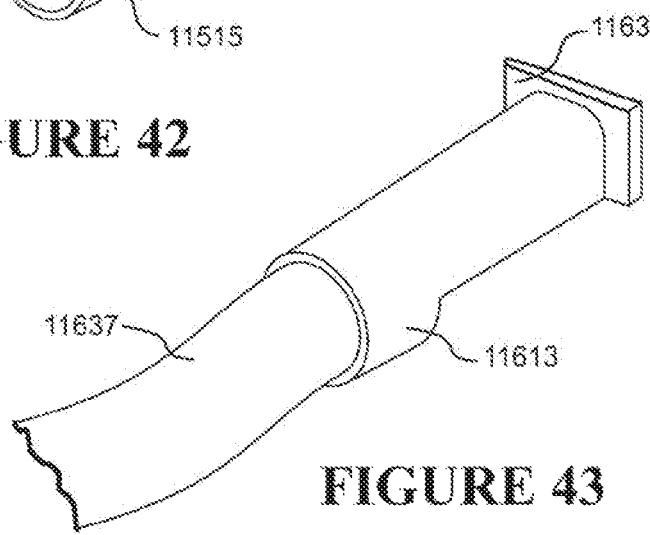
FIG. 43 is an exploded view of a sixth embodiment manifold assembly.

The embodiment of FIG. 43 is a modification of the embodiment of FIG. 42 in which the conduit or tube 11637 is incorporated with the manifold inlet portion 11613.

Figure 44:
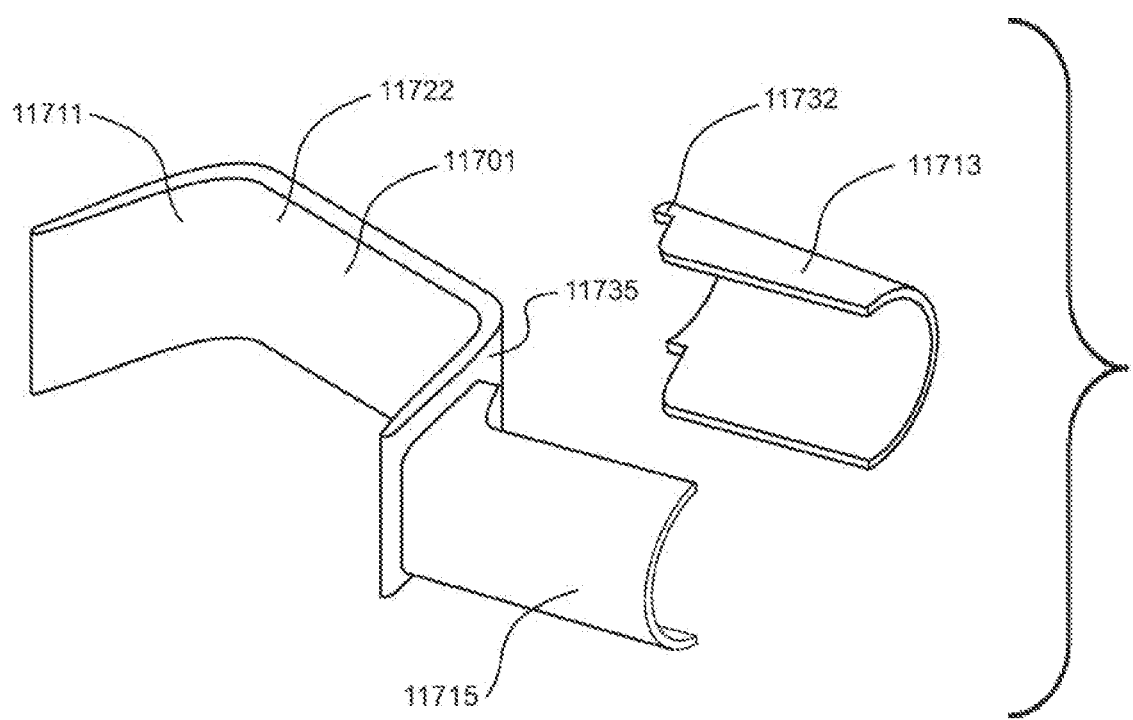
FIG. 44 is an exploded view of a seventh embodiment manifold assembly.

The embodiment of FIG. 44 has a first component 11711 with a manifold portion 11722 forming the manifold 11701 and a manifold inlet portion 11715. The second component is a manifold inlet portion 11713. The manifold inlet portion 11713 has an integrally formed protrusion 11732. The protrusion 11732 engages a surface 11735 of the manifold portion 11722.

Figure 45:
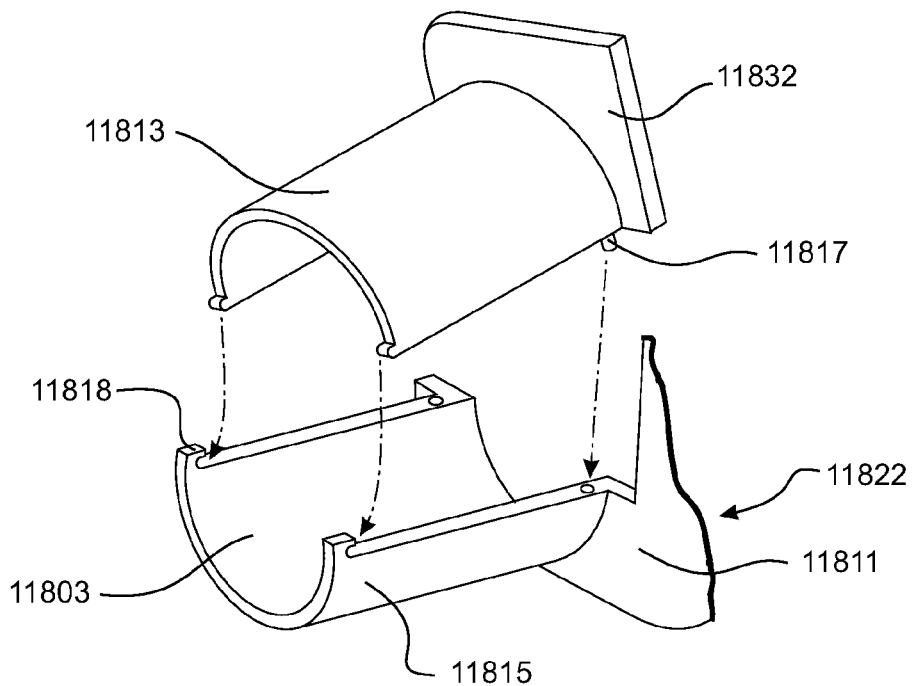
FIG. 45 is an exploded view of an eighth embodiment manifold assembly.

The embodiment of FIG. 45 has a first component 11811 with a manifold portion 11822 forming the manifold and a manifold inlet portion 11815. The second component is a manifold inlet portion 11813; the first component forms a portion of the manifold inlet and the second component is a portion of the manifold inlet. The manifold inlet portion 11813 has an integrally formed flange 11832. The flange engages the manifold portion 11822 of the first component 11811 to form the manifold. This embodiment includes protrusions 11817 on one of the first and second components and complementary hooks 11818 on the other of the first and second components. This embodiment also includes pins and/or bosses together with complementary recesses.

The embodiment of FIG. 46 has a first component 11911 with a manifold portion 11922 forming the manifold 11901 and a manifold inlet portion 11915. The second component is a manifold inlet portion 11913 (comprising portions 11913a and 11913b). The manifold inlet portion 11913 has an integrally formed flange 11932. The flange 11932 engages the manifold portion 11922 of the first component 11911 to form the manifold 11901. This embodiment also includes pins and/or bosses 11917 together with complementary recesses 11918. The manifold assembly further comprises a fourth component that acts as a fastening component. In the embodiment shown in FIG. 46, the fastening component comprises a collar 11927 that engages with the external surfaces of the manifold inlet portions 11913a, 11913b.

With reference to the embodiments shown in FIGS. 47 to 50, the first component has a manifold portion and the second component has a manifold portion. The manifold portion of the first component and the manifold portion of the second component are engageable to form at least part of the manifold. In the embodiments shown in FIGS. 48 to 51, the manifold portion of the first component and the manifold portion of the second component are engageable to form the entire manifold.

Figure 47:
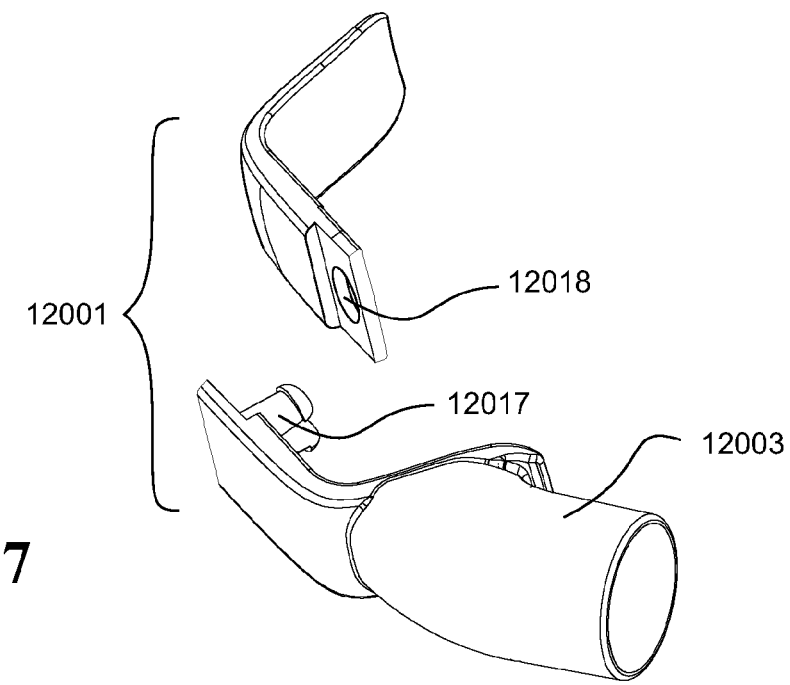
FIG. 47 is an exploded view of a tenth embodiment manifold assembly.

In the embodiment of FIG. 47, the first component has a manifold inlet portion forming at least part of the manifold inlet 12003. In particular, the first component has a manifold inlet portion forming the entire manifold inlet 12003; that is, the first component forms the manifold inlet 12003 and part of the manifold and the second component forms the remainder of the manifold 12001. The manifold assembly has flexibly resilient legs 12017 that are received by aperture 12018.

Figure 48:
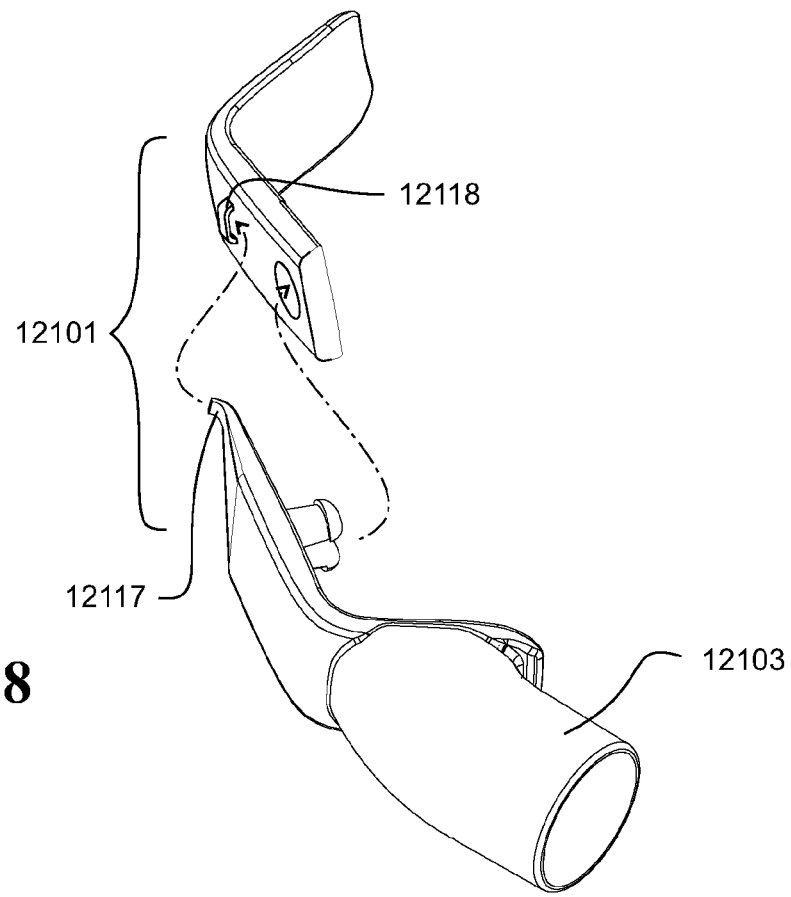
FIG. 48 is an exploded view of an eleventh embodiment manifold assembly.

The embodiment of FIG. 48 is similar to that of FIG. 47 with the addition of complementary hooks 12117 and protrusions 12118 that are engageable to assemble the manifold.

Figure 49:
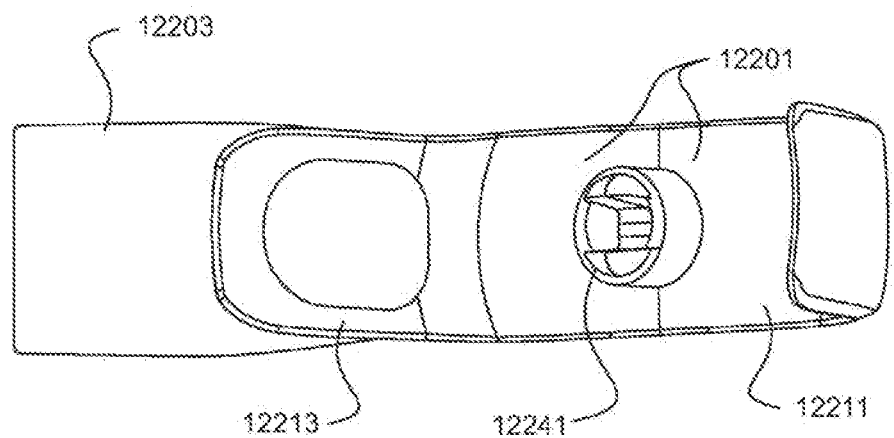
FIG. 49 is a perspective view of a twelfth embodiment manifold assembly.
Figure 50:
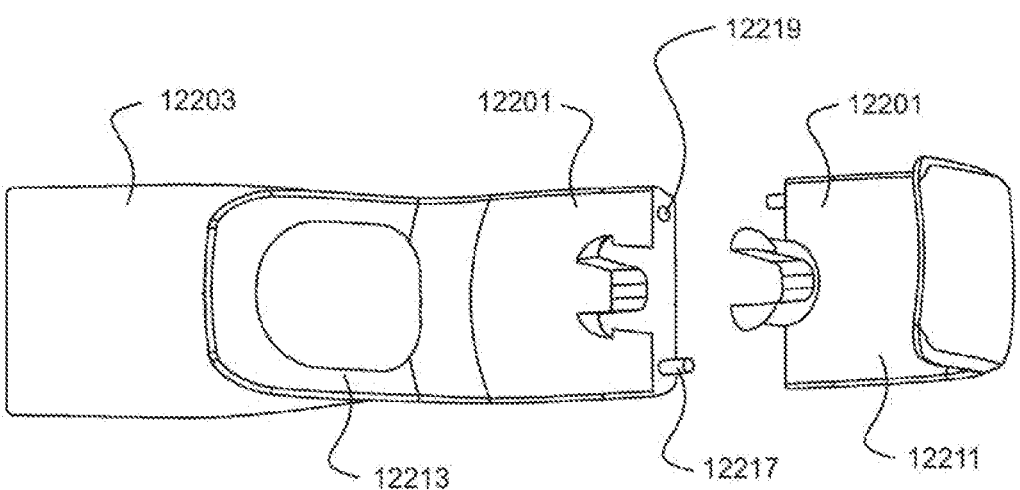
FIG. 50 is an exploded view of the manifold assembly of FIG. 49.

The embodiment of FIGS. 49 and 50 is one in which the manifold is split through a vertically extending plane that intersects the axis of the axle 12241, when viewed from the position of FIG. 49. This embodiment comprises pins and/or bosses 12217 together with complementary recesses 12219 for engaging the first component with the second component.

In an alternative embodiment, the manifold assembly further comprises a third component engageable with the first component and/or second component to form at least part of the manifold. In a further alternative embodiment, the patient interface further comprises a third component engageable with the first component and/or second component to form the entire manifold.

With reference to the embodiments shown in FIGS. 51 to 57, the first component forms at least a major portion of the manifold and the second component forms at least a major portion of the manifold inlet. In the embodiments shown in FIGS. 51 to 57, the first component forms the entire manifold and the second component forms the entire manifold inlet.

Figure 51:
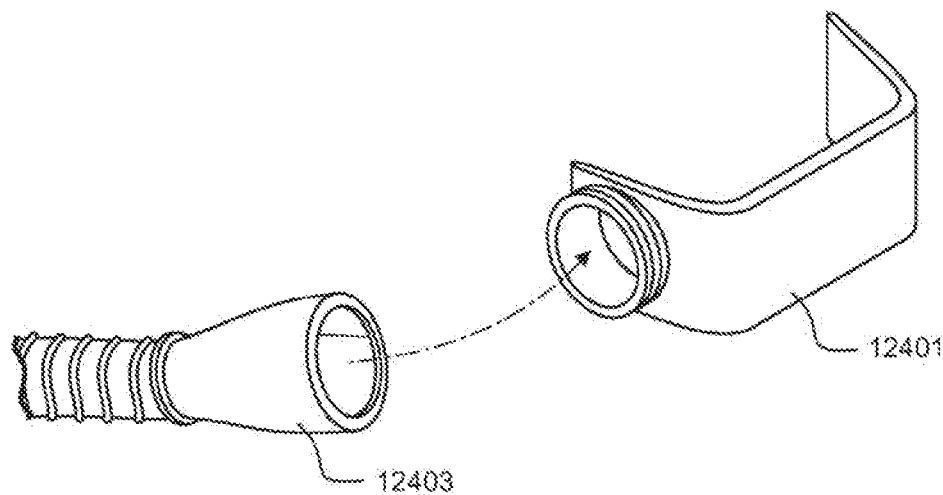
FIG. 51 is an exploded view of a thirteenth embodiment manifold assembly.
Figure 52:
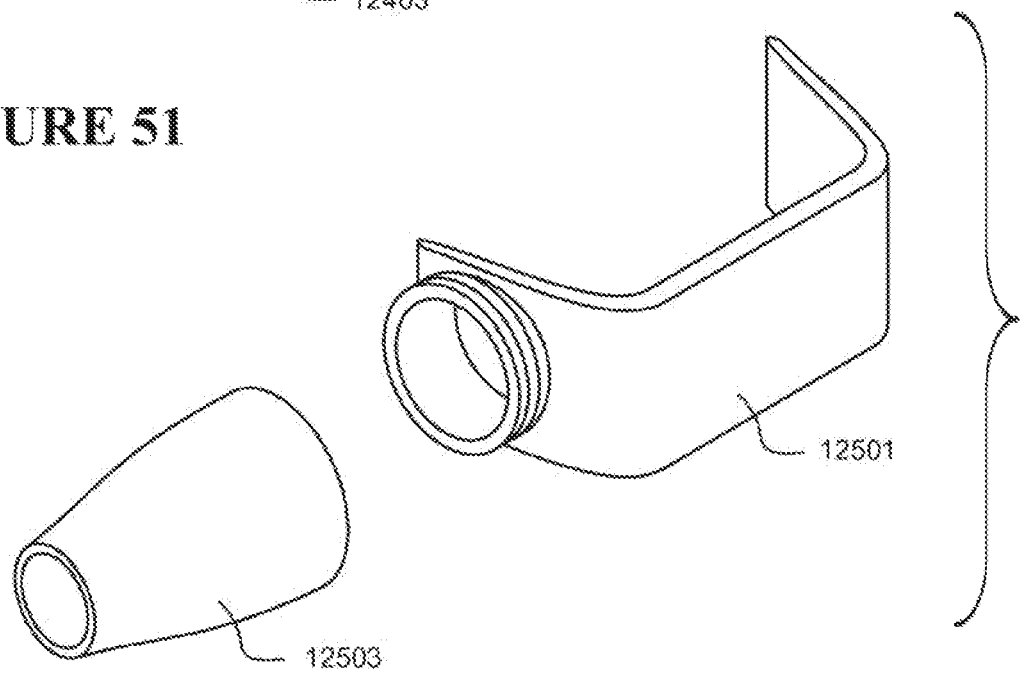
FIG. 52 is an exploded view of a fourteenth embodiment manifold assembly.
Figure 53:
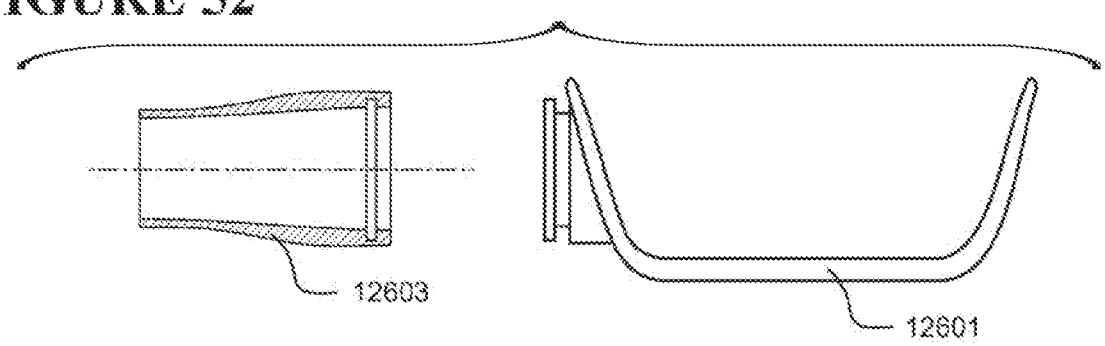
FIG. 53 is an exploded cross sectional view of a fifteenth preferred embodiment manifold assembly.
Figure 54:
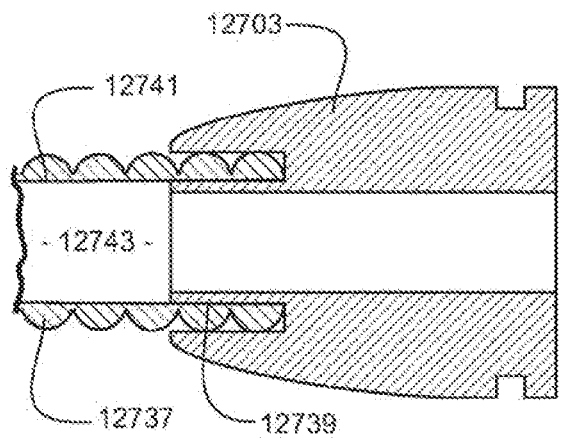
FIG. 54 is a cross sectional view of a sixteenth embodiment manifold assembly.
Figure 55:
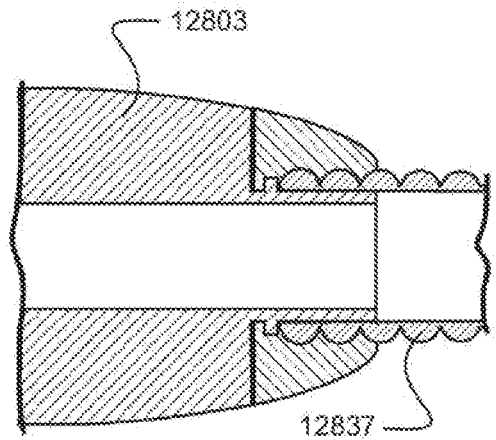
FIG. 55 is a cross sectional view of a seventeenth embodiment manifold assembly.

The embodiment of FIGS. 51 to 53 have a manifold inlet 12403, 12503, 12603 (or as for example 12703 as shown in FIG. 54, 12803 as shown in FIG. 55) that is a snap fit on to a manifold 12401, 12501, 12601. The embodiment of FIG. 51 has a manifold inlet integrally formed with the conduit or tube.

The embodiments of FIGS. 54 and 55 show alternative methods for attaching the conduit or tube to the manifold inlet. The embodiment of FIG. 54 has a smooth bore conduit 12737 and the manifold inlet has a smooth inner surface 12739 to engage the bore 12743 of the conduit. Alternatively, the inner surface of the manifold inlet could have surface features to engage with the troughs or crest of the conduit, if the conduit is corrugated or threaded, for example.

Figure 60:
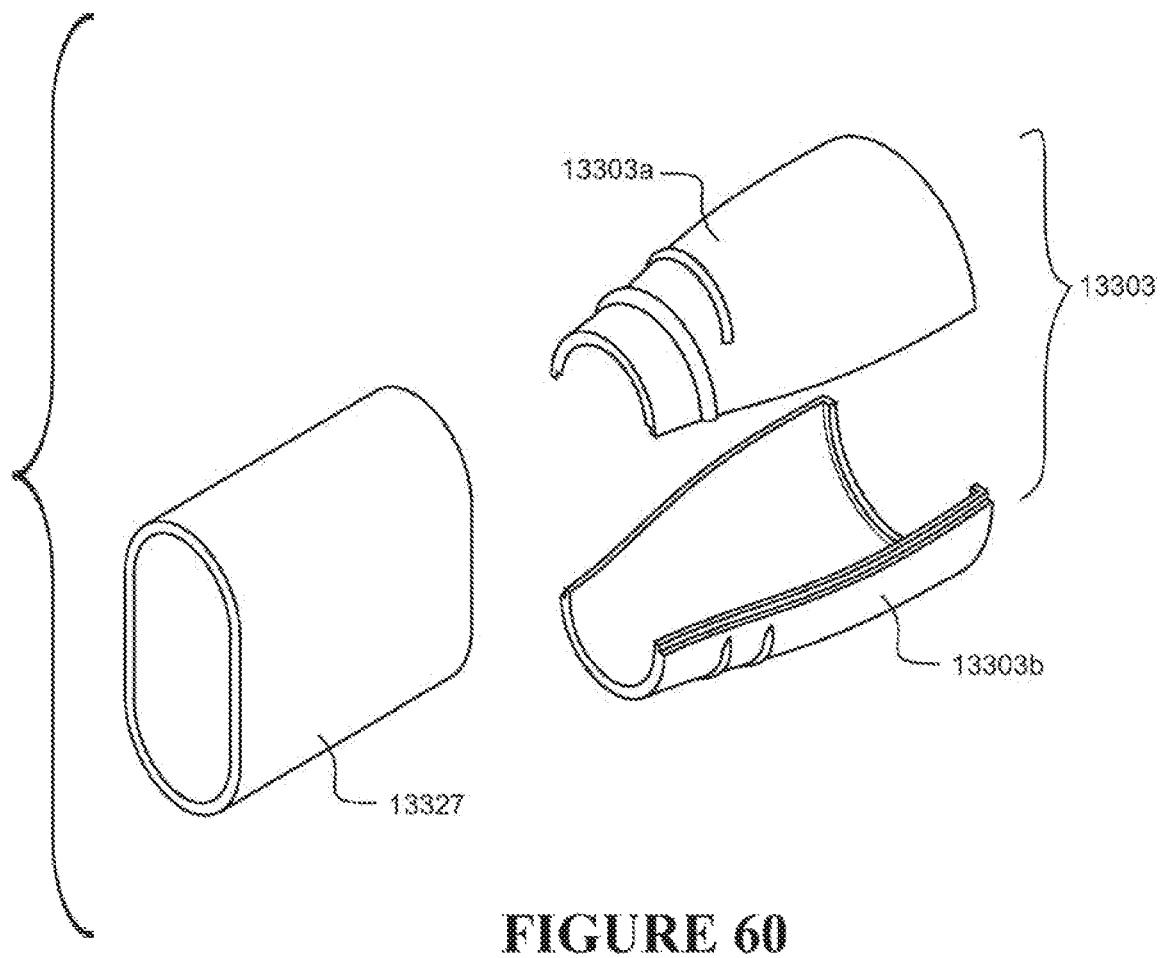
FIGS. 60 and 60A show a twenty-first embodiment manifold assembly.
Figure 60A:
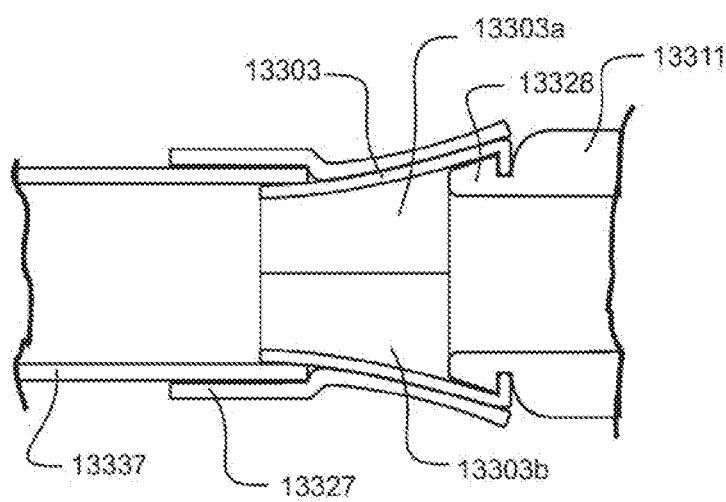

The embodiment of FIG. 55 is similar to the embodiment shown in FIG. 54, except that the first component of the manifold inlet is formed from a relatively rigid material and the second component of the manifold inlet is formed from a relatively flexible or resilient material that snaps over the manifold inlet and/or conduit 12837 (or as for example 13337, as shown in FIG. 60A).

Figure 56:
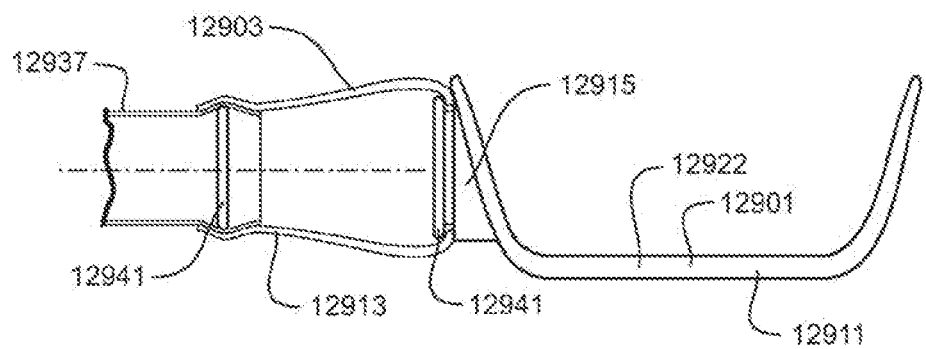
FIG. 56 is a cross sectional view of an eighteenth embodiment manifold assembly.

The embodiment of FIG. 56 has a first component 12911 with a manifold portion 12922 forming the manifold 12901 and a manifold inlet portion 12915. The second component 12913 is relatively soft material, preferably TPE, which forms a manifold inlet 12903 with the manifold inlet portion 12915 of the first component 12911. The second component 12913 covers and joins the conduit or tube 12937 to the first component 12911. This embodiment also includes O-rings 12941 for sealing the second component 12913 to each of the conduit 12937 and the manifold inlet portion 12915.

The embodiment of FIG. 57 is similar to the embodiment of FIG. 51, except that the manifold inlet is a separate and distinct component to the conduit or tube. The manifold inlet is a snap-fit with the manifold with a rib 13017 of the engaging a channel 13019 of the manifold.

Figure 58:
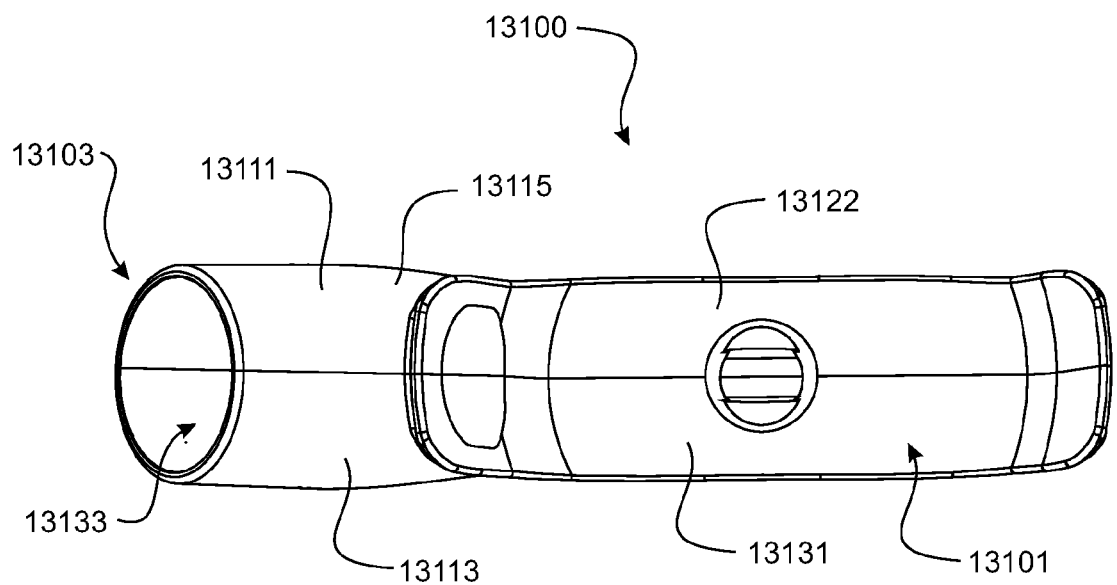
FIGS. 58 and 59 shows a twentieth embodiment manifold assembly.
Figure 59:
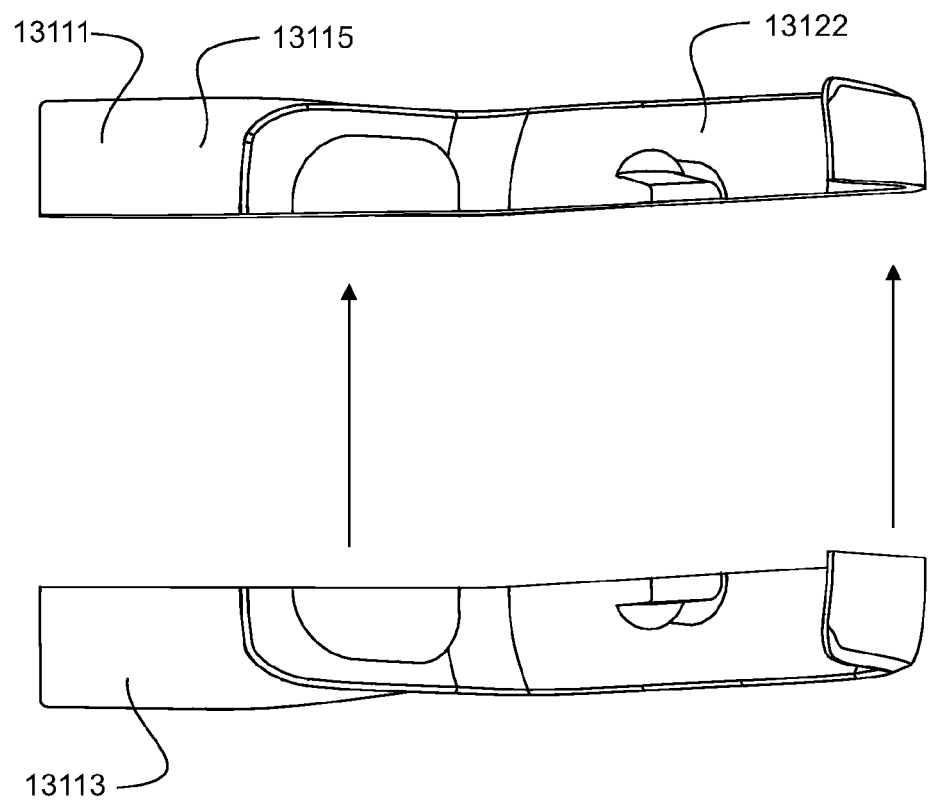

With reference to the embodiment shown in FIGS. 58 and 59, the first component 13111 (or as for example 13311, as shown in FIG. 60A) has a manifold portion 13122 and a manifold inlet portion 13115, and the second component 13113 has a manifold portion 13131 and a manifold inlet portion 13133. The manifold portion 13131 of the first component 13111 and the manifold portion 13133 of the second component 13113 are engageable to form at least part of the manifold 13101. The manifold inlet portion 13115 of the first component 13111 and the manifold inlet portion 13133 of the second component 13113 are engageable to form at least part of the manifold inlet 13103.

The embodiment of FIGS. 58 and 59 has a manifold inlet 13103 and a manifold 13101. In this embodiment, the first component 13111 and second component 13113 form half of each of the manifold and the manifold inlet. The first component 13111 and second component 13113 are substantially similar components. The first component 13111 may be a mirror image of the second component 13113. In this embodiment, the manifold assembly 13100 is split horizontally along a plane that is coincident with a longitudinal axis of the manifold assembly. The plane may be positioned higher or lower than the position of the plane when viewed from the position of FIG. 58. In an alternative embodiment, the manifold assembly may further comprise an additional component that secures the first and second components together at the axle. The additional component may comprise a flexible or resilient material.

With reference to the embodiments shown in FIGS. 60 to 75, the patient interface comprises first and second components forming at least part of the manifold inlet and a third component forming at least part of the manifold. In the embodiments shown, the third component forms the entire manifold.

The embodiment of FIGS. 60 and 60a has a two part manifold inlet 13303 in which the two parts are engageable together and with other components (not shown) to form a manifold assembly. A first component (not shown) forms at least part of or the entire manifold. A second component 13303a and a third component 13303b engage to form the manifold inlet 13303. In this embodiment, the first and second components of the manifold inlet fit over a flange 13328 of the manifold. The manifold assembly further comprises a fourth component that acts as a fastening component. In the embodiment shown in FIG. 60, the fastening component comprises a collar 13327 that is or comprises shrink wrap material.

Figure 61:
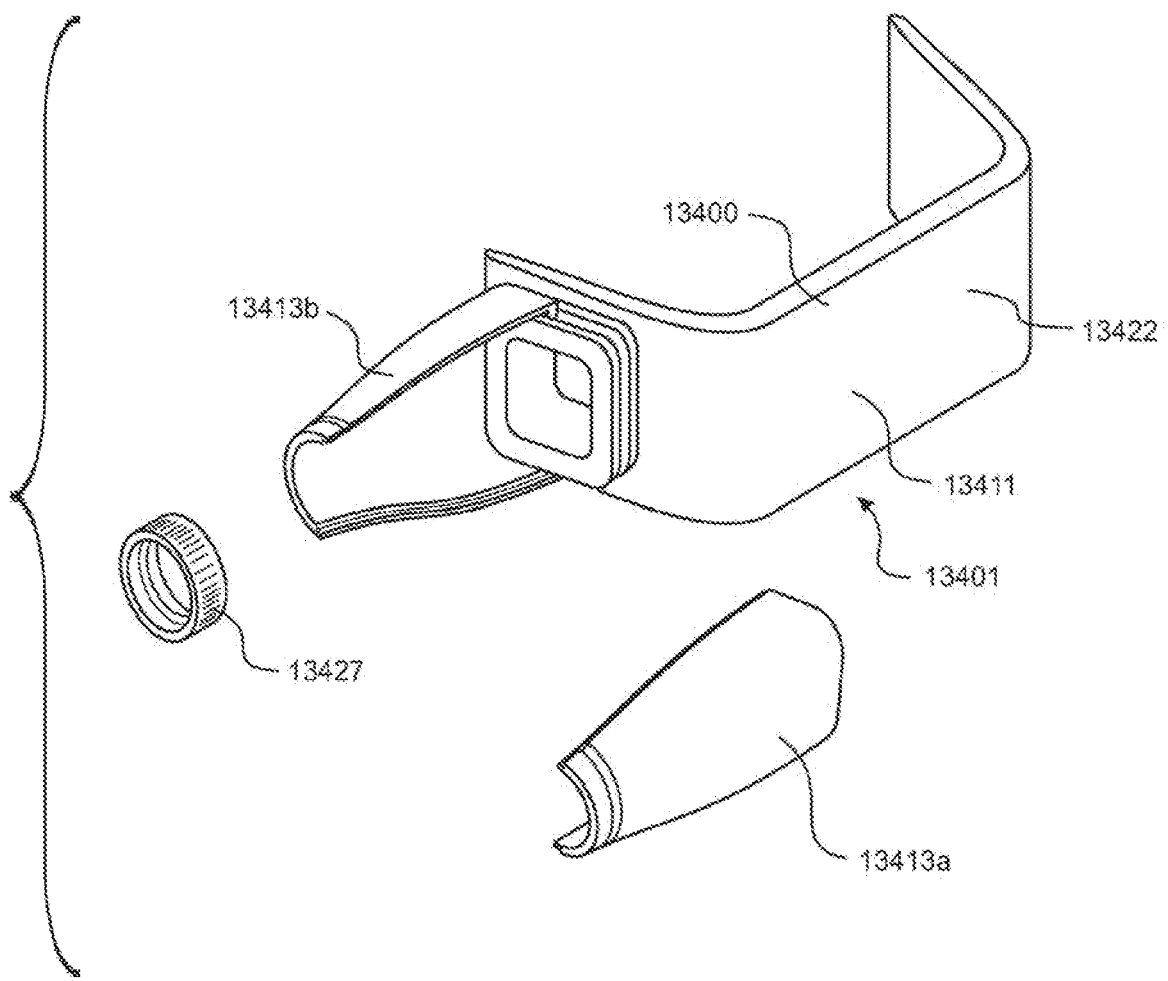
FIG. 61 shows another embodiment of a manifold assembly.

The embodiment of FIG. 61 has a first component 13411 with a manifold portion 13422 forming the entire manifold 13401. The second component is a manifold inlet portion 13413a and the third component is a manifold inlet portion 13413b. The manifold assembly further comprises a fourth component that acts as a fastening component. In the embodiment shown in FIG. 45, the fastening component comprises a collar 13427 with internal threads that engage with complementary external threads of the manifold inlet portions 13413a, 13413b.

Figure 62:
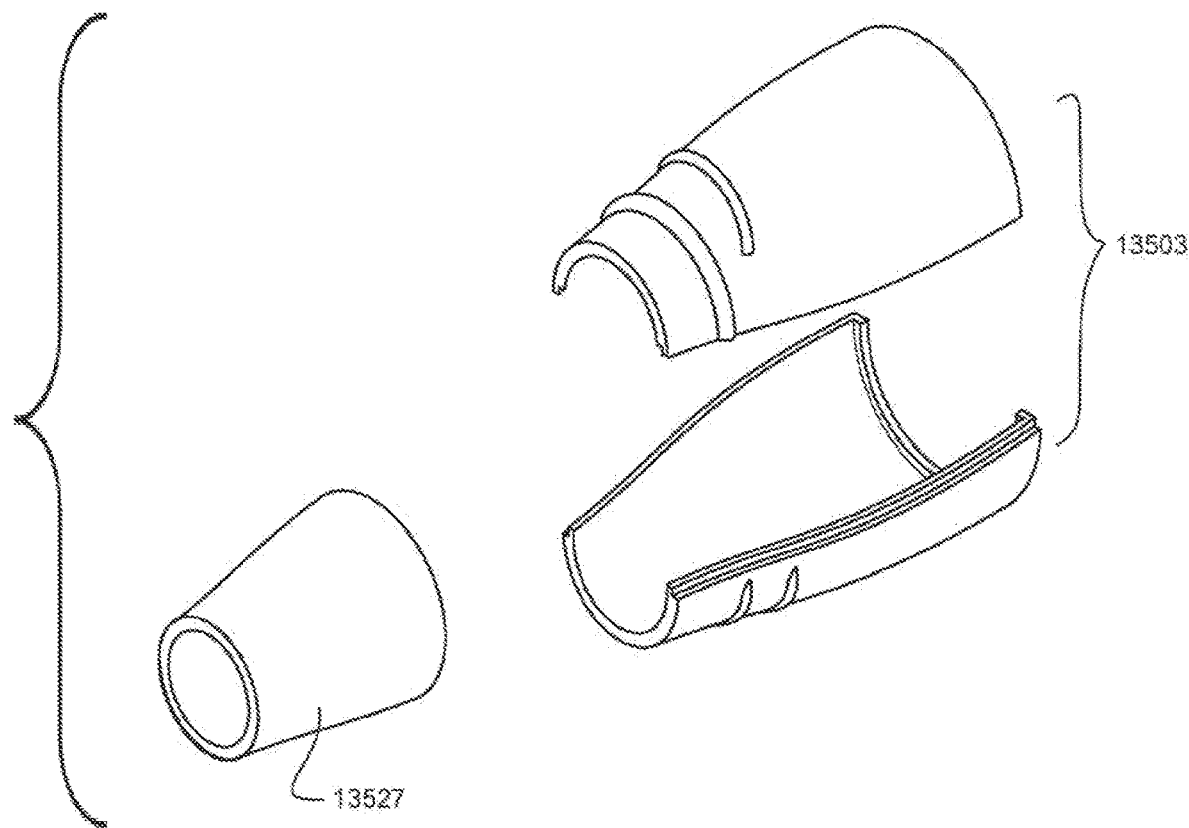
FIGS. 62 and 63 show twenty-second embodiment manifold assembly.
Figure 63:
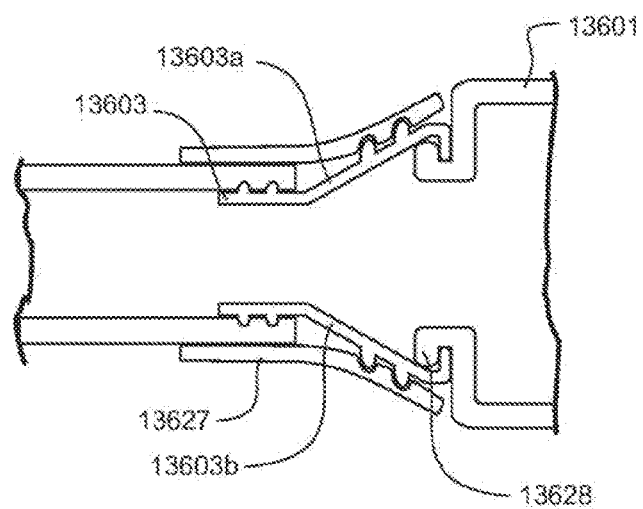
Figure 64:
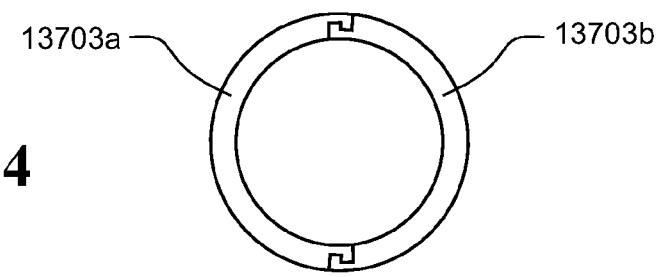
FIG. 64 is a cross sectional view of a twenty-third embodiment manifold assembly.
Figure 65:
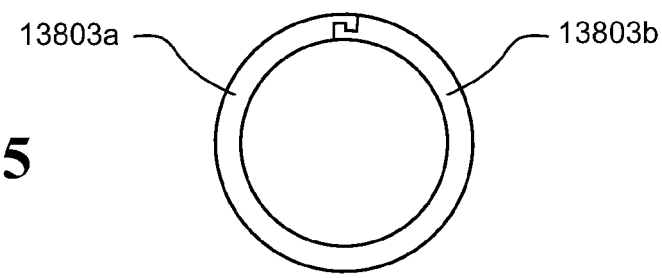
FIG. 65 is a cross sectional view of a twenty-fourth embodiment manifold assembly.

The embodiment of FIGS. 62 and 63 has a two part manifold inlet 13503 in which the two parts are engageable together and with other components (not shown) to form a manifold assembly. A first component 13511 forms at least part of or the entire manifold 13501. A second component 13503a (or as for example 13703a, as shown in FIG. 64, or 13803a as shown in FIG. 65) and a third component 13503b (or as for example 13703b, as shown in FIG. 64, or 13803b as shown in FIG. 65) engage to form the manifold inlet 13503. In this embodiment, the first and second components of the manifold inlet fit over a flange 13528 of the manifold. The manifold assembly further comprises a fourth component that acts as a fastening component. In the embodiment shown in FIG. 62, the fastening component comprises a threaded collar 13527 that engages with threads of the components that form the manifold inlet.

Figure 66:
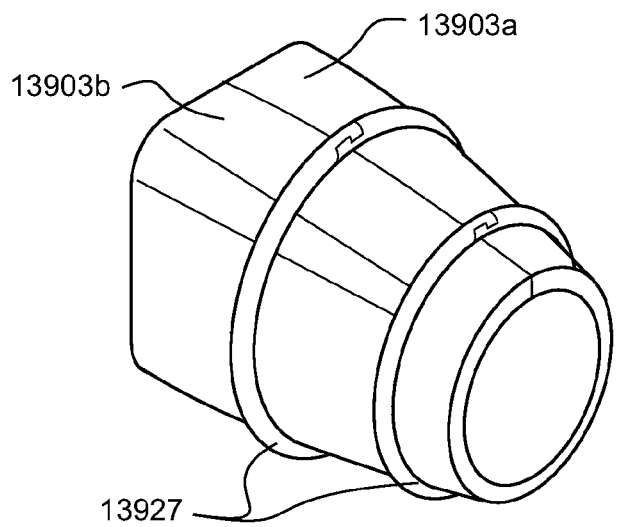
FIG. 66 is a perspective view of a twenty-fifth embodiment manifold assembly.

The embodiment of FIG. 66 is similar to the embodiment of FIG. 60. One difference is that the manifold assembly comprises two or more rings 13927 that act as fastening components.

FIGS. 64 and 65 show cross-sections of embodiments having a two piece inlet.

Figure 67:
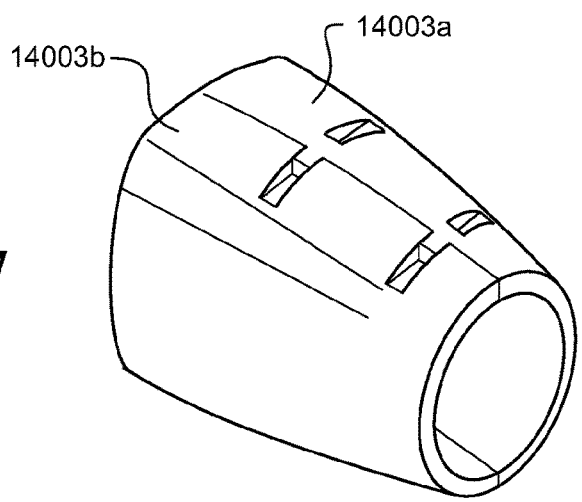
FIGS. 67 and 68 show a twenty-sixth embodiment manifold assembly.
Figure 68:
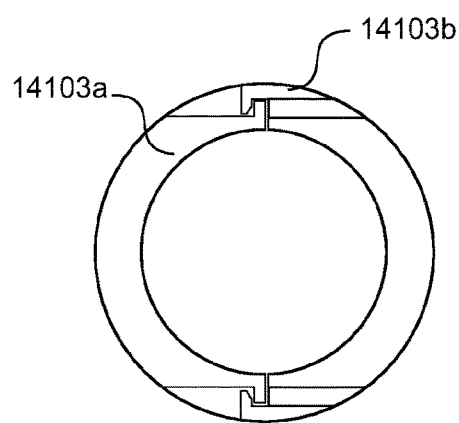

The embodiment of FIGS. 67 and 68 has a manifold inlet formed by the first component 14003a, 14103a and second component 14003b, 14103b.

Figure 69:
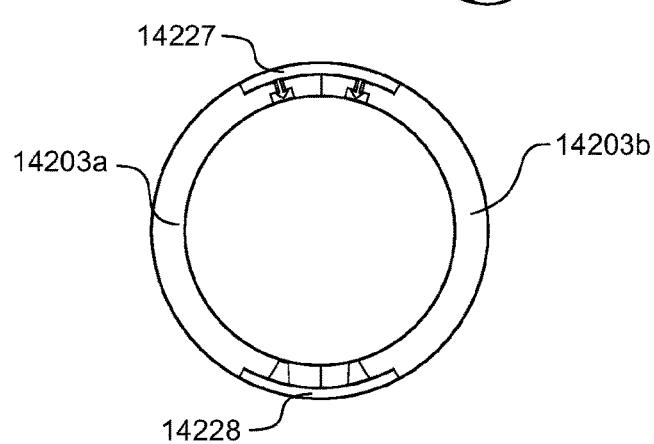
FIG. 69 is a cross sectional view of a twenty-seventh embodiment manifold assembly.

The embodiment of FIG. 69 has a manifold inlet formed by the first component 14203a and second component 14203b together with a third component 14227 and fourth component 14228 that connect the first and second components together.

Figure 70:
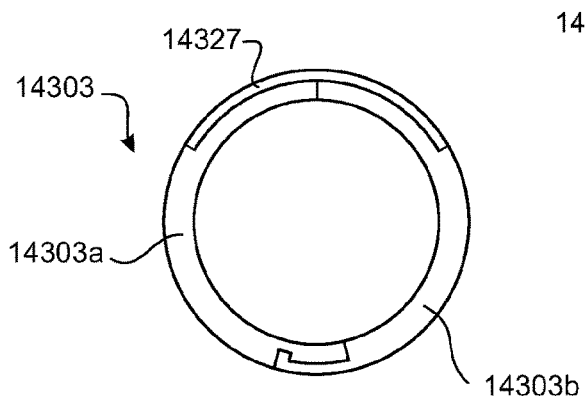
FIG. 70 is a cross sectional view of a twenty-eighth embodiment manifold assembly.
Figure 71:
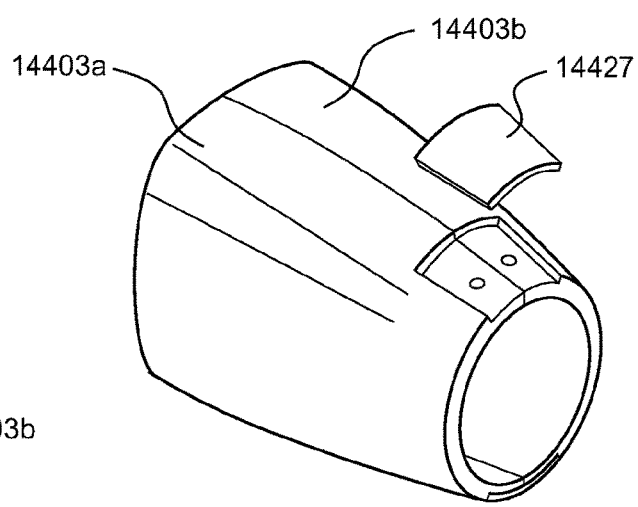
FIG. 71 is a perspective view of a twenty-ninth embodiment manifold assembly.

The embodiment of FIG. 70 has a two part manifold inlet 14303 in which the two parts are engageable together and with other components (not shown) to form a manifold assembly. The manifold inlet 14303 has a first component 14303a (or as for example 14403a as shown in FIG. 71) and a second component 14303b (or as for example 14403b as shown in FIG. 71) that engage to form the manifold inlet 14303. The manifold assembly further comprises a third component that acts as a fastening component. In the embodiment shown in FIG. 70, the fastening component comprises a patch 14327.

The embodiment of FIG. 71 is similar to that of FIG. 70, except that this embodiment has two patches and each of the patch is relatively smaller 14427.

Figure 72:
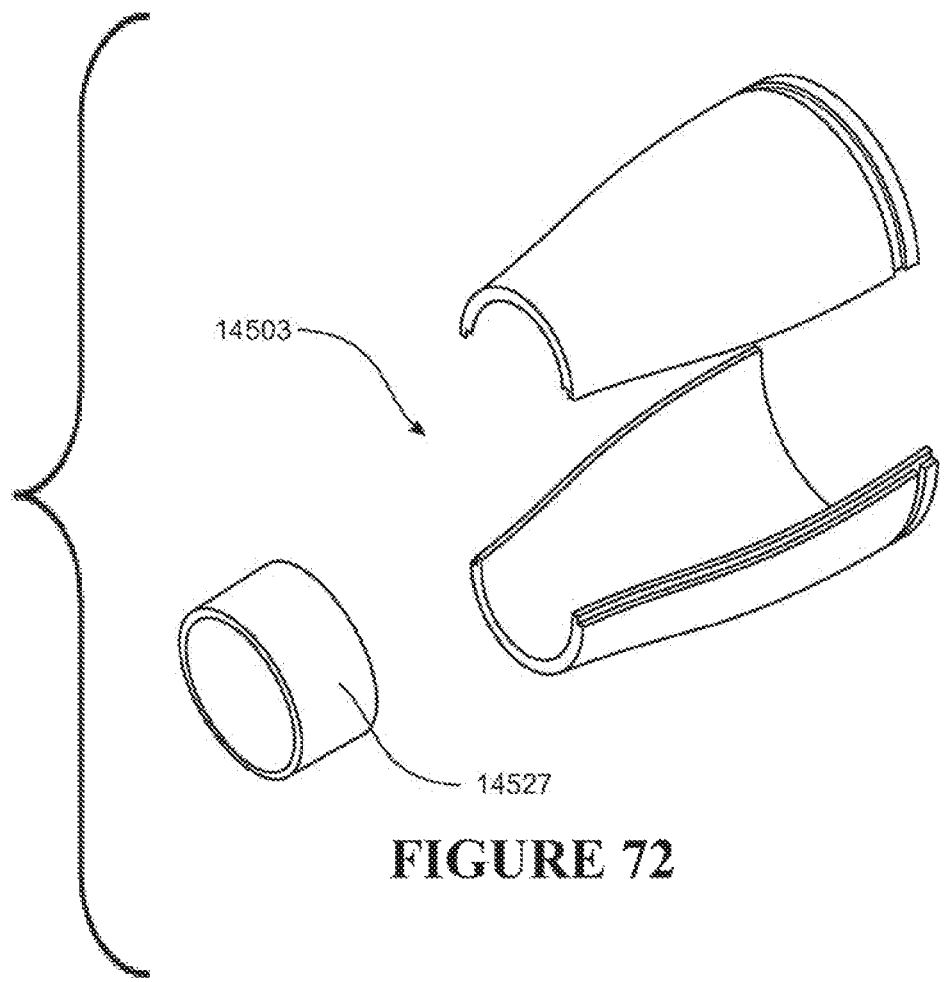
FIGS. 72 and 73 show a thirtieth embodiment manifold assembly.
Figure 73:
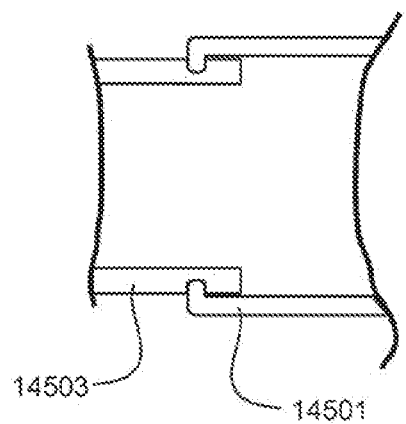
Figure 74:
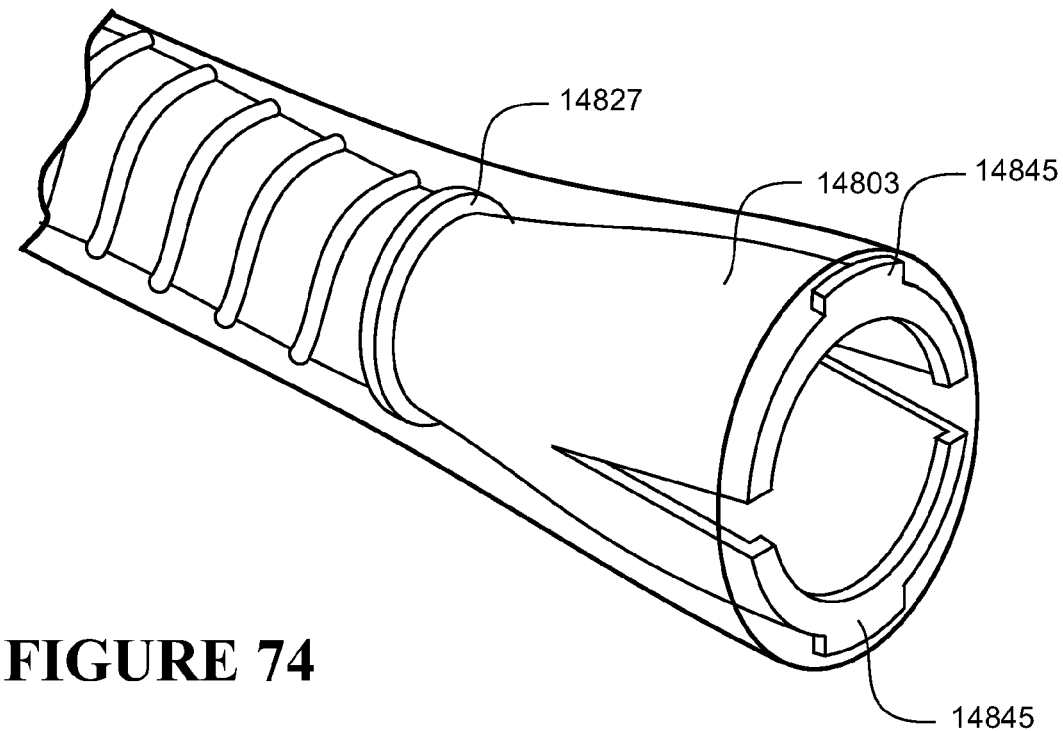
FIG. 74 shows a thirty-first embodiment manifold assembly.

The embodiment of FIGS. 72 and 73 is similar to the embodiment of FIG. 60. In this embodiment a tube 14527 holds the components of the manifold inlet together. The manifold inlet 14503 is a snap-fit with the manifold 14501.

Figure 75:
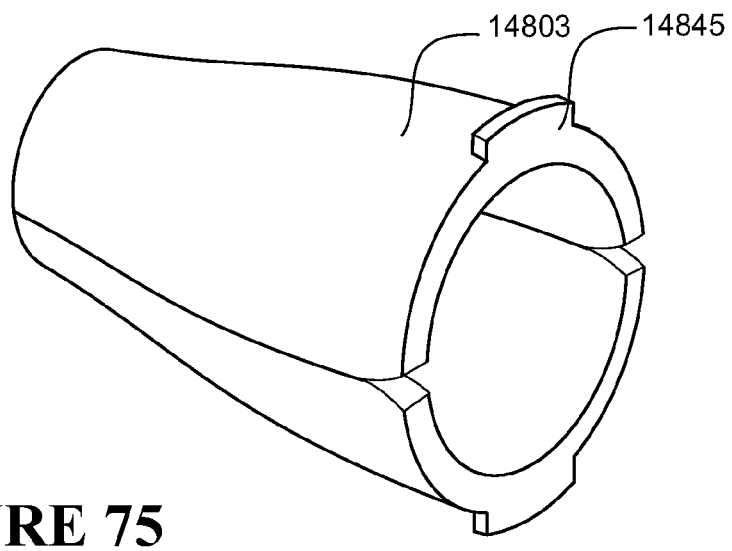
FIG. 75 shows a thirty-second embodiment manifold assembly.

The embodiment of FIG. 75 has a two part manifold inlet 14803 in which the two parts are engageable together and with other components (not shown) to form a manifold assembly. The manifold inlet 14803 has a second component 14303a and a third component in the form of a collar 14827 that engage to form the manifold inlet 14803. The collar 14827 may be longer than shown in FIG. 75. The manifold inlet 14803 has curved lips 14845 that are receivable by an annular recess of the manifold (not shown). The manifold assembly also has a relatively soft material, preferably TPE, which covers the manifold inlet 14803.

With reference to the embodiment shown in FIGS. 76a to 81, a number of alternative methods for connecting the manifold and manifold inlet together are shown.

The embodiment of FIGS. 76a to 76c comprises a connector 14947 or 14947' that extends between the first component 14911 and second component. The connector is formed in two halves with an integrally formed live hinge 14948/14948' between the halves. The two halves are joined together with complementary ribs 14917/14917' and channels 14918/14918'. When the connector of FIGS. 76a to 76c is assembled with the manifold 14901 and manifold inlet, the manifold is spaced away from the manifold inlet.

Figure 77:
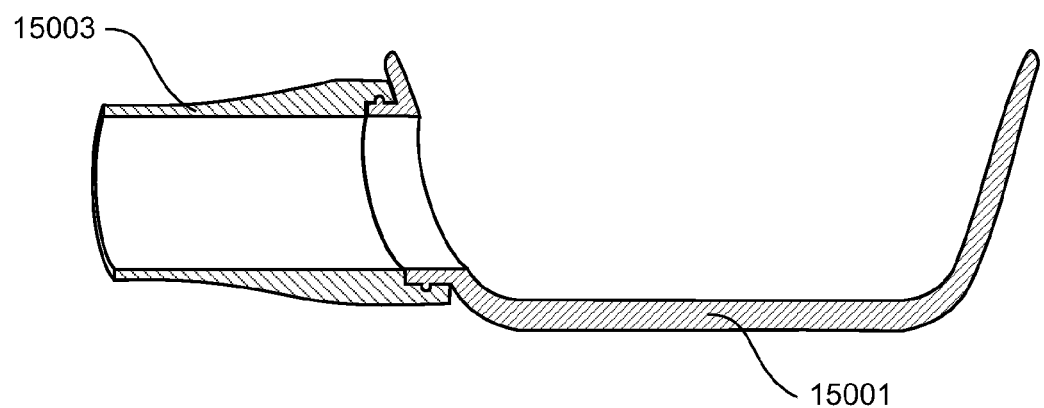
FIG. 77 is a cross sectional view of a thirty-fourth embodiment manifold assembly.
Figure 78:
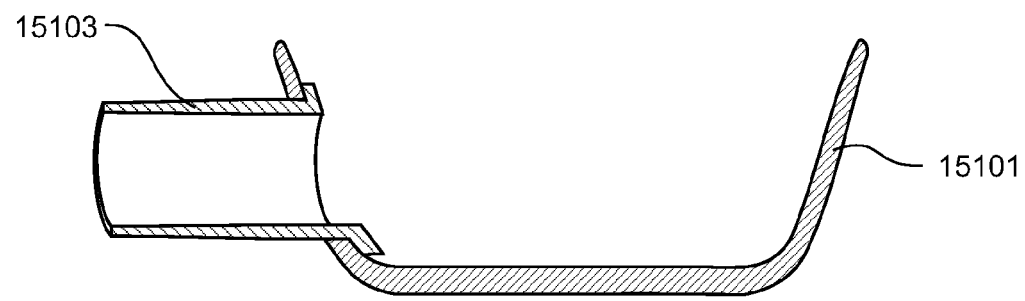
FIG. 78 is a cross sectional view of thirty-fifth embodiment manifold assembly.

The embodiment of FIG. 77 has a snap fit between the manifold inlet 15003 and the manifold 15001. The embodiment of FIG. 78 is assembled by the manifold inlet 15103 being pushed through an aperture in the manifold 15101 from the interior of the manifold.

Figure 79:
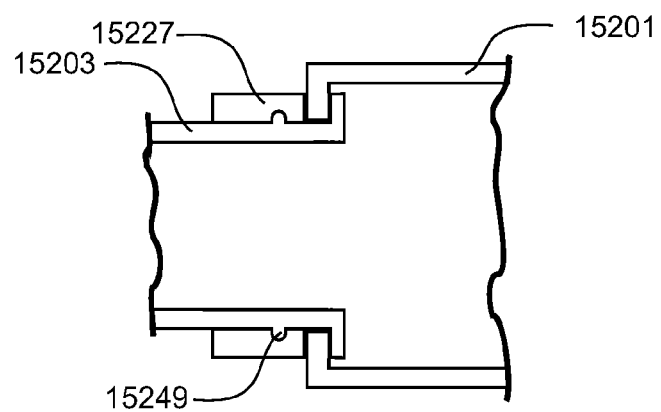
FIG. 79 is a cross sectional view of a thirty-sixth embodiment manifold assembly.

The embodiment of FIG. 79 has a manifold inlet 15203 with a relatively thin wall. The manifold inlet 15203 has a flange that engages the side wall of the manifold 15201 to form a seal. The manifold assembly further comprises a collar 15227 that engages with protrusions 15249 of the manifold inlet 15203. That engagement secures the manifold inlet to the manifold and prevents the manifold inlet form sliding relative to the manifold.

Figure 80:
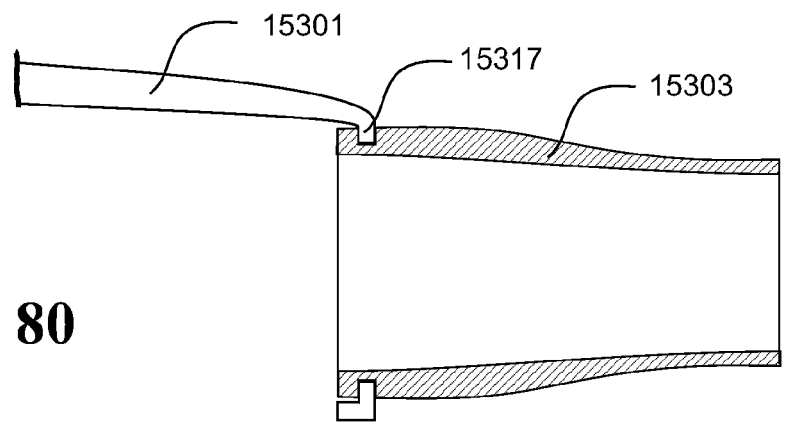
FIG. 80 is a cross sectional view of a thirty-seventh embodiment manifold assembly.

The embodiment of FIG. 80 shows an assembly in which the manifold inlet 15303 is pushed through an aperture in the manifold 15301. The manifold inlet 15303 has an annular recess adapted to receive a flange 15317 of the manifold. When assembled, a seal is formed between the manifold 15301 and the manifold inlet 15303.

Figure 81:
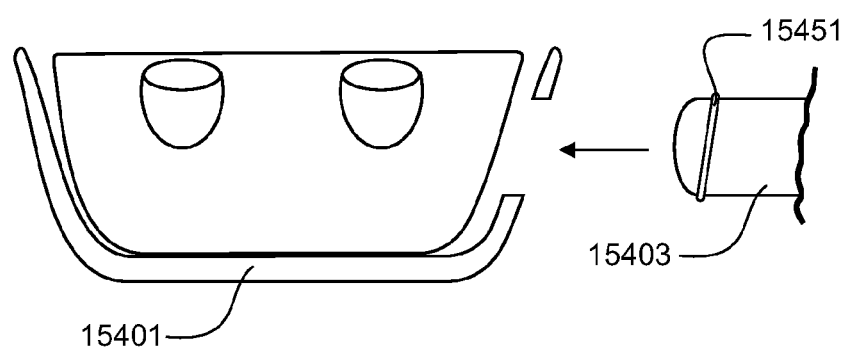
FIG. 81 is a cross sectional view of a thirty-eighth embodiment manifold assembly.

The embodiment of FIG. 81 is a snap fit between the manifold 15401 and the manifold inlet 15403. The manifold inlet 15403 may have an annular groove or annular rib 15451 for engaging with a complementary feature of the manifold. In the embodiment shown, a surface of the rib 15451 engages with a side wall of the manifold 15401.

Any of the embodiments described above may have a first component in which a part of the component is a relatively rigid material and another part of the first component is a relatively soft and/or flexible material. The first component may comprise a relatively rigid component. Alternatively, the first component may comprise a relatively soft and/or flexible component. Part of the second component may comprise a relatively rigid material and another part of the second component may comprise a relatively soft and/or flexible material. The second component may be a relatively rigid component. Alternatively, the second component may comprise a relatively soft and/or flexible component. The manifold assembly may comprise one or more seals and/or gaskets for at least substantially sealing the connection between the components of the manifold assembly. The seal may be integrally formed with the first and/or second component. Alternatively, the seal is a separate component from the first and second components.

The first component and second component may be integrally formed with a live hinge. Alternatively, the first component and second component may separate components. When the manifold assembly comprises a third, fourth, or further components, two or more, or all of, those components may be integrally formed. An example is with a live hinge arrangement. Alternatively, all of the components may be separate and distinct components.

When assembled, the first component is engaged with the second component. The first component is engaged with the second component by one or more of: ultrasonic welding, RF welding, stitching, an adhesive substance, hook and loop fasteners, zip fasteners, clips, snap fits, and press fits. When a third or further component(s) is/are engaged with the first component and/or second component, the third or further component(s) is/are engaged with the complementary component by one or more of: ultrasonic welding, RF welding, stitching, an adhesive substance, hook and loop fasteners, zip fasteners, clips, snap fits, and press fits. Additionally or alternatively, the complementary surfaces of two or more of the components are shaped to have a tight, snug fit to form a seal between the components.

Preferably the conduit or tube is a medical breathing tube, including a corrugated tube or a tube with a helically recessed surface region. For example, a medical breathing tube as defined by International standard ISO 5367:2000(E) (Fourth edition, Jun. 6, 2000). Preferably the conduit or tube is an insufflation tube.

Any one or more features from any embodiment may be combined with any one or more features from any one or more other embodiments. For example, a patient interface, such as but not limited to, a nasal cannula, may comprise or include either as integrated componentry or as parts or portions any one or more of the embodiment features as described herein, whether solely or in combination thereof.

In terms of a further embodiment, a patient interface will be described below and with reference to an in-hospital respiratory care system to be used by adults and/or in paediatrics. It will be appreciated that the described patient interface and/or headgear embodiments can alternatively be used in delivering CPAP therapy or other therapies as described herein.

It will also be appreciated that various aspects of the invention may be applied to any form of patient interface including, but not limited indirect nasal masks (which covers the nose), direct nasal masks including nozzles or pillows enter or engage the nares of the wearer, oral masks (which cover the mouth), or full face masks (which cover the nose and mouth), and mouthpieces but will be described with reference to a nasal cannula. Similarly, various aspects of the present invention may be applied to any form of headgear but these will be described with reference to a head strap.

Figure 1A:
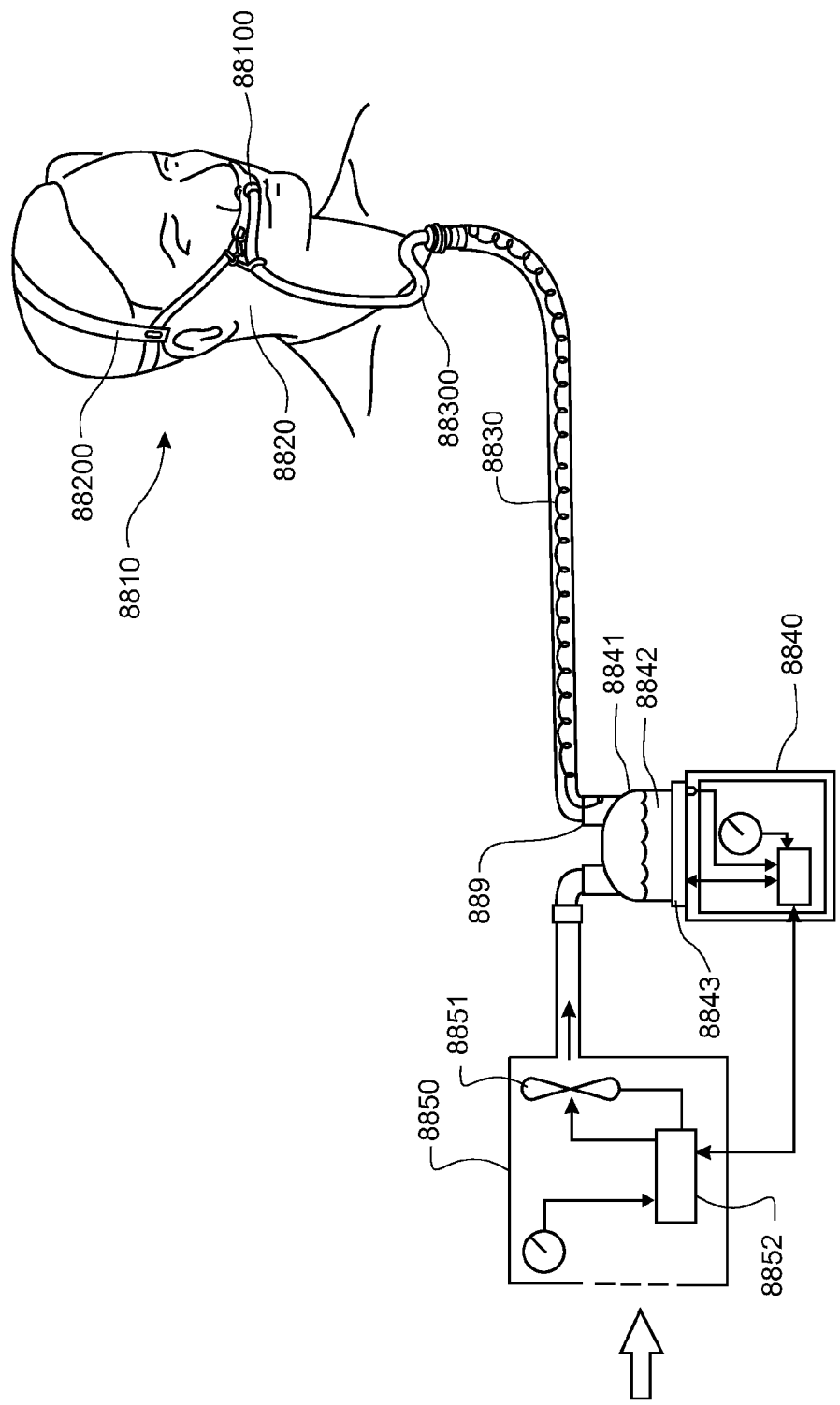
FIG. 1A illustrates a generalised setup of a humidification system for delivering a flow of humidified gas to a patient interface being worn by a user.
Figure 1B:
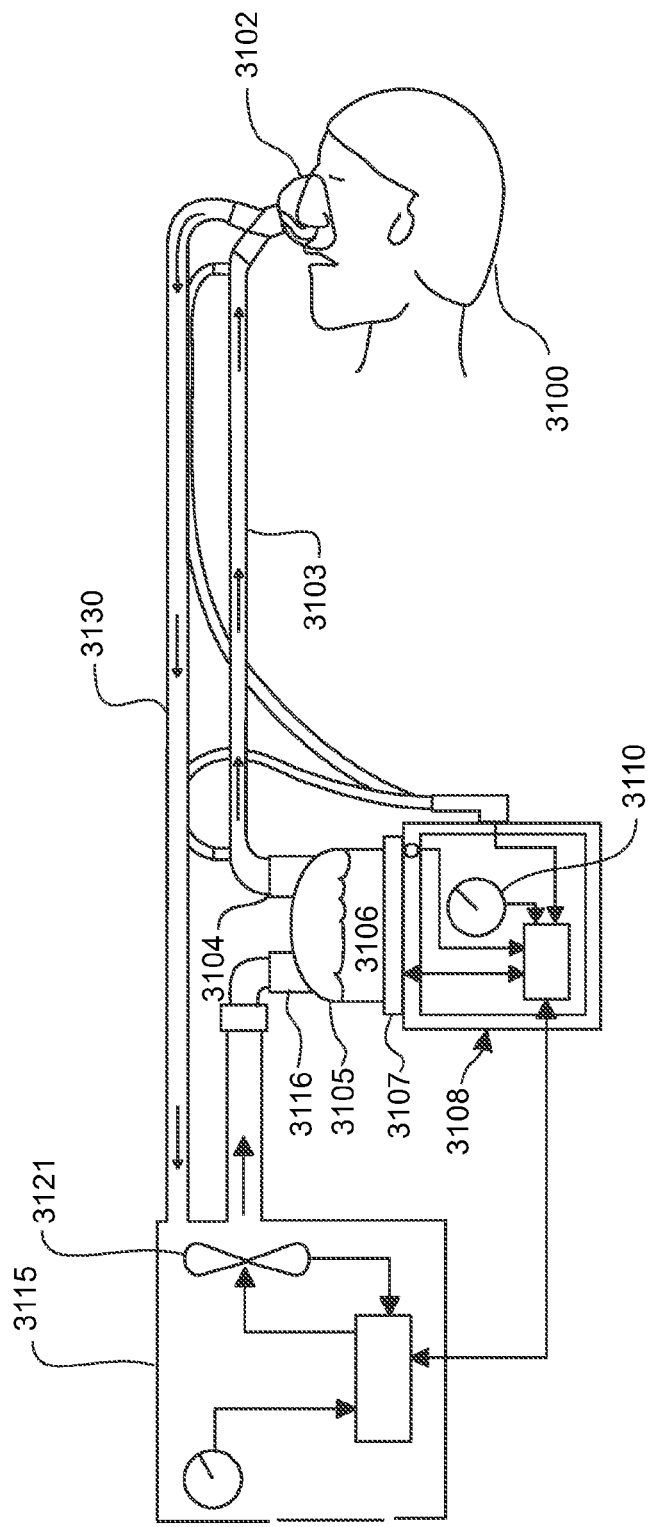
FIG. 1B generally illustrates one form of a medical circuit provided for a user, in providing a source of humidified breathing gas.

Referring to FIG. 1A, a ventilation and humidification system (a respiratory system 8810) as may be used with the present invention is shown. In such a system 8810, a patient 8820 is supplied with a humidified flow of gases through a patient interface 88100. The patient interface 88100 is retained in an operational position upon the patient's face using associated headgear 88200. The interface 88200 is connected to a humidified gases transportation pathway or inspiratory conduit 8830. The inspiratory conduit 8830 is connected at one end (either directly or indirectly) to the patient interface 88100 and at an opposing end to the outlet of a humidifier 8840. In the preferred embodiment the inspiratory conduit is connected to the patient interface via an extension tube/conduit 88300. The humidifier 8840 receives and humidifies gas supplied from a gases supply source 8850, preferably including a blower 8851. The humidifier 8840 may comprise a humidification chamber 8841 filled with water 8842 and a heating means 8843 for heating the water to humidify the gas path through the humidifier. A controller 8852 may be provided to control and possibly vary one or more properties of the supplied gas, including but not limited to the pressure profile of the gas, the flow rate profiles of the gas at the patient interface, the temperature of the gas and/or the humidity of the gas. It will be appreciated that the control capabilities are dependent on the purpose and application of the respiratory system 8810. For example, in the preferred application of in-hospital respiratory care, the flow rate of supplied gas is monitored and controlled according to the patient's requirements but the pressure of the supplied gas is not necessarily monitored and controlled. In alternative embodiments, such as the use of the invention in a CPAP, the pressure profile of the supplied gas may be monitored and controlled.

Referring to FIGS. 151 to 154, a preferred form of patient interface 88100 is shown. The patient interface 88100 is configured to deliver breathing gases from a gases supply and humidification source (not shown) to the patient, and headgear 88200 is configured to support and retain the patient interface against the patient's face in use. The patient interface 88100 of the preferred embodiment is in the form of a nasal cannula 88100 that is adapted to couple an inspiratory conduit 88300 and that comprises at least one, but preferably two, nasal prongs 88111 and 88112 configured to fit within the nares of a patient to deliver a flow of gases to the patient. The headgear 88200 is in the form of a head strap 88200 that is adapted to extend in use along the patient's cheeks, above the ears and about the back of the head, and may be adjustable in length to customise the size of the strap to the patient. The gas supply tube shown as item 88300 is preferably a breathable tube.

The nasal cannula 88100 provides a patient with a patient interface suitable for the delivery of high airflow, high humidity gas flow to the patient's nasal cavity/nares. In some configurations, the cannula is adapted to deliver a high flow of gases over a wide flow range (e.g. may preferably be about 8 L/min or about 30 L/min or may be higher depending on other preferred therapy applications, perhaps such as 10-50 L/min, or up to 60 or up to about 80 L/min). In some configurations, the cannula is adapted to deliver relatively low pressure gases.

The nasal cannula 88100 comprises a face mount part 88105 including at least one, but preferably a pair of tubular nasal prongs 88111 and 88112, integrally moulded with or removably attached to the body 106 having a face mount part 88105, and a gases flow manifold part 88110 that is removably attached or integrally moulded to the conduit 88300. The gases flow manifold part 88110 is connectable, such as by being insertable, into the body 106 of the face mount part 88105 from either one of two opposing horizontal directions, i.e. from either left side or the right side. In this manner, the position or location of the gases flow manifold part 88110 is reversible with respect to the body 88106 and face mount part 88105. In other words, a user may choose to have the manifold part 88110 (and essentially the conduit 88300 extending therefrom) extend from either the left side or the right side of the cannula 88100 depending on what is most convenient, for example depending on which side of the user the gas source or ventilator is located. In an alternative embodiment the gases flow manifold 88110 is attached to the body 88106 and face mount part 88105 by a swivel mount so that the gases flow manifold part 88110 is a permanent or semi-permanent part of the nasal cannula 88100, but can swivel about an axle part and thereby rotate relative to the body 88106 and face mount part 88105 to move the conduit 88300 from the left to right side or vice versa, i.e. to allow the side of the manifold inlet 88120 to be varied.

The face mount part 88105 of the body 88106 may be formed from a soft, flexible and material such as Silicone or other cannula material known in the art. The nasal prongs 88111 and 88112 are preferably supple and may be formed from a sufficiently thin layer of Silicone to achieve this property. The gases flow manifold part 88110 may be formed from a relatively harder material such as Polycarbonate, a High-Density Polyethylene (HDPE) or any other suitable plastics material known in the art. The face mount part 88105 provides a soft interfacing component to the patient for comfortably delivering the flow of gases through the nasal prongs 88111 and 88112, while the gases flow manifold part 88110 fluidly couples the conduit 88300 to the nasal prongs 88111 and 88112 via the body 88106.

The nasal prongs 88111 and 88112 may be curved to extend into the patient's nares in use and to provide a smooth flow path for gases to flow through. The inner surfaces of the prongs 88111 and 88112 may be contoured to reduce noise. The bases of the prongs 88111 and 88112 may include curved surfaces to provide for smoother gases flow. This may reduce the noise level during operation. The nasal prongs 88111 and 88112 are substantially hollow and substantially tubular in shape. The nasal prongs 88111 and 88112 may be consistent, or may vary, in diameter or cross-sectional area along their lengths but are preferably shaped to fit the contours of the nares. Each prong 88111/88112 has an elongate opening at the distal end. In alternative embodiments the nasal prongs 88111 and 88112 may have a tapered profile of a wider end at the base portion 88118 and a narrower end at the openings 88111*a* and 88112*a*. The openings 88111*a* and 88112*a* may be scooped to direct the flow of gases up the patient's nares. The face mount part 88105, body 88106, and in particular the nasal prongs 88111 and 88112 are preferably designed not to seal about the patient's nares to avoid excessive and potentially harmful build up of pressure during high flow therapy. The nasal prongs 88111 and 88112 are therefore sized to maintain a sufficient gap between the outer surface of the prongs 88111 and 88112 and the patient's skin to avoid sealing the gas path between the cannula 88100 and patient.

The face mount part 88105 of the body 88106 is shaped to generally follow the contours of a patient's face around the upper lip area. The face mount part 88105 is moulded or pre-formed to be able to conform to and/or is pliable to adapt, accommodate and/or correspond with the contours of the user's face, in the region of the face where the cannula is to be located.

The face mount part 88105 comprises an elongate base portion of the body 88106 from which the nasal prongs 88111 and 88112 extend, and two side arms 88113 and 88114 extending laterally from either side. The side arms 88113 and 88114 are integrally formed with the base portion but may alternatively be separate parts.

A pair of elongate side arms 88113 and 88114 extend laterally from opposite sides of the generally centrally located body part 88106 or face mount part 88105 to contact a user's face in use to aid in stabilising the body on the user's face, with the side arms having any one or more of the following features:

Referring particularly to FIG. 151, the side arms 88113 and 88114 also comprise a bend upwardly along their length. In particular an outer second portion 88113*a*/88114*a* of each of said side arm upwardly extends at an angle to an inner first portion 88114*b*. In at least some embodiments the first portion 88114*b* and second portion 88114*a* of the side arms are joined by an intermediate curved portion 88114*c*. The side arms may be thus shaped to engage the wearer's face below the cheek bones.

Referring particularly to FIGS. 153 and 154, the side arms comprise an inner first portion 88114*d* extending laterally and rearwardly from the generally centrally located body part 88106 or face mount 88105 at a first angle to the body 88106 and an outer second portion 88114e extending from the first portion 114d and rearwardly at a relatively shallower angle relative to the body part 88106. The inner first portion 88114d of each side arm may extend at an angle to the body part 88106 of between 30 and about 50 or about 70 degrees for example and the outer second portion 88114e at an angle of between about 150 and about 170 or about 180 degrees for example to the body part 88106.

Referring particularly to FIGS. 152 to 154, the side arms also comprise a part twist, such that a cross-section shape orthogonally through the side arm is part twisted, part twisted either anti-clockwise or clockwise depending on whether the side arms are viewed as a top view or a bottom view of the patient interface 88100 and depending on whether it is a left or a right side arm being considered, at a part of the wing portion or side arm portion closer to an outer end thereof than a part closer to the body 88106. The cross-section shape orthogonally through the side arms may be part twisted anti-clockwise or clockwise up to about 60 degrees or up to about 45 degrees, or between about 2 and about 20 degrees or between about 2 and 50 degrees, when considered from a top or a bottom view of the interface, and depending on which side arm is being considered.

Typically the side arms are resiliently flexible or semi-rigid side arms.

In at least some embodiments a cross-section area of each side arm substantially reduces along the length of the side arm.

Typically a distal end of each side arm comprises a formation configured to releasably couple a complementary connector of a headgear. Alternatively or additionally adhesive pads may be provided on each side arm 88113 and 88114 to facilitate coupling of the cannula 88100 to the patient—especially for younger children (e.g. under 5 years old).

Primary end portions 88201 and 88202 of the head strap 88200 are adapted to releasably connect respective formations 88101 and 88102 at the ends of the side arms 88113 and 88114 to hold the cannula 88100 in position during use. In a preferred embodiment, a clip or buckle component is provided at each end portion 88201/88202 capable of being received and retained within the corresponding formation 88101/88102. The clip component may be coupled to the strap at the respective primary end portion in accordance with one of two preferred embodiments (as will be described in further detail below). Furthermore, the head strap 88200 may be adjustable in length to help customise the strap to the wearer's head. The strap 88200 is preferably formed from a soft and stretchable/elastic material such as an elastic, textile material/fabric that is comfortable to the wearer. Alternatively, the strap 88200 may be formed from a substantially more rigid, or less flexible, material such as a hard plastics material. The headgear 88200 may further comprise an additional strap or other headgear component that couples the strap 88200 to extend over the patient's crown in use. In some embodiments the headgear strap may be a bifurcated strap, the strap comprising two sub straps that are arranged to engage a rear portion of the head or a top portion of the head. In some embodiments the headgear strap 88200 may be a tearable or separable strap, having weakened sections that allow a user to tear the strap apart to form a bifurcated strap.

FIGS. 155-161 illustrate an embodiment of a patient interface (or frame thereof) having elongate side arms 88113, 88114 extending from opposite sides of a manifold or central body part 88106 and which are, in-use, provided with an inner surface or patient-side surface for contact with a user's face.

Figure 155:
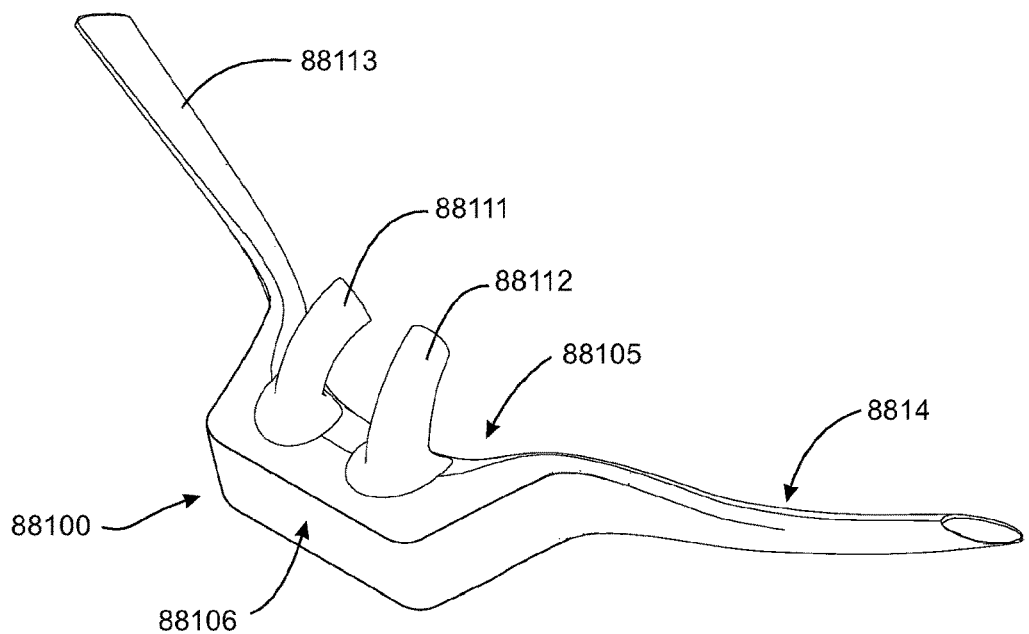
Figure 156:
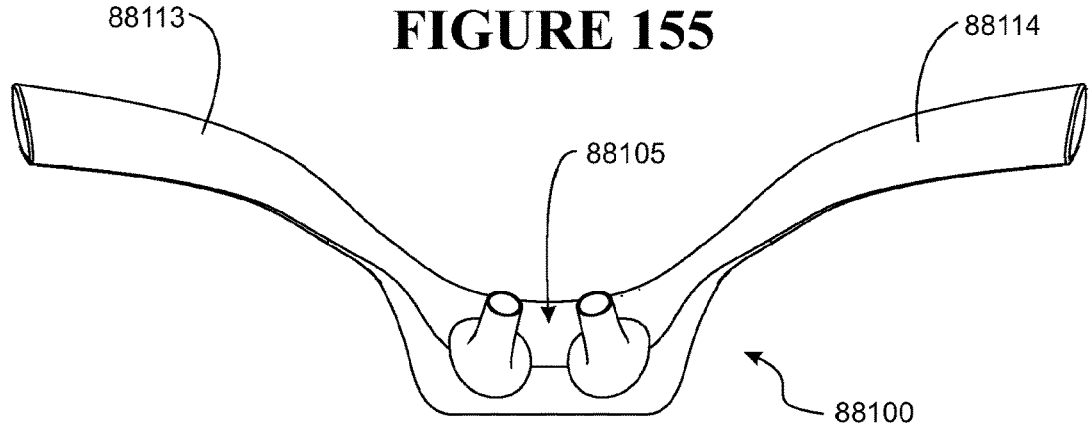
Figure 157:
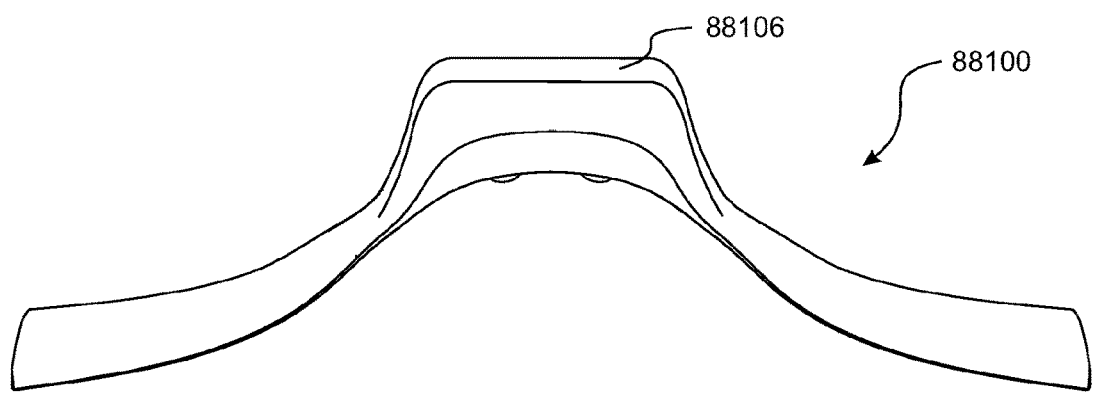
Figure 158:
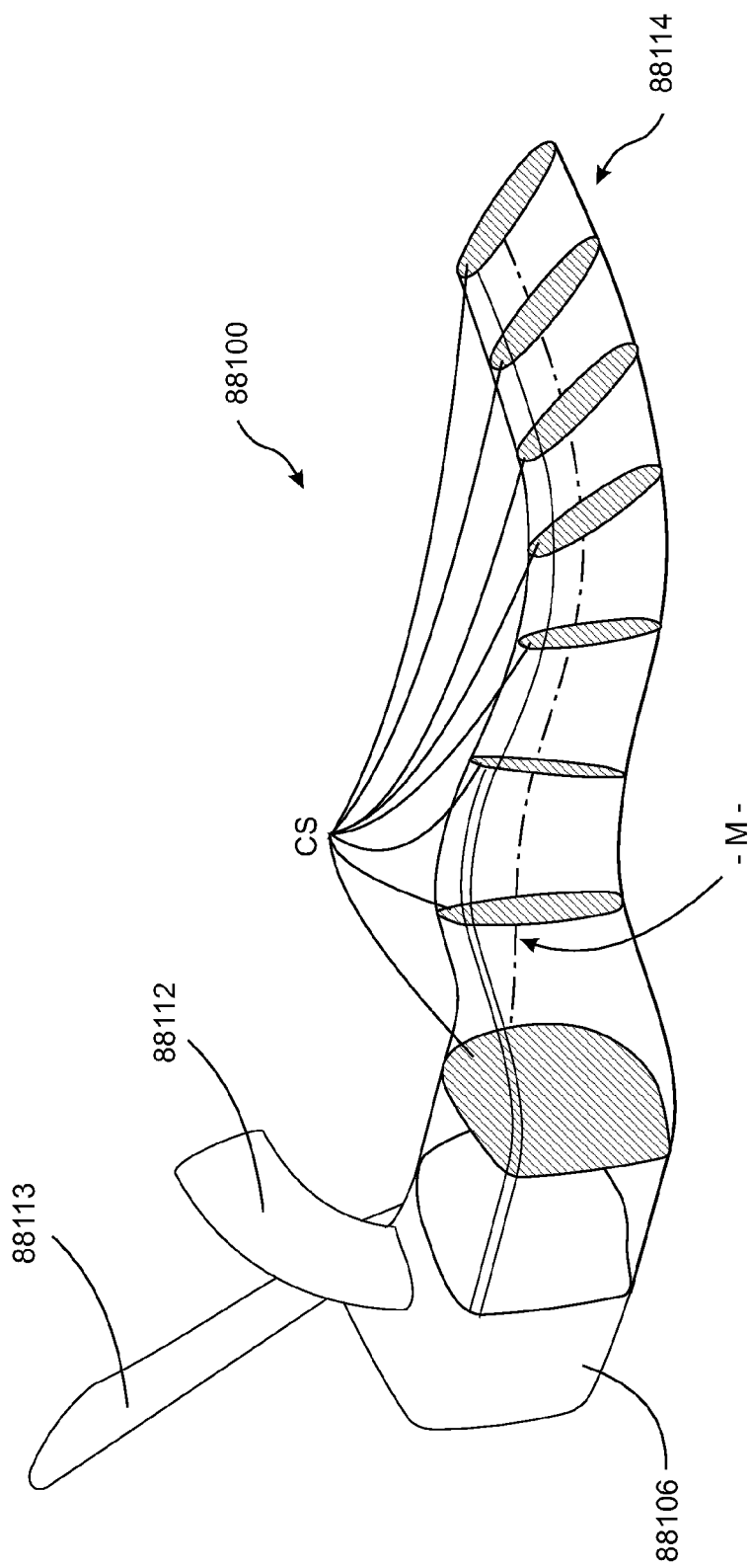
Figure 159:
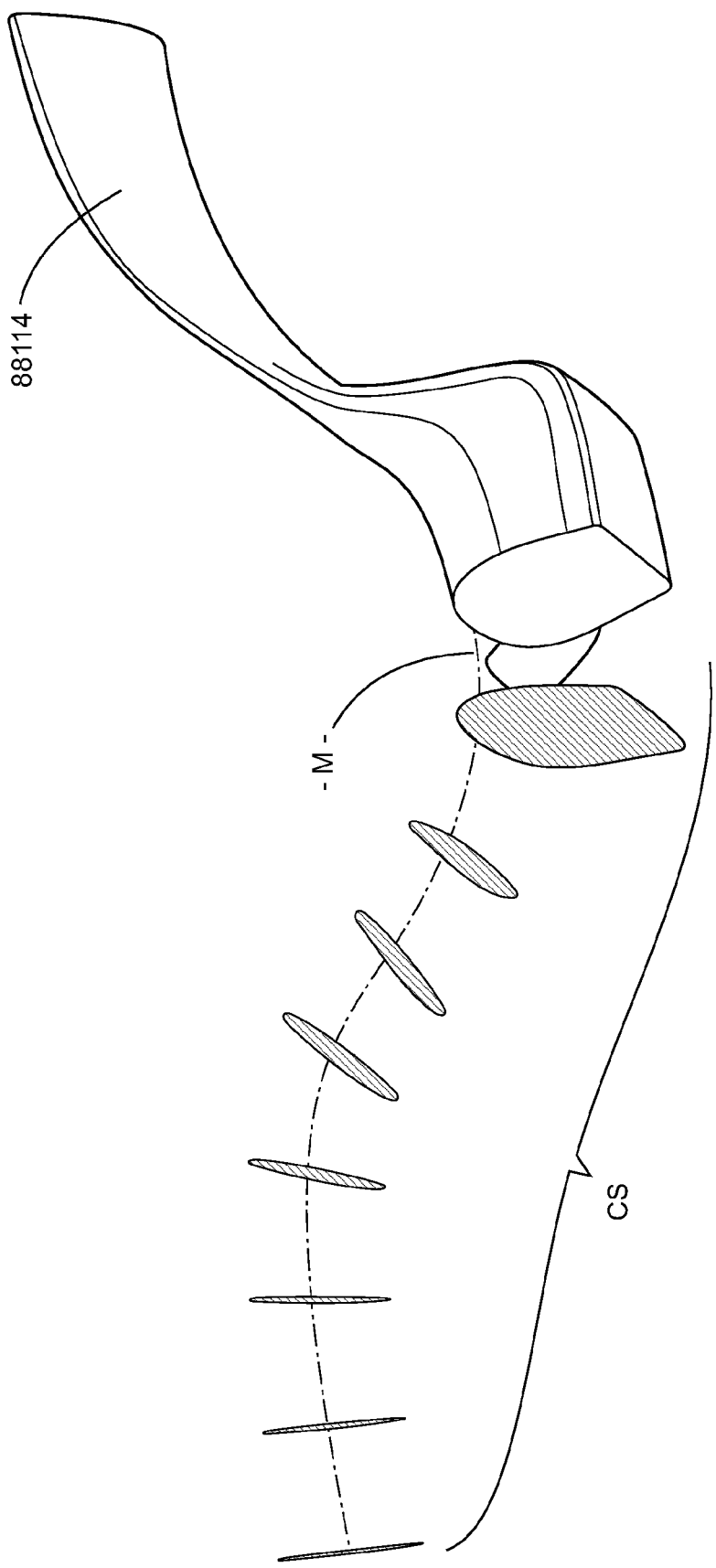
Figure 160:
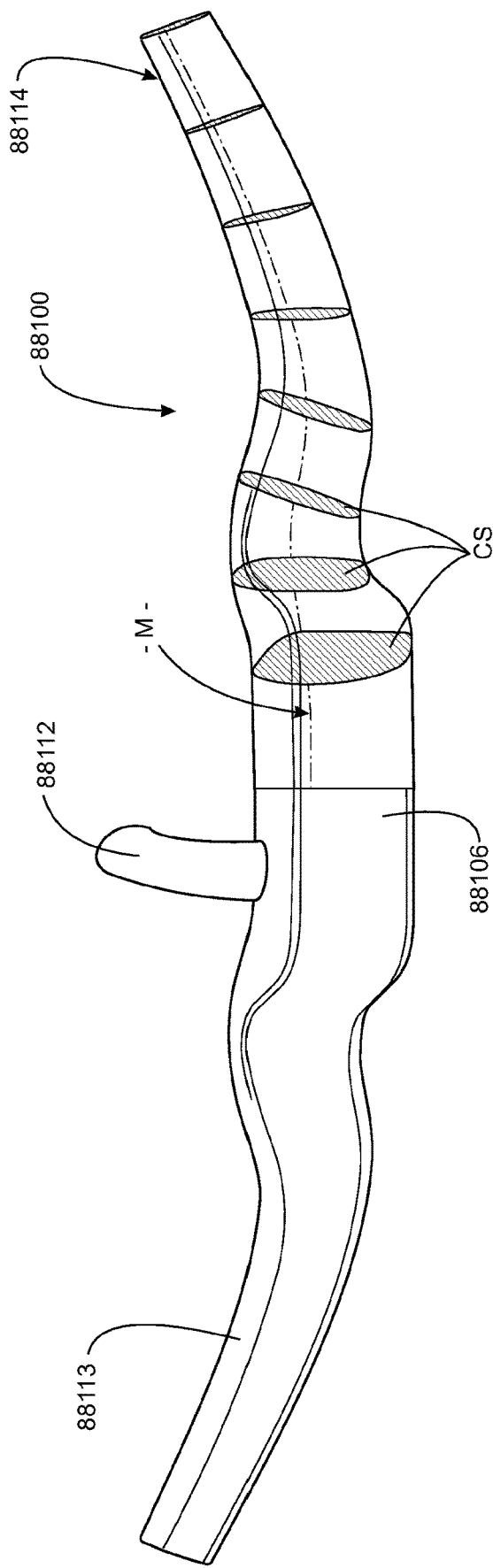
Figure 161:
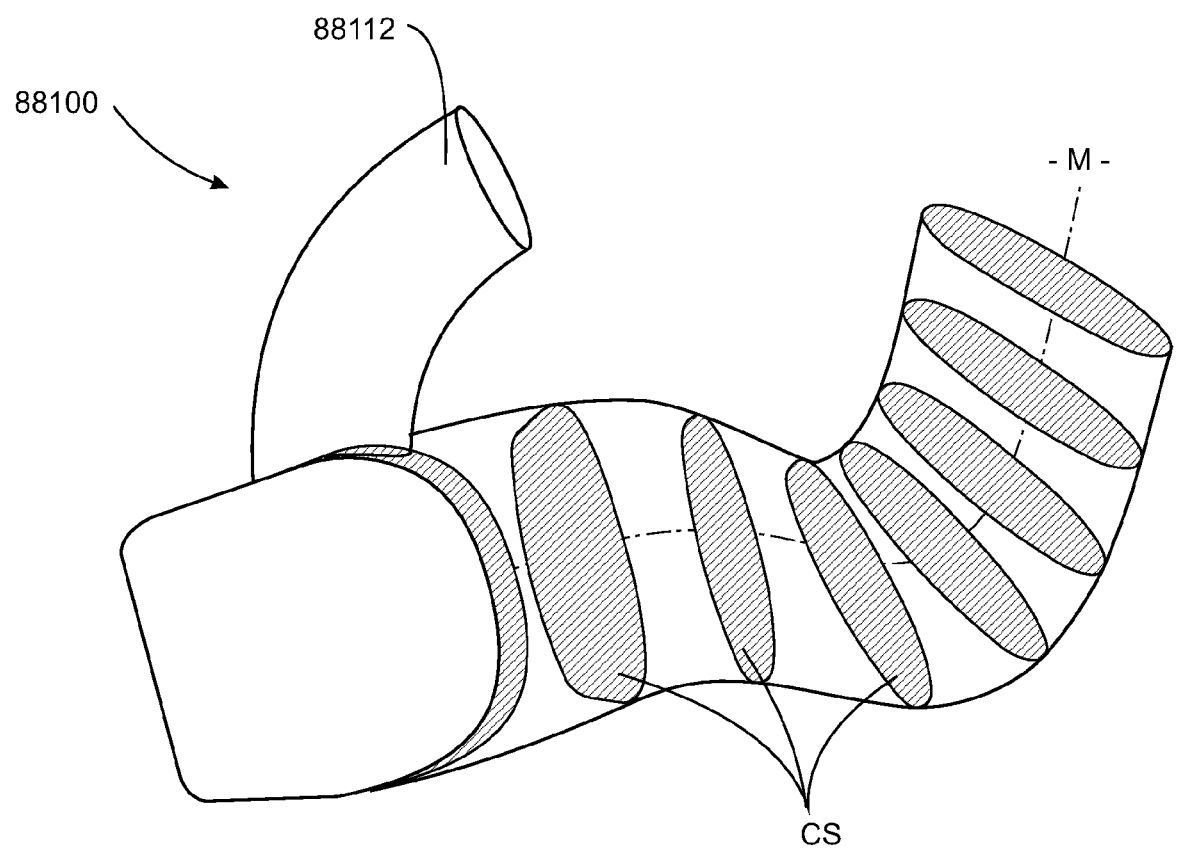

FIG. 155 is a top perspective view of such a generalised interface, FIG. 156 is a top view down onto the interface, while FIG. 157 is a bottom view up onto the bottom of the interface. The figures help show the relative curvature of each of the side arms and how they may be at least in part twisted relative to the manifold section or remainder of the interface body.

FIGS. 158-161 illustrate cross-sections CS through the interface, generally a side arm extends from a substantially centralised manifold region or central body part 88106 out towards an outer end of a side arm. The various cross-sections CS are a section of the arm along a mid-line trajectory or path or line of travel, M. The various cross-sections show a surface or slice through the interface as the cross-sections change orientation through a longitudinal trajectory or line or path of travel indicated by the dot-dash line in the figures, such a trajectory or line or path of travel being positioned or located upon and extending along the rear surface or rear face (i.e. the patient side) of the interface and which is a located as substantially a mid-point of the height of that rear surface or face that contacts the user's face. It will be appreciated such cross-sections or slices vary along the side arm in accordance with the bending or twists of the side arm.

Each cross-section plane or slice shown (CS) is a transverse plane along the mid-line trajectory or path or line of travel (M) and orthogonal to the tangent plane at each point when each section or slice is taken.

A purpose of such illustrations is to help show how the side arms traverse through a series of bends and twists as side arm extends from the manifold body to an outer end of each such side arm.

In relation to FIGS. 151-161, an outline of a patient interface is provided, yet without details which may otherwise be included for formation of a final patient interface. For example, such a patient interface may optional additionally comprise one or more of: headgear or heat straps for retaining or maintaining a patient interface upon a user during use, such a headgear or head strap being of a type which, in-use, may be bifurcated or which is bifurcatable to provide for an upper and a lower strap of such a headgear, clips for supporting or retaining or securing a gas supply tube or conduit (or accessories such as feeding tubes or measurement wires or conduit, or buckles for releasably connecting the ends of headgear or straps to an end of each side arm) a manifold which can be adjusted as to orientation or position relative to the use (or the interface depending on the perspective to be taken), such as for example a manifold or manifold assembly as described herein including but not limited to a rotatably coupled manifold or a manifold which is of a push-fit type configuration each of which allow for a re-orientation of side of a gases supply conduit or tube or the delivery point of a manifold to a gases chamber of such a patient interface). It will be appreciated the patient interface as illustrated in FIGS. 155-161 can be supplemented with the features of the embodiments as described herein to provide for a patient interface assembly or combination of assembled features.

FIG. 146 illustrates a patient interface 5100 that is similar in some ways to the patient interface illustrated in FIG. 2. Aspects or features of the interface of FIG. 146 that are the same or similar to aspects or features of the interface of FIG. 2 are identified by the same reference numerals used in FIG. 2 and are not described again in relation to FIG. 146.

The patient interface 5100 of FIG. 146 may also be used in a respiratory therapy system 400 as described for earlier embodiments with reference to FIG. 9.

As described with reference to FIG. 2, the frame portion 102 of the interface 5100 illustrated in FIG. 146 comprises a first side arm 106 and a second side arm 108. The side arms 106, 108 comprise headgear retaining mechanisms adapted to hold headgear 124. In the illustrated embodiment of FIG. 146 the retaining mechanism are buckles or connectors 3200 comprising a first connector part in the form of a clip 3201 (shown in FIG. 148) and a second connector part in the form of a carrier 3203, for example as described with reference to FIGS. 123 to 132.

As shown in FIG. 146, the headgear 124 is similar to the headgear shown in FIG. 2. However in FIG. 146 the headgear is illustrated without frictional elements 138 as shown in FIG. 2. In some embodiments the interface 5100 may be provided with headgear comprising such frictional elements 138 illustrated in FIG. 2, to help to prevent undesired sliding of the headgear 124 around the head of the user.

As described with reference to FIGS. 3A and 3B, the embodiment of FIG. 2 comprises a manifold 114 that is rotationally coupled to the frame portion 102, so that the manifold inlet 116 may be positioned over or near the first or second frame gas inlets 110, 112 of the frame portion. This arrangement provides for the conduit 146 to be oriented to the left or right side of the patient interface to provide for convenient configurability of the interface. One embodiment of a rotationally coupled (swiveling) manifold assembly 11100 is described with reference to FIGS. 29 to 31

Like the embodiment of FIG. 2, the embodiment of FIG. 146 is also provided with a manifold assembly 51100 that may be arranged to position the conduit 146 to either the left or right side of the patient interface. However, unlike the embodiment of FIG. 2 comprising a swiveling manifold 114, the embodiment of FIG. 146 comprises a manifold 51100 that may be pushed into or received in the gases chamber 109 of the frame portion 102. In some embodiments, the manifold 51100 may be received in the gases chamber 109 in two orientations—either via the first frame gas inlet 110 or via the second frame gas inlet 112. If a user desires the conduit to extend from the interface on the right hand side then the manifold assembly 51100 may be inserted into the chamber 109 via the first gas inlet 110. Alternatively if the user desires the conduit to extend from the interface on the left hand side then the manifold assembly 51100 may be inserted into the chamber 109 via the second gas inlet 112, as illustrated in FIG. 149.

The manifold assembly 51110 is illustrated in FIG. 150 and in an exploded view in FIG. 148. With reference to FIG. 150, one end of the manifold assembly comprises a manifold inlet 51103, for interfacing with or attaching to a conduit 146. An opposite end of the manifold assembly 51110 is closed to form a plug or cap 51104 to close the first and second frame gas inlets 110, 112 (depending on orientation in use). The manifold assembly comprises an outlet or opening 51107 to communicate with the gas chamber and nasal prongs 105A, 105B when inserted into the gas chamber 109 of the frame portion. A sealing surface 51106, 51109 is provided at or towards each end of the manifold assembly to seal with the first and second frame gas inlets so that when the manifold assembly is inserted into the gas chamber 109 of the frame 102 the manifold assembly 51100 forms a seal with both the first and second frame inlets 110, 112. With the manifold inserted into the chamber 109 the manifold inlet 51103 is in fluid communication with the chamber 109 via the manifold outlet 51107. In some embodiments the frame 102 or the manifold assembly may comprise resilient material to form a seal between the manifold part and the frame 102 to substantially prevent gas flow through the first and second frame gas inlets between the frame and the manifold assembly. For example, in the illustrated embodiment the frame 102 may comprise a resilient material 51108 within the gases chamber 109 to contact sealing surfaces 51106, 51109 of the manifold part. In some embodiments the resilient material 51108 may be integrally formed with the face contacting part 104 of the frame 102.

In some embodiments the manifold outlet 51107 may be formed rearwardly, and in some embodiments may extend for a substantial length of the manifold. With the outlet 51107 formed rearwardly, the resilient face contacting part 104 of the frame is unsupported by the manifold assembly in an upper lip (between upper lip and nose) area so that the face contacting part in the region of the manifold assembly outlet provides a cushion to sit against the user's upper lip. The face contacting portion in the area of the manifold assembly outlet may act as an air filled cushion (104A in FIG. 147) to contact the user's upper lip region.

In some embodiments the manifold inlet has a tapered lumen 51105, for example as described with reference to FIG. 38. Particular advantageous combinations may be provided for such a patient interface, for example combination of the "clip" integrated or as an attachment component to a part of an interface (such as a side arm), the ability to provide for a side swapping manifold (whether as a "swivel manifold" or being of a push-fit type configuration manifold or manifold assembly), the usefulness of a "tapered lead in" to allow for ease or manufacture as well as improved patient experience by reducing noise of gases flowing through a manifold part or less turbulent flow of gases being delivered to an outlet or outlets (e.g. nasal prongs of a nasal cannula), as well as the ability to provide for ease of release and connection of a headgear via "buckles" to the patient interface.

In some embodiments the manifold assembly 51100 comprises a first component 51111, a second component 51113 engageable with the first component. The manifold assembly may comprise a third component 51127 that acts as a fastening component to hold the first and second components 51111, 51113 together. The manifold assembly may be formed from a series of modular components that allow for relatively simple tool designs to be used to create the smooth transition between the manifold inlet and a manifold 51101 of the manifold assembly. In particular, using a modular design allows a combination of relatively simple components to be assembled together to form a more complex shape.

The first, second and third components 51111, 51113 and 51127 may fit together in the same way as components 11111, 11113 and 11127 as described with reference to FIGS. 29 to 38. Further, the first, second and third components 51111, 51113 and 51127 may comprise any one or more of the features of the first, second and third components 11111, 11113 and 11127 as described earlier with reference to FIGS. 29 to 38.

In some embodiments, the patient interface 5100 may comprise a component 23300 to secure the tube to the patient interface 5100 via a mounting portion 23340 on the frame 102 of the patient interface, as described with reference to FIGS. 117 to 121B. As shown, the frame 102 may comprise a mounting portion on each of the first and second arms 106, 108 to interface with component 23300 to hold the tube either to the left or right hand side of the patient interface.

With reference to the various embodiments described herein, and for example, in combination with any one or more of the above aspects or other embodiments, a conduit or tube may be provided. Such a conduit or tube providing gases to the patient interface, or that which is provided in fluid communication or in connection with a manifold or manifold assembly. Such a conduit may be formed of a breathable and flexible type. Such a gases conduit may be additionally crush-resistant and/or may be made of a material that reduces or may minimise noise generation when the conduit is moved or bent, such noises are sometimes referred to as a "crinkling" sound. In this embodiment, the conduit may comprise of an elongate film spirally wrapped with an elongate reinforcing member to form the conduit's lumen. The conduit may also be of the type which is extruded to form the conduit. In various embodiments, breathable material(s) can be used in the construction of the conduit to assist with expelling of any accumulated condensate (e.g. from "rain-out") in the conduit. In various embodiments, the reinforcing member may help to prevent or reduce crushing and/or kinking of the tube, or at least the potential for crushing and/or kinking during use. The lumen of the conduit may comprise of an inner bore that is substantially smooth so as to reduce resistance to flow and/or minimise surface features upon which condensation may accumulate or pool.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

Embodiment Combinations

TC1. A component comprising
a body for receiving at least one tube and/or at least one cable, optionally such as in a medical breathing circuit, and
an attachment for removeably engaging a mounting portion of a patient interface.

TC2. A component as defined in TC1 wherein the body is movable along a length of the at least one tube and/or the at least one cable, is fixed relative to the at least one tube and/or the at least one cable, and/or is rotatable about the periphery of the at least one tube and/or the at least one cable.

TC3. A component as defined in TC1 or TC2 wherein the body is arranged to at least partially surround a perimeter of the at least one tube and/or the at least one cable.

TC4. A component as defined in TC1 or TC2 wherein the body is arranged to surround a perimeter of the at least one tube and/or the at least one cable.

TC5. A component as defined in any one of TC1 to TC4 wherein the body comprises at least one arm that is arranged to at least partially surround a perimeter of the at least one tube and/or the at least one cable.

TC6. A component as defined in any one of TC1 to TC4 wherein the body comprises at least one arm that is arranged to surround a perimeter of the at least one tube and/or the at least one cable.

TC7. A component as defined in any one of TC1 to TC4 wherein the body comprises two arms that are arranged to at least partially surround or, separately or together, surround a perimeter of the at least one tube and/or the at least one cable.

TC8. A component as defined in any one of TC1 to TC4 wherein the body comprises an annular, substantially annular, square, substantially square, or rectilinear portion that is arranged to at least partially surround or to surround a perimeter of the at least one tube and/or the at least one cable.

TC9. A component as defined in any one of TC1 to TC8 wherein an internal surface of the body is engageable with the one or more external surface recesses of the at least one tube.

TC10. A component as defined in any one of TC1 to TC9 wherein the body is pivotably, rotatably, or removably connected to the attachment, or any combination of any two or more thereof.

TC11. A component as defined in any one of TC1 to TC10 wherein the attachment comprises at least one arm or at least one lug that is arranged to engage a mounting portion on a patient interface.

TC12. A component as defined in TC11 wherein the at least one arm comprises a projection or lug.

TC13. A component as defined in any one of TC1 to TC10 wherein the attachment comprises two arms that are arranged to engage a mounting portion.

TC14. A component as defined in TC13 wherein the two arms extend from the body to define a space therebetween.

TC15. A component as defined in TC14 wherein one arm comprises a projection or lug or both arms comprise a projection or lug.

TC16. A component as defined in TC15 wherein the projection or lug engages a corresponding recess on the mounting portion, optionally with a snap engagement.

TC17. A component as defined in TC1 to TC10 wherein the attachment comprises two arms and one arm is shaped, or both arms are shaped to engage a corresponding projection on the mounting portion, optionally with a snap engagement.

TC18. A component as defined in TC17 wherein the arm or arms comprise an angled or lug portion shaped to engage a corresponding projection on the mounting portion, optionally with a snap engagement.

TC19. A component as defined in TC17 wherein the attachment comprises two arms, each arm comprises an angled or lug portion, and each angled or lug portion extends towards the other arm, or into or towards the space between the arms.

TC20. A component as defined in TC17 wherein the attachment comprises two arms, each arm extending from the same point or substantially adjacent points on the body, each arm initially extending from the body in a direction away from the other arm, and each arm comprising an angled or lug portion that extends substantially towards the other arm, or into or towards the space between the arms.

TC21. A component as defined in TC17 wherein the attachment comprises two arms, each arm extending from the same point or substantially adjacent points on the body, each arm extending from the body in a direction toward the other arm, and each arm comprising a projection or lug that extends substantially outwardly or away from the other arm.

TC22. A component as defined in any one of TC1 to TC21 wherein the mounting portion comprises one or more shaped projections, and/or one or more slots or recesses arranged to engage the attachment.

TC23. A component as defined in any one of TC1 to TC22 wherein the mounting portion comprises one or more slots or recesses or apertures as a female part of the mounting portion for receiving of an engagement by the attachment TC24. A component as defined in any one of TC1 to TC23 wherein the mounting portion is integral with a patient interface.

TC25. A component as defined in any one of TC1 to TC24 wherein the mounting portion is removably attachable to a patient interface.

TC26. A component as defined in any one of TC1 to TC25 wherein the mounting portion comprises at least one projection arranged to engage at least one arm of the attachment.

TC27. A component as defined in any one of TC1 to TC26 wherein the mounting portion comprises a projection arranged to engage each arm.

TC28. A component as defined in TC26 or TC27 wherein the projection or projections are arranged to engage the arms with a snap engagement.

TC29. A component as defined in any one of TC1 to TC28 wherein the attachment provides sensory feedback to an operator when the attachment engages the mounting portion, optionally with a snap engagement.

TC30. A component as defined in any one of TC1 to TC29 wherein the attachment is arranged to emit a readily audible sound when the attachment engages the mounting portion, optionally with a snap engagement.

TC31. A component as defined in any one of TC1 to TC30 wherein the attachment is arranged to undergo a readily tactile movement or emit a readily tactile vibration when the attachment engages the mounting portion, optionally with a snap engagement.

TC32. A component as defined in any one of TC1 to TC31 wherein the component further comprises at least one retainer portion for retaining of at least one accessory.

TC33. A component as defined in TC32 wherein the retainer portion is a recessed region of the component or extends from the body.

TC34. A component as defined in any one of TC1 to TC33 wherein the patient interface is a nasal mask, oral mask, oronasal mask, nasal cannula, or full-face mask.

TC35. A component as defined in any one of TC1 to TC34 wherein the patient interface is a nasal cannula.

TC36. A component as defined in any one of TC1 to TC35 wherein the component comprises
a body for receiving at least one tube and/or at least one cable, such as in a medical breathing circuit, the body comprising an annular, substantially annular, square, substantially square, or rectilinear portion that is arranged to at least partially surround or to surround a perimeter of the at least one tube and/or the at least one cable, and
an attachment for removeably engaging a mounting portion on a patient interface associated with the at least one tube and/or the at least one cable, the attachment comprising one or two arms that extend from the body to define a space therebetween, each arm comprising an angled portion extending into or towards the space defined by the arms, such that the arms are arranged to engage a mounting portion on a patient interface, and each angled portion engages a corresponding projection on the mounting portion with a snap engagement.

TC37. A component as defined in any one of TC1 to TC35 wherein the component comprises
a body for receiving at least one tube and/or at least one cable, such as in a medical breathing circuit, the body comprising an annular, substantially annular, square, substantially square, or rectilinear portion that is arranged to at least partially surround or to surround a perimeter of the at least one tube and/or the at least one cable, and
an attachment for removeably engaging a mounting portion on a patient interface associated with the at least one tube and/or the at least one cable, the attachment comprising one or two arms that extend from the body to define a space therebetween, each arm comprising a projection or lug extending into or towards the space defined by the arms, such that the arms are arranged to engage a mounting portion on a patient interface, and each projection or lug engages a corresponding recess on the mounting portion with a snap engagement.

TC38. A component as defined in any one of TC1 to TC35, wherein the component comprises
a body for receiving at least one tube and/or at least one cable, such as a tube in a medical breathing circuit, the body comprising an annular, substantially annular, square, substantially square, or rectilinear portion that is arranged to at least partially surround or to surround a perimeter of the at least one tube and/or the at least one cable, and
an attachment for removeably engaging a mounting portion on a patient interface associated with the at least one tube and/or the at least one cable, the attachment comprising one or two arms that extend from the body to define a space therebetween, each arm comprising a projection or lug extending away from or outwardly from the arms, such that the arms are arranged to engage a mounting portion on a patient interface, and each projection or lug engages a corresponding recess on the mounting portion with a snap engagement.

TC39. A tube, such as for use in a medical breathing circuit, the tube being coupled a component of any one of TC1 to TC38, the component being optionally removeably engaged to a mounting portion according, the mounting portion being removably attachable to a patient interface in a medical breathing circuit.

TC40. A patient interface, such as for use in a medical breathing circuit, the patient interface comprising a mounting portion, integral with or removably attached to the patient interface, and a component defined by any one of TC1 to TC38 removeably engaged to the mounting portion.

TC41. A kit comprising a component as defined by any one of TC1 to TC38 and any two or more of
- a patient interface, optionally comprising an integral mounting portion,
- a mounting portion, and
- instructions for assembly and/or use.

B1. A connector comprising:
- a first connector part;
- a second connector part;
- a detent for securing the first connector part and the second connector part together;
- a slide moveable relative to the first connector part and/or the second connector part between:
- a secured position in which the detent is substantially inhibited from moving and releasing the first connector part from the second connector part; and
- a free position in which the detent is able to move to release the first connector part from the second connector part.

B2. A connector as defined by B1, further comprising a biasing means for urging the slide towards the secured position.

B3. A connector as defined by B2, wherein the biasing means comprises a resilient leg.

B4. A connector as defined by B2, wherein the biasing means comprises a pair of resilient legs.

B5. A connector as defined by B4, wherein the legs move away from each other as the slide moves towards the free position.

B6. A connector as defined by B4, wherein the legs move towards each other as the slide moves towards the free position.

B7. A connector as defined by any one of B2 to B6, wherein the biasing means and detent are integrally formed together.

B8. A connector as defined by any one of B1 to B7, wherein the detent comprises a resilient arm.

B9. A connector as defined by B8, wherein the resilient arm is biased towards engagement with the first connector part.

B10. A connector defined by any one of B1 to B7, wherein the detent comprises a pair of resilient arms.

B11. A connector as defined by B10, wherein the pair of resilient arms are biased towards engagement with the first connector part.

B12. A connector as defined by B10 or B11, wherein the resilient arms are spaced apart and are biased towards each other.

B13. A connector as defined by any one of B8 to B12, wherein the or each resilient arm comprises a protrusion for engagement with a complementary notch of the first connector part.

B14. A connector as defined by any one of B2 to B13, wherein the slide comprises a lug for engagement with the biasing means.

B15. A connector as defined by B14 wherein the lug comprises outwardly tapered surfaces.

B16. A connector as defined by any one of B1 to B15, wherein the slide comprises a protrusion for engagement with the detent for substantially inhibiting movement and release of the first connector part from the second connector part.

B17. A connector as defined by any one of B1 to B16, wherein the slide comprises two protrusions for engagement with the detent for substantially inhibiting movement and release of the first connector part from the second connector part.

B18. A connector as defined by any one of B1 to B17, wherein the slide comprises a stop for locating the slide and second connector part in the secured configuration.

B19. A connector as defined by any one of B1 to B18, wherein the slide comprises a sleeve.

B20. A connector as defined by any one of B1 to B19, wherein the first connector part comprises a notch.

B21. A connector as defined by any one of B1 to B19, wherein the first connector part comprises a pair of notches.

B22. A connector as defined by any one of B1 to B19, wherein the first connector part comprises a plurality of notches.

B23. A connector as defined by any one of B1 to B22, wherein the first connector part is a substantially planar component.

B24. A connector as defined by any one of B1 to B23, wherein the first connector part is a substantially rigid component.

B25. A connector as defined by any one of B1 to B24, wherein the first connector part comprises a clip.

B26. A connector as defined by any one of B1 to B25, wherein the second connector part comprises a location feature for locating the biasing means.

B27. A connector as defined by any one of B1 to B26, wherein the second connector part comprises a guide feature for guiding the first connector part.

B28. A connector as defined by any one of B1 to B27, wherein the second connector part has a guide feature for guiding the slide.

B29. A connector as defined in any one of B1 to B27 wherein the second connector part comprises a carrier for carrying the detent and/or biasing means.

B30. A connector as defined in any one of B1 to B29, wherein the first connector part is located on a patient interface.

B31. A connector as defined in any one of B1 to B30, wherein the first connector part is attached to, or integrally formed with or as, a patient interface or a part of a patient interface.

B32. A connector as defined in any one of B1 to B31, wherein attached or attachable to the second connector part is a headgear or a part of a headgear or system for securing a patient interface in place about a user's head.

B33. A connector as defined in B32, wherein the carrier is formed with a slot and a headstrap of the headgear has an opening, the slot and opening being arranged for receiving the first connector part.

B34. A connector comprising:
- a first connector part;
- a detent for securing the first connector part and a second connector part together;
- a slide moveable relative to the first connector part between:
- a secured position in which the detent is substantially inhibited from moving and releasing the first connector part from the second connector part; and
- a free position in which the detent is able to move to release the first connector part from the second connector part.

B35. A patient interface for use in a medical breathing circuit, the patient interface comprising a connector defined by any one of B1 to 34.

SM1. A patient interface comprising:

a frame section adapted to be positioned on the face of a user, the frame section comprising a gases chamber adapted to channel gases to the user and a nasal delivery element extending from the gases chamber adapted to be located in a nare of the user; and a manifold rotatably secured to the frame section, the manifold being configured to rotate relative to the frame section, the manifold comprising an axle structure about which rotational motion between the manifold and frame section can occur.

SM2. The patient interface as defined in SM1, wherein the axle structure protrudes through an aperture in the frame section.

SM3. The patient interface as defined in SM1, wherein the manifold is rotatably secured to the frame section in such a way that the range of rotary motion between the manifold and the frame section is limited.

SM4. The patient interface as defined by SM1, wherein the frame section comprises a stop that limits the range of rotary motion.

SM5. The patient interface as defined by SM1, further comprising a nasal delivery element extending from the gases chamber adapted to be located in a nare of the user.

SM6. The patient interface as defined by SM1, wherein the frame section further comprising a track, the track configured to guide rotation of the manifold relative to the frame section.

SM7. The patient interface as defined by SM1, wherein the interface further comprises a retention mechanism, the retention mechanism being disposed on the frame section, the retention mechanism configured to retain the manifold in an operational position such that a pneumatic seal is created between the manifold and the gases chamber.

SM8. The patient interface as defined by SM7, wherein the retention mechanism is a post extending outwardly from the frame section, the post being configured to retain the manifold between the frame section and the post when the manifold is in the operational position.

SM9. The patient interface as defined by any one SM1 to SM8, wherein the patient interface comprises a release mechanism, the release mechanism configured to release the manifold from an operational position such that the manifold can rotate relative to the frame section.

SM10. The patient interface as defined by SM9, wherein the release mechanism comprises a button, the button disposed on the manifold, the button comprising a boss portion that is configured to engage with and move within a substantial portion of the track as the manifold rotates.

SM11. The patient interface as defined by SM9 or SM10, wherein the track comprises one or more detention regions positioned at the end of the track, the boss configured engage the detention regions to lock the manifold in the operational position.

SM12. The patient interface as defined by any one of SM9 to SM11 wherein the release mechanism comprises a release body, the release body moveable within a recess within the manifold, the release body being moveable from an unbiased position to a biased position, the release body being in the unbiased position when the manifold is in the operational position.

SM13. The patient interface as defined by SM12 wherein the release body comprises one or side arms, the recess comprising one or more end regions shaped to correspond to the one or more side arms, the side arms being configured to move into the end regions to release the boss portion from the detention regions and allow the manifold to rotate.

SM14. The patient interface as defined by SM13, wherein the side arms are configured to splay outwardly to release the boss portion from the detention regions.

SM15. The patient interface as defined by SM13, wherein the side arms are configured to splay inwardly to release the boss portion from the detention regions.

SM16. The patient interface as defined by SM1, further comprising at least one nasal delivery element extending from the gases chamber, each nasal delivery adapted to be located in a nare of the user.

SM17. The patient interface as defined by SM16, wherein the at least one nasal delivery element comprises two nasal delivery elements.

SM18. A patient interface comprising:

a frame section adapted to be positioned on the face of a user, the frame section comprising a gases chamber adapted to channel gases to the user;

a manifold rotatably relative to the frame section and adapted to receive gases from a gases source; and a retention mechanism, the retention mechanism being disposed on the frame section and/or the manifold and the retention mechanism configured to limit the non-rotational motion of the manifold relative to the frame section.

SM19. The patient interface as defined by SM18, wherein the retention mechanism comprises a post adapted to retain the manifold.

SM20. The patient interface as defined by SM18, wherein the retention mechanism limits non-rotational motion of the manifold relative to the frame section only in some rotational orientations.

SM21. The patient interface as defined by SM18, wherein the retention mechanism seals a gases passageway extending between the manifold and the gases chamber only in some rotational orientations.

SM22. The patient interface as defined by SM18, further comprising a nasal delivery element extending from the gases chamber, the nasal delivery element being adapted to be located in a nare or the nares of the user.

SM23. The patient interface as defined by any one of SM18 to 22, wherein the manifold is rotatably secured to the frame section.

SM24. The patient interface as defined by any one of SM18 to SM23, wherein the retention mechanism is disposed on the frame section.

SM25. The patient interface as defined by SM24, wherein the retention mechanism is integrally formed with the frame section.

SM26. The patient interface as defined by any one of SM18 to SM25, wherein the retention mechanism is disposed on the manifold.

SM27. The patient interface as defined by SM26, wherein the retention mechanism is integrally formed with the manifold.

SM28. The patient interface as defined by any one of SM18 to SM27, wherein the retention mechanism comprises a first retention feature disposed on the manifold and a second retention feature disposed on the frame section.

SM29. The patient interface as defined by SM28, wherein the first retention feature comprises a first hook having a generally vertically extending portion and a generally horizontally extending portion extending from the generally vertically extending portion in a direction towards the manifold and the second retention features comprises a second hook having a generally vertically extending portion and a generally horizontally extending portion extending from the generally vertically extending portion in a direction away from the manifold.

SM30. The patient interface as defined by SM28, wherein the first retention feature comprises a first hook having a generally vertically extending portion and a generally horizontally extending portion extending from the generally vertically extending portion in a direction away from the manifold and the second retention features comprises a second hook having a generally vertically extending portion and a generally horizontally extending portion extending from the generally vertically extending portion in a direction towards from the manifold.

SM31. The patient interface as defined by any one of SM15 to SM30, wherein the first retention feature is integrally formed with the manifold.

SM32. The patient interface as defined by any one of SM18 to SM31, wherein the second retention feature is integrally formed with the frame section.

SM33. The patient interface as defined by any one of SM18 to SM30, wherein the first retention feature is integrally formed with the frame section.

SM34. The patient interface as defined by any one of SM18 to SM31, wherein the second retention feature is integrally formed with the manifold.

SM35. A patient interface comprising:
a frame section adapted to be positioned on the face of a user, the frame section comprising a gases chamber adapted to channel gases to the user; and
a manifold rotatably rotatable relative to the frame section and adapted to receive gases from a gases source; and
a release mechanism;
wherein the patient interface is configured such that the manifold is rotationally locked in at least one rotational orientation of the manifold relative to the frame section, and
wherein the release mechanism is adapted to unlock motion of the manifold relative to the frame section when the manifold is rotationally locked.

SM36. The patient interface as defined by SM35, wherein the release mechanism comprises a button.

SM37. The patient interface as defined by SM36, wherein the button is positioned on the manifold.

SM38. The patient interface as defined by SM37, wherein the button is linked to a release body comprising a boss configured to rotatably move in a track located on the frame.

SM39. The patient interface as defined by SM38, wherein the track comprises a detention region that locks the rotational movement of the boss, and wherein actuating the button causes the boss to leave the detention region.

SM40. The patient interface as defined by SM39, wherein the release body comprises an biased state and an unbiased state, and wherein actuating the button causes the release body to transition from the biased state to the unbiased state.

SM41. The patient interface as defined by SM40, wherein releasing the button causes the release body to transition from the unbiased state to the biased state.

SM42. The patient interface as defined by SM40, wherein the release body comprises at least one side arm that is forced around a lug bump section in the frame in the biased state.

SM43. The patient interface as defined by SM42, wherein the release mechanism comprises a lever or arm.

SM44. The patient interface as defined by SM43, wherein the lever or arm is positioned on the frame.

SM45. The patient interface as defined by SM43 or SM44, wherein the lever or arm comprises a protuberance and the manifold has a complementary recess, slot, or aperture for receiving the protuberance.

SM46. The patient interface as defined by SM45, wherein the lever or arm is positioned on the manifold.

SM47. The patient interface as defined by SM46, wherein the manifold comprises a flexible section or hinge.

SM48. The patient interface as defined by SM46 or SM47, wherein the lever or arm comprises a protuberance and the frame has a complementary recess, slot, or aperture for receiving the protuberance.

SM49. The patient interface as defined by any one of SM46 to SM48, wherein the lever or arm comprises a biased state and an unbiased state, and wherein actuating the lever or arm causes the lever or arm to transition from the biased state to the unbiased state.

SM50. The patient interface as defined by SM49, wherein releasing the lever or arm causes the lever or arm to transition from the unbiased state to the biased state.

SM51. The patient interface as defined by SM43 to SM50, wherein the lever or arm has a flexible section.

SM52. The patient interface as defined by any one of SM43 to SM51, wherein the entire lever or arm is flexible.

SM53. The patient interface as defined by any one of SM35 to SM52, wherein the manifold is rotatably secured to the frame section.

SM54. A patient interface comprising:
a frame section adapted to be positioned on the face of a user, the frame section comprising a gases chamber adapted to channel a gas to the user;
a manifold rotatable relative to the frame section and adapted to receive gases from a gases source; and
a retention mechanism, the retention mechanism being disposed on the frame section and the retention mechanism configured to limit the non-rotational motion of the manifold relative to the frame section; and
a release mechanism;
wherein the patient interface is configured such that the manifold is rotationally locked in at least one rotational orientation of the manifold relative to the frame section, and
wherein the release mechanism is adapted to unlock motion of the manifold relative to the frame section when the manifold is rotationally locked.

SM55. The patient interface as defined by SM54, wherein the retention mechanism and release mechanism are a combined mechanism that limits the non-rotational motion of the manifold relative to the frame section and is adapted to unlock motion of the manifold relative to the frame section when the manifold is rotationally locked.

SM56. A patient interface comprising:
a frame section adapted to be positioned on the face of a user, the frame section comprising a gases chamber adapted to channel gases to the user;
a manifold secured to the frame section and adapted to receive gases from a gases source; and
headgear adapted to secure the frame section to the head of the user, wherein the headgear comprises a bifurcatable section.

SM57. The patient interface as defined by SM56, wherein the bifurcatable section rests on the back of the head of the user.

SM58. The patient interface as defined by SM56, wherein the bifurcatable strap comprises a pair of straps linked by bridging regions.

SM59. The patient interface as defined by SM56, wherein the bridging regions are thinner or integrally weaker than the straps.

SM60. A patient interface comprising:
a frame section adapted to be positioned on the face of a user, the frame section comprising a gases chamber adapted to channel gases to the user;
a manifold secured to the frame section and adapted to receive gases from a gases source; and
headgear adapted to secure the frame section to the head of the user, wherein the headgear comprises a user-contacting section with frictional elements.

SM61. The patient interface as defined by SM60, wherein the user-contacting section rests on the back and/or sides of the head of the user.

SM62. The patient interface as defined by SM60, wherein the frictional elements comprise markings.

SM63. A patient interface comprising:
a frame section adapted to be positioned on the face of a user, the frame comprising a gas chamber adapted to channel a gas to the user;
a manifold secured to the frame and adapted to receive a gas from a gas source;
headgear adapted to secure the frame to the head of the user; and
a headgear retaining mechanism actuatable to tighten or loosen the headgear,
wherein the headgear comprises markings adapted to inform the user as to the tightness or fit of the headgear when used in cooperation with the headgear retaining mechanism.

SM64. The patient interface as defined by any one of SM1 to SM63, wherein the frame comprises a relatively rigid section and a relatively flexible section.

SM65. The patient interface as defined by SM64, wherein the relatively flexible section of the frame is overmoulded onto a face contacting portion of the relatively rigid section of the frame.

SM66. The patient interface as defined by SM65, further comprising a nasal delivery element adapted to be inserted into a nare or the nares of a patient, the nasal delivery element extending from the relatively flexible section of the frame.

SM67. The patient interface as defined by any one of SM1 to SM66, further comprising a nasal delivery element adapted to be inserted into a nare or the nares of a patient, the nasal delivery element extending from the gases chamber.

TL1. A patient interface comprising:
a frame section adapted to be positioned on the face of a user, the frame section comprising a gases chamber adapted to channel gases to the user and a nasal delivery element extending from the gases chamber adapted to be located in a nare of the user;
a manifold assembly operatively securable to the frame section, the manifold assembly having a manifold and a manifold inlet, the manifold inlet having a tapered lumen in which an end proximal to the manifold has an area greater than an area of an end of the lumen distal the manifold.

TL2. The patient interface as defined by TL1, wherein the manifold assembly comprises a first component and a second component engageable with the first component such that:
the first component forms at least part of the manifold, at least part of the manifold inlet, or at least part of the manifold and at least part of the manifold inlet, and the second component forms at least part of the manifold, at least part of the manifold inlet, or at least part of the manifold and at least part of the manifold inlet.

TL3. The patient interface as defined by TL2, wherein the first component has a manifold inlet portion, and the second component is a or has a manifold inlet portion, the manifold inlet portion of the first component and the manifold inlet portion of the second component being engageable to form the manifold inlet.

TL4. The patient interface as defined by TL2 or TL3, wherein the manifold portion is formed by the first component having a manifold portion.

TL5. The patient interface as defined by any one of TL2 to TL4, wherein the first component comprises at least one location feature and the second component comprises at least one complementary location feature.

TL6. The patient interface as define by any one of TL2 to TL5, wherein the at least one location feature of the first component comprises a protrusion and the at least one location feature of the second component comprises a complementary recess or aperture.

TL7. The patient interface as defined by any one of TL2 to TL6, wherein the first component has an internally threaded portion corresponding to an externally threaded portion of a conduit or tube.

TL8. The patient interface as defined by any one of TL2 to TL7, wherein the first component has a smooth, non-threaded portion.

TL9. The patient interface as defined by any one of TL2 to TL8, wherein the second component has an internally threaded portion corresponding to an externally threaded portion of a conduit or tube.

TL10. The patient interface as defined by any one of TL2 to TL9, wherein the second component has a smooth, non-threaded portion.

TL11. The patient interface as defined by any one of TL2 to TL10, further comprising a fastening component.

TL12. The patient interface as defined by TL11, wherein the fastening component comprises a collar.

TL13. The patient interface as defined by TL12, wherein the collar is a substantially annular component.

TL14. The patient interface as defined by TL12 or TL13, wherein the collar has a tapered internal surface for engaging with an exterior surface of the manifold inlet portion of the first component and an exterior surface of the manifold inlet portion of the second component.

TL15. The patient interface as defined by TL2, wherein the first component has a manifold portion, and the second component has a manifold portion, the manifold portion of the first component and the manifold portion of the second component being engageable to form at least part of the manifold.

TL16. The patient interface as defined by TL15, wherein the manifold portion of the first component and the manifold portion of the second component are engageable to form the entire manifold.

TL17. The patient interface as defined by TL15, further comprising a third component engageable with the first component and/or second component to form at least part of the manifold.

TL18. The patient interface as defined by TL14, further comprising a third component engageable with the first component and/or second component to form the entire manifold.

TL19. The patient interface as defined by any one of TL15 to TL18, wherein the first component has a manifold inlet portion forming at least part of the manifold inlet.

TL20. The patient interface as defined by any one of TL18 to TL19, wherein the first component has a manifold inlet portion forming the entire manifold inlet.

TL21. The patient interface as defined by TL2, wherein the first component forms at least a major portion of the manifold and the second component forms at least a major portion of the manifold inlet.

TL22. The patient interface as defined by TL21, wherein the first component forms the entire manifold and the second component forms the entire manifold inlet.

TL23. The patient interface as defined by TL2, wherein the first component has a manifold portion and a manifold inlet portion, and the second component has a manifold portion and a manifold inlet portion, the manifold portion of the first component and the manifold portion of the second component being engageable to form at least part of the manifold, and the manifold inlet portion of the first component and the manifold inlet portion of the second component being engageable to form at least part of the manifold inlet.

TL24. The patient interface as defined by TL2, wherein the first component forms at least a major part of the manifold, the second component forms at least part of the manifold inlet.

TL25. The patient interface as defined by TL24, further comprising a third component, the third component engageable with the second component to form at least part of the manifold inlet.

TL26. The patient interface as defined by TL24 or TL25, wherein the first component forms the entire manifold.

TL27. The patient interface as defined by TL2, wherein the first component forms at least part of the manifold, the second component forms at least a major part of the manifold inlet.

TL28. The patient interface as defined by TL27, further comprising a third component, the third component engageable with the first component to form at least part of the manifold.

TL29. The patient interface as defined by TL27 or TL28, wherein the second component forms the entire manifold inlet.

TL30. The patient interface as defined by any one of TL2 to TL29, wherein part of the first component comprises a relatively rigid material and another part of the first component comprises a relatively soft and/or flexible material.

TL31. The patient interface as defined by any one of TL2 to TL29, wherein the first component comprises a relatively rigid component.

TL32. The patient interface as defined by any one of TL2 to TL30, wherein the first component comprises a relatively soft and/or flexible component.

TL33. The patient interface as defined by any one of TL2 to TL32, wherein part of the second component comprises a relatively rigid material and another part of the second component comprises a relatively soft and/or flexible material.

TL34. The patient interface as defined by any one of TL2 to TL30, wherein the second component is a relatively rigid component.

TL35. The patient interface as defined by any one of TL2 to TL30, wherein the second component is a relatively soft and/or flexible component.

TL36. The patient interface as defined by any one of TL2 to TL30, wherein part of the second component comprises a relatively rigid material and another part of the second component comprises a relatively soft and/or flexible material.

TL37. The patient interface as defined by any one of TL2 to TL36, further comprising one or more seals and/or gaskets.

TL38. The patient interface as defined by TL37, wherein the one or more seals and/or gaskets is/are integrally formed with the first and/or second component.

TL39. The patient interface as defined by any one of TL2 to TL37, wherein the one or more seals and/or gaskets is/are a separate component from the first and second components.

TL40. The patient interface as defined by any one of TL2 to TL39, wherein the first component and second component are integrally formed together with a live hinge.

TL41. The patient interface as defined by any one of TL2 to TL39, wherein the first component and second component are separate components.

TL42. The patient interface as defined by any one of TL2 to TL41, wherein the first component is engaged with the second component.

TL43. The patient interface as defined by TL42, wherein the first component is engaged with the second component by one or more of: ultrasonic welding, RF welding, heat staking, stitching, an adhesive substance, hook and loop fasteners, zip fasteners, clips, snap fits, and press fits.

TL44. The patient interface as defined by any one of TL2 to TL43, wherein the manifold assembly is formed from a series of modular components.

FA1. A patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms comprising a curve or bend upwardly along their length.

FA2. A patient interface as defined by FA1 wherein each side arm has an inner first portion and an outer second portion which extends at an angle upwardly relative to the inner first portion.

FA3. A patient interface as defined by FA2 wherein at least a part of the outer second portion extends at an angle of between 20 and 70 degrees to the inner first portion.

FA4. A patient interface as defined by any one of FA1 to FA3 wherein the side arms are shaped to engage the wearer's face below the cheek bones.

FA5. A patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms having an inner first portion extending laterally and rearwardly from the manifold at a first angle to the manifold and an outer second portion extending from the first portion and rearwardly at a relatively shallower angle to the manifold, optionally including the interface as defined by FA1.

FA6. A patient interface as defined by FA5 wherein the inner first portion of each of said side arm extends at an angle to the manifold of between about 30 or about 50 or about 70 degrees and the outer second portion extends from the first portion at an angle of between about 150 and about 170 or about 180 degrees relative to the angle of the inner first portion, or the outer second portion extends from the first portion at an angle of between about 30 and 10 or about 0 degrees relative to the manifold or the outer second.

FA7. A patient interface as defined by FA5 or FA6 wherein the side arms also comprise a curve or bend upwardly along their length.

FA8. A patient interface as defined by any one of FA5 to FA7 wherein the side arms also comprise a part twisted portion, such that a cross-section shape orthogonally through the side arms is part twisted anti-clockwise or clockwise at a part of the side arm closer to an outer end relative to a part of the side arm closer to the manifold, the twist being when considered from a top or bottom view of the interface and said respective side arm(s).

FA9. A patient interface for delivering a supply of gases to a patient, comprising a gas supply manifold for receiving and directing to an outlet or outlets to a patient a gas supply, and a pair of elongate side arms extending from opposite sides of the manifold to contact a user's face in use to aid in stabilising the interface on the user's face, each of said side arms comprising a part twisted portion, such that a cross-section shape orthogonally through the side arm is part twisted anti-clockwise or clockwise at a part of the side arm closer to an outer end relative to a part of the side arm closer to the manifold, the twist being when considered from a top or bottom view of the interface and said respective side arm(s), optionally including the interface as defined by FA1 or FA5.

FA10. A patient interface as defined by FA8 wherein the cross-section shape orthogonally through the side arm is part twisted anti-clockwise or clockwise up to about 45 degrees, or between about 2 and about 20 degrees.

FA11. A patient interface as defined by FA10 wherein a major part or all of the part twisted shape is in said second outer portion of each side arm.

FA12. A patient interface as defined by FA10 or FA11 wherein each of said side arms comprises a curve or bend upwardly along their length and/or each of said side arms has an inner first portion extending laterally and rearwardly from the manifold at a first angle to the manifold and an outer second portion extending from the first portion and rearwardly at a relatively shallower or a relatively deeper angle relative to the manifold.

FA13. A patient interface as defined by any one of FA1 to FA12 wherein a cross-section area of each side arm reduces along the length of the side arm.

FA14. A patient interface as defined by any one of FA1 to FA13 wherein a distal end of each side arm comprises a formation configured to releasably couple with a complementary connector of a headgear.

FA15. A patient interface as defined by any one of FA1 to FA15 wherein the interface outlet or outlets comprise a nasal cannula or cannulae.

A1. A patient interface, optionally as a nasal cannula, comprising any one or more of: TC1 to TC41, B1 to B35, SM1 to SM67, TL1 to TL44, FA1 to FA15.

The invention claimed is:
1. A connector comprising:
a first connector part;
a second connector part;
a detent for securing the first connector part and the second connector part together wherein the detent comprises a pair of resilient arms;
a slide moveable relative to the first connector part and/or the second connector part between:
  a secured position in which the detent is substantially inhibited from moving and releasing the first connector part from the second connector part; and
  a free position in which the detent is able to move to release the first connector part from the second connector part; and
at least two resilient legs for urging the slide towards the secured position,
wherein the at least two resilient legs:
  a) move away from each other as the slide moves towards the free position, or
  b) towards each other as the slide moves towards the free position, and
wherein the at least two resilient legs are positioned between the pair of resilient arms.

2. The connector of claim 1, wherein the pair of resilient arms spaced apart and biased towards each other, and biased towards engagement with the first connector part, and wherein the or each resilient arm comprises a protrusion for engagement with a complementary notch of the first connector part.

3. The connector of claim 1, wherein the slide comprises a protrusion for engagement with the detent for substantially inhibiting movement and release of the first connector part from the second connector part.

4. The connector of claim 1, wherein the slide comprises a stop for locating the slide and second connector part in the secured position.

5. The connector of claim 1, wherein the first connector part comprises a plurality of notches.

6. The connector of claim 1, wherein the second connector part comprises the slide and a carrier configured to be assembled with the at least two resilient legs, the second connector part configured to inhibit release of a first component when the slide is in the secured position.

7. The connector of claim 1, wherein the second connector part comprises a carrier for carrying the detent and/or the at least two resilient leers.

8. The connector of claim 7, wherein the carrier is formed with a slot arranged for receiving the first connector part.

9. The connector of claim 1, wherein the first connector part is located on a patient interface, and attached or attachable to the second connector part is a headgear or a part of a headgear or system for securing the patient interface in place about a user's head.

10. The connector of claim 1, wherein the at least two resilient legs and detent are integrally formed together.

11. The connector of claim 1, wherein the resilient arms are biased towards engagement with the first connector part.

12. The connector of claim 1, wherein the slide comprises two protrusions for engagement with the detent for substantially inhibiting movement and release of the first connector part from the second connector part.

13. The connector of claim 1, wherein the slide comprises a sleeve.

14. The connector or claim 1, wherein the first connector part comprises a notch.

15. The connector of claim 1, wherein the first connector part comprises a pair of notches.

16. The connector of claim 1, wherein the first connector part comprises a clip.

17. The connector of claim 1, wherein the first connector part is attached to, or integrally formed with or as, a patient interface or a part of a patient interface.

18. The connector of claim 1, wherein the connector is connected to a patient interface for use in a medical breathing circuit.

19. The connector of claim 18, wherein the patient interface comprises a pair of side arms and a headgear strap and wherein the connector connects an end of the headgear strap to at least one of the side arms.

20. A connector comprising:
a first connector part;
a second connector part;
a centerline extending along the length of the connector;
a detent for securing the first connector part and the second connector part together wherein the detent comprises a pair of resilient arms, wherein the centerline bisects the pair of resilient arms;
a slide moveable relative to the first connector part and/or the second connector part between:
  a secured position in which the detent is substantially inhibited from moving and releasing the first connector part from the second connector part; and
  a free position in which the detent is able to move to release the first connector part from the second connector part;
and
at least two resilient legs for urging the slide towards the secured position,
  wherein the at least two resilient legs: a) move away from each other as the slide moves towards the free position, or b) towards each other as the slide moves towards the free position,
wherein the centerline bisects the at least two resilient legs, and
wherein the at least two resilient legs are closer to the centerline than the pair of resilient arms.

* * * * *

UNITED STATES PATENT AND TRADEMARK OFFICE
CERTIFICATE OF CORRECTION

PATENT NO. : 10,806,887 B2
APPLICATION NO. : 15/319657
DATED : October 20, 2020
INVENTOR(S) : Mathew Ian Peacock et al.

It is certified that error appears in the above-identified patent and that said Letters Patent is hereby corrected as shown below:

In the Specification

In Column 7, Line 63, delete "Jun. 6," and insert --Jun. 1,--.

In Column 10, Line 25, delete "the or".

In Column 32, Line 23, delete "Jun. 6," and insert --Jun. 1,--.

In Column 45, Line 47, delete "the or".

In Column 45, Line 66, delete "the or".

In Column 57, Line 65, delete "medium, for" and insert --medium, 'L' for--.

In Column 67, Line 31, delete "carer." and insert --carrier.--.

In Column 68, Line 10, delete "FIG." and insert --FIGS.--.

In Column 71, Line 22, delete "FIG." and insert --FIGS.--.

In Column 85, Line 47, delete "that that" and insert --that--.

In Column 89, Line 53, delete "the or".

In the Claims

In Column 100, Line 17, Claim 2, delete "the or".

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,806,887 B2

In Column 100, Line 36, Claim 7, delete "leers" and insert --legs--.

In Column 100, Line 54, Claim 14, delete "or" and insert --of--.